US012029736B2

(12) United States Patent
Li

(10) Patent No.: US 12,029,736 B2
(45) Date of Patent: Jul. 9, 2024

(54) CAMPTOTHECIN DERIVATIVES AND CONJUGATES THEREOF

(71) Applicant: MediBoston Limited, Causeway Bay (HK)

(72) Inventor: Wei Li, Acton, MA (US)

(73) Assignee: MediBoston Limited, Causeway Bay (HK)

( * ) Notice: Subject to any disclaimer, the term of this patent is extended or adjusted under 35 U.S.C. 154(b) by 500 days.

(21) Appl. No.: 17/185,012

(22) Filed: Feb. 25, 2021

(65) Prior Publication Data

US 2021/0283125 A1 Sep. 16, 2021

Related U.S. Application Data

(60) Provisional application No. 62/981,197, filed on Feb. 25, 2020.

(51) Int. Cl.
| | |
|---|---|
| A61K 31/4745 | (2006.01) |
| A61K 47/54 | (2017.01) |
| A61K 47/65 | (2017.01) |
| A61K 47/68 | (2017.01) |
| A61P 35/00 | (2006.01) |
| C07D 491/22 | (2006.01) |

(52) U.S. Cl.
CPC ........ *A61K 31/4745* (2013.01); *A61K 47/545* (2017.08); *A61K 47/65* (2017.08); *A61K 47/6803* (2017.08); *A61K 47/6855* (2017.08); *A61K 47/6889* (2017.08); *A61P 35/00* (2018.01); *C07D 491/22* (2013.01)

(58) Field of Classification Search
CPC .. A61K 31/4745; A61K 47/545; A61K 47/65; A61K 47/6803; A61K 47/6855; A61K 47/6889; A61P 35/00; C07D 491/22
See application file for complete search history.

(56) References Cited

U.S. PATENT DOCUMENTS

| | | | |
|---|---|---|---|
| 5,049,668 A | 9/1991 | Wall et al. | |
| 5,834,476 A | 11/1998 | Terasawa et al. | |
| 6,403,604 B1 | 6/2002 | Yang et al. | |
| 6,512,118 B1 | 1/2003 | Tsujihara et al. | |
| 9,840,627 B2 | 12/2017 | Feng et al. | |
| 2015/0017246 A1 | 1/2015 | Huang | |
| 2015/0297748 A1 | 10/2015 | Masuda et al. | |
| 2022/0378929 A1 | 12/2022 | Li | |

FOREIGN PATENT DOCUMENTS

| | | |
|---|---|---|
| CN | 100406460 | 11/2003 |
| CN | 100354279 C | 6/2004 |
| CN | 1704416 A | 12/2005 |
| CN | 1246323 C | 3/2006 |
| CN | 102477042 A | 11/2010 |
| CN | 103289461 B1 | 7/2013 |
| CN | 109467563 A | 6/2018 |
| EP | 0325247 A1 | 7/1989 |
| EP | 1383772 B1 | 1/2004 |
| EP | 3524267 A1 | 8/2019 |
| EP | 3130608 B1 | 9/2019 |
| JP | H03232888 A | 10/1991 |
| WO | WO 1992/005785 A1 | 4/1992 |
| WO | WO 1992/011263 A1 | 7/1992 |
| WO | WO 1993/011770 A1 | 6/1993 |
| WO | WO 2005/044821 A1 | 5/2005 |
| WO | WO 2007/095389 A2 | 8/2007 |
| WO | WO 2011/154574 A1 | 5/2011 |
| WO | WO 2012/007619 A1 | 1/2012 |
| WO | WO 2015/000240 A1 | 1/2015 |
| WO | WO 2015/155998 A1 | 10/2015 |
| WO | WO 2019/034176 | 2/2019 |
| WO | WO 2019/195655 A1 | 10/2019 |
| WO | WO 2019/195665 A1 | 10/2019 |
| WO | WO 2020/219287 A1 | 10/2020 |
| WO | WO 2021/173773 A1 | 9/2021 |
| WO | WO 2021/212638 A1 | 10/2021 |

OTHER PUBLICATIONS

Wang, et al., Int. J. Mol. Sci. (2017) 18:1860 (Year: 2017).*
Li, et al., ACS Med. Chem. 2019 10:1386-1392 (Year: 2019).*
Yang, et al., Bioorg. and Medi. Chem. Lett. 2017 27:3959 (Year: 2017).*
Gisela, et al., Anti-Cancer Drugs 2003 (14)7:569 (Year: 2003).*
Dallavalle, et al., J. Med. Chem 2001 44:3264 (Year: 2001).*
Chen et al., "Enhancement and destruction of antibody function by somatic mutation: unequal occurrence is controlled by V gene combinatorial associations", The EMBO Journal, vol. 14, No. 12, 1995, pp. 2784-2794, DOI: 10.1002/j.1460-2075.1995.tb07278.x, (11 pages).
Hansch et al., "20-(S)-Camptothecin Analogues as DNA Topoisomerase I Inhibitors: a QSAR Study", ChemMedChem, vol. 2, No. 12, Dec. 10, 2007, pp. 1807-1813, DOI: 10.1002/cmdc.200700138, (7 pages).
Hyz et al., "Topotecan dynamics, tautomerism and reactivity—1H/13C NMR and ESI MS study", Magnetic Resonance in Chemistry, vol. 48, No. 8, Aug. 2010, pp. 575-584, DOI: 10.1002/mrc.2625, (10 pages).
International Search Report and Written Opinion for PCT/US2021/019565 dated Jun. 14, 2021 (13 pages).
International Search Report and Written Opinion for PCT/IB2022/051660 dated Sep. 12, 2022 (9 pages).
Kussie et al., "A single engineered amino acid substitution changes antibody fine specificity", The Journal of Immunology, vol. 152, No. 1, Jan. 1994, pp. 146-152, DOI: 10.4049/jimmunol.152.1.146 (8 pages).
Li et al., "Synthesis and Evaluation of Camptothecin Antibody-Drug Conjugates", ACS Medicinal Chemistry Letters, vol. 10, No. 10, 2019, pp. 1386-1392, DOI: 10.1021/acsmedchemlett.9b00301, Supplementary Section (21 pages).

(Continued)

*Primary Examiner* — Julie Wu
*Assistant Examiner* — John L Van Druff
(74) *Attorney, Agent, or Firm* — Proskauer Rose LLP; Fangli Chen

(57) ABSTRACT

The invention provides, camptothecins, camptothecin payloads, and camptothecin conjugates, methods of preparing and using, and intermediates useful in the preparation thereof. Also provided herein are methods of treating cancer and autoimmune diseases with the camptothecin conjugates described herein.

33 Claims, 5 Drawing Sheets

(56) References Cited

OTHER PUBLICATIONS

Nakada et al., "Novel antibody drug conjugates containing exatecan derivative-based cytotoxic payloads", Bioorganic & Medicinal Chemistry Letters, vol. 26, No. 6, Mar. 15, 2016, pp. 1542-1545, DOI: 10.1016/j.bmcl.2016.02.020, (4 pages).

Li, et al. "Synthesis and Evaluation of Camptothecin Antibody-Drug Conjugates." Sep. 6, 2019. ACS Medical Chemistry Letters. 10 (10), 1386-1392 DOI: 10.1021/acsmedchemlett.9b00301.

* cited by examiner

CAMPTOTHECIN DERIVATIVES AND CONJUGATES THEREOF

CROSS-REFERENCE TO RELATED APPLICATIONS

The present application claims benefit of U.S. Provisional Patent Application No. 62/981,197, filed Feb. 25, 2020, which is hereby incorporated by reference in its entirety.

BACKGROUND

Antibody Drug Conjugates (ADCs) have attracted significant interest as a new class of therapeutics. For example, ADCs can leverage monoclonal antibodies (mAbs) for the targeted delivery of cytotoxic agents to tumor cells, thereby permitting the use of highly cytotoxic drugs that could not be used using conventional, non-targeted modes. The design of ADCs-which typically features attachment of a cytotoxic agent to antibody, typically via a linker-involves consideration of a variety of factors, including the presence of a conjugation handle on the drug for attachment to the linker and linker technology for attaching the drug to an antibody in a conditionally stable manner. Non-optimal design can result in reduced ADC potency, insufficient immunologic specificity of the conjugate and increased toxicity due to non-specific release of the drug from the conjugate.

Camptothecin (CPT) is a pentacyclic quinoline alkaloid originally isolated from the wood and bark of a native tree of China called *Camptotheca acuminata* (*Camptotheca*, Happy tree) in latin and xi shu in chinese. Camptothecin exhibits significant antitumor activity by inhibiting topoisomerase I, an enzyme that is overexpressed in a variety of tumor cell lines and essential for DNA synthesis. Because of its broad-spectrum antitumor activity and unique mechanism of action, there have been substantial efforts towards developing clinical analogues of camptothecin. However, camptothecin and most of its derivatives have poor solubility and inactivity at physiological conditions, which have limited the clinical development of suitable camptothecin analogues.

Accordingly, camptothecin as toxin used in ADCs may overcome those limitations and there remains a need for therapeutically effective camptothecin derivatives and a need for new ADCs for therapeutic use.

SUMMARY OF INVENTION

Described herein are new cytotoxic agents according to Formula (I). These cytotoxic agents can then be combined with peptide linkers to form payloads according to Formula (II), which in turn can be used to prepare conjugates with cell binding agents (Formula (III)). Compounds of Formula (III) include ADCs that are useful for treating cell proliferative diseases such as cancers.

Accordingly, in one aspect, the invention features a compound of Formula (I), $$D\text{-}L_1\text{-}L_2\text{-}Q \quad (I),$$

or a pharmaceutically acceptable salt thereof, wherein:

D is represented by the following structural formula:

wherein
$R^1$ independently is —H, $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, $C_2$-$C_6$ halogenated alkenyl, or $C_2$-$C_6$ halogenated alkynyl;

$R^2$ independently is —H, —F, —N($R^4$)$_2$, —N($R^4$)(R'), —OR$^4$, —SR$^4$, —S(=O)R$^5$, —SO$_2$R$^5$, $C_1$-$C_6$ alkyl, or $C_1$-$C_6$ fluoroalkyl; and $R^3$ independently is —H, —F, —CN, —OCH$_3$, —CH$_3$, or —CF$_3$; or $R^2$ and $R^3$ together form a group of the formula —O(CH$_2$)$_n$O— or —O(CF$_2$)$_n$O— wherein n is 1 or 2;

$R^4$ independently is —H or $C_1$-$C_4$ alkyl;

$R^5$ independently is $C_1$-$C_4$ alkyl;

$L_1$ independently is absent or —($C_1$-$C_{10}$ alkylene)-;

$L_2$ independently is absent or is —OCH$_2$-$L_3$-*, —SCH$_2$-$L_3$-*, —S(=O)-$L_3$-*, —SO$_2$-$L_3$-*, —C(=O)-$L_3$-*, —N(R$^6$)CH$_2$-$L_3$-*, —N(R$^6$)C(=O)-$L_3$-*, —N(R$^6$)C(=O)N(R$^7$)-$L_3$-*, —C(=O)N(R$^6$)CH$_2$-$L_3$-*, —OC(=O)N(R$^6$)CH$_2$-$L_3$-*, or —N(R$^6$)C(=O)OCH$_2$-$L_3$-*; wherein * denotes the site covalently linked to Q;

$L_3$ independently is —($C_1$-$C_{10}$ alkylene)-, —CH$_2$OCH$_2$CH$_2$—, or —CH$_2$CH$_2$OCH$_2$CH$_2$—;

each $R^6$ and $R^7$ independently is —H, $C_1$-$C_6$ alkyl, $C_1$-$C_6$ fluoroalkyl, $C_3$-$C_6$ cycloalkyl, aryl, heteroaryl, or benzyl; and Q is —OH or —SH; and wherein when $R^2$ and $R^3$ combine to form —OCH$_2$O—, $R^1$ is not —CH$_2$CH$_2$CH$_2$CH$_3$; and when $R^1$ is —H or —CH$_2$CH$_3$, $R^2$ is —OH or alkoxy and $R^3$ is —H, then -$L_1$-$L_2$-Q is not —CH(R')CH$_2$OH or —CH(R')(CH$_2$)$_2$OH, wherein R' is —H or $C_1$-$C_6$ alkyl, alkoxy, substituted alkyl, phenyl or PhCH$_2$—.

In embodiments, at least one of $R^1$, $R^2$ and $R^3$, is not —H.

In embodiments, at least one of $L_1$ and $L_2$ is present.

In embodiments, $R^1$ independently is $C_1$-$C_6$ alkyl, silyl, $C_2$-$C_6$ alkenyl, $C_2$-$C_6$ alkynyl, $C_3$-$C_6$ cycloalkyl, $C_1$-$C_6$ halogenated alkyl, alkene or alkyne.

In embodiments, $R^1$ independently is —H or $C_1$-$C_6$ alkyl.

In embodiments, $R^2$ independently is —H, —F, —N($R^4$)$_2$, —N($R^4$)($R^5$), —OR$^4$, —SR$^4$, —S(=O)R$^5$, —SO$_2$R$^5$, $C_1$-$C_6$ alkyl, or $C_1$-$C_6$ fluoroalkyl; and $R^3$ independently is —H, —F, —CN, —OCH$_3$, —CH$_3$, or —CF$_3$.

In embodiments, $R^2$ independently is $C_1$-$C_6$ alkyl, $C_1$-$C_6$ fluoroalkyl, or —F.

In embodiments, $R^3$ independently is —H, —F, —CN, or —CF$_3$.

In embodiments, $R^3$ independently is —F, —CN, —OCH$_3$, —CH$_3$, or —CF$_3$.

In embodiments, $R^2$ and $R^3$ combine to form —O(CH$_2$)$_n$O— or —O(CF$_2$)$_n$O—, wherein n is 1 or 2.

In embodiments, D is represented by one of the following structures:
(D-I)
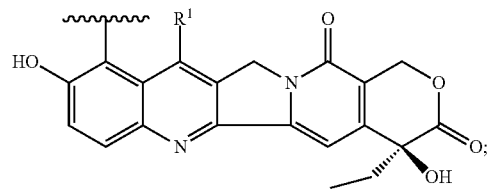
(D-II)
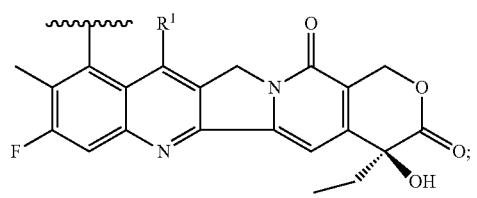
(D-III)
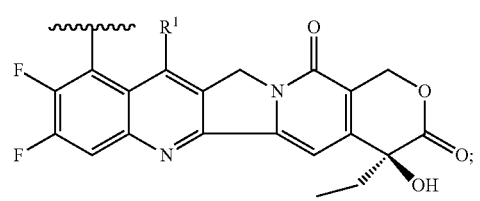
(D-IV)
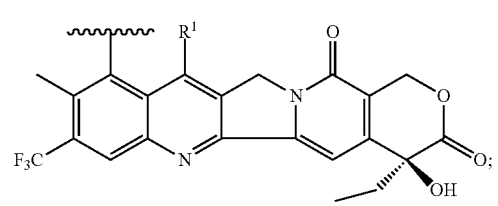
(D-V)
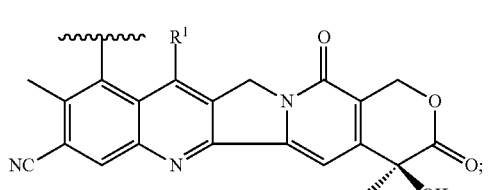
(D-VI)
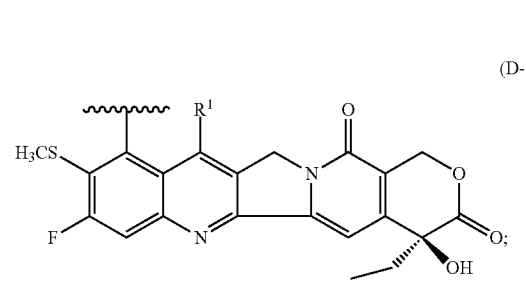
(D-VII)
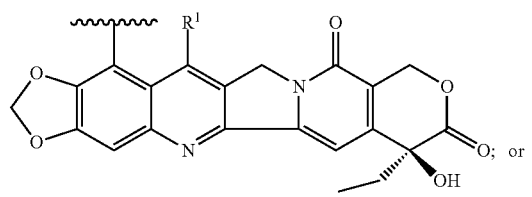
-continued
(D-VIII)
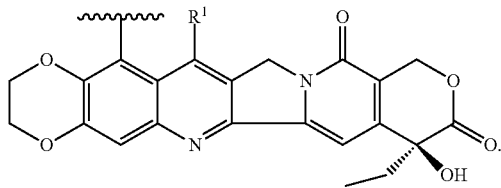
In embodiments, $R^1$ is —H or $C_1$-$C_6$ alkyl.
In embodiments, D is represented by one of the following structures:
(D1)
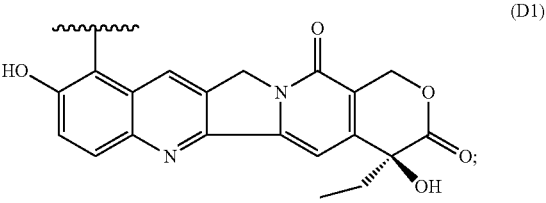
(D2)
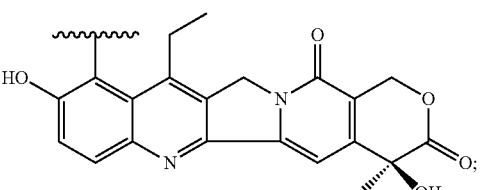
(D3)
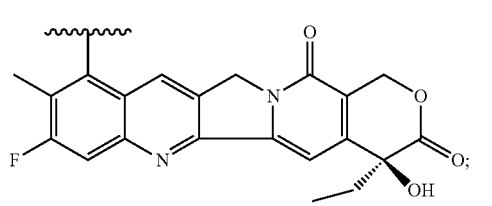
(D4)
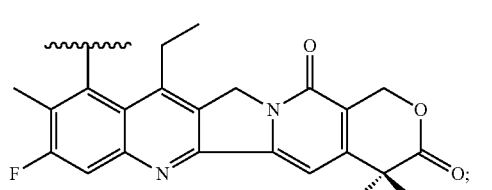
(D5)
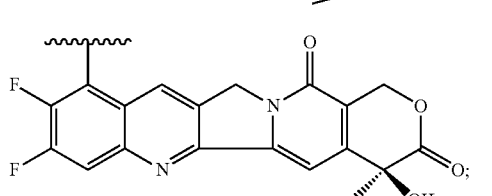
(D6)
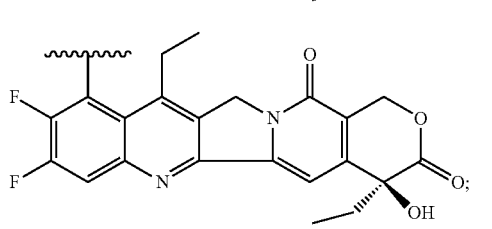

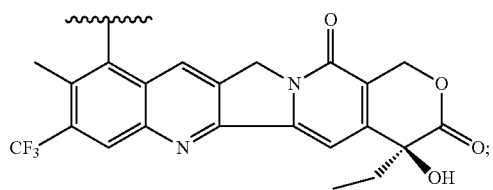 (D7)

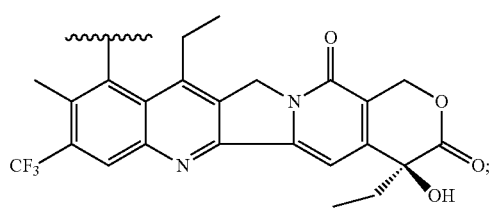 (D8)

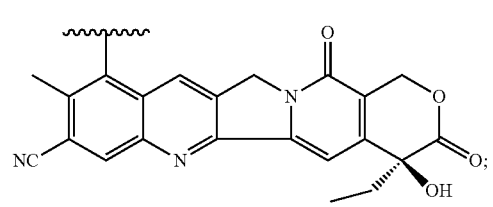 (D9)

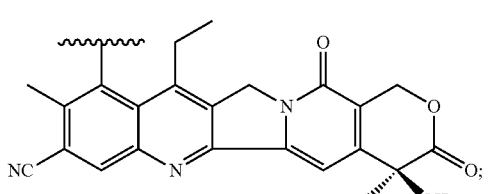 (D10)

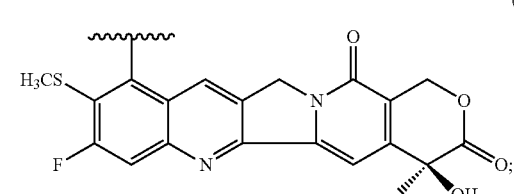 (D11)

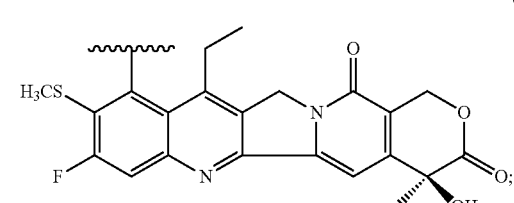 (D12)

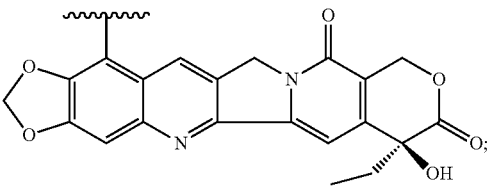 (D13)

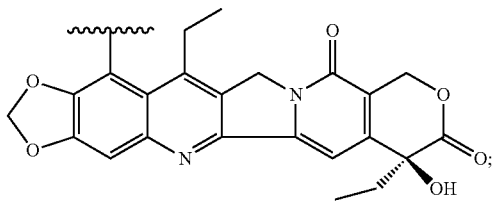 (D14)

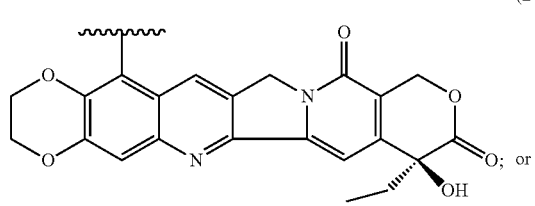 (D15)

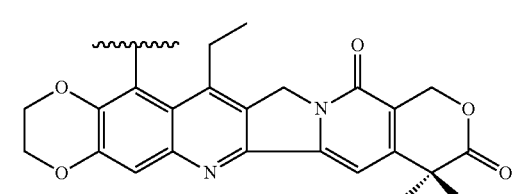 (D16)

In embodiments, $L_1$ is —($C_1$-$C_{10}$ alkylene)- and $L_2$ is absent.

In embodiments, $L_1$ is —($C_1$-$C_{10}$ alkylene)- and $L_2$ is —N($R^6$)CH$_2$-L$_3$-* or —N($R^6$)C(=O)-L$_3$-*, wherein * denotes the site covalently linked to Q.

In embodiments, $L_1$ is absent and $L_2$ is —N($R^6$)CH$_2$-L$_3$-* or —N($R^6$)C(=O)-L$_3$-*, wherein * denotes the site covalently linked to Q.

In embodiments, $L_3$ is —($C_1$-$C_{10}$ alkylene)-.

In embodiments, $R^6$ is —H or —CH$_3$.

In embodiments, $L_1$-$L_2$ is —CH$_2$—, —CH$_2$CH$_2$—, —CH$_2$CH$_2$CH$_2$—, or —CH$_2$CH$_2$CH$_2$CH$_2$—.

In embodiments, $L_1$-$L_2$ is —OCH$_2$CH$_2$—*, —OCH$_2$CH$_2$OCH$_2$CH$_2$—*, —SCH$_2$CH$_2$—*, —SCH$_2$CH$_2$OCH$_2$CH$_2$—*, —S(=O)CH$_2$—*, —SO$_2$CH$_2$—*, —C(=O)CH$_2$—*, —NHCH$_2$CH$_2$—*, —N(CH$_3$)CH$_2$CH$_2$—*, —N(CF$_3$)CH$_2$CH$_2$—*, —NHC(=O)CH$_2$—*, —CH$_2$NHC(=O)CH$_2$—*, —CH$_2$CH$_2$NHC(=O)CH$_2$—*, CH$_2$N(CH$_3$)C(=O)CH$_2$—*, —N(CH$_3$)C(=O)CH$_2$—*, —N(CH$_3$)C(=O)CH$_2$CH$_2$—*, —C(=O)NHCH$_2$CH$_2$—*, —NHC(=O)NHCH$_2$CH$_2$—*, —NHC(=O)OCH$_2$CH$_2$—*, —CH$_2$OC(=O)NHCH$_2$CH$_2$—*, or —C(=O)N(CH$_3$)CH$_2$CH$_2$—*, wherein * denotes the site covalently linked to Q.

In embodiments, $L_1$-$L_2$-Q is —CH$_2$CH$_2$CH$_2$CH$_2$OH, —CH$_2$CH$_2$CH$_2$OH, —CH$_2$CH$_2$OH, —CH$_2$CH$_2$OCH$_2$CH$_2$OH, —CH$_2$SCH$_2$CH$_2$OH, —CH$_2$NHC(=O)CH$_2$OH, —CH$_2$CH$_2$NHC(=O)CH$_2$OH, —CH$_2$N(CH$_3$)C(=O)CH$_2$OH, —OCH$_2$CH$_2$OH, —OCH$_2$CH$_2$CH$_2$OH, —SCH$_2$CH$_2$CH$_2$OH, —SCH$_2$CH$_2$OH, —NHCH$_2$CH$_2$OH, —NHCH$_2$CH$_2$CH$_2$OH, —N(CH$_3$)CH$_2$CH$_2$OH, —C(=O)NHCH$_2$CH$_2$OH, —NHC(=O)CH$_2$OH, —CH$_2$S(=O)CH$_2$OH, —CH$_2$SO$_2$CH$_2$OH, —CH$_2$CH$_2$CH$_2$CH$_2$SH, —CH$_2$CH$_2$CH$_2$SH, —CH$_2$CH$_2$SH, —CH$_2$CH$_2$OCH$_2$CH$_2$SH, —CH$_2$SCH$_2$CH$_2$SH, —CH$_2$NHC(=O)CH$_2$SH, —OCH$_2$CH$_2$CH$_2$SH, —SCH$_2$CH$_2$SH, —SCH$_2$CH$_2$SH, —NHCH$_2$CH$_2$CH$_2$SH, —N(CH$_3$)

CH₂CH₂SH, —C(=O)NHCH₂CH₂SH, —NHC(=O)CH₂SH, —CH₂S(=O)CH₂SH, or —CH₂SO₂CH₂SH.
In embodiments, D-L₁-L₂ is represented by a structure that is
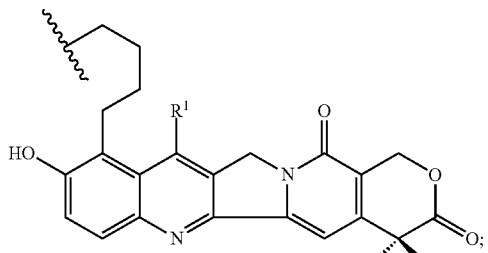
(P-I)
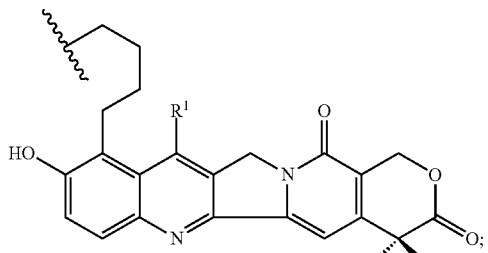
In embodiments, R¹ is —H or C₁-C₆ alkyl.
In embodiments, R¹ is H or —CH₂CH₃.
In embodiments, Q is —OH.
In embodiments, Q is —SH.
In embodiments, the compound has one of the following structures,
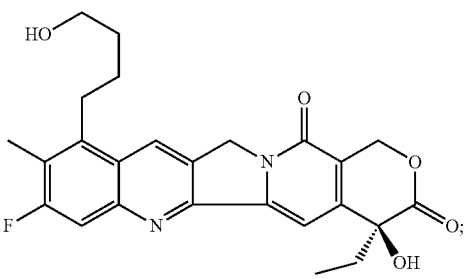
(P1)
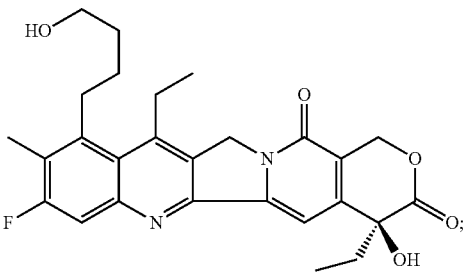
(P2)
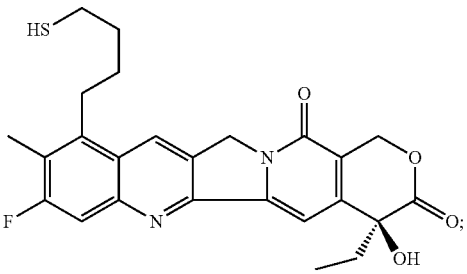
(P3)
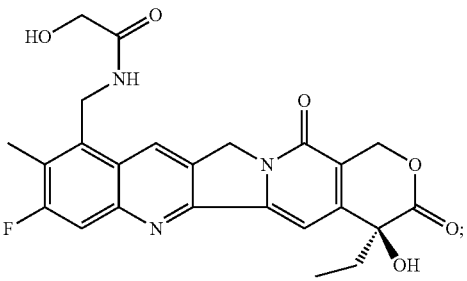
(P4)
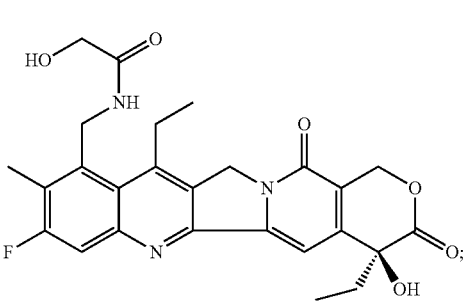
(P5)

-continued (P6)

[Chemical structure of P6]

or a pharmaceutically acceptable salt thereof.

In another aspect, the invention features a compound of Formula (II), $$D-L_1-L_2-Q'-CH_2-NH-E-Z \quad (II),$$

or a pharmaceutically acceptable salt thereof, wherein:

D is represented by the following structural formula:

[Chemical structure]

$R^1$ independently is —H, $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, $C_2$-$C_6$ halogenated alkenyl, or $C_2$-$C_6$ halogenated alkynyl;

$R^2$ independently is —H, —F, —N($R^4$)$_2$, —N($R^4$)($R^5$), —O$R^4$, —S$R^4$, —S(=O)$R^5$, —SO$_2R^5$, $C_1$-$C_6$ alkyl, or $C_1$-$C_6$ fluoroalkyl; and $R^3$ is —H, —F, —CN, —OCH$_3$, —CH$_3$, —CF$_3$; or $R^2$ and $R^3$ together form a group of the formula —O(CH$_2$)$_n$O— or —O(CF$_2$)$_n$O— wherein n is 1 or 2;

$R^4$ independently is —H or $C_1$-$C_4$ alkyl;

$R^5$ independently is $C_1$-$C_4$ alkyl;

$L_1$ independently is absent or —($C_1$-$C_{10}$ alkylene)-;

$L_2$ independently is absent or is —OCH$_2$-$L_3$-*, —SCH$_2$-$L_3$-*, —S(=O)-$L_3$-*, —SO$_2$-$L_3$-*, —C(=O)-$L_3$-*, —N($R^6$)CH$_2$-$L_3$-*, —N($R^6$)C(=O)-$L_3$-*, —N($R^6$)C(=O)N($R^7$)-$L_3$-*, —C(=O)N($R^6$)CH$_2$-$L_3$-*; —OC(=O)N($R^6$)CH$_2$-$L_3$-*, or —N($R^6$)C(=O)OCH$_2$-$L_3$-* wherein * denotes the site covalently linked to Q';

$L_3$ independently is —($C_1$-$C_{10}$ alkylene)-, —CH$_2$OCH$_2$CH$_2$—, or —CH$_2$CH$_2$OCH$_2$CH$_2$—;

each $R^6$ and $R^7$ independently is —H, $C_1$-$C_6$ alkyl, $C_1$-$C_6$ fluoroalkyl, $C_3$-$C_6$ cycloalkyl, aryl, heteroaryl, or benzyl; and Q' is —O— or —S—;

E is a peptide comprising 2 to 10 amino acids; wherein E is optionally substituted with one or more polyol; and wherein the N terminal of the peptide is covalently attached to Z;

Z is —C(=O)-$L_4$-Y,

[Chemical structure], or

[Chemical structure];

wherein m represents an integer of 1-10;

$L_4$ is —($C_1$-$C_{10}$ alkylene)-*, —CH$_2$CH$_2$(OCH$_2$CH$_2$)$_n$N($R^8$)C(=O)-$L_5$-*, or —CH$_2$(OCH$_2$CH$_2$)$_n$N($R^8$)C(=O)-$L_5$-*; wherein n represents an integer of 1-10; and wherein * denotes the site covalently linked to Y;

$L_5$ is —($C_1$-$C_{10}$ alkylene)-;

$R^8$ is —H or —CH$_3$; and

Y is an electrophilic group; and wherein when $R^2$ and $R^3$ combine to form —OCH$_2$O—, $R^1$ is not —CH$_2$CH$_2$CH$_2$CH$_3$.

In embodiments, E is a peptide of 2, 3, or 4 amino acids. Each amino acid in said peptide is an L amino acid, or at least one amino acid in said peptide is a D amino acid.

In embodiments, E comprises one or more amino acids selected from glycine, alanine, valine, glutamine, glutamic acid, phenylalanine, and leucine, and wherein said glutamine or glutamic acid is optionally substituted by a polyol.

In embodiments, E comprises amino acids selected from glycine, alanine, valine, glutamine, glutamic acid, phenylalanine, and leucine, and wherein said glutamine or glutamic acid is optionally substituted by a polyol.

In embodiments, E comprises an amino acid having the following structure,

[Chemical structure]

wherein $R^9$ is —H or $C_1$-$C_6$ alkyl.

In embodiments, E comprises an amino acid having the following structure,

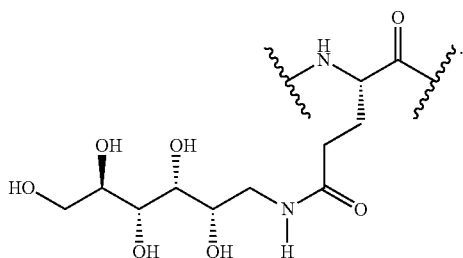 [SMILES: *N[C@@H](CCC(=O)NC[C@H](O)[C@@H](O)[C@H](O)[C@H](O)CO)C(*)=O]

In embodiments, E is selected from the group consisting of -Ala-Val-*, -Val-Ala-*, -Gly-Gly-*, -Val-Cit-*, -Cit-Val-*, -Leu-Ala-*, -Ala-Leu-*, -Leu-Cit-*,-Cit-Leu-*, -Leu-Ala-*, -Ala-Leu-*, -Lys-Lys-*, -Ala-Lys-*, -Lys-Ala-*, -Val-Lys-*, -Lys-Val-*, -Tyr-Arg-*, -Arg-Tyr-*, -Arg-Arg-*, -Ala-Ala-*, -Phe-Lys-*, -Lys-Phe-*, -Thr-Thr-*, -Thr-Met-*, -Met-Thr-*, -Met-Tyr-*, -Tyr-Met-*, -Phe-Gln-*, -Gln-Phe-*, -Gly-Ser-*, -Leu-Gln-*, -Gln-Leu-*, -Ser-Ala-*, -Ser-Gly-*, -Val-Thr-*, -Thr-Val-*, -Val-Gln-*, -Ser-Val-*, -Val-Ser-*, -Ala-Met-*, -Met-Ala-*, -Val-Arg-*, -Arg-Val-*, -Phe-Ala-*,-Ala-Phe-*, -Cit-Val-*, -Gln-Val-*, -Phe-Arg-*, -Arg-Phe-*, -Ala-Ala-Ala-*, -Gly-Gly-Gly-*, -Ala-Val-Ala-*, -Gly-Val-Gly-*, -Ala-Val-Gly-*, -Gly-Phe-Lys-*, -Lys-Phe-Gly-*, -Leu-Ala-Leu-*, -Val-Ala-Leu-*, -Leu-Ala-Val-*, -Val-Ala-Val-*, -Ala-Val-Ala-Gly-*, -Gly-Phe-Gly-Gly-*, -Gly-Gly-Phe-Gly-*, -Ala-Val-Gly-Gly-*, -Ala-Ala-Ala-Ala-*, -Ala-Val-Ala-Ala-*, -Ala-Leu-Ala-Leu-*,-Leu-Ala-Leu-Ala-*, -Gly-Phe-Leu-Gly-* and -Gly-Leu-Phe-Gly-*, wherein * denotes the N-terminal of the peptides covalently attached to Z.

In embodiments, E is selected from the group consisting of -L-Ala-D-Val-*, -L-Val-D-Ala-*, -L-Val-D-Lys-*, -L-Val-D-Arg-*, -L-Val-D-Cit-*, -L-Val-D-Arg-*, -L-Val-D-Cit-*, -L-Val-D-Lys-*, -L-Val-D-Arg-*, -L-Arg-D-Arg-*, -L-Ala-D-Ala-*, -L-Ala-D-Lys-*, -L-Ala-D-Arg-*, -L-Ala-D-Ala-L-Ala-*, -L-Ala-D-Val-L-Ala-*, -L-Ala-D-Ala-Gly-*, and -L-Ala-D-Val-Gly-*, wherein * denotes the N-terminal of the peptides covalently attached to Z.

In embodiments, -E-NH—CH$_2$— has one of the following structures, wherein * denotes the N-terminal of the peptides covalently attached to Z:

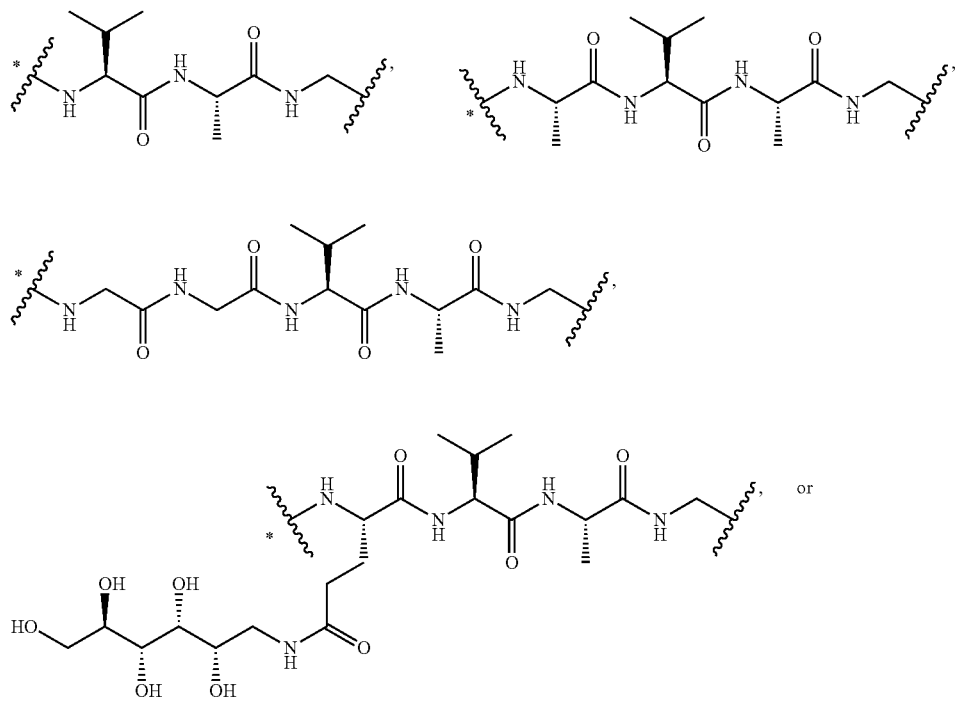

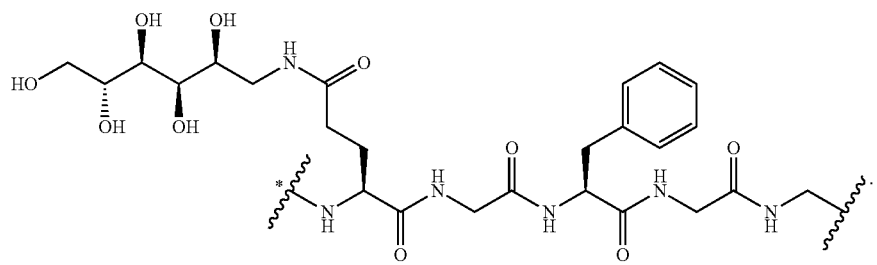

In embodiments, $L_4$ is —($C_1$-$C_{10}$ alkylene)-.

In embodiments, $L_4$ is —$CH_2CH_2(OCH_2CH_2)_nN(R^8)C(=O)$-$L_5$-* or —$CH_2(OCH_2CH_2)_nN(R^8)C(=O)$-$L_5$-*, wherein n represents an integer of 1-10; and wherein* denotes the site covalently linked to Y.

In embodiments, $L_4$ is —$CH_2CH_2CH_2CH_2CH_2$—, —$CH_2CH_2$—, —$CH_2$—, —$CH_2CH_2OCH_2CH_2OCH_2CH_2NHC(=O)CH_2CH_2$—* or —$CH_2OCH_2CH_2OCH_2CH_2NHC(=O)CH_2CH_2$—*, wherein* denotes the site covalently linked to Y.

In embodiments, Y is a Michael acceptor group, a succinimide, an epoxide, or a halogen.

In embodiments, Y is

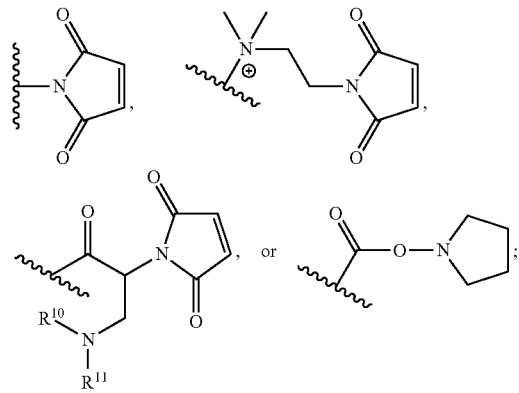

wherein $R^{10}$ and $R^{11}$ are each independently H or $C_1$-$C_3$ alkyl.

In embodiments, Z is —C(=O)-$L_4$-Y.

In embodiments, Z is

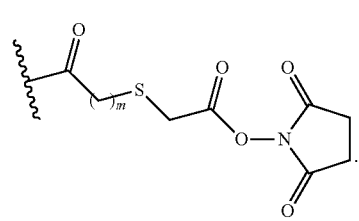

In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z is

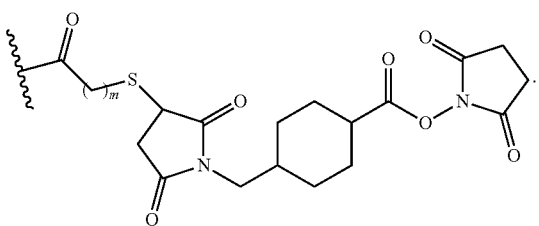

In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z is

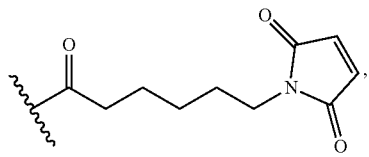

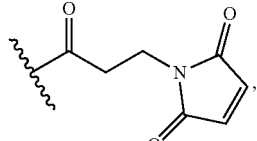

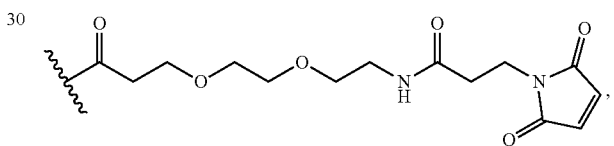

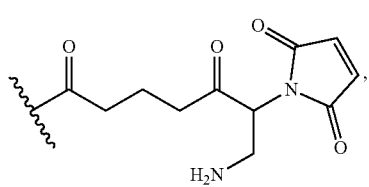

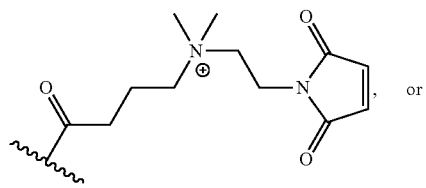, or

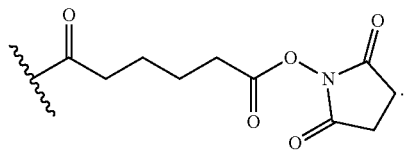

In embodiments, Z-E-NH—CH$_2$— has one of the following structures,

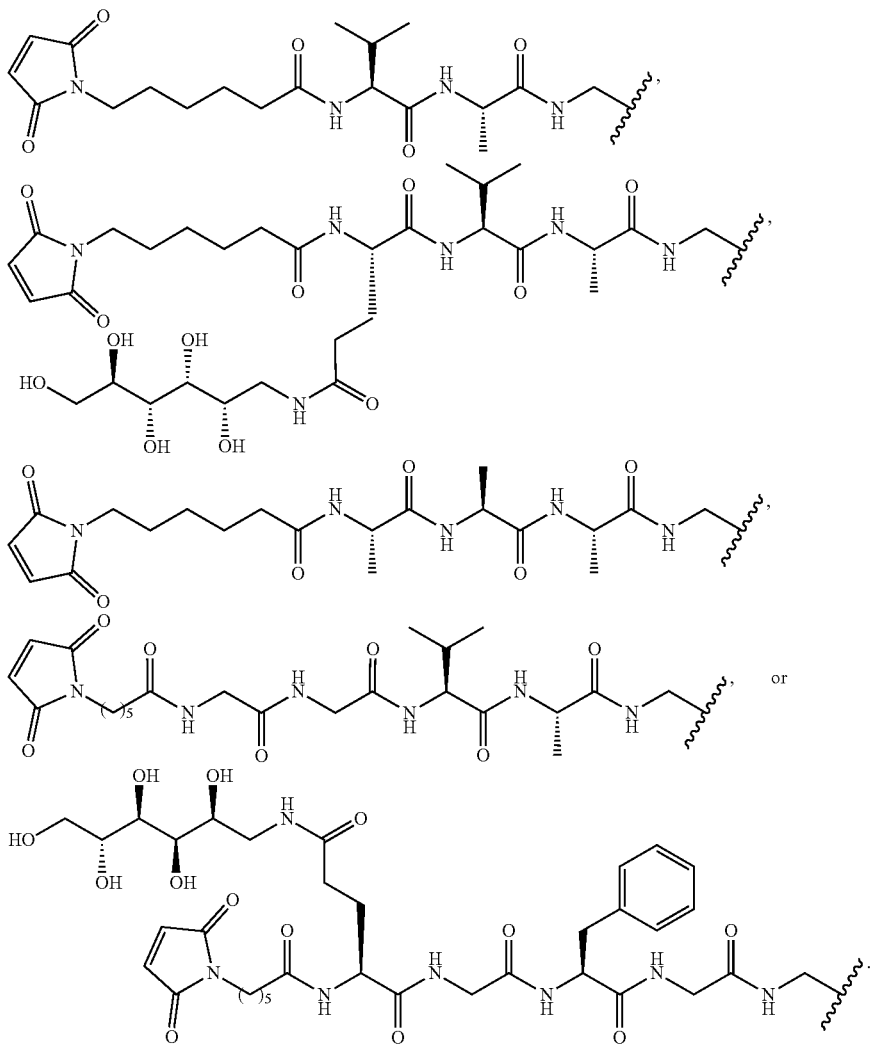

In embodiments, when R$^1$ is —H or —CH$_2$CH$_3$, R$^2$ is —OH or alkoxy and R$^3$ is —H, then -L$_1$-L$_2$-Q'— is not -CH(R')CH$_2$O— or —CH(R')(CH$_2$)$_2$O—, wherein R' is —H or C$_1$-C$_6$ alkyl, alkoxy, substituted alkyl, phenyl or PhCH$_2$—.

In embodiments, at least one of L$_1$ and L$_2$ is present.

In embodiments, at least one of R$^1$, R$^2$ and R$^3$, is not —H.

In embodiments, R$^1$ independently is C$_1$-C$_6$ alkyl, C$_2$-C$_6$ alkenyl, C$_2$-C$_6$ alkynyl, silyl, C$_3$-C$_6$ cycloalkyl, C$_1$-C$_6$ halogenated alkyl, alkene or alkyne.

In embodiments, R$^1$ independently is —H or C$_1$-C$_6$ alkyl.

In embodiments, R$^2$ independently is —H, —F, —N(R$^4$)$_2$, —N(R$^4$)(R$^5$), —OR$^4$, —SR$^4$, —S(=O)R$^5$, —SO$_2$R$^5$, C$_1$-C$_6$ alkyl, or C$_1$-C$_6$ fluoroalkyl; and R$^3$ independently is —H, —F, —CN, —OCH$_3$, —CH$_3$, or —CF$_3$.

In embodiments, R$^2$ independently is C$_1$-C$_6$ alkyl, C$_1$-C$_6$ fluoroalkyl, or —F.

In embodiments, R$^3$ independently is —H, —F, —CN, or —CF$_3$.

In embodiments, R$^3$ independently is —F, —CN, —OCH$_3$, —CH$_3$, or —CF$_3$.

In embodiments, R$^2$ and R$^3$ combine to form —O(CH$_2$)$_n$O— or —O(CF$_2$)$_n$O—, wherein n is 1 or 2.

In embodiments, D is represented by one of the following structures:

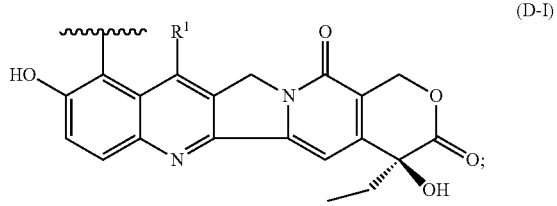

(D-I)

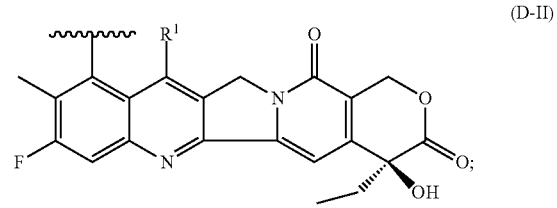

(D-II)

(D-III)
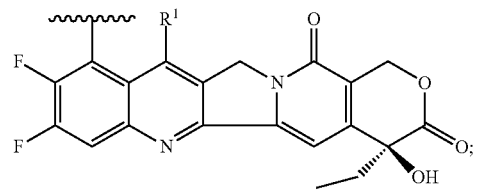
(D-IV)
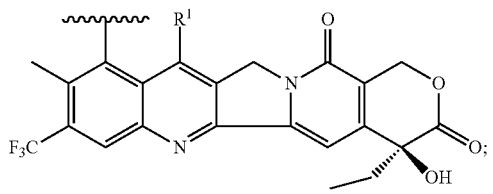
(D-V)
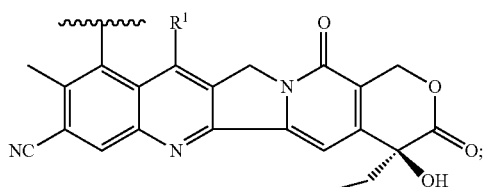
(D-VI)
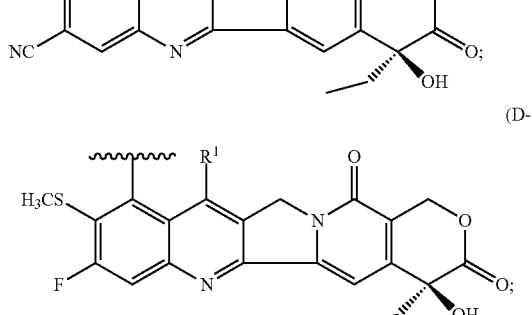
(D-VII)
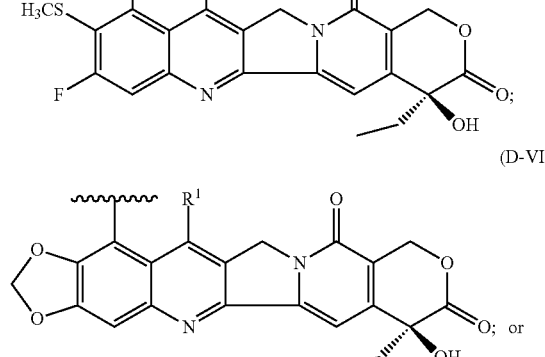
(D-VIII)
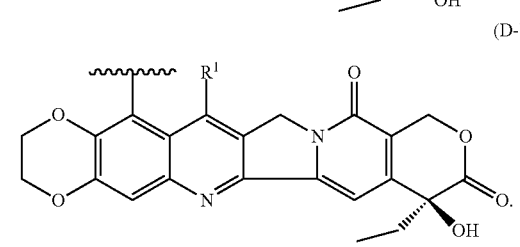
In embodiments, $R^1$ is —H or $C_1$-$C_6$ alkyl.
In embodiments, D is represented by one of the following structures:
(D1)
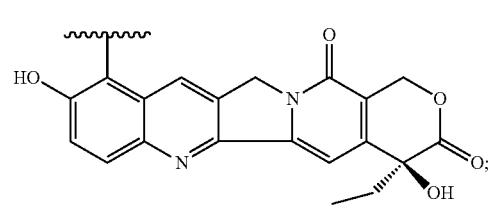
(D2)
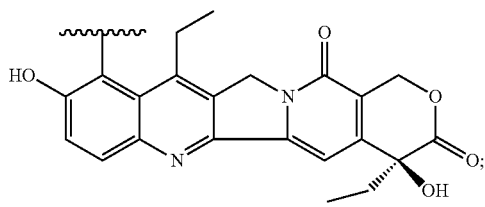
(D3)
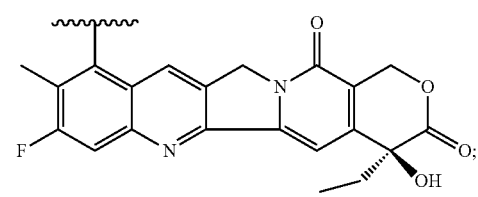
(D4)
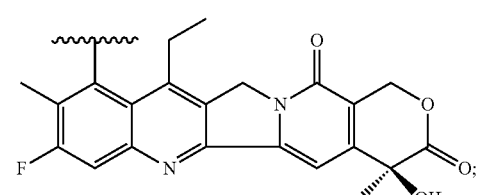
(D5)
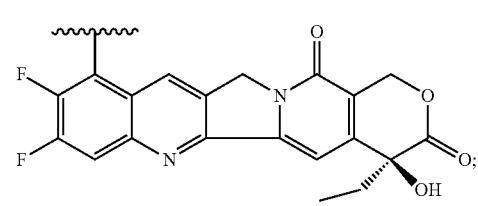
(D6)
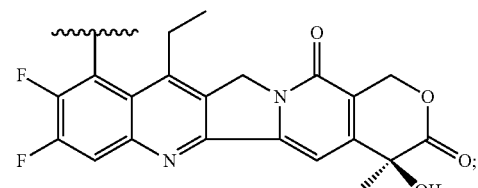
(D7)
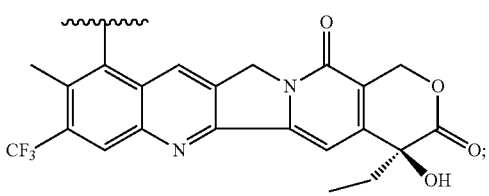
(D8)
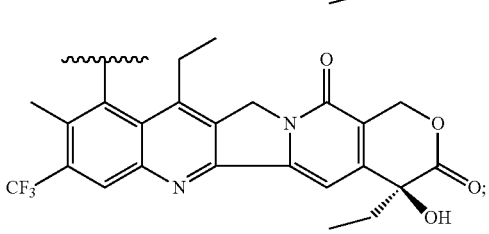
(D9)
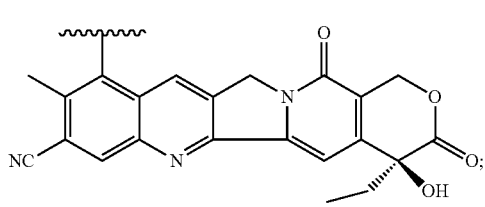

-continued

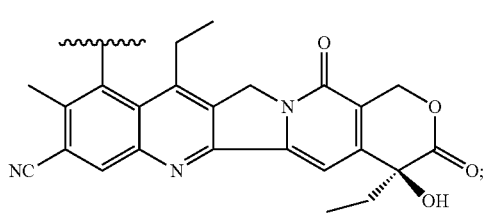 (D10)

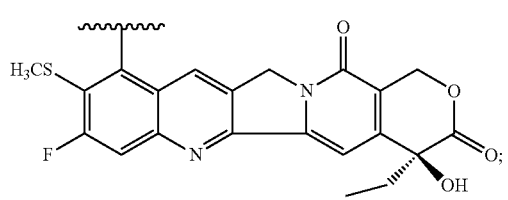 (D11)

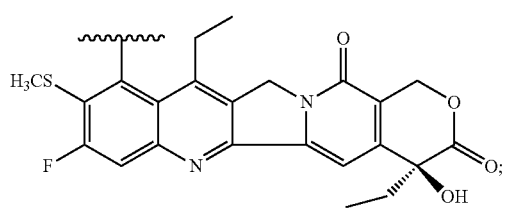 (D12)

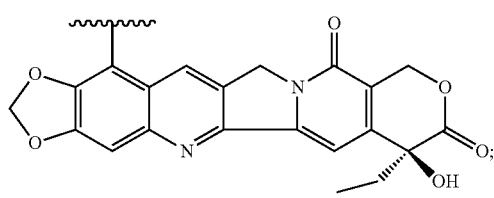 (D13)

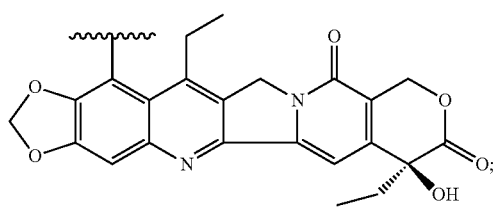 (D14)

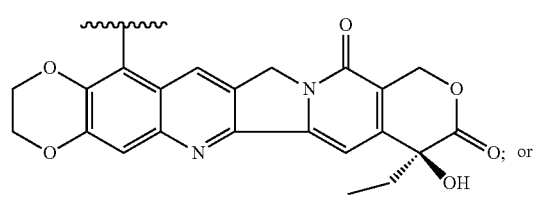 (D15)

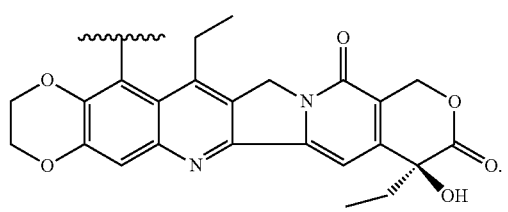 (D16)

In embodiments, $L_1$ is —($C_1$-$C_{10}$ alkylene)- and $L_2$ is absent.

In embodiments, $L_1$ is —($C_1$-$C_{10}$ alkylene)- and $L_2$ is —N($R^6$)CH$_2$-$L_3$-* or —N($R^6$)C(=O)-$L_3$-* wherein * denotes the site covalently linked to Q'.

In embodiments, $L_1$ is absent and $L_2$ is —N($R^6$)CH$_2$-$L_3$-* or —N($R^6$)C(=O)-$L_3$-*, wherein * denotes the site covalently linked to Q'.

In embodiments, $L_3$ is —($C_1$-$C_{10}$ alkylene)-.

In embodiments, $R^6$ is —H or —CH$_3$.

In embodiments, $L_1$-$L_2$ is —CH$_2$—, —CH$_2$CH$_2$—, —CH$_2$CH$_2$CH$_2$—, or —CH$_2$CH$_2$CH$_2$CH$_2$—.

In embodiments, $L_1$-$L_2$ is —OCH$_2$CH$_2$—*, —OCH$_2$CH$_2$OCH$_2$CH$_2$—*, —SCH$_2$CH$_2$—*, —SCH$_2$CH$_2$OCH$_2$CH$_2$—*, —S(=O)CH$_2$—*, —SO$_2$CH$_2$—*, —C(=O)CH$_2$—*, —NHCH$_2$CH$_2$—*, —N(CH$_3$)CH$_2$CH$_2$—*, —N(CF$_3$)CH$_2$CH$_2$—*, —NHC(=O)CH$_2$—*, —CH$_2$NHC(=O)CH$_2$—*, —CH$_2$CH$_2$NHC(=O)CH$_2$—*, —CH$_2$N(CH$_3$)C(=O)CH$_2$—*, —N(CH$_3$)C(=O)CH$_2$—*, —N(CH$_3$)C(=O)CH$_2$CH$_2$—*, —C(=O)NHCH$_2$CH$_2$—*, —NHC(=O)NHCH$_2$—*, —NHC(=O)OCH$_2$CH$_2$—*, —CH$_2$OC(=O)NHCH$_2$CH$_2$—*, or —C(=O)N(CH$_3$)CH$_2$CH$_2$—*, wherein * denotes the site covalently linked to Q'.

In embodiments, $L_1$-$L_2$-Q' is —CH$_2$CH$_2$CH$_2$CH$_2$O—, —CH$_2$CH$_2$CH$_2$O—, —CH$_2$CH$_2$O—, —CH$_2$CH$_2$OCH$_2$CH$_2$O—, —CH$_2$SCH$_2$CH$_2$O—, —CH$_2$NHC(=O)CH$_2$O—, —CH$_2$CH$_2$NHC(=O)CH$_2$O—, —CH$_2$N(CH$_3$)C(=O)CH$_2$O—, —OCH$_2$CH$_2$O—, —OCH$_2$CH$_2$CH$_2$O—, —SCH$_2$CH$_2$CH$_2$O—, —SCH$_2$CH$_2$O—, —NHCH$_2$CH$_2$O—, —NHCH$_2$CH$_2$CH$_2$O—, —N(CH$_3$)CH$_2$CH$_2$O—, —C(=O)NHCH$_2$CH$_2$O—, —NHC(=O)CH$_2$O—, —CH$_2$S(=O)CH$_2$O—, —CH$_2$SO$_2$CH$_2$O—, —CH$_2$CH$_2$CH$_2$CH$_2$S—, —CH$_2$CH$_2$CH$_2$S—, —CH$_2$CH$_2$S—, —CH$_2$CH$_2$OCH$_2$CH$_2$S—, —CH$_2$SCH$_2$CH$_2$S—, —CH$_2$NHC(=O)CH$_2$S—, —OCH$_2$CH$_2$CH$_2$S—, —SCH$_2$CH$_2$CH$_2$S—, —SCH$_2$CH$_2$S—, —NHCH$_2$CH$_2$CH$_2$S—, —N(CH$_3$)CH$_2$CH$_2$S—, —C(=O)NHCH$_2$CH$_2$S—, —NHC(=O)CH$_2$S—, —CH$_2$S(=O)CH$_2$S—, or —CH$_2$SO$_2$CH$_2$S—.

In embodiments, D-$L_1$-$L_2$ is represented by a structure that is

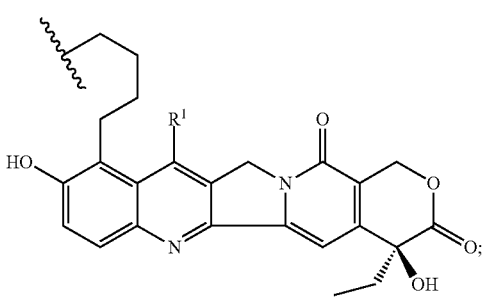 (P-I)

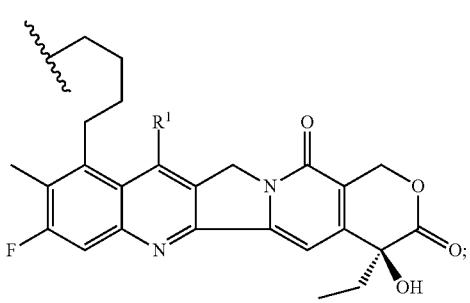 (P-II)

(P-III)
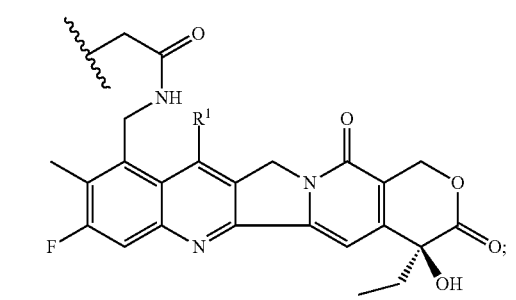
(P-IV)
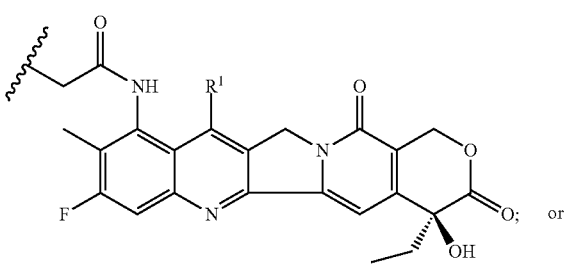
or
(P-V)
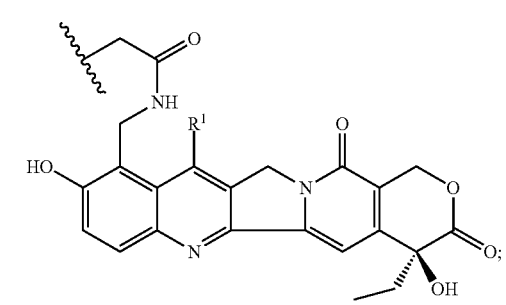
In embodiments, $R^1$ is —H or $C_1$-$C_6$ alkyl.
In embodiments, $R^1$ is —H or —CH$_2$CH$_3$.
In embodiments, Q' is —O—.
In embodiments, Q' is —S—.
In embodiments, D-$L_1$-$L_2$-Q'— has one of the following structures:
(P1')
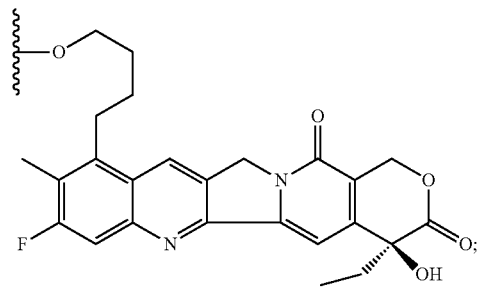
(P2')
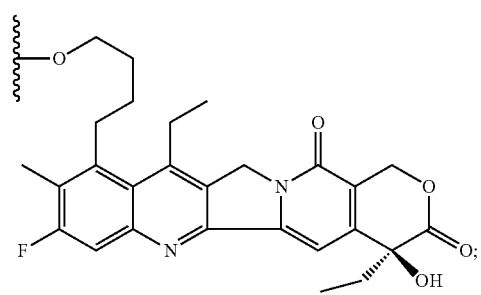
(P3')
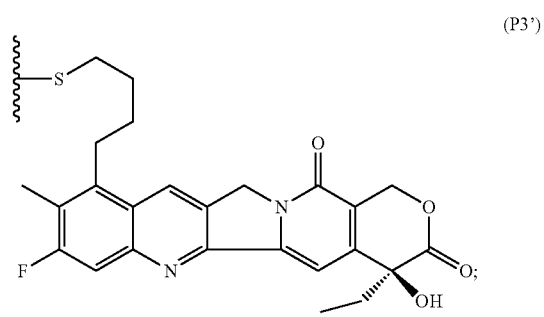
(P4')
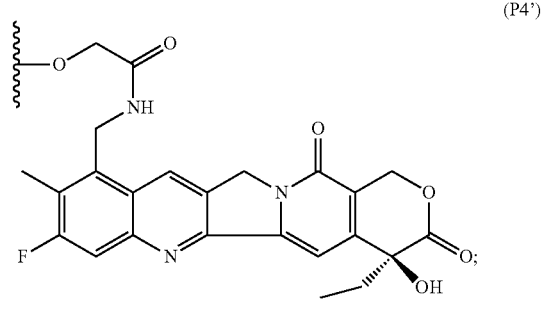
(P5')
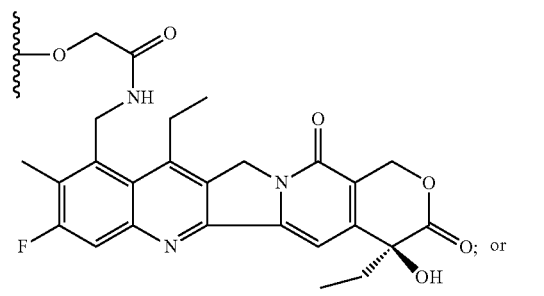
or
(P6')
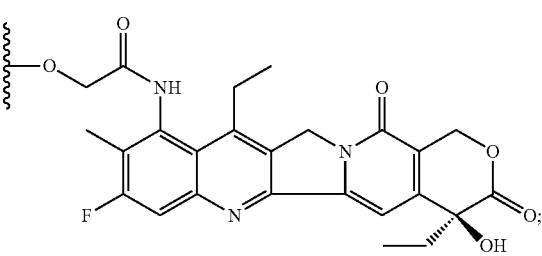

In embodiments, the compound has one of the following structures,
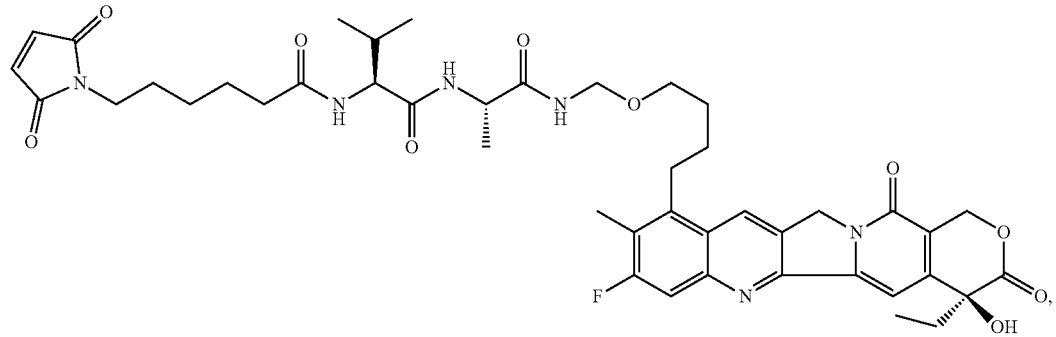
(PL1)
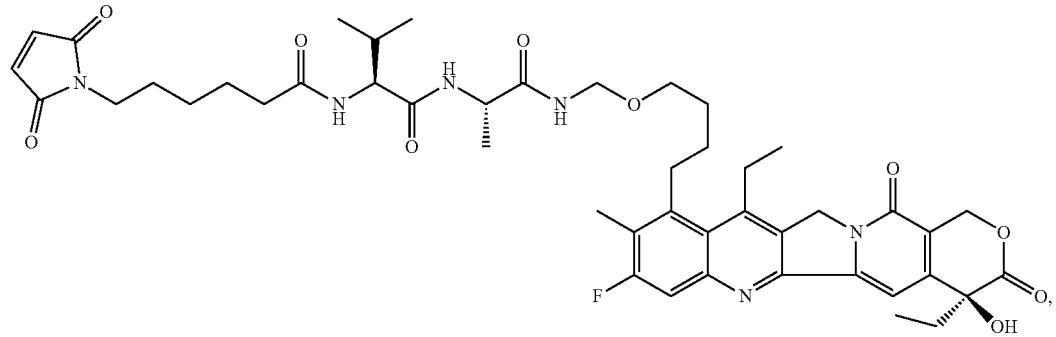
(PL2)
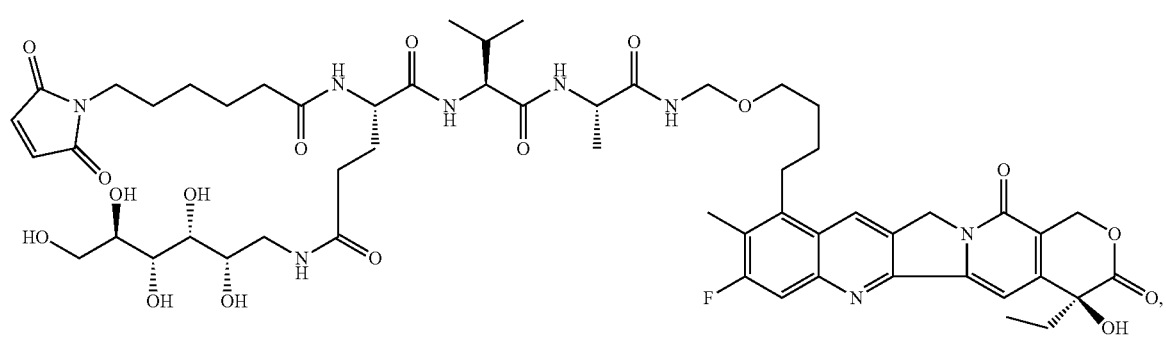
(PL3)
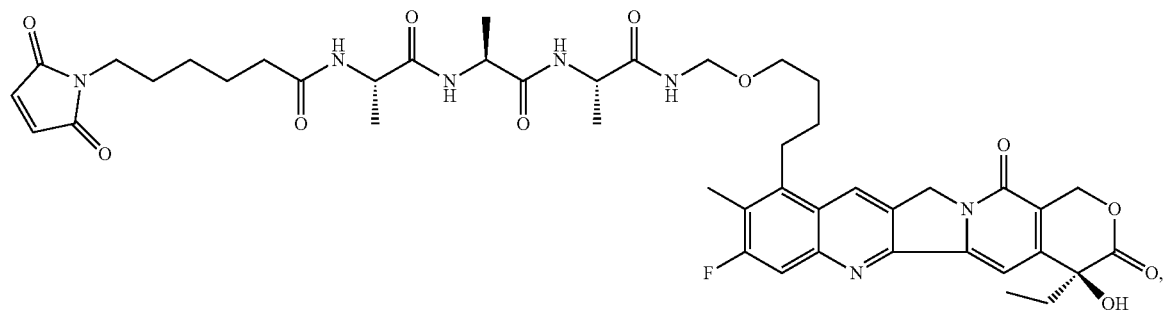
(PL4)

(PL5)
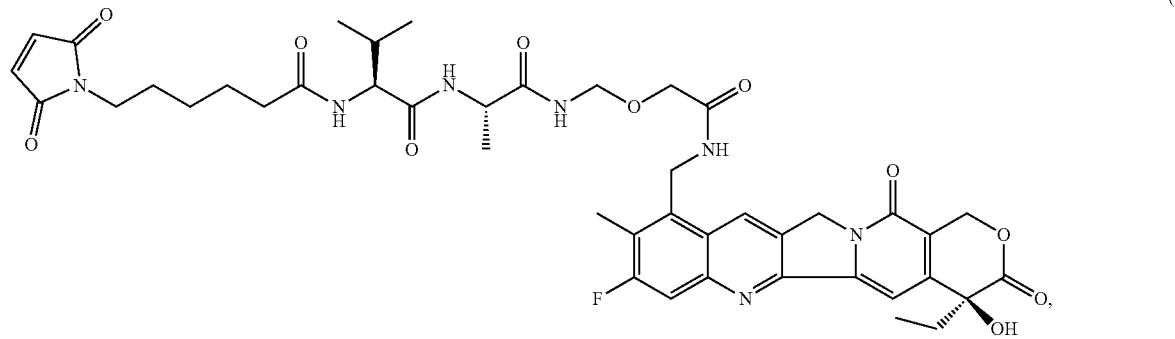
(PL6)
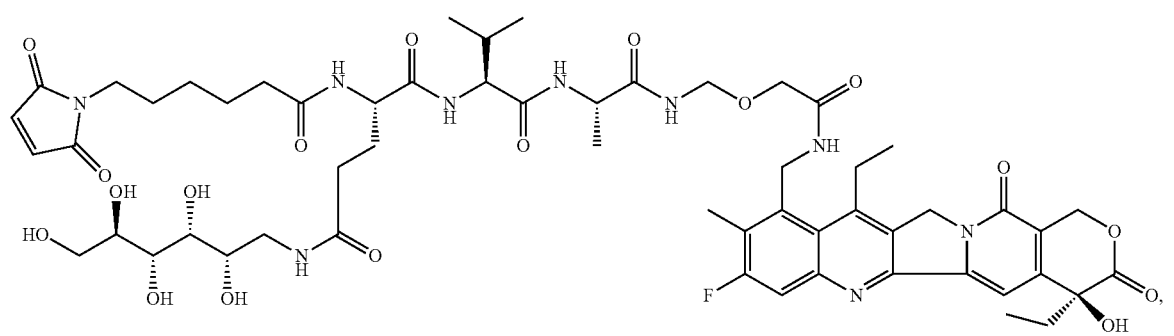
(PL7)
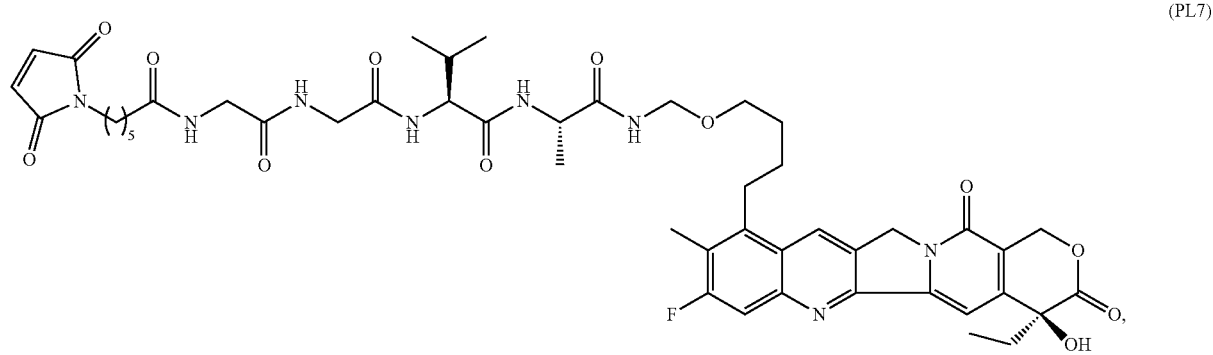
(PL8)
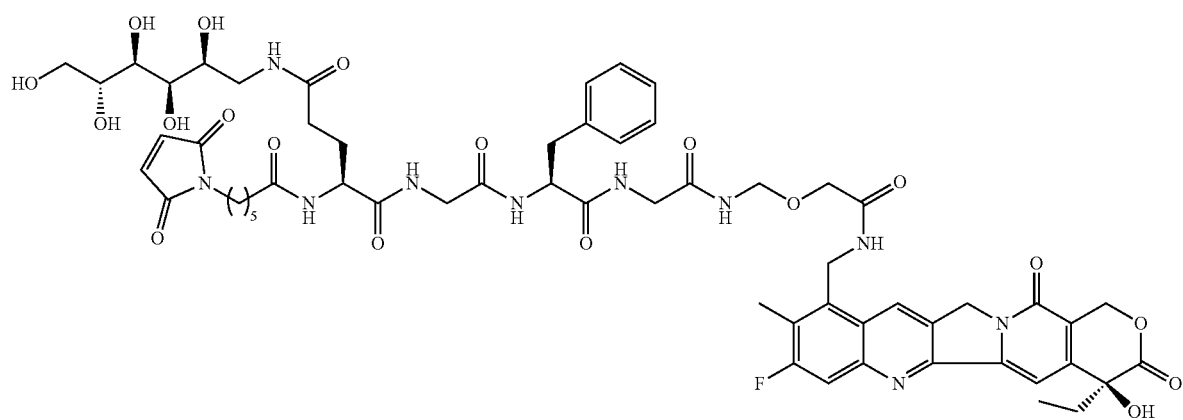

(PL9)
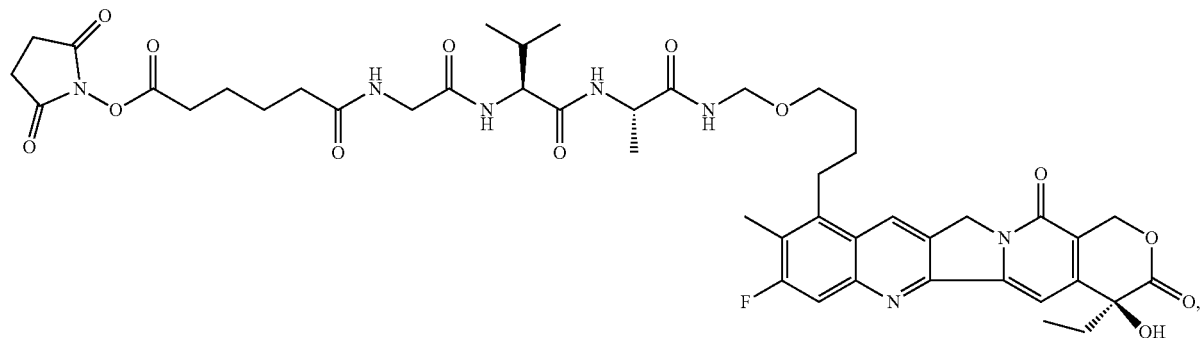
(PL10)
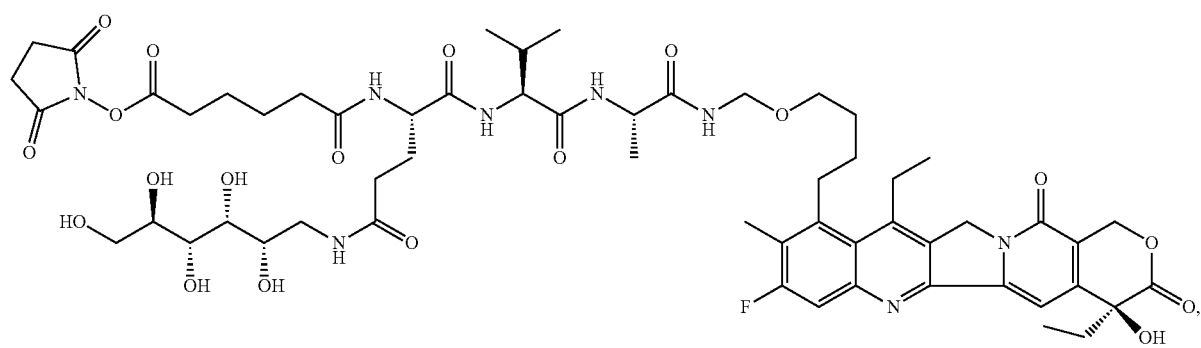
(PL11)
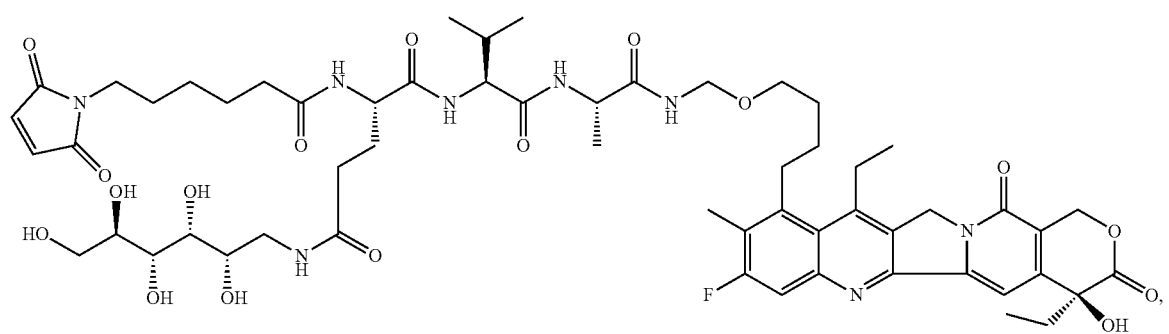
(PL12)
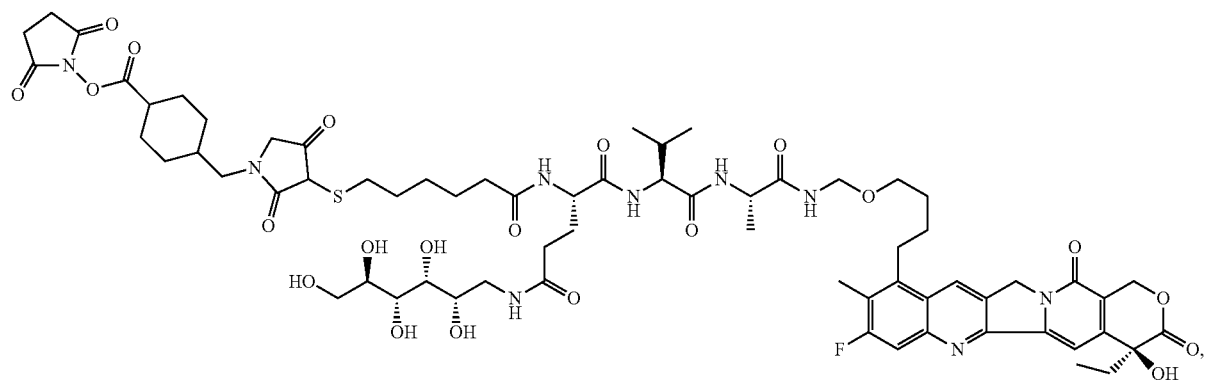

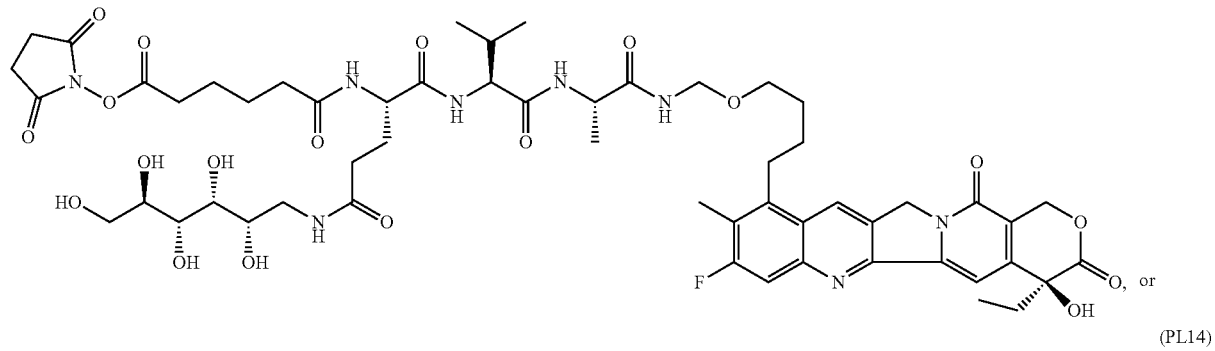
(PL13)

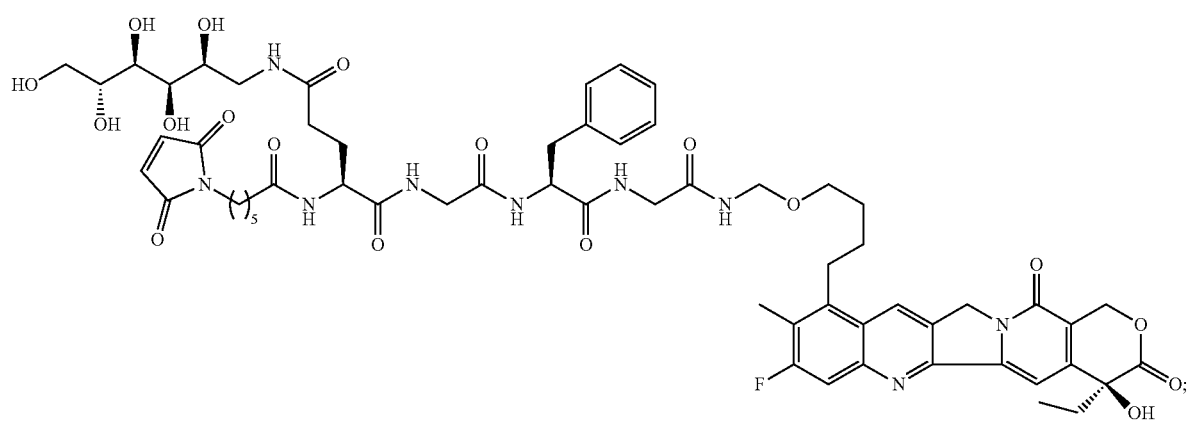
(PL14)

or a pharmaceutically acceptable salt thereof.

In a still further aspect, the invention features a compound of Formula (III), $$\{D-L_1-L_2-Q'-CH_2-NH-E-Z'\}_p-C \quad \text{(III)},$$

or a pharmaceutically acceptable salt thereof, wherein:

D is represented by the following structural formula:

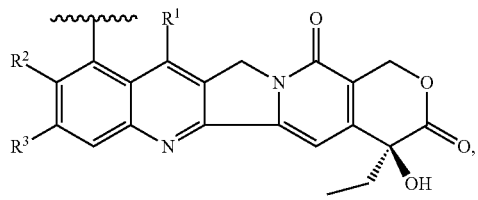

wherein
- $R^1$ independently is —H, $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, $C_2$-$C_6$ halogenated alkenyl, or $C_2$-$C_6$ halogenated alkynyl;
- $R^2$ independently is —H, —F, —N($R^4$)$_2$, —N($R^4$)($R^5$), —O$R^4$, —S$R^4$, —S(=O)$R^5$, —SO$_2R^5$, $C_1$-$C_6$ alkyl, or $C_1$-$C_6$ fluoroalkyl; and $R^3$ is —H, —F, —CN, —OCH$_3$, —CH$_3$, or —CF$_3$; or $R^2$ and $R^3$ together form a group of the formula —O(CH$_2$)$_n$O— or —O(CF$_2$)$_n$O— wherein n is 1 or 2;
- $R^4$ independently is —H or $C_1$-$C_4$ alkyl;
- $R^5$ independently is $C_1$-$C_4$ alkyl;
- $L_1$ independently is absent or —($C_1$-$C_{10}$ alkylene)-;
- $L_2$ independently is absent or is —OCH$_2$-$L_3$-*, —SCH$_2$-$L_3$-*, —S(=O)-$L_3$-*, —SO$_2$-$L_3$-*, —C(=O)-$L_3$-*, —N($R^6$)CH$_2$-$L_3$-*, —N($R^6$)C(=O)-$L_3$-*, —N($R^6$)C(=O)N($R^7$)-$L_3$-*, —C(=O)N($R^6$)CH$_2$-$L_3$-*, —OC(=O)N($R^6$)CH$_2$-$L_3$-*, or —N($R^6$)C(=O)OCH$_2$-$L_3$-*; wherein * denotes the site covalently linked to Q';
- $L_3$ independently is —($C_1$-$C_{10}$ alkylene)-, —CH$_2$OCH$_2$CH$_2$—, or —CH$_2$CH$_2$OCH$_2$CH$_2$—;
- each $R^6$ and R' independently is —H, $C_1$-$C_6$ alkyl, $C_1$-$C_6$ fluoroalkyl, $C_3$-$C_6$ cycloalkyl, aryl, heteroaryl, or benzyl;
- Q' is —O— or —S—;
- E is a peptide comprising 2 to 10 amino acids; wherein E is optionally substituted with one or more polyol; and wherein the N terminal of the peptide is covalently attached to Z';
- Z' is —C(=O)-$L_4$-Y',

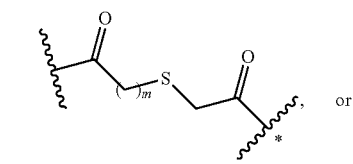, or

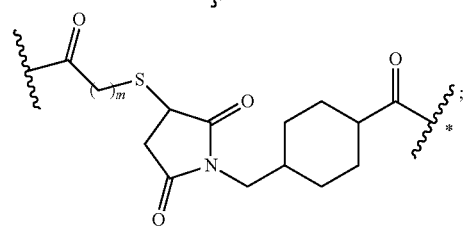;

wherein m represents an integer of 1-10 and * denotes the site covalently linked to said C;

- $L_4$ is —($C_1$-$C_{10}$ alkylene)-, —$CH_2CH_2(OCH_2CH_2)_nN(R^8)C(=O)$-$L_5$-*, or —$CH_2(OCH_2CH_2)_nN(R^8)C(=O)$-$L_5$-*; wherein n represents an integer of 1-10; and wherein * denotes the site covalently linked to Y';
- $L_5$ is —($C_1$-$C_{10}$ alkylene)-;
- $R^8$ is —H or —$CH_3$;
- C represents a cell binding agent;
- Y' is a group formed by the reaction of an electrophilic group with a reactive nucleophilic group present on said cell binding agent; and
- wherein when $R^2$ and $R^3$ combine to form —$OCH_2O$—, $R^1$ is not —$CH_2CH_2CH_2CH_3$; and
- p has a value between 1 to 18.

In embodiments, $L_4$ is —($C_1$-$C_{10}$ alkylene)-.

In embodiments, $L_4$ is —$CH_2CH_2(OCH_2CH_2)_nN(R^8)C(=O)$-$L_5$-* or —$CH_2(OCH_2CH_2)_nN(R^8)C(=O)$-$L_5$-*, wherein n represents an integer of 1-10; and wherein * denotes the site covalently linked to Y'.

In embodiments, $L_4$ is —$CH_2CH_2CH_2CH_2CH_2$—, —$CH_2CH_2$—, —$CH_2$—, —$CH_2CH_2OCH_2CH_2OCH_2CH_2NHC(=O)CH_2CH_2$—* or —$CH_2OCH_2CH_2OCH_2CH_2NHC(=O)CH_2CH_2$—*, wherein * denotes the site covalently linked to Y'.

In embodiments, Y' is formed from a Michael acceptor group, a succinimide, an epoxide, or a halogen.

In embodiments, Y' is formed from

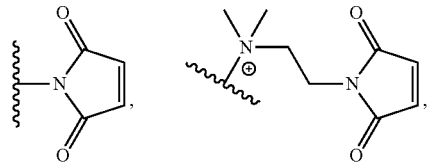

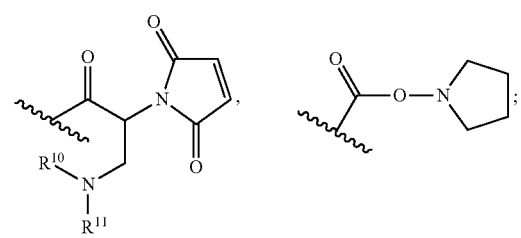

wherein $R^{10}$ and $R^{11}$ are each independently —H or $C_1$-$C_3$ alkyl.

In embodiments, Y' is

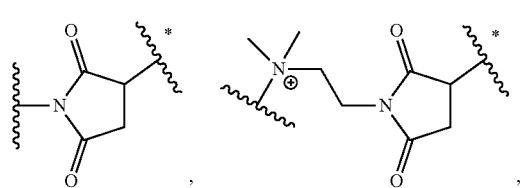

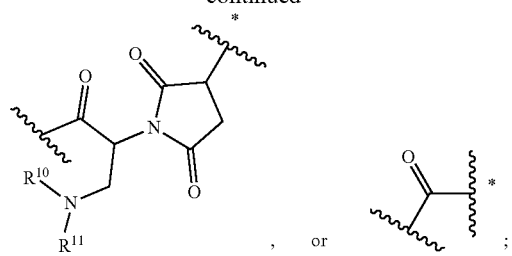

wherein $R^{10}$ and $R^{11}$ are each independently —H or $C_1$-$C_3$ alkyl and * denotes the site covalently linked to said C.

In embodiments, Z' is formed from:

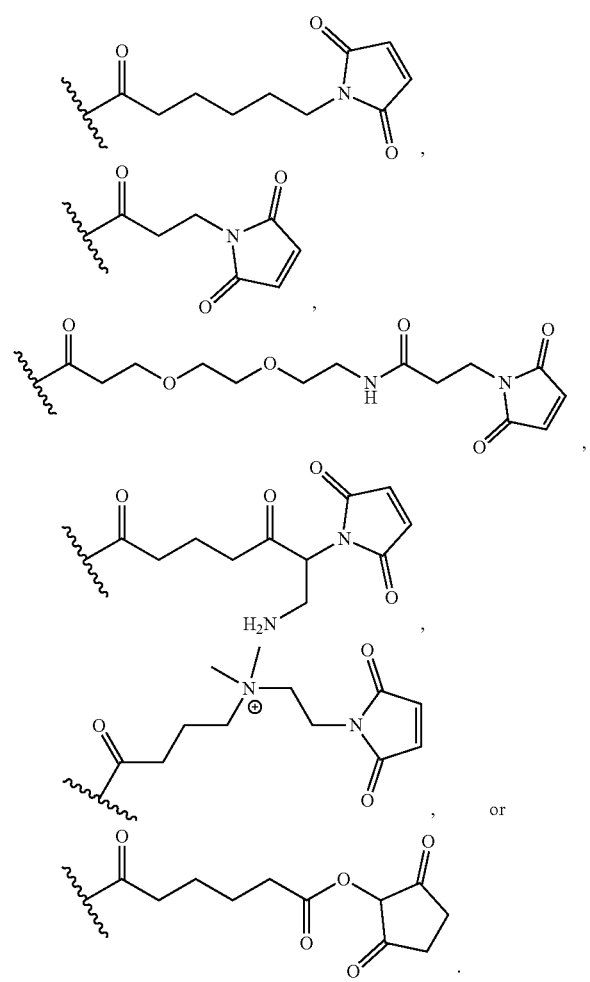

In embodiments, Z' is —C(=O)-$L_4$-Y'.

In embodiments, Z' is

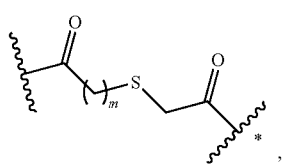

and * denotes the site covalently linked to said C. In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z' is

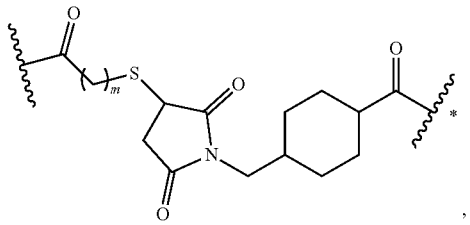

and * denotes the site covalently linked to said C. In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z' is:

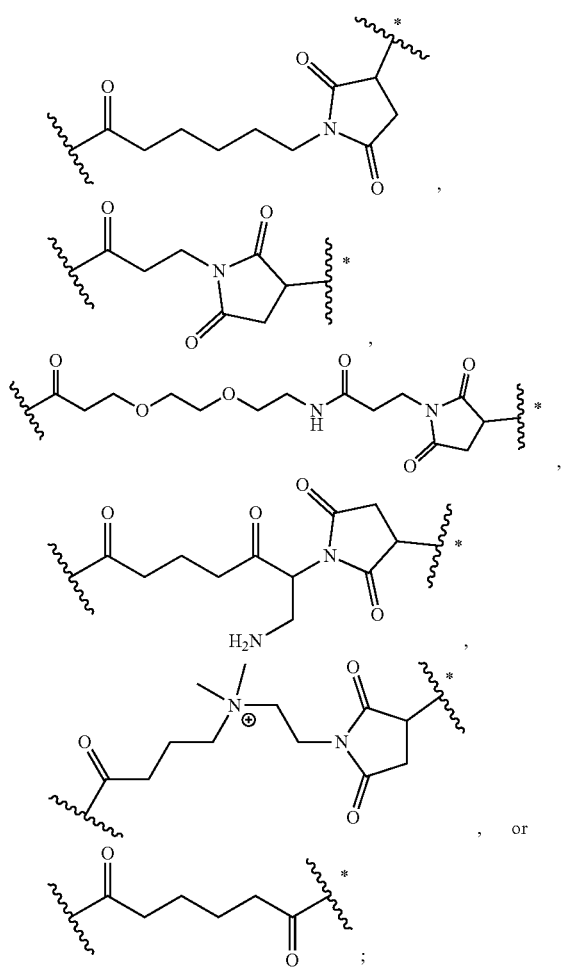

wherein * denotes the site covalently linked to C.

In embodiments, E is a peptide of 2, 3, or 4 amino acids. Each amino acid in said peptide is an L amino acid, or at least one amino acid in said peptide is a D amino acid.

In embodiments, E comprises one or more amino acids selected from glycine, alanine, valine, glutamine, glutamic acid, phenylalanine, and leucine, and wherein said glutamine or glutamic acid is optionally substituted by a polyol.

In embodiments, E comprises amino acids selected from glycine, alanine, valine, glutamine, glutamic acid, phenylalanine, and leucine, and wherein said glutamine or glutamic acid is optionally substituted by a polyol.

In embodiments, E comprises an amino acid having the following structure,

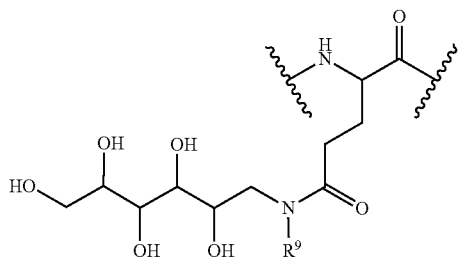

wherein $R^9$ is —H or $C_1$-$C_6$ alkyl.

In embodiments, E comprises an amino acid having the following structure,

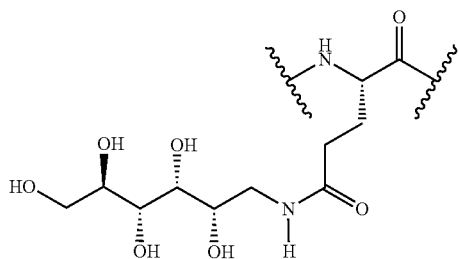

In embodiments, E is selected from the group consisting of -Ala-Val-*, -Val-Ala-*, -Gly-Gly-*, -Val-Cit-*, -Cit-Val-*, -Leu-Ala-*, -Ala-Leu-*, -Leu-Cit-*,-Cit-Leu-*, -Leu-Ala-*, -Ala-Leu-*, -Lys-Lys-*, -Ala-Lys-*, -Lys-Ala-*, -Val-Lys-*, -Lys-Val-*, -Tyr-Arg-*, -Arg-Tyr-*, -Arg-Arg-*, -Ala-Ala-*, -Phe-Lys-*, -Lys-Phe-*, -Thr-Thr-*, -Thr-Met-*, -Met-Thr-*, -Met-Tyr-*, -Tyr-Met-*, -Phe-Gln-*, -Gln-Phe-*, -Gly-Ser-*, -Leu-Gln-*, -Gln-Leu-*, -Ser-Ala-*, -Ser-Gly-*, -Val-Thr-*, -Thr-Val-*, -Val-Gln-*, -Ser-Val-*, -Val-Ser-*, -Ala-Met-*, -Met-Ala-*, -Val-Arg-*, -Arg-Val-*, -Phe-Ala-*,-Ala-Phe-*, -Cit-Val-*, -Gln-Val-*, -Phe-Arg-*, -Arg-Phe-*, -Ala-Ala-Ala-*, -Gly-Gly-Gly-*, -Ala-Val-Ala-*, -Gly-Val-Gly-*, -Ala-Val-Gly-*, -Gly-Phe-Lys-*, -Lys-Phe-Gly-*, -Leu-Ala-Leu-*, -Val-Ala-Leu-*, -Leu-Ala-Val-*, -Val-Ala-Val-*, -Ala-Val-Ala-Gly-*, -Gly-Phe-Gly-Gly-*, -Gly-Gly-Phe-Gly-*, -Ala-Val-Gly-Gly-*, -Ala-Ala-Ala-Ala-*, -Ala-Val-Ala-Ala-*, -Ala-Leu-Ala-Leu-*,-Leu-Ala-Leu-Ala-*, -Gly-Phe-Leu-Gly-* and -Gly-Leu-Phe-Gly-*, wherein * denotes the N-terminal of the peptides covalently attached to Z'.

In embodiments, E is selected from the group consisting of -L-Ala-D-Val-*, -L-Val-D-Ala-*, -L-Val-D-Lys-*, -L-Val-D-Arg-*, -L-Val-D-Cit-*, -L-Val-D-Arg-*, -L-Val-D-Cit-*, -L-Val-D-Lys-*, -L-Val-D-Arg-*, -L-Arg-D-Arg-*, -L-Ala-D-Ala-*, -L-Ala-D-Lys-*, -L-Ala-D-Arg-*, -L-Ala-D-Ala-L-Ala-*, -L-Val-D-Val-L-Ala-*, -L-Ala-D-Ala-Gly-*, and -L-Ala-D-Val-Gly-*, wherein * denotes the N-terminal of the peptides covalently attached to Z'.

In embodiments, -E-NH—CH$_2$— has one of the following structures, wherein * denotes the N-terminal of the peptides covalently attached to Z':
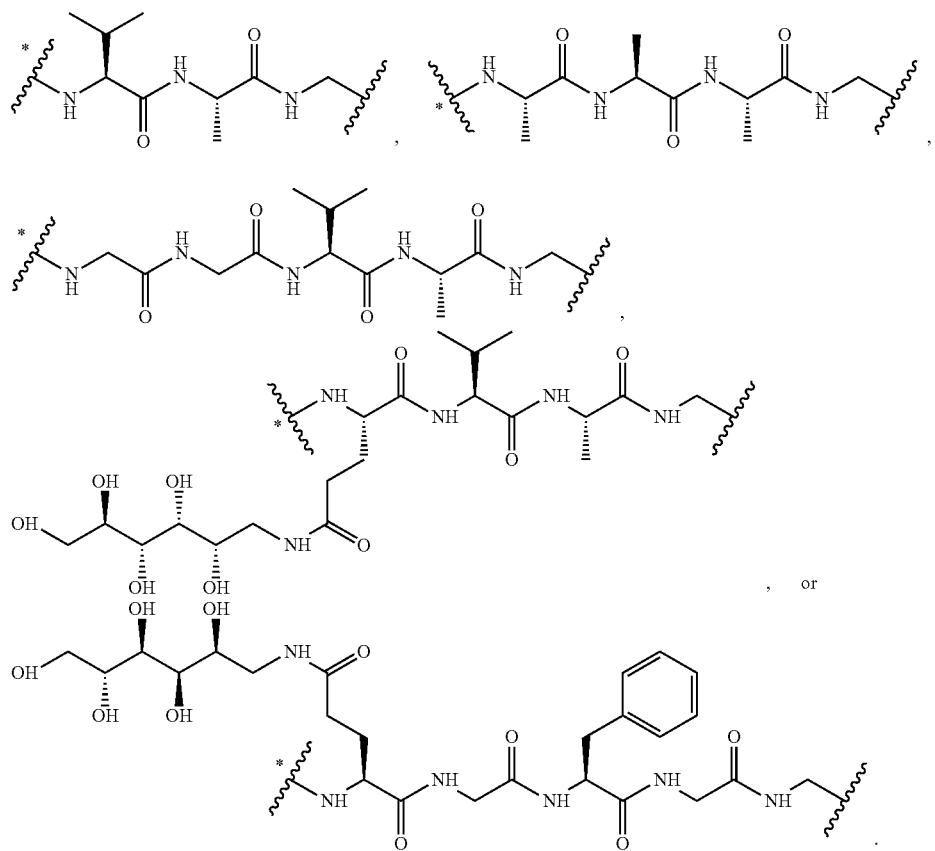
In embodiments, Z'-E-NH—CH$_2$ is formed from one of the following structures:
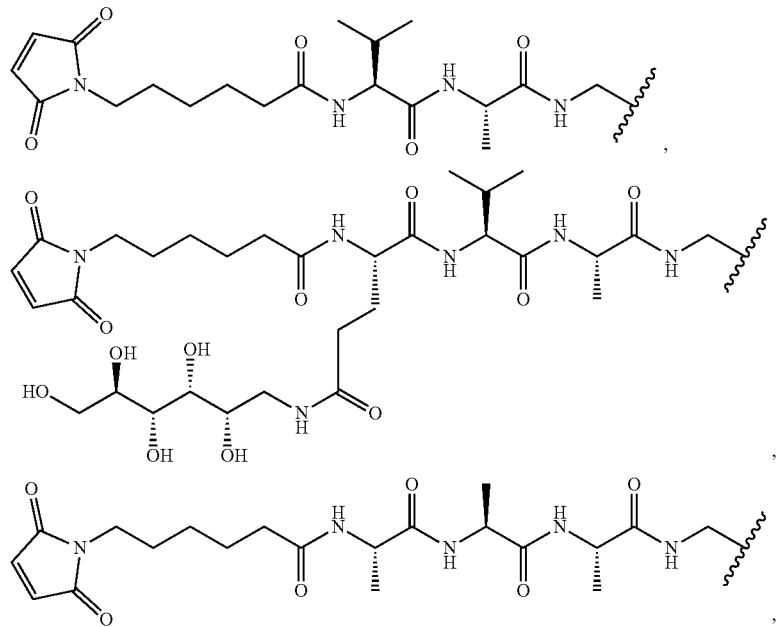

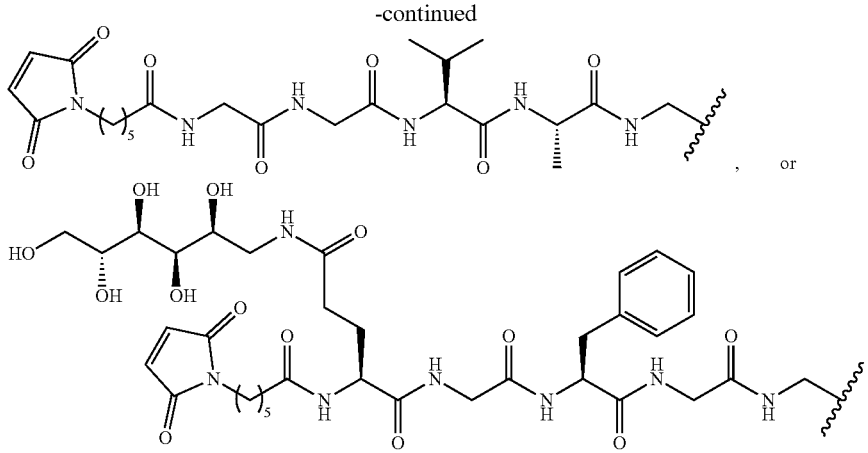
In embodiments, Z'-E-NH—CH$_2$ is one of the following structures, wherein * denotes the point of attachment to the C:
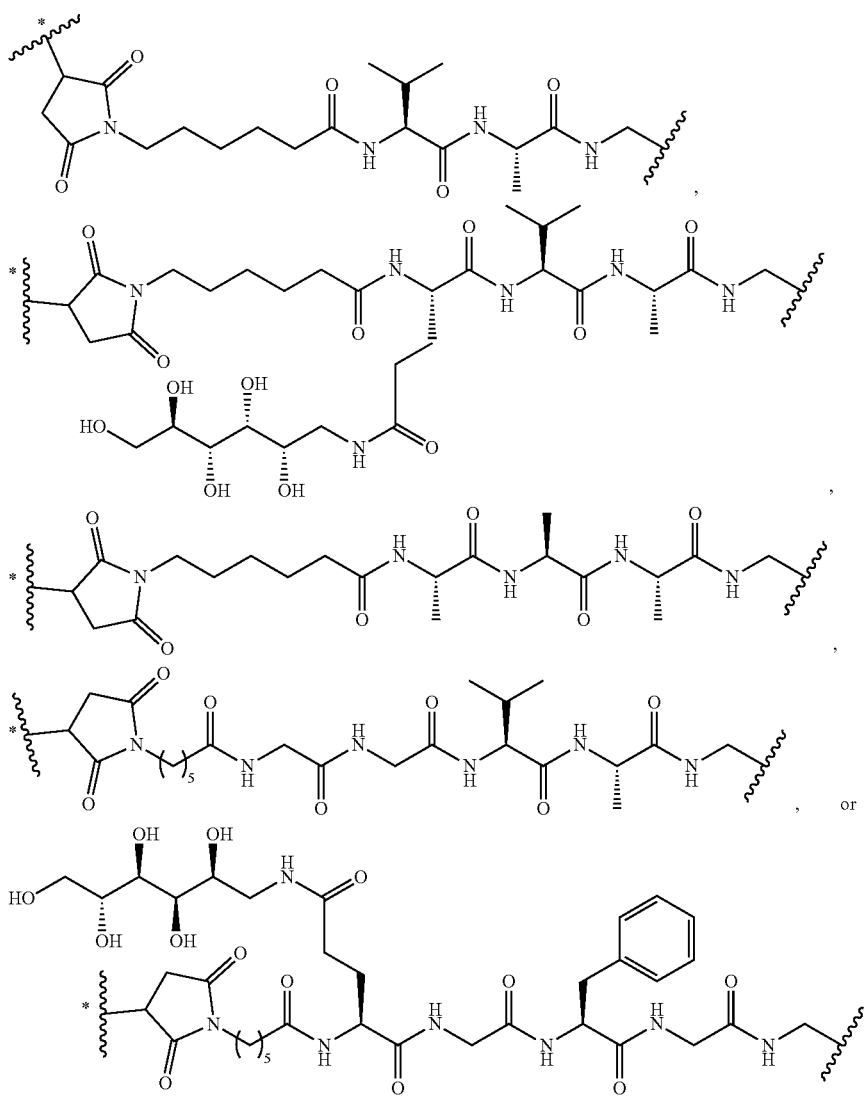

In embodiments, when R¹ is —H or —CH₂CH₃, R² is —OH or alkoxy and R³ is —H, then -L₁-L₂-Q'— is not —CH(R')CH₂O— or —CH(R')(CH₂)₂O—, wherein R' is —H or $C_1$-$C_6$ alkyl, alkoxy, substituted alkyl, phenyl or PhCH₂—. In embodiments, when R¹ is —H or —CH₂CH₃, R² is —OH or alkoxy and R³ is —H, then -L₁-L₂-Q'— is not —CH(R')CH₂O— or —CH(R')(CH₂)₂O—, wherein R' is —H or $C_1$-$C_6$ alkyl, alkoxy, substituted alkyl, phenyl or PhCH₂—.

In embodiments, at least one of L₁ and L₂ is present.

In embodiments, at least one of R¹, R² and R³, is not —H.

In embodiments, R¹ independently is $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, alkene or alkyne.

In embodiments, R¹ independently is —H or $C_1$-$C_6$ alkyl.

In embodiments, R² independently is —H, —F, —N(R⁴)₂, —N(R⁴)(R⁵), —OR⁴, —SR⁴, —S(=O)R⁵, —SO₂R⁵, $C_1$-$C_6$ alkyl, or $C_1$-$C_6$ fluoroalkyl; and R³ independently is —H, —F, —CN, —OCH₃, —CH₃, or —CF₃.

In embodiments, R² independently is $C_1$-$C_6$ alkyl, $C_1$-$C_6$ fluoroalkyl, or —F.

In embodiments, R³ independently is —H, —F, —CN, or —CF₃.

In embodiments, R³ independently is —F, —CN, —OCH₃, —CH₃, or —CF₃.

In embodiments, R² and R³ combine to form —O(CH₂)ₙO— or —O(CF₂)ₙO—, wherein n is 1 or 2.

In embodiments, D is represented by one of the following structures:

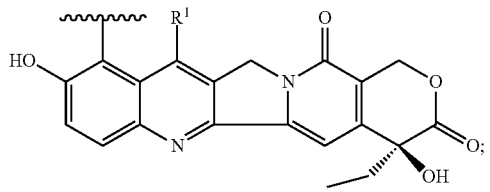

(D-I)

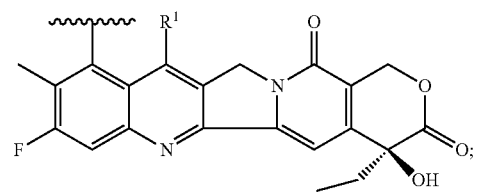

(D-II)

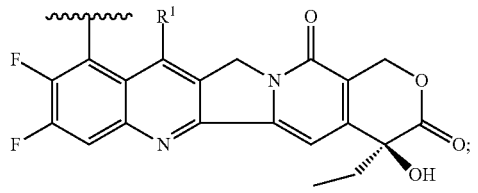

(D-III)

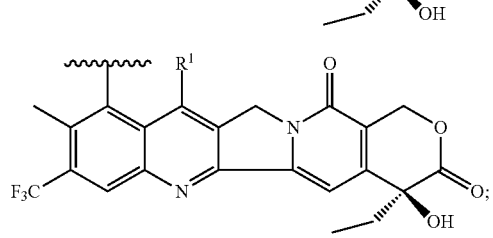

(D-IV)

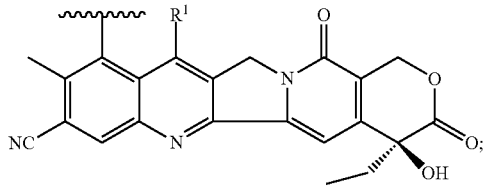

(D-V)

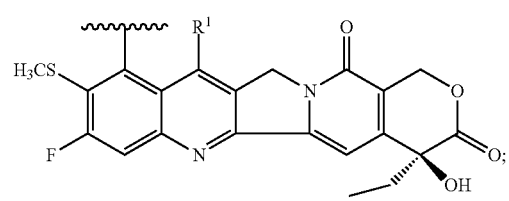

(D-VI)

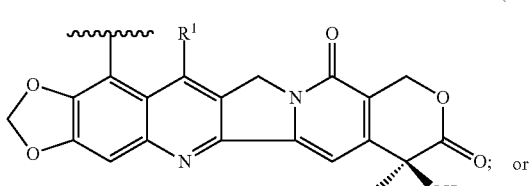

(D-VII)

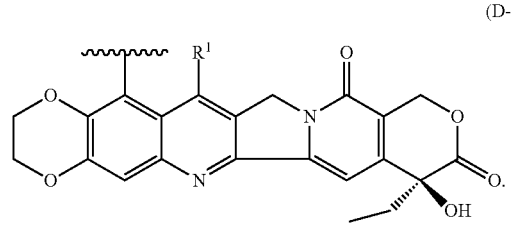

(D-VIII)

In embodiments, R¹ is —H or $C_1$-$C_6$ alkyl.

In embodiments, D is represented by one of the following structures:

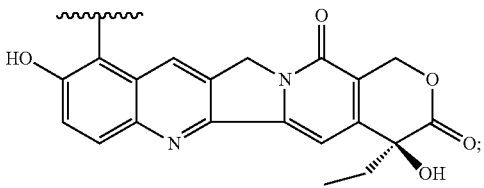

(D1)

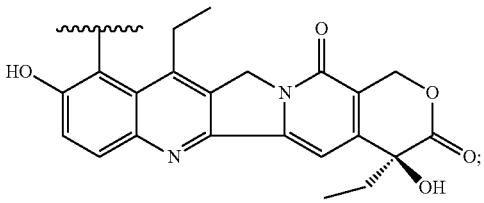

(D2)

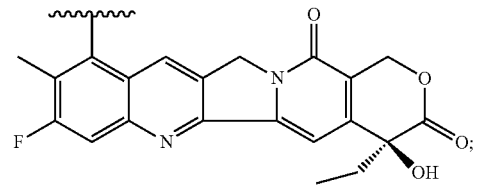

(D3)

-continued (D4)
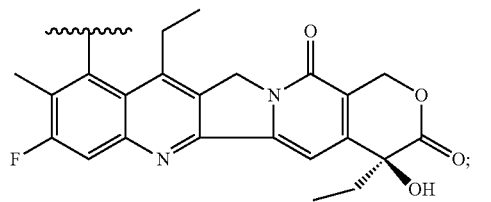

(D5)
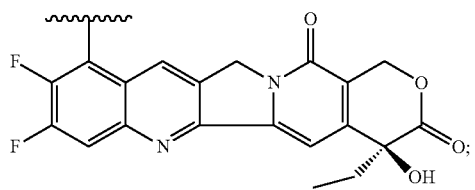

(D6)
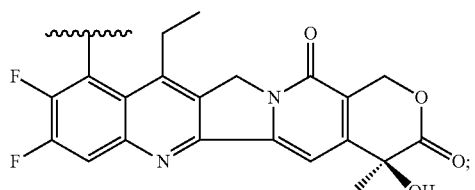

(D7)
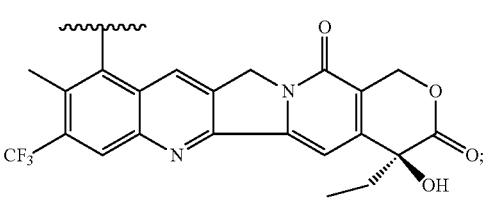

(D8)
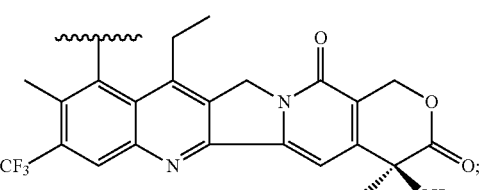

(D9)
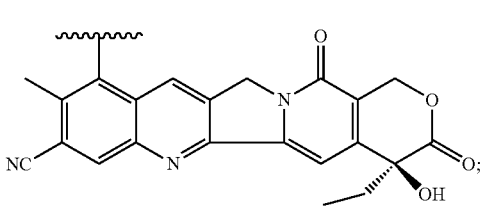

(D10)
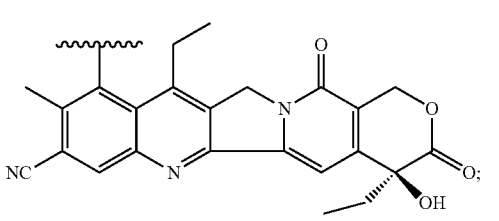

(D11)
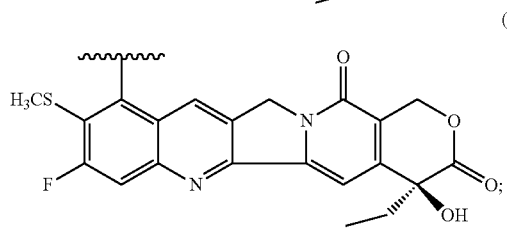

-continued (D12)
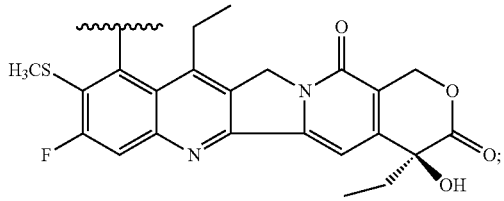

(D13)
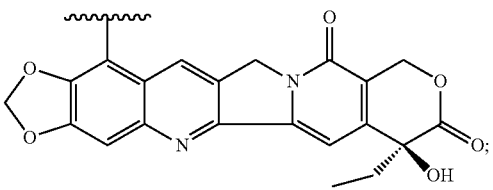

(D14)
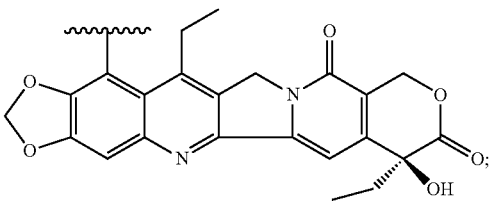

(D15)
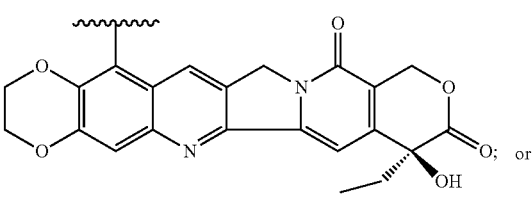

or (D16)
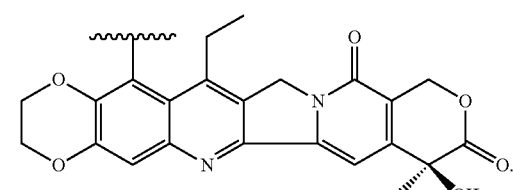

In embodiments, $L_1$ is —($C_1$-$C_{10}$ alkylene)- and $L_2$ is absent.

In embodiments, $L_1$ is —($C_1$-$C_{10}$ alkylene)- and $L_2$ is —N($R^6$)CH$_2$-$L_3$-* or —N($R^6$)C(=O)-$L_3$-*, wherein * denotes the site covalently linked to Q'.

In embodiments, $L_1$ is absent and $L_2$ is —N($R^6$)CH$_2$-$L_3$-* or —N($R^6$)C(=O)-$L_3$-*, wherein * denotes the site covalently linked to Q'.

In embodiments, $L_3$ is —($C_1$-$C_{10}$ alkylene)-.

In embodiments, $R^6$ is —H or —CH$_3$.

In embodiments, $L_1$-$L_2$ is —CH$_2$—, —CH$_2$CH$_2$—, —CH$_2$CH$_2$CH$_2$—, or —CH$_2$CH$_2$CH$_2$CH$_2$—.

In embodiments, $L_1$-$L_2$ is —OCH$_2$CH$_2$—*, —OCH$_2$CH$_2$OCH$_2$CH$_2$—*, —SCH$_2$CH$_2$—*, —SCH$_2$CH$_2$OCH$_2$CH$_2$—*, —S(=O)CH$_2$—*, —SO$_2$CH$_2$—*, —C(=O)CH$_2$—*, —NHCH$_2$CH$_2$—*, —N(CH$_3$)CH$_2$CH$_2$—*, —N(CF$_3$)CH$_2$CH$_2$—*, —NHC(=O)CH$_2$—*, —CH$_2$NHC(=O)CH$_2$—*, —CH$_2$CH$_2$NHC(=O)CH$_2$—*, —CH$_2$N(CH$_3$)C(=O)CH$_2$—* —N(CH$_3$)C(=O)CH$_2$—*, —N(CH$_3$)C(=O)CH$_2$CH$_2$—*, —C(=O)NHCH$_2$CH$_2$—*, —NHC(=O)NHCH$_2$CH$_2$—*, —NHC (=O)OCH₂CH₂—*, —CH₂OC(=O)NHCH₂CH₂—*, or —C(=O)N(CH₃)CH₂CH₂—*, wherein * denotes the site covalently linked to Q'.

In embodiments, $L_1$-$L_2$-Q' is —CH₂CH₂CH₂CH₂O—, —CH₂CH₂CH₂O—, —CH₂CH₂O—, —CH₂CH₂OCH₂CH₂O—, —CH₂SCH₂CH₂O—, —CH₂NHC(=O)CH₂O—, —CH₂CH₂NHC(=O)CH₂O—*, —CH₂N(CH₃)C(=O)CH₂O—, —OCH₂CH₂O—, —OCH₂CH₂CH₂O—, —SCH₂CH₂CH₂O—, —SCH₂CH₂O—, —NHCH₂CH₂O—, —NHCH₂CH₂CH₂O—, —N(CH₃)CH₂CH₂O—, —C(=O)NHCH₂CH₂O—, —NHC(=O)CH₂O—, —CH₂S(=O)CH₂O—, —CH₂SO₂CH₂O—, —CH₂CH₂CH₂CH₂S—, —CH₂CH₂CH₂S—, —CH₂CH₂S—, —CH₂CH₂OCH₂CH₂S—, —CH₂SCH₂CH₂S—, —CH₂NHC(=O)CH₂S—, —OCH₂CH₂CH₂S—, —SCH₂CH₂CH₂S—, —SCH₂CH₂S—, —NHCH₂CH₂CH₂S—, —N(CH₃)CH₂CH₂S—, —C(=O)NHCH₂CH₂S—, —NHC(=O)CH₂S—, —CH₂S(=O)CH₂S—, or —CH₂SO₂CH₂S—.

In embodiments, D-$L_1$-$L_2$ is represented by a structure that is (P-I)

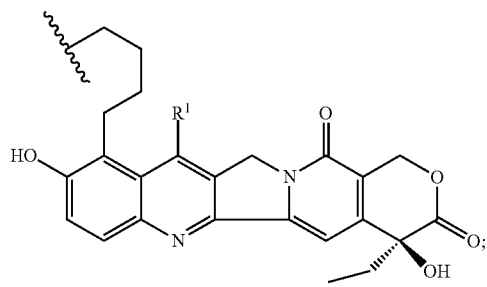

(P-II)

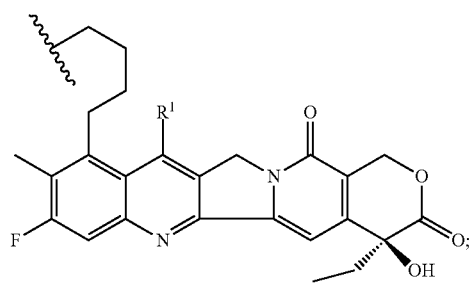

(P-III)

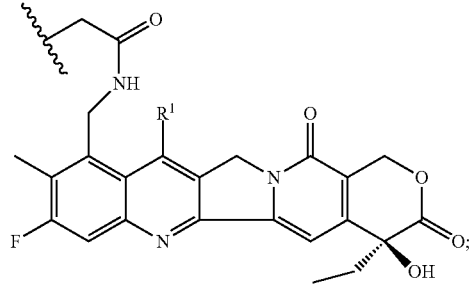

(P-IV)

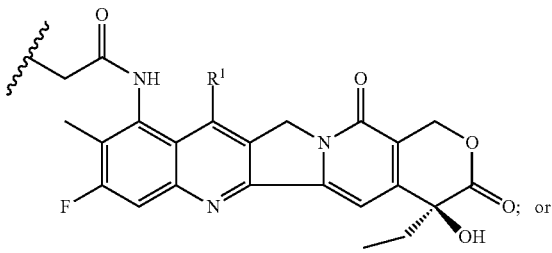

(P-V)

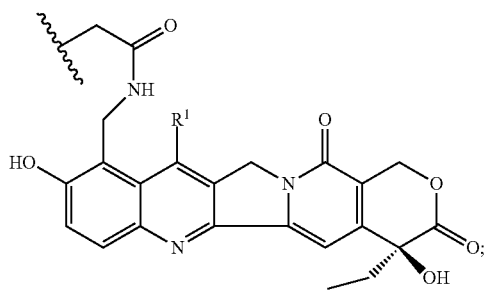

In embodiments, $R^1$ is —H or $C_1$-$C_6$ alkyl.

In embodiments, $R^1$ is —H or —CH₂CH₃.

In embodiments, Q' is —O—.

In embodiments, Q' is —S—.

In embodiments, D-$L_1$-$L_2$-Q'— has one of the following structures:

(P1')

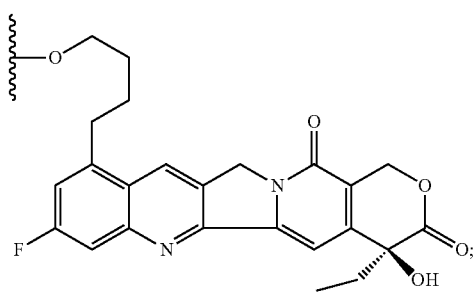

(P2')

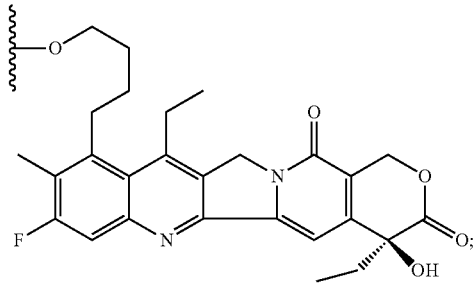

(P3')
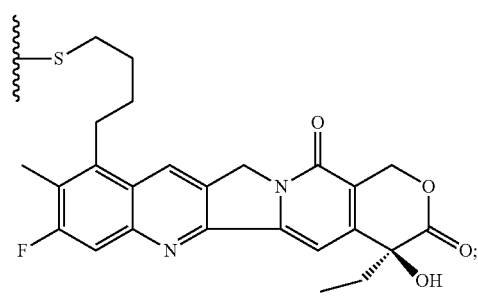
(P5')
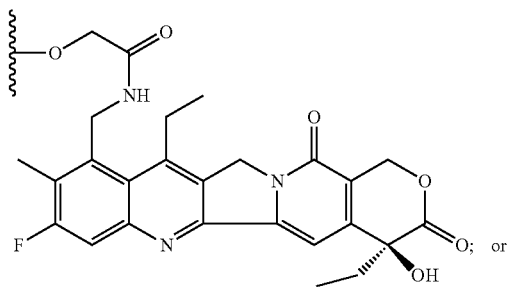
or
(P4')
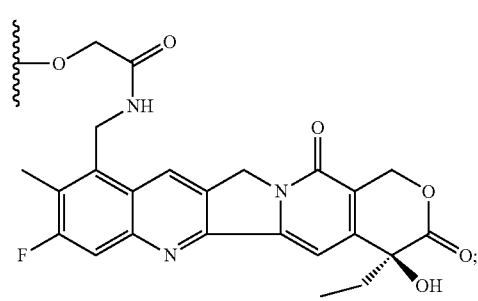
(P6')
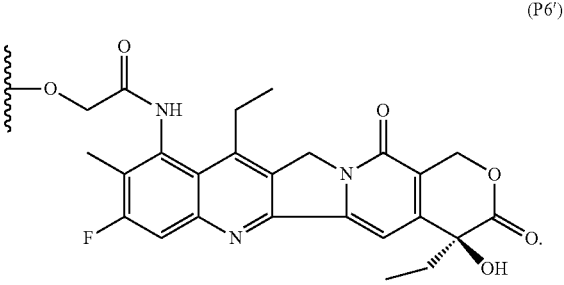
In embodiments, D-$L_1$-$L_2$-Q'—$CH_2$—NH-E-Z'— is formed from one of the following structures,
(PL1)
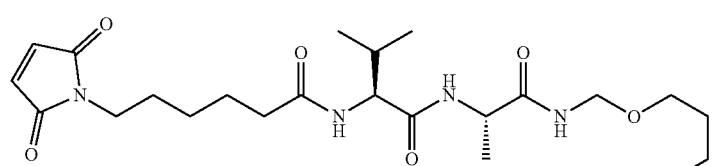
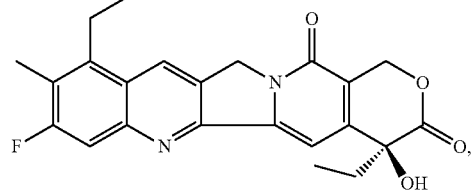
(PL2)
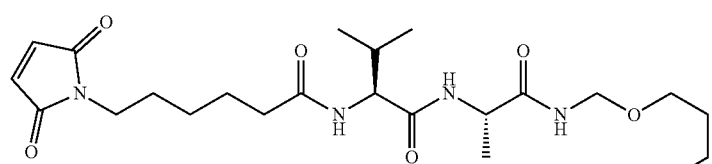
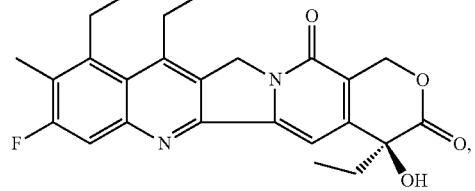

(PL3)
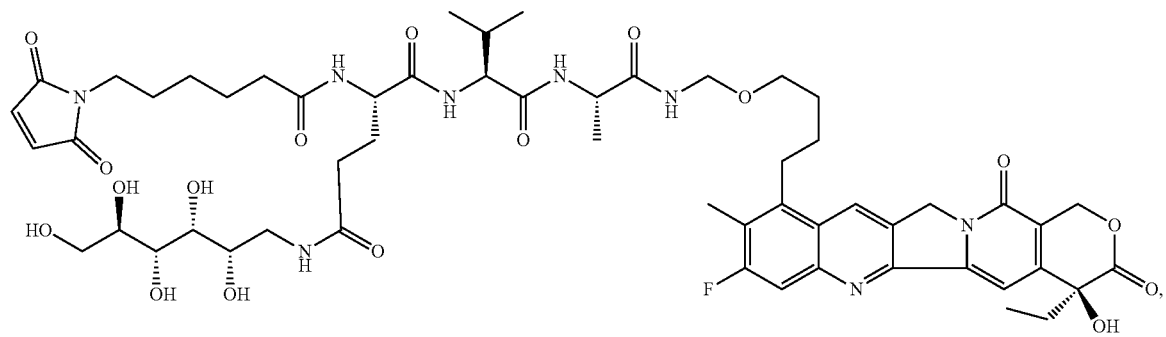
(PL4)
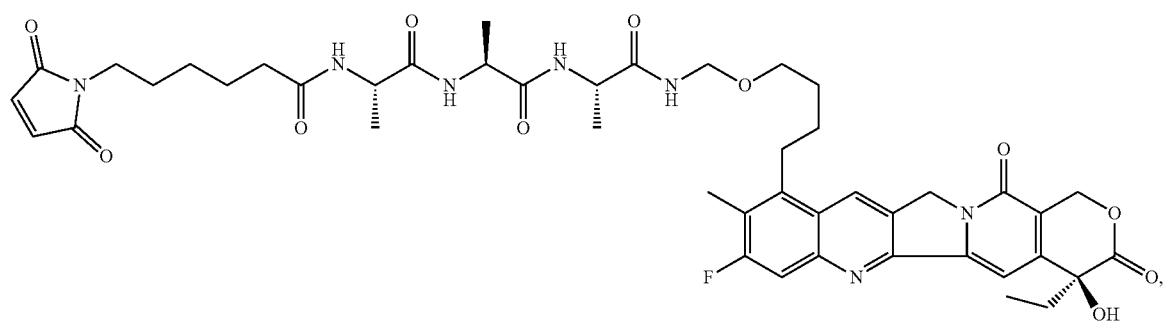
(PL5)
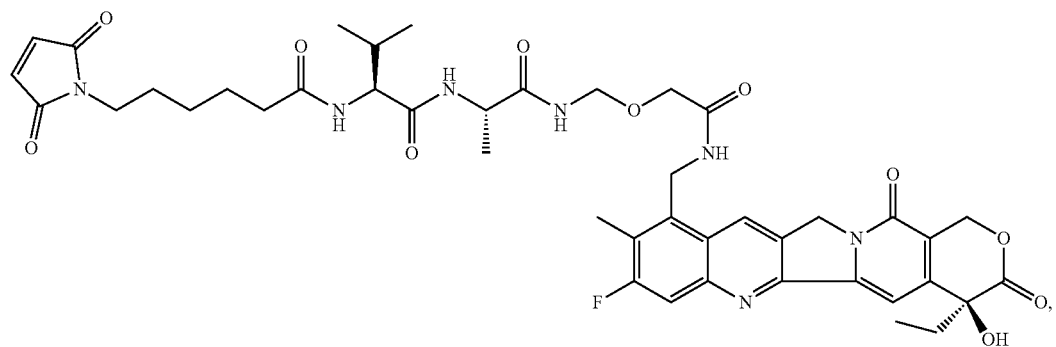
(PL6)
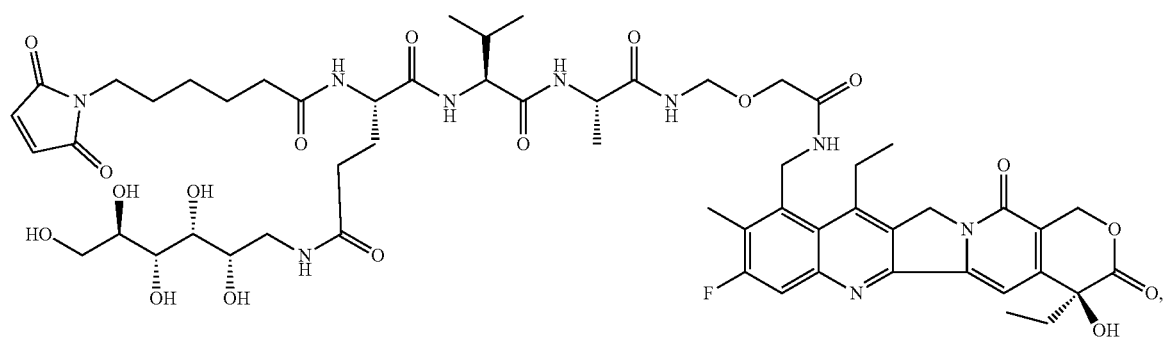

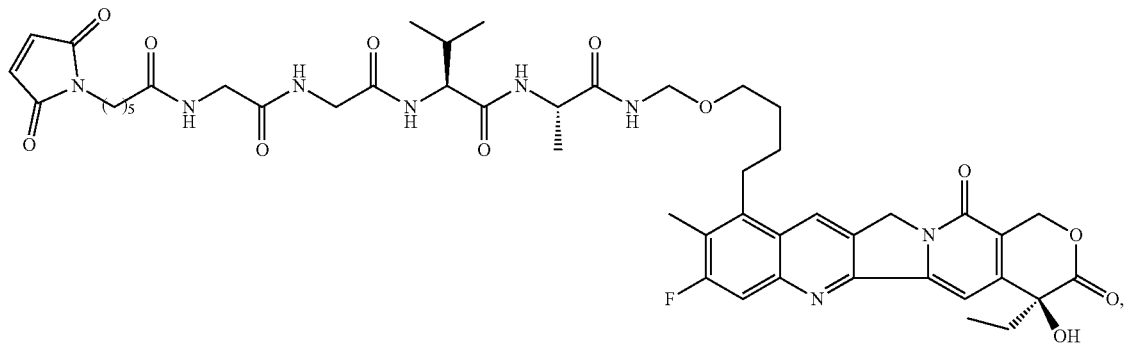
(PL7)
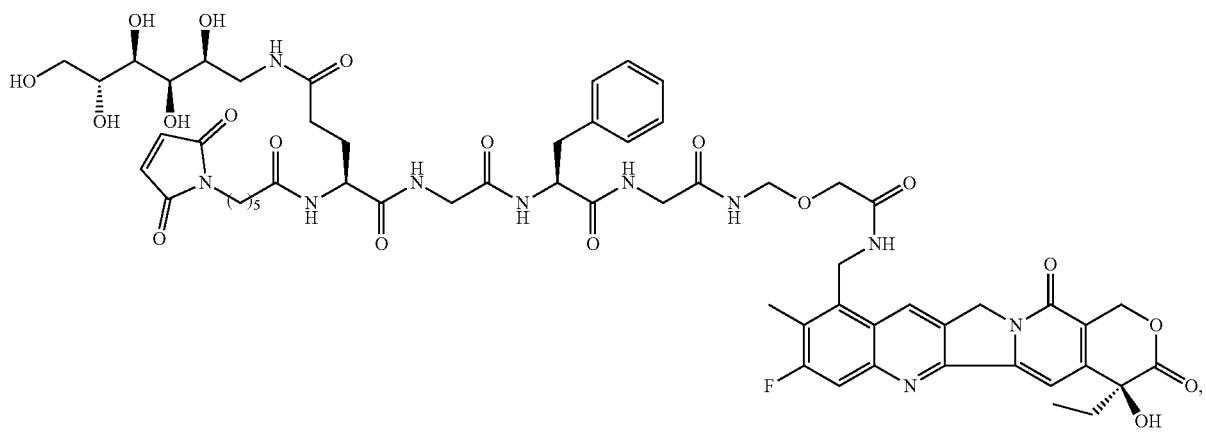
(PL8)
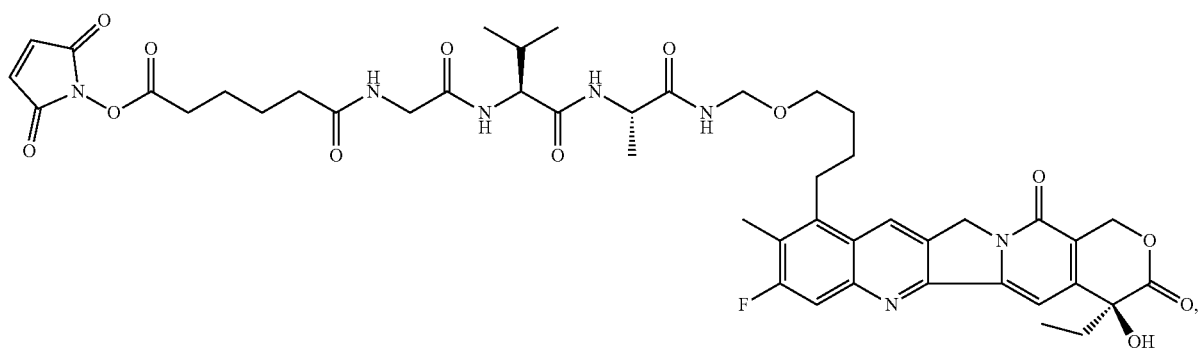
(PL9)
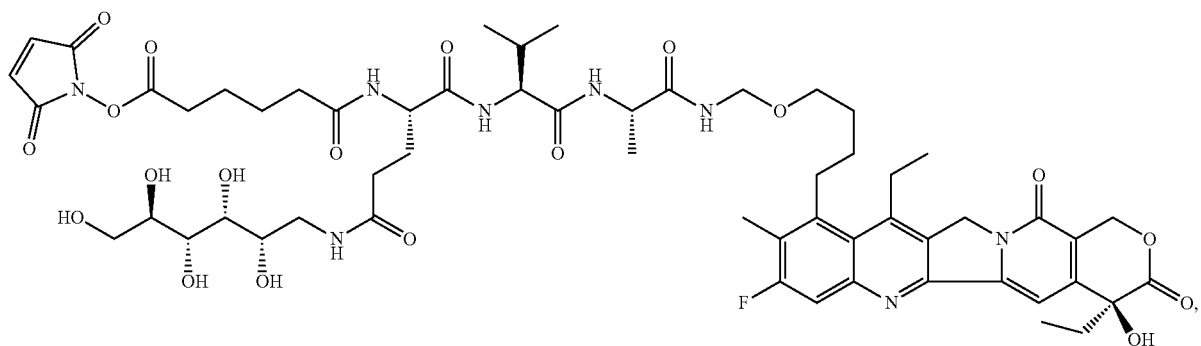
(PL10)

-continued
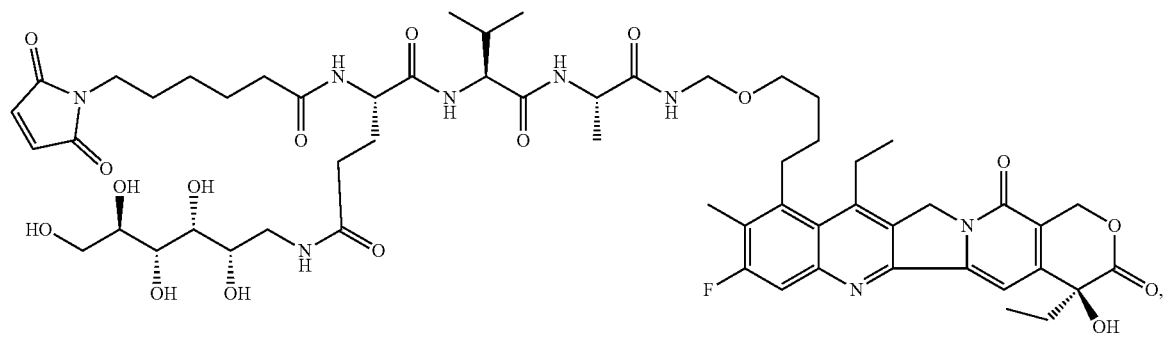
(PL11)
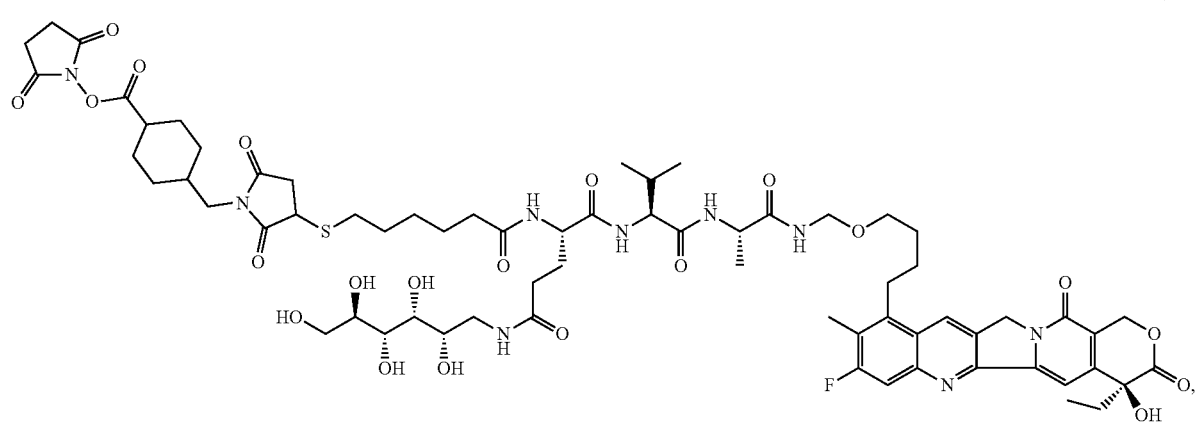
(PL12)
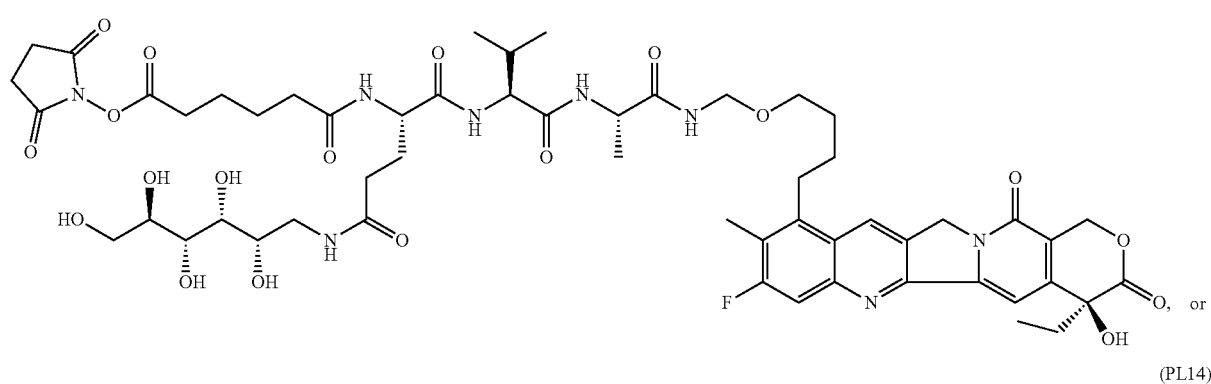
(PL13) or
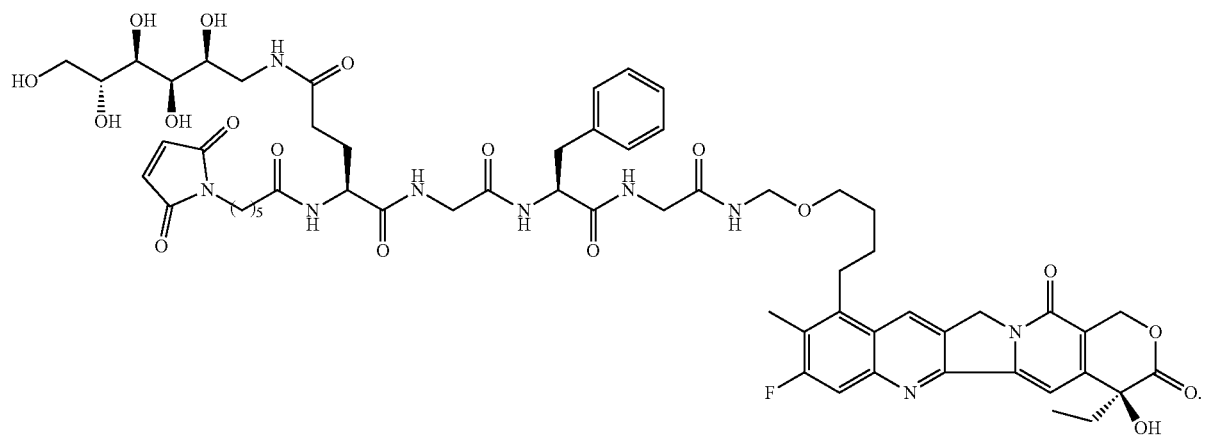
(PL14)

In embodiments, {D-L$_1$-L$_2$-Q'—CH$_2$—NH-E-Z'}$_p$—C is one of the following structures, wherein C is a monoclonal antibody and p is the drug to antibody ratio (DAR) and p is a average number ranging from about 2-10, 4-8, 7-8, or 3.2 to 8.0,
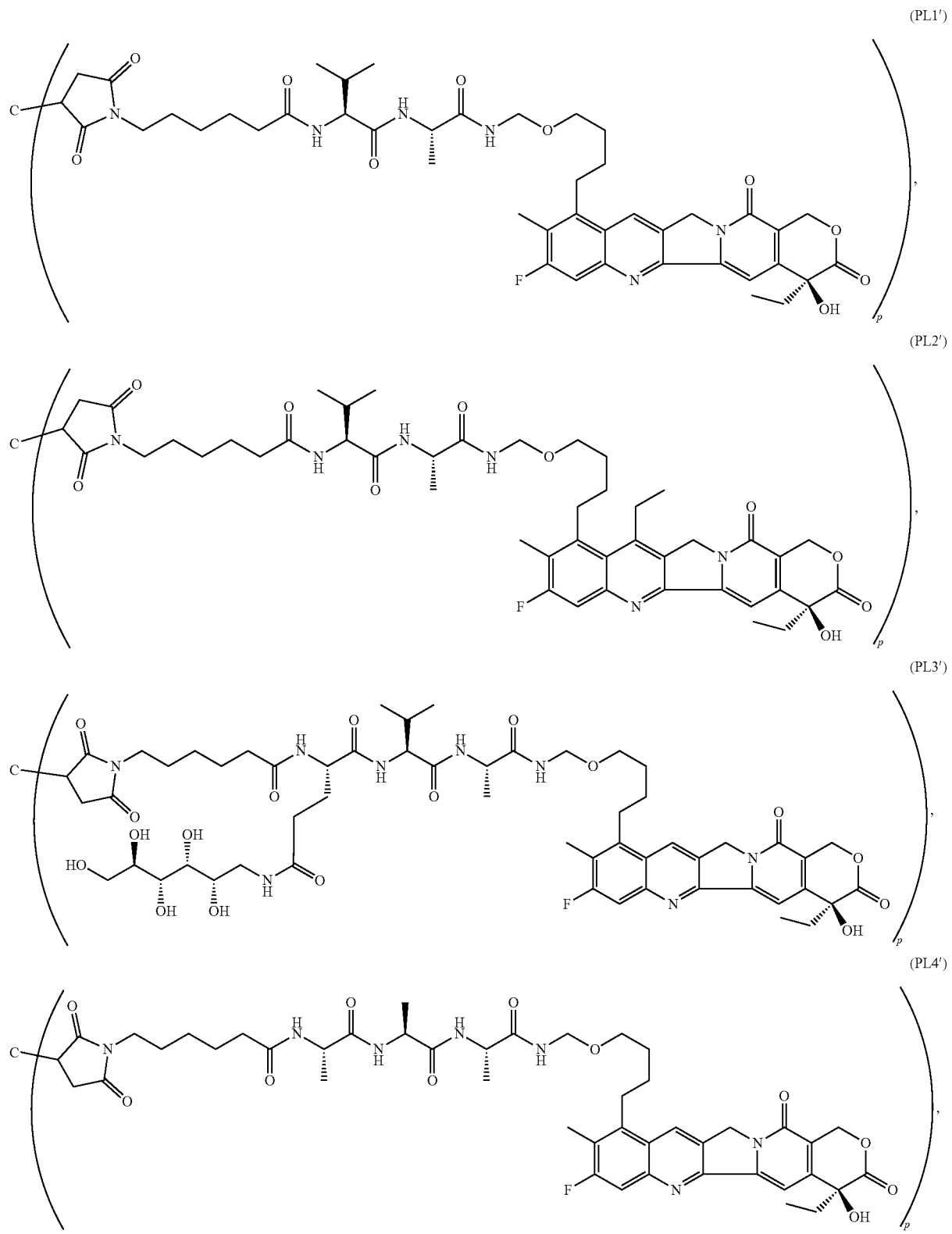

(PL5′)
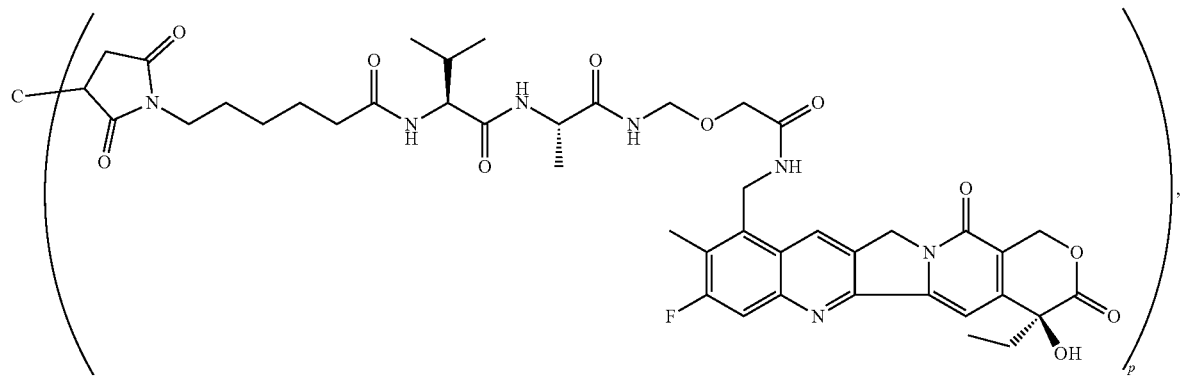
(PL6′)
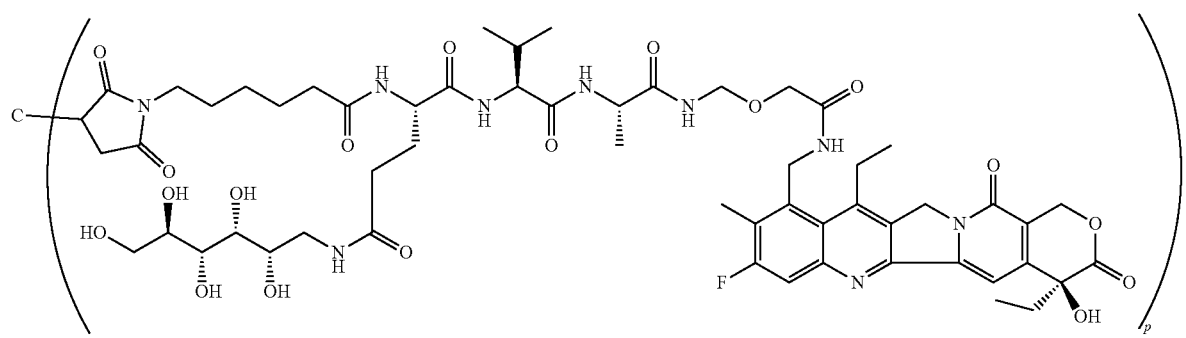
(PL7′)
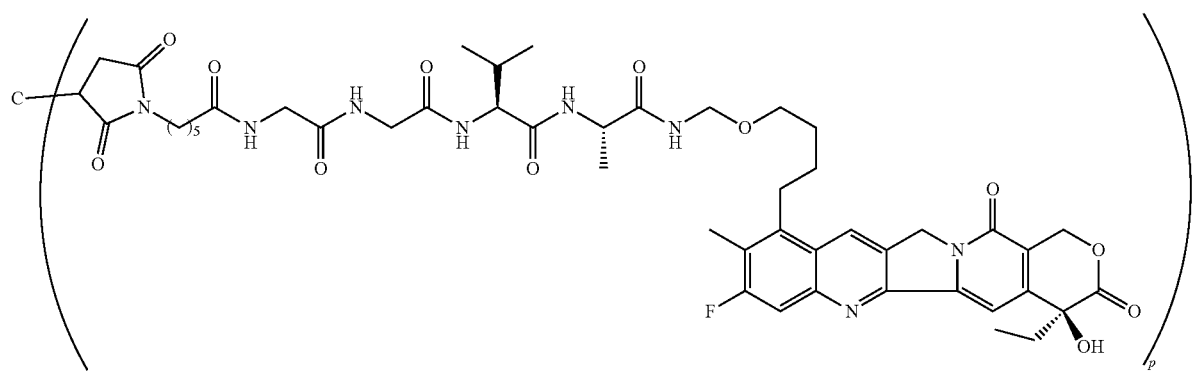
(PL8′)
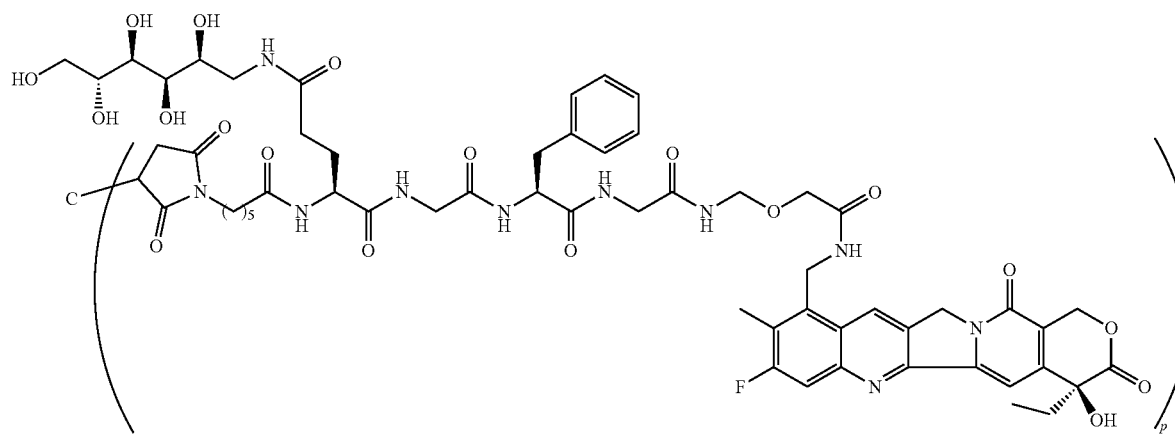

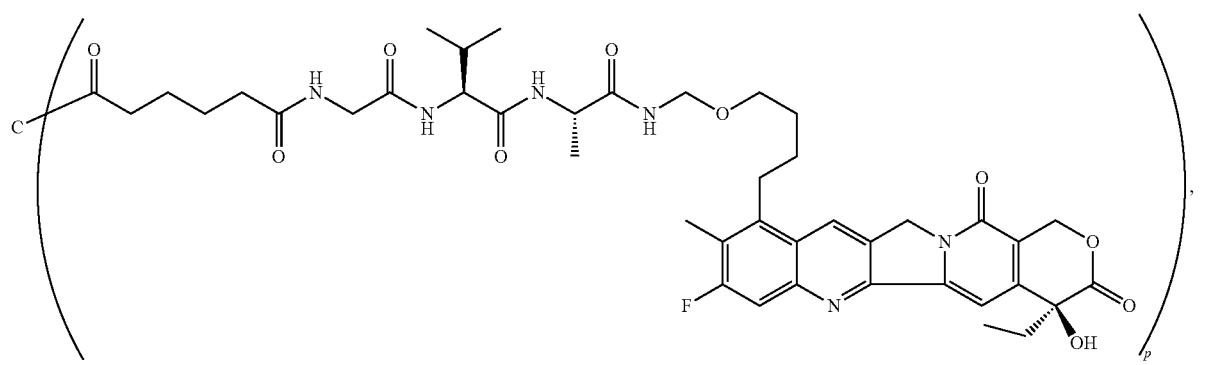
(PL9′)
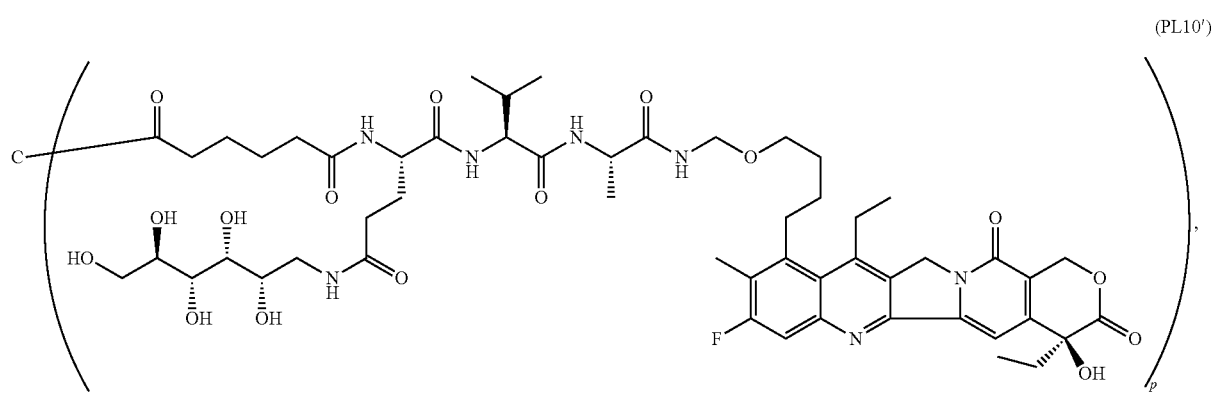
(PL10′)
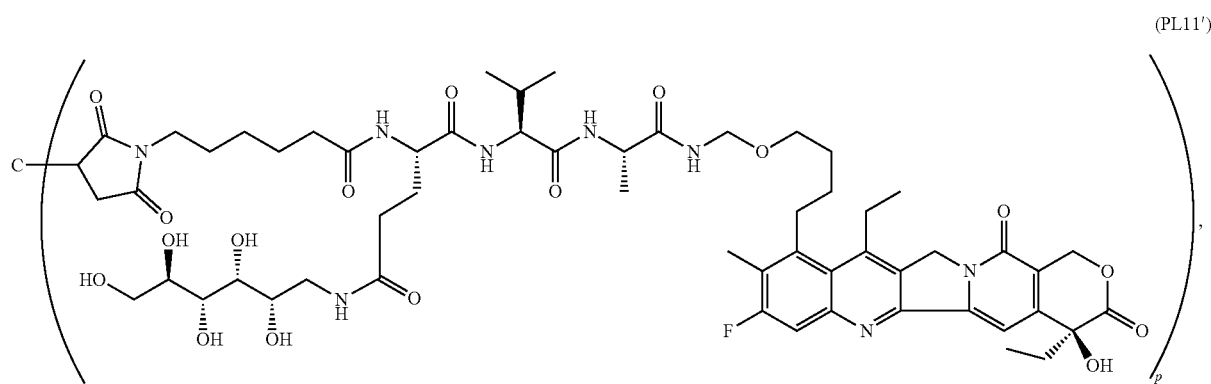
(PL11′)
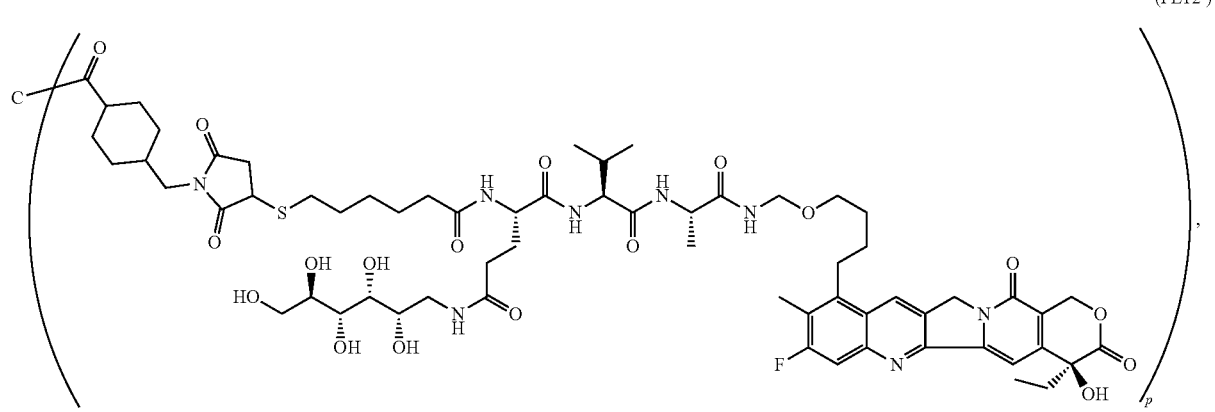
(PL12′)

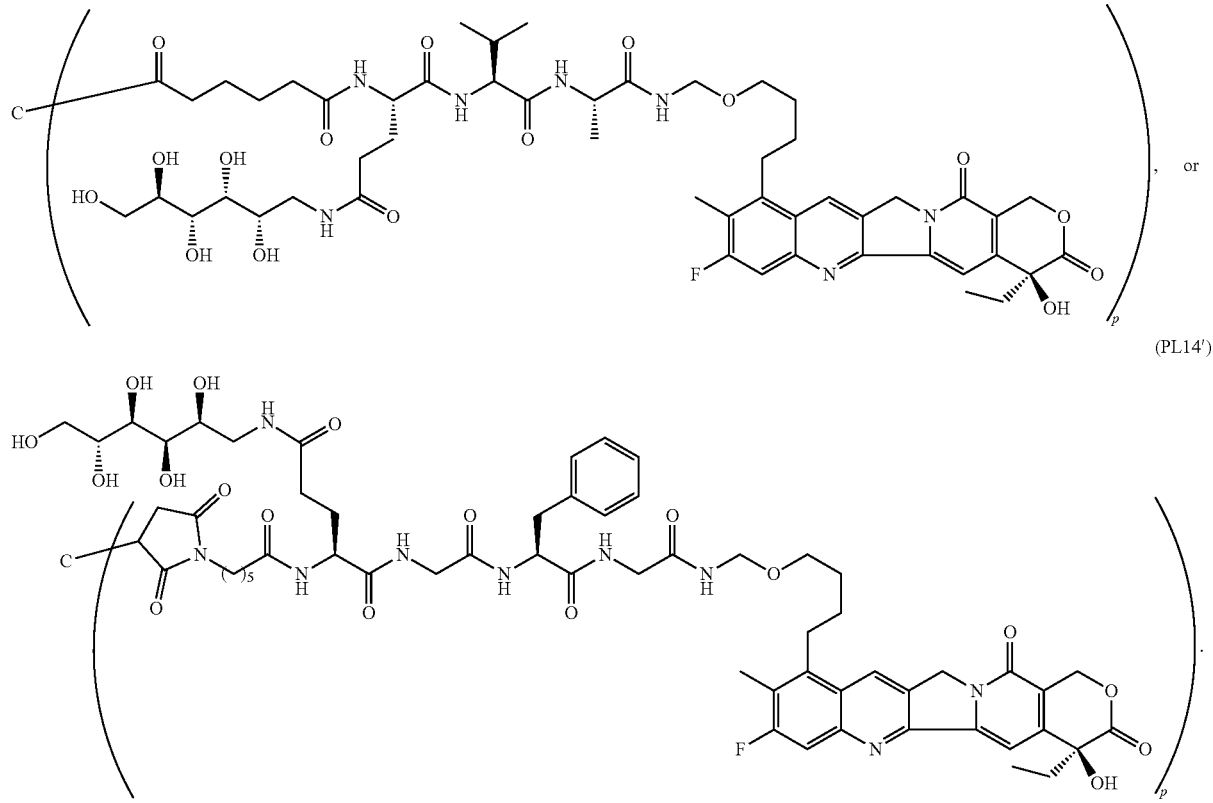

In another aspect, the invention features a method of preparing a conjugate of Formula (III) which comprises a cell binding agent and a drug and, said method comprising contacting a cell binding agent with a compound of Formula (II), such that a covalent bond forms between said cell binding agent and said compound of Formula (II).

In still another aspect, the invention features a conjugate comprising a cell binding agent and a drug. In embodiments, the conjugate is prepared according to any method described herein.

In embodiments, a conjugate comprises a cell binding agent that is an antibody or an antigen-binding fragment thereof.

In embodiments, a conjugate comprises a cell binding agent that is a monoclonal antibody or an antigen-binding fragment thereof.

In embodiments, the cell binding agent is an antibody or an antigen-binding fragment thereof; p is the drug to antibody ratio (DAR) and has a value between 1 to 18. In embodiments, p is a average number ranging from about 2-10, 4-8, or 7-8 (e.g., 3.2 to 8.0).

In embodiments, the cell binding agent is a monoclonal antibody or an antigen-binding fragment thereof; p is the drug to antibody ratio (DAR) and has a value between 1 to 18. In embodiments, p is a average number ranging from about 2-10, 4-8, or 7-8 (e.g., 3.2 to 8.0).

In another aspect, the invention features a pharmaceutical composition comprising any conjugate described herein.

In still another aspect, the invention features a method of treating a cell proliferative disease or disorder or inhibiting abnormal cell growth, where the method comprises administering any conjugate described herein or any pharmaceutical composition comprising any conjugate described herein.

In another aspect, the invention features a pharmaceutical composition comprising any compound of Formula (III), or a pharmaceutically acceptable salt thereof, as described herein.

In another aspect, the invention features a method of treating a cell proliferative disease or disorder or inhibiting abnormal cell growth, said method comprising administering any compound of Formula (III), or a pharmaceutically acceptable salt thereof, as described herein, or a pharmaceutical composition comprising any compound of Formula (III), or a pharmaceutically acceptable salt thereof, as described herein.

In embodiments, the method is for treating cancer.

In embodiments, a cancer is adenocarcinoma, brain cancer, bladder cancer, breast cancer, cervical cancer, choriocarcinoma, a CNS tumor, colon or colorectal cancer, diffuse intrinsic pontine glioma (DIPG), endometrial cancer, esophageal cancer, Ewing's sarcoma, fallopian tube cancer, gall bladder cancer, gastric cancer, glioblastoma, head and neck cancer, hematological cancer, Hodgkin's lymphoma, kidney cancer, laryngeal cancer, leukemia, liver cancer, lung cancer, lymphoma, melanoma, Merkel cell carcinoma, mesothelioma, multiple myeloma, myelodysplastic syndrome (MDS), neuroblastoma, non-Hodgkin's lymphoma, osteosarcoma, pancreatic cancer, peritoneal cancer, prostate cancer, ovarian cancer, renal cancer, rhabdomyosarcoma salivary gland cancer, sarcoma, skin cancer, small intestine cancer, squamous cell carcinoma, testicular cancer, thyroid cancer, uterine cancer, or Wilms tumor.

In embodiments, a cancer is breast cancer.

BRIEF DESCRIPTION OF DRAWINGS

FIG. 3 illustrates a selection of data from FIG. 2 showing the antitumor effect using 2.5 mg/kg IV single doses of MB-2a and MB-3a.

FIG. 4 illustrates a selection of data from FIG. 2 showing the antitumor effect using 5 mg/kg IV single doses of MB-2a and MB-3a.

FIG. 5 illustrates a selection of data from FIG. 2 showing the antitumor effect using 10 mg/kg IV single doses of MB-2a and MB-3a.

DETAILED DESCRIPTION OF THE INVENTION

Definitions

Figure 1:
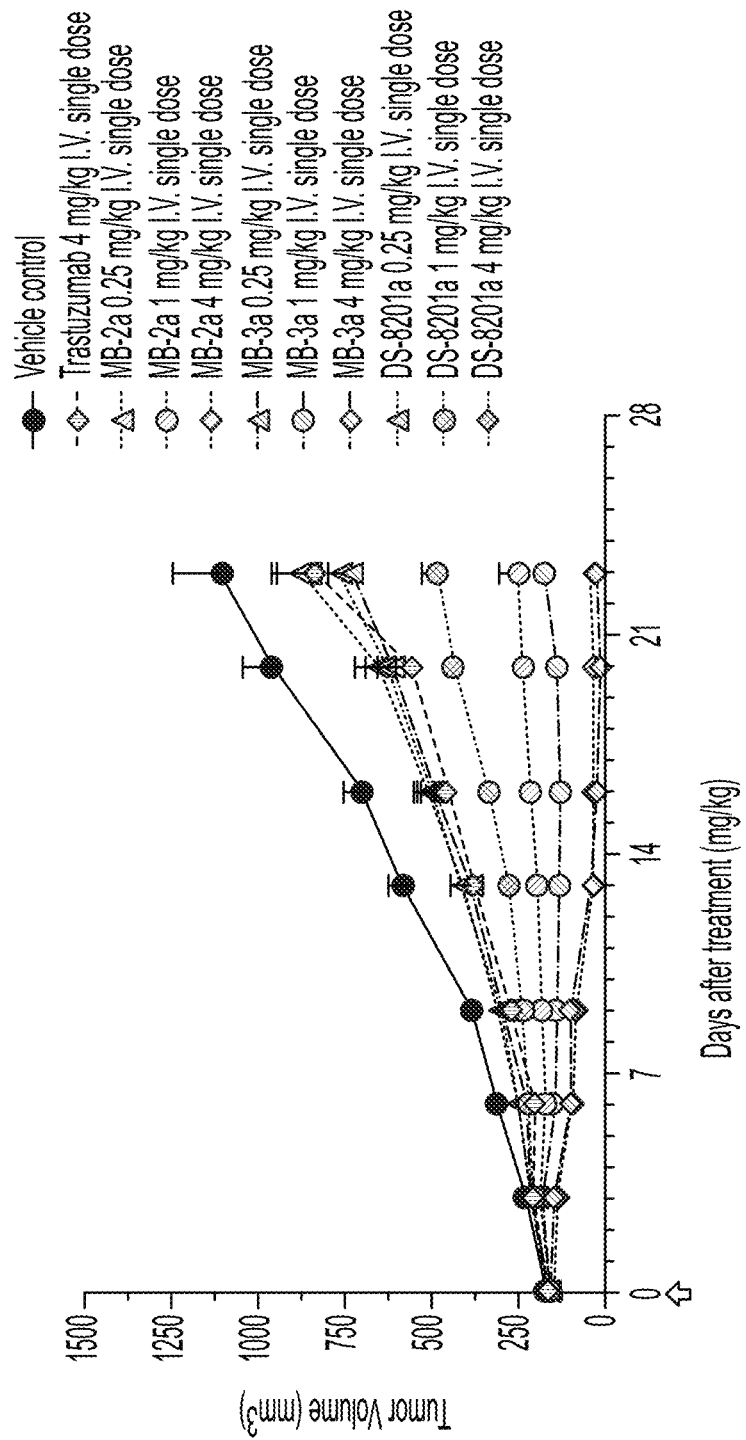
FIG. 1 illustrates effects of antibody drug conjugates (ADCs) in the NCI-N87 CDX model. MB-2a and MB-3a are ADCs encompassed by the present formula, which were studied along with a vehicle control, trastuzumab, and the ADC DS-8201a. As shown in this figure MB-2a (1 mg/kg and 4 mg/kg) and MB-3a (1 mg/kg and 4 mg/kg) demonstrated a strong antitumor effect.

Unless stated otherwise, the following terms and phrases as used herein are intended to have the following meanings. When trade names are used herein, the trade name includes the product formulation, the generic drug, and the active pharmaceutical ingredient(s) of the trade name product, unless otherwise indicated by context.

As used herein, the term "antibody" refers to an agent that specifically binds to a particular antigen. In some embodiments, the term encompasses any polypeptide or polypeptide complex that includes immunoglobulin structural elements sufficient to confer specific binding. Exemplary antibodies include, but are not limited to monoclonal antibodies or polyclonal antibodies. In some embodiments, an antibody may include one or more constant region sequences that are characteristic of mouse, rabbit, primate, or human antibodies. In some embodiments, an antibody may include one or more sequence elements are humanized, primatized, chimeric, etc., as is known in the art. In many embodiments, the term "antibody" is used to refer to one or more of the art-known or developed constructs or formats for utilizing antibody structural and functional features in alternative presentation. For example, embodiments, an antibody utilized in accordance with the present invention is in a format selected from, but not limited to, intact IgA, IgG, IgE or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof; single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc], or other pendant group [e.g., polyethylene glycol, etc.]). In many embodiments, an antibody is or comprises a polypeptide whose amino acid sequence includes one or more structural elements recognized by those skilled in the art as a complementarity determining region (CDR); in some embodiments, an antibody is or comprises a polypeptide whose amino acid sequence includes at least one CDR (e.g., at least one heavy chain CDR and/or at least one light chain CDR) that is substantially identical to one found in a reference antibody. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

The term "monoclonal antibody" as used herein refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

As used herein, the term "human antibody" is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

As is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $CH_1$, hinge, $CH_2$, $CH_3$, and, optionally, a $CH_4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

An "intact antibody" is one which comprises an antigen-binding variable region as well as a light chain constant domain ($C_L$) and heavy chain constant domains, $C_H1$, $C_H2$, $C_H3$ and $C_H4$, as appropriate for the antibody class. The constant domains may be native sequence constant domains (e.g., human native sequence constant domains) or amino acid sequence variant thereof.

An "antibody fragment" comprises a portion of an intact antibody, comprising the antigen-binding or variable region thereof. Examples of antibody fragments include Fab, Fab', F(ab')$_2$, and Fv fragments, diabodies, triabodies, tetrabodies, linear antibodies, single-chain antibody molecules, scFv, scFv-Fc, multispecific antibody fragments formed from antibody fragment(s), a fragment(s) produced by a Fab expression library, or an epitope-binding fragments of any of the above which immunospecifically bind to a target antigen (e.g., a cancer cell antigen, a viral antigen or a microbial antigen).

An "antigen" is an entity to which an antibody specifically binds.

It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell). In some embodiments, "binding" refers to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473).

The terms "specific binding" and "specifically binds" mean that the antibody or antibody derivative will bind, in a highly selective manner, with its corresponding epitope of a target antigen and not with the multitude of other antigens. Typically, the antibody or antibody derivative binds with an affinity of at least about $1 \times 10^{-7}$ M, and preferably $10^{-8}$ M to $10^{-9}$ M, $10^{-10}$ M, $10^{-11}$ M, or $10^{-12}$ M and binds to the predetermined antigen with an affinity that is at least two-fold greater than its affinity for binding to a non-specific antigen (e.g., BSA, casein) other than the predetermined antigen or a closely-related antigen. The term "specificity" refers to the ability of a cell binding agent (e.g., as described herein such as an antibody or a fragment thereof) to specifically bind (e.g., immunoreact with) a given target antigen, e.g., a human target antigen.

In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

The term "inhibit" or "inhibition of" means to reduce by a measurable amount, or to prevent entirely.

The term "substantial" or "substantially" refers to a majority, i.e. >50% of a population, of a mixture or a sample, preferably more than 50%, 55%, 60%, 65%, 70%, 75%, 80%, 85%, 90%, 91%, 92%, 93%, 94%, 95%, 96%, 97%, 98%, or 99% of a population.

The term "cytotoxic activity" refers to a cell-killing effect of a drug or Camptothecin Conjugate or an intracellular metabolite of a Camptothecin Conjugate. Cytotoxic activity may be expressed as the $IC_{50}$ value, which is the concentration (molar or mass) per unit volume at which half the cells survive.

The term "cytostatic activity" refers to an antiproliferative effect of a drug or Camptothecin Conjugate or an intracellular metabolite of a Camptothecin Conjugate.

The term "cytotoxic agent" as used herein refers to a substance that has cytotoxic activity and causes destruction of cells. The term is intended to include chemotherapeutic agents, and toxins such as small molecule toxins or enzymatically active toxins of bacterial, fungal, plant or animal origin, including synthetic analogs and derivatives thereof.

The term "cytostatic agent" as used herein refers to a substance that inhibits a function of cells, including cell growth or multiplication. Cytostatic agents include inhibitors such as protein inhibitors, e.g., enzyme inhibitors. Cytostatic agents have cytostatic activity.

The terms "cancer" and "cancerous" refer to or describe the physiological condition or disorder in mammals that is typically characterized by unregulated cell growth. A "tumor" comprises one or more cancerous cells.

An "autoimmune disease" as used herein refers to a disease or disorder arising from and directed against an individual's own tissues or proteins.

As used herein, the term "patient" or "subject" refers to any organism to which provided compound or compounds described herein are administered in accordance with the present invention e.g., for experimental, diagnostic, prophylactic, and/or therapeutic purposes. Typical subjects include animals. The term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone. In embodiments, animals are mammals such as mice, rats, rabbits, non-human primates, and humans; insects; worms; etc. In embodiments, a subject is a human. In some embodiments, a subject may be suffering from, and/or susceptible to a disease, disorder, and/or condition (e.g., cancer). As used herein, a "patient population" or "population of subjects" refers to a plurality of patients or subjects.

As used herein, the term "normal," when used to modify the term "individual" or "subject" refers to an individual or group of individuals who does not have a particular disease or condition and is also not a carrier of the disease or condition. The term "normal" is also used herein to qualify a biological specimen or sample isolated from a normal or wild-type individual or subject, for example, a "normal biological sample."

An individual who is "suffering from" a disease, disorder, and/or condition (e.g., any cancer described herein) has been diagnosed with or displays one or more symptoms of the disease, disorder, and/or condition.

An individual who is "susceptible to" a disease, disorder, and/or condition has not been diagnosed with and/or may not exhibit symptoms of the disease, disorder, and/or condition. In some embodiments, an individual who is susceptible to a disease, disorder, and/or condition (for example, cancer) may be characterized by one or more of the following: (1) a genetic mutation associated with development of the disease, disorder, and/or condition; (2) a genetic polymorphism associated with development of the disease, disorder, and/or condition; (3) increased and/or decreased expression and/or activity of a protein associated with the disease, disorder, and/or condition; (4) habits and/or lifestyles associated with development of the disease, disorder, and/or condition; (5) a family history of the disease, disorder, and/or condition; (6) reaction to certain bacteria or viruses; (7) exposure to certain chemicals. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

The terms "treat" or "treatment", unless otherwise indicated by context, refer to any administration of a therapeutic molecule (e.g., any compound described herein) that partially or completely alleviates, ameliorates, relieves, inhibits, delays onset of, delays progression of, reduces severity of and/or reduces incidence of one or more symptoms or features of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. Alternatively, the pharmacologic and/or physiologic effect may be prophylactic, i.e., the effect of completely or partially prevents a disease or symptom thereof (e.g., delaying onset or slowing progression of a disease or symptom thereof). In this respect, the inventive method comprises administering a "prophylactically effective amount" of the binding agent. A "prophylactically effective amount" refers to an amount effective, at dosages and for periods of time necessary, to achieve a desired prophylactic result. Accordingly, treatment (including prophylactic treatment) where the object is to inhibit or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Treatment can also include the prolonging of survival as compared to expected survival if not receiving treatment. Those in need of treatment include those already with the condition or disorder as well as those prone to have the condition or disorder.

In the context of cancer, the term "treating" includes any or all of: killing tumor cells; inhibiting growth of tumor cells, cancer cells, or of a tumor; inhibiting replication of tumor cells or cancer cells, lessening of overall tumor burden or decreasing the number of cancerous cells, and ameliorating one or more symptoms associated with the disease.

In the context of an autoimmune disease, the term "treating" includes any or all of: inhibiting replication of cells associated with an autoimmune disease state including, but not limited to, cells that produce an autoimmune antibody, lessening the autoimmune-antibody burden and ameliorating one or more symptoms of an autoimmune disease.

The term "therapeutically effective amount" or "effective amount" refers to an amount of a conjugate effective to treat or prevent a disease or disorder in a mammal (e.g., as described herein). In the case of cancer, the therapeutically effective amount of the conjugate may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may inhibit growth and/or kill existing cancer cells, it may be cytostatic and/or cytotoxic. For cancer therapy, efficacy can, for example, be measured by assessing the time to disease progression (TTP) and/or determining the response rate (RR).

The term "pharmaceutically acceptable form" as used herein refers to a form of a disclosed compound including, but is not limited to, pharmaceutically acceptable salts, esters, hydrates, solvates, polymorphs, isomers, prodrugs, and isotopically labeled derivatives thereof. In one embodiment, a "pharmaceutically acceptable form" includes, but is not limited to, pharmaceutically acceptable salts, esters, prodrugs and isotopically labeled derivatives thereof. In embodiments, a "pharmaceutically acceptable form" includes, but is not limited to, pharmaceutically acceptable isomers and stereoisomers, prodrugs and isotopically labeled derivatives thereof.

In embodiments, the pharmaceutically acceptable form is a pharmaceutically acceptable salt. The term "pharmaceutically acceptable salt," as used herein, refers to pharmaceutically acceptable organic or inorganic salts of a compound (e.g., a camptothecin, a camptothecin payload, or a camptothecin conjugate). In some aspects, the compound can contain at least one amino group, and accordingly acid addition salts can be formed with the amino group. Exemplary salts include, but are not limited to, sulfate, trifluoroacetate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-touenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

As used herein, the term "pharmaceutical composition" refers to a composition in which an active agent (e.g., a compound according to any of Formulas (I)-(III) as described herein) is formulated together with one or more pharmaceutically acceptable carriers. In some embodiments, the active agent is present in unit dose amount appropriate for administration in a therapeutic regimen that shows a statistically significant probability of achieving a predetermined therapeutic effect when administered to a relevant population. In some embodiments, a pharmaceutical composition may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

As used herein, a "carrier" or a "pharmaceutically acceptable carrier" refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components. In some embodiments, the carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In some cases, it may be desirable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

As used herein, the term "kit" refers to any delivery system for delivering materials. Such delivery systems may include systems that allow for the storage, transport, or delivery of various diagnostic or therapeutic reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes, cartridges, bottles, ampoules, etc.) containing the relevant reaction reagents and/or supporting materials. As used herein, the term "fragmented kit" refers to a delivery systems comprising two or more separate containers that each contain a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components in a single container (e.g., in a single box housing each of the desired components). The term "kit" includes both fragmented and combined kits.

As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. Examples of routes of administration include parenteral, e.g., intravenous, intradermal, subcutaneous, oral (e.g., inhalation), transdermal (i.e., topical), transmucosal, and rectal administration. For example, in some embodiments, administration may be ocular, oral, parenteral, topical, etc. In embodiments, administration is parenteral (e.g., intravenous administration). In embodiments, intravenous administration is intravenous infusion. In some particular embodiments, administration may be bronchial (e.g., by bronchial instillation), buccal, dermal (which may be or comprise, for example, one or more of topical to the dermis, intradermal, interdermal, transdermal, etc.), enteral, intraarterial, intradermal, intragastric, intramedullary, intramuscular, intranasal, intraperitoneal, intrathecal, intravenous, intraventricular, within a specific organ (e.g. intrahepatic), mucosal, nasal, oral, rectal, subcutaneous, sublingual, topical, tracheal (e.g., by intratracheal instillation), vaginal, vitreal, etc.

As used herein, the term "nucleophilic" refers to a reactive group that is electron rich, has an unshared pair of electrons acting as a reactive site, and reacts with a positively charged or electron-deficient site. Examples of nucleophilic groups suitable for use in the invention include, without limitation, amino groups (e.g., primary amines, secondary amines, hydroxyamines, and/or hydrazines), thiols, phenols, and alcohols. In embodiments, a nucleophilic functional group comprises: amino, hydrazino, hydroxyamino, hydroxy, or thio. In embodiments, a nucleophilic functional group is carboxamide, N-hydroxycarboxamide, carboxyl hydrazide, or guanidino. In embodiments, a nucleophilic group is a thiol group or comprises a thiol group. Certain nucleophilic groups must be activated with a base so as to be capable of reaction with an electrophilic group. For example, when there are nucleophilic thiol and hydroxyl groups in the multifunctional compound, the compound must be admixed with an aqueous base in order to remove a proton and provide a thiolate or hydroxylate anion to enable reaction with the electrophilic group. Unless it is desirable for the base to participate in the reaction, a non-nucleophilic base is preferred. In some embodiments, the base may be present as a component of a buffer solution.

As used herein, the term "electrophilic" refers to a reactive group that is susceptible to nucleophilic attack; that is, susceptible to reaction with an incoming nucleophilic group. Selection of electrophilic group can be made such that reaction is possible with the nucleophilic groups of the paired reactant. For example, when a nucleophilic reactive group is an amino group, the electrophilic group(s) can be selected so as to react with amino groups. Analogously, when the nucleophilic reactive group is a thiol moiety, a corresponding electrophilic group can be thiol-reactive groups, and the like. Examples of electrophilic groups suitable for use in the invention include, without limitation, carboxylic acid esters, acid chloride groups, anhydrides, isocyanato, thioisocyanato, epoxides, activated hydroxyl groups, succinimidyl ester, sulfosuccinimidyl ester, maleimido, and ethenesulfonyl. In embodiments, an electrophilic group is an aldehyde, an α-halo ketone, a maleimide, a succinimide, a hydroxysuccinimide, an isothiocyanate, an isocyanate, an acyl azide, a sulfonyl chloride, a tosylate ester, a glyoxal, an epoxide, an oxirane, a carbonate, an imidoester, an anhydride, a fluorophenyl ester, a hydroxymethyl phosphine derivative, a carbonate, a haloacetyl, a chlorotriazine, a haloacetyl, an alkyl halide, an aziridine, an acryloyl derivative, ketone, carboxylic acid, ester, acetyl chloride, or acetic anhydride. In embodiments, an electrophilic group is or comprises a maleimide or succinimide group. Carboxylic acid groups may be activated so as to be reactive with a nucleophile, including reaction with a suitable hydroxyl-containing compound in the presence of a dehydrating agent such as dicyclohexylcarbodiimide (DCC) or dicyclohexylurea (DHU). For example, a carboxylic acid can be reacted with an alkoxy-substituted N-hydroxysuccinimide or N-hydroxysulfosuccinimide in the presence of DCC to form reactive electrophilic groups, the N-hydroxysuccinimide ester and the N-hydroxysulfosuccinimide ester, respectively. Carboxylic acids may also be activated by reaction with an acyl halide such as an acyl chloride (e.g., acetyl chloride), to provide a reactive anhydride group. In a further example, a carboxylic acid may be converted to an acid chloride group using, e.g., thionyl chloride or an acyl chloride capable of an exchange reaction.

Unless otherwise indicated, the term "alkyl" by itself or as part of another term refers to a substituted or unsubstituted straight chain or branched, saturated or unsaturated hydrocarbon having the indicated number of carbon atoms (e.g., "—$C_1$-$C_8$ alkyl" or "—$C_1$-$C_{10}$" alkyl refer to an alkyl group having from 1 to 8 or 1 to 10 carbon atoms, respectively). When the number of carbon atoms is not indicated, the alkyl group has from 1 to 8 carbon atoms. Representative straight chain "—$C_1$-$C_8$ alkyl" groups include, but are not limited to, -methyl, -ethyl, -n-propyl, -n-butyl, -n-pentyl, -n-hexyl, -n-heptyl and -n-octyl; while branched —$C_3$-$C_8$ alkyls include, but are not limited to, -isopropyl, -sec-butyl, -isobutyl, -tert-butyl, -isopentyl, and -2-methylbutyl; unsaturated —$C_2$-$C_8$ alkyls include, but are not limited to, -vinyl, -allyl, -1-butenyl, -2-butenyl, -isobu-tylenyl, -1 pentenyl, -2 pentenyl, -3-methyl-1-butenyl, -2 methyl-2-butenyl, -2,3 dimethyl-2-butenyl, -1-hexyl, 2-hexyl, -3-hexyl, -acetylenyl, -propynyl, -1 butynyl, -2 butynyl, -1 pentynyl, -2 pentynyl and -3 methyl 1 butynyl. Sometimes an alkyl group is unsubstituted. An alkyl group can be substituted with one or more groups. In other aspects, an alkyl group will be saturated.

Unless otherwise indicated, "alkylene", by itself of as part of another term, refers to a substituted or unsubstituted saturated, branched or straight chain or cyclic hydrocarbon radical of the stated number of carbon atoms, typically 1-10 carbon atoms, and having two monovalent radical centers derived by the removal of two hydrogen atoms from the same or two different carbon atoms of a parent alkane. Typical alkylene radicals include, but are not limited to: methylene (—$CH_2$—), 1,2-ethylene (—$CH_2CH_2$—), 1,3-propylene (—$CH_2CH_2CH_2$—), 1,4-butylene (—$CH_2CH_2CH_2CH_2$—), and the like. In preferred aspects, an alkylene is a branched or straight chain hydrocarbon (i.e., it is not a cyclic hydrocarbon).

Unless otherwise indicated, "aryl", by itself or as part of another term, means a substituted or unsubstituted monovalent carbocyclic aromatic hydrocarbon radical of the stated number of carbon atoms, typically 6-20 carbon atoms, derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like. An exemplary aryl group is a phenyl group.

Unless otherwise indicated, an "arylene", by itself or as part of another term, is an aryl group as defined above which has two covalent bonds (i.e., it is divalent) and can be in the ortho, meta, or para orientations.

Unless otherwise indicated, a "$C_3$-$C_8$ heterocycle" by itself or as part of another term, refers to a monovalent substituted or unsubstituted aromatic or non-aromatic monocyclic or bicyclic ring system having from 3 to 8 carbon atoms (also referred to as ring members) and one to four heteroatom ring members independently selected from N, O, P or S, and derived by removal of one hydrogen atom from a ring atom of a parent ring system. One or more N, C or S atoms in the heterocycle can be oxidized. The ring that includes the heteroatom can be aromatic or nonaromatic. Heterocycles in which all of the ring atoms are involved in aromaticity are referred to as heteroaryls and otherwise are referred to heterocarbocycles. Unless otherwise noted, the heterocycle is attached to its pendant group at any heteroatom or carbon atom that results in a stable structure. As such a heteroaryl may be bonded through an aromatic carbon of its aromatic ring system, referred to as a C-linked heteroaryl, or through a non-double-bonded N atom (i.e., not=N—) in its aromatic ring system, which is referred to as an N-linked heteroaryl. Thus, nitrogen-containing heterocycles may be C-linked or N-linked and include pyrrole moieties, such as pyrrol-1-yl (N-linked) and pyrrol-3-yl (C-linked), and imidazole moieties such as imidazol-1-yl and imidazol-3-yl (both N-linked), and imidazol-2-yl, imidazol-4-yl and imidazol-5-yl moieties (all of which are C-linked).

Unless otherwise indicated, a "$C_3$-$C_8$ heteroaryl" is an aromatic $C_3$-$C_8$ heterocycle in which the subscript denotes the total number of carbons of the cyclic ring system of the heterocycle or the total number of aromatic carbons of the aromatic ring system of the heteroaryl and does not implicate the size of the ring system or the presence or absence of ring fusion. Representative examples of a $C_3$-$C_8$ heterocycle include, but are not limited to, pyrrolidinyl, azetidinyl, piperidinyl, morpholinyl, tetrahydrofuranyl, tetrahydropyranyl, benzofuranyl, benzothiophene, indolyl, benzopyrazolyl, pyrrolyl, thiophenyl (thiophene), furanyl, thiazolyl, imidazolyl, pyrazolyl, pyrimidinyl, pyridinyl, pyrazinyl, pyridazinyl, isothiazolyl, and isoxazolyl. When explicitly given, the size of the ring system of a heterocycle or heteroaryl is indicated by the total number of atoms in the ring. For example, designation as a 5- or 6-membered heteroaryl indicates the total number or aromatic atoms (i.e., 5 or 6) in the heteroaromatic ring system of the heteroaryl, but does not imply the number of aromatic heteroatoms or aromatic carbons in that ring system. Fused heteroaryls are explicitly stated or implied by context as such and are typically indicated by the number of aromatic atoms in each aromatic ring that are fused together to make up the fused heteroaromatic ring system. For example a 5,6-membered heteroaryl is an aromatic 5-membered ring fused to an aromatic 6-membered ring in which one or both of the rings have aromatic heteroatom(s) or where a heteroatom is shared between the two rings.

A heterocycle fused to an aryl or heteroaryl such that the heterocycle remains non-aromatic and is part of a larger structure through attachment with the non-aromatic portion of the fused ring system is an example of an optionally substituted heterocycle in which the heterocycle is substituted by ring fusion with the aryl or heteroaryl. Likewise, an aryl or heteroaryl fused to heterocycle or carbocycle that is part of a larger structure through attachment with the aromatic portion of the fused ring system is an example of an optionally substituted aryl or heterocycle in which the aryl or heterocycle is substituted by ring fusion with the heterocycle or carbocycle.

Unless otherwise indicated, "$C_3$-$C_8$ heterocyclo" by itself or as part of another term, refers to a $C_3$-$C_8$ heterocyclic defined above wherein one of the hydrogen atoms of the heterocycle is replaced with a bond (i.e., it is divalent). Unless otherwise indicated, a "$C_3$-$C_8$ heteroarylene," by itself or as part of another term, refers to a $C_3$-$C_8$ heteroaryl group defined above wherein one of the heteroaryl group's hydrogen atoms is replaced with a bond (i.e., it is divalent).

Unless otherwise indicated, a "$C_3$-$C_8$ carbocycle" by itself or as part of another term, is a 3-, 4-, 5-, 6-, 7- or 8-membered monovalent, substituted or unsubstituted, saturated or unsaturated non-aromatic monocyclic or bicyclic carbocyclic ring derived by the removal of one hydrogen atom from a ring atom of a parent ring system. Representative —$C_3$-$C_8$ carbocycles include, but are not limited to, cyclopropyl, cyclobutyl, cyclopentyl, cyclopentadienyl, cyclohexyl, cyclohexenyl, 1,3-cyclohexadienyl, 1,4-cyclohexadienyl, cycloheptyl, 1,3-cycloheptadienyl, 1,3,5-cycloheptatrienyl, cyclooctyl, and cyclooctadienyl.

Unless otherwise indicated, a "$C_3$-$C_8$ carbocyclo" by itself or as part of another term, refers to a $C_3$-$C_8$ carbocycle group defined above wherein another of the carbocycle groups' hydrogen atoms is replaced with a bond (i.e., it is divalent).

Unless otherwise indicated, the term "heteroalkyl" by itself or in combination with another term, means, unless otherwise stated, a stable straight or branched chain hydrocarbon, or combinations thereof, fully saturated or containing from 1 to 3 degrees of unsaturation, consisting of the stated number of carbon atoms and from one to ten, preferably one to three, heteroatoms selected from the group consisting of O, N, Si and S, and wherein the nitrogen and sulfur atoms may optionally be oxidized and the nitrogen heteroatom may optionally be quaternized. The heteroatom (s) O, N and S may be placed at any interior position of the heteroalkyl group or at the position at which the alkyl group is attached to the remainder of the molecule. The heteroatom Si may be placed at any position of the heteroalkyl group, including the position at which the alkyl group is attached to the remainder of the molecule. Examples include —$CH_2$— $CH_2$—O—$CH_3$, —$CH_2$—$CH_2$—NH—$CH_3$, —$CH_2$— $CH_2$—N($CH_3$)—$CH_3$, —$CH_2$—S—$CH_2$—$CH_3$, —$CH_2$—$CH_2$—S(O)—$CH_3$, —NH—$CH_2$—$CH_2$—NH—C(O)—$CH_2$—$CH_3$, —$CH_2$—$CH_2$—S(O)$_2$—$CH_3$, —CH=CH—O—$CH_3$, —Si($CH_3$)$_3$, —$CH_2$—CH=N—O—$CH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Typically, a $C_1$ to $C_4$ heteroalkyl or heteroalkylene has 1 to 4 carbon atoms and 1 or 2 heteroatoms and a $C_1$ to $C_3$ heteroalkyl or heteroalkylene has 1 to 3 carbon atoms and 1 or 2 heteroatoms. In some aspects, a heteroalkyl or heteroalkylene is saturated.

Unless otherwise indicated, the term "heteroalkylene" by itself or in combination with another term means a divalent group derived from heteroalkyl (as discussed above), as exemplified by —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

Unless otherwise indicated, "aminoalkyl" by itself or in combination with another term means a heteroalkyl wherein an alkyl moiety as defined herein is substituted with an amino, alkylamino, dialkylamino or cycloalkylamino group. Exemplary non-limiting aminoalkyls are —$CH_2NH_2$, —$CH_2CH_2NH_2$, —$CH_2CH_2NHCH_3$ and —$CH_2CH_2N(CH_3)_2$ and further includes branched species such as —CH($CH_3$)$NH_2$ and —C($CH_3$)$CH_2NH_2$ in the (R)- or (S)-configuration. Alternatively, an aminoalkyl is an alkyl moiety, group, or substituent as defined herein wherein a $sp^3$ carbon other than the radical carbon has been replaced with an amino or alkylamino moiety wherein its $sp^3$ nitrogen replaces the $sp^3$ carbon of the alkyl provided that at least one $sp^3$ carbon remains. When referring to an aminoalkyl moiety as a substituent to a larger structure or another moiety the aminoalkyl is covalently attached to the structure or moiety through the carbon radical of the alkyl moiety of the aminoalkyl.

Unless otherwise indicated "alkylamino" and "cycloalkylamino" by itself or in combination with another term means an alkyl or cycloalkyl radical, as described herein, wherein the radical carbon of the alkyl or cycloalkyl radical has been replaced with a nitrogen radical, provided that at least one $sp^3$ carbon remains. In those instances where the alkylamino is substituted at its nitrogen with another alkyl moiety the resulting substituted radical is sometimes referred to as a dialkylamino moiety, group or substituent wherein the alkyl moieties substituting nitrogen are independently selected. Exemplary and non-limiting amino, alkylamino and dialkylamino substituents, include those having the structure of —N(R')$_2$, wherein R' in these examples are independently selected from hydrogen or $C_{1-6}$ alkyl, typically hydrogen or methyl, whereas in cycloalkyl amines, which are included in heterocycloalkyls, both R' together with the nitrogen to which they are attached define a heterocyclic ring. When both R' are hydrogen or alkyl, the moiety is sometimes described as a primary amino group and a tertiary amine group, respectively. When one R' is hydrogen and the other is alkyl, then the moiety is sometimes described as a secondary amino group. Primary and secondary alkylamino moieties are more reactive as nucleo-philes towards carbonyl-containing electrophilic centers whereas tertiary amines are more basic.

"Substituted alkyl" and "substituted aryl" mean alkyl and aryl, respectively, in which one or more hydrogen atoms, typically one, are each independently replaced with a substituent. Typical substituents include, but are not limited to a —X, —R', —OH, —OR', —SR', —N(R')$_2$, —N(R')$_3$, =NR', —CX$_3$, —CN, —NO$_2$, —NR'C(=O)R', —C(=O) R', —C(=O)N(R')$_2$, —S(=O)$_2$R', —S(=O)$_2$NR, —S(=O)R', —OP(=O)(OR')$_2$, —P(=O)(OR')$_2$, —PO$_3$=, PO$_3$H$_2$, —C(=O)R', —C(=S)R', —CO$_2$R', —CO$_2$—, —C(=S)OR', —C(=O)SR', —C(=S)SR', —C(=O)N (R')$_2$, —C(=S)N(R')$_2$, and —C(=NR)N(R')$_2$, where each X is independently selected from the group consisting of a halogen: —F, —CI, —Br, and —I; and wherein each R' is independently selected from the group consisting of —H, —C$_1$-C$_{20}$ alkyl, —C$_6$-C$_{20}$ aryl, —C$_3$-C$_{14}$ heterocycle, a protecting group, and a prodrug moiety.

More typically substituents are selected from the group consisting of —X, —R', —OH, —OR', —SR', —N(R')$_2$, —N(R')$_3$, =NR', —NR'C(=O)R, —C(=O)R', —C(=O) N(R')$_2$, —S(=O)$_2$R', —S(=O)$_2$NR', —S(=O) R', —C(=O)R', —C(=S)R, —C(=O)N(R')$_2$, —C(=S)N (R')$_2$, and —C(=NR)N(R')$_2$, wherein each X is independently selected from the group consisting of —F and —CI, or are selected from the group consisting of —X, —R, —OH, —OR', —N(R')$_2$, —N(R')$_3$, —NR' C(=O)R', —C(=O)N(R')$_2$, —S(=O)$_2$R', —S(=O)$_2$NR', —S(=O) R', —C(=O)R', —C(=O)N(R')$_2$, —C(=NR)N(R')$_2$, a protecting group, and a prodrug moiety wherein each X is —F; and wherein each R' is independently selected from the group consisting of hydrogen, —C$_1$-C$_{20}$ alkyl, —C$_6$-C$_{20}$ aryl, —C$_3$-C$_{14}$ heterocycle, a protecting group, and a prodrug moiety. In some aspects, an alkyl substituent is selected from the group consisting —N(R')$_2$, —N(R')$_3$ and —C(=NR)N(R')$_2$, wherein R is selected from the group consisting of hydrogen and —C$_1$-C$_{20}$ alkyl. In other aspects, alkyl is substituted with a series of ethyleneoxy moieties to define a PEG unit. Alkylene, carbocycle, carbocyclo, arylene, heteroalkyl, heteroalkylene, heterocycle, heterocyclo, heteroaryl, and heteroarylene groups as described above may also be similarly substituted.

"Protecting group" as used here means a moiety that prevents or reduces the ability of the atom or functional group to which it is linked from participating in unwanted reactions. Typical protecting groups for atoms or functional groups are given in Greene (1999), "PROTECTIVE GROUPS IN ORGANIC SYNTHESIS, 3$^{RD}$ ED.", Wiley Interscience. Protecting groups for heteroatoms such as oxygen, sulfur and nitrogen are used in some instances to minimize or avoid unwanted their reactions with electrophilic compounds. In other instances, the protecting group is used to reduce or eliminate the nucleophilicity and/or basicity of the unprotected heteroatom. Non-limiting examples of protected oxygen are given by —OR$^{PR}$, wherein R$^{PR}$ is a protecting group for hydroxyl, wherein hydroxyl is typically protected as an ester (e.g. acetate, propionate or benzoate). Other protecting groups for hydroxyl avoid interfering with the nucleophilicity of organometallic reagents or other highly basic reagents, where hydroxyl is typically protected as an ether, including alkyl or heterocycloalkyl ethers, (e.g., methyl or tetrahydropyranyl ethers), alkoxymethyl ethers (e.g., methoxymethyl or ethoxymethyl ethers), optionally substituted aryl ethers, and silyl ethers (e.g., trimethylsilyl (TMS), triethylsilyl (TES), tert-butyldiphenylsilyl (TBDPS), tert-butyldimethylsilyl (TBS/TBDMS), triisopropylsilyl (TIPS) and [2-(trimethylsilyl)ethoxy]-methylsilyl (SEM)). Nitrogen protecting groups include those for primary or secondary amines as in —NHR$^{PR}$ or —N(R$^{PR}$)$_2$—, wherein least one of R$^{PR}$ is a nitrogen atom protecting group or both R$^{PR}$ together comprise a protecting group.

A protecting group is suitable when it is capable of preventing or avoiding unwanted side-reactions or premature loss of the protecting group under reaction conditions required to effect desired chemical transformation elsewhere in the molecule and during purification of the newly formed molecule when desired, and can be removed under conditions that do not adversely affect the structure or stereochemical integrity of that newly formed molecule. By way of example and not limitation, a suitable protecting group may include those previously described for protecting functional groups. A suitable protecting group is sometimes a protecting group used in peptide coupling reactions.

"Aromatic alcohol" by itself or part of a larger structure refers to an aromatic ring system substituted with the hydroxyl functional group —OH. Thus, aromatic alcohol refers to any aryl, heteroaryl, arylene and heteroarylene moiety as described herein having a hydroxyl functional group bonded to an aromatic carbon of its aromatic ring system. The aromatic alcohol may be part of a larger moiety as when its aromatic ring system is a substituent of this moiety, or may be embedded into the larger moiety by ring fusion, and may be optionally substituted with moieties as described herein including one or more other hydroxyl substitutents. A phenolic alcohol is an aromatic alcohol having a phenol group as the aromatic ring.

"Aliphatic alcohol" by itself or part of a larger structure refers to a moiety having a non-aromatic carbon bonded to the hydroxyl functional group —OH. The hydroxy-bearing carbon may be unsubstituted (i.e., methyl alcohol) or may have one, two or three optionally substituted branched or unbranched alkyl substituents to define a primary alcohol, or a secondary or tertiary aliphatic alcohol within a linear or cyclic structure. When part of a larger structure, the alcohol may be a substituent of this structure by bonding through the hydroxy bearing carbon, through a carbon of an alkyl or other moiety as described herein to this hydroxyl-bearing carbon or through a substituent of this alkyl or other moiety. An aliphatic alcohol contemplates a non-aromatic cyclic structure (i.e., carbocycles and hetero-carbocycles, optionally substituted) in which a hydroxy functional group is bonded to a non-aromatic carbon of its cyclic ring system.

"Arylalkyl" or "heteroarylalkyl" as used herein means a substituent, moiety or group where an aryl moiety is bonded to an alkyl moiety, i.e., aryl-alkyl-, where alkyl and aryl groups are as described above, e.g., C$_6$H$_5$—CH$_2$— or C$_6$H$_5$—CH(CH$_3$)CH$_2$—. An arylalkyl or heteroarylalkyl is associated with a larger structure or moiety through a sp$^3$ carbon of its alkyl moiety.

"Succinimide moiety" as used herein refers to an organic moiety comprised of a succinimide ring system, which is present in one type of Y' in the compounds of Formula (III) that is typically further comprised of an alkylene-containing moiety bonded to the imide nitrogen of that ring system. A succinimide moiety typically results from Michael addition of a thiol group of a cell binding agent to the maleimide ring system of a camptothecin payload compound (Formula II). A succinimide moiety is therefore comprised of a thio-substituted succinimide ring system and when present in a camptothecin conjugate has its imide nitrogen substituted with the remainder of the cell binding agent of the camptothecin conjugate and is optionally substituted with substituent(s) that were present on the maleimide ring system of the compounds of Formula II.

"Acid-amide moiety" as used herein refers to succinic acid having an amide substituent that results from the thio-substituted succinimide ring system of a succinimide moiety having undergone breakage of one of its carbonyl-nitrogen bonds by hydrolysis. Hydrolysis resulting in a succinic acid-amide moiety provides a linker less likely to suffer premature loss of the linker to which it is bonded through elimination of the antibody-thio substituent. Hydrolysis of the succinimide ring system of the thio-substituted succinimide moiety is expected to provide regiochemical isomers of acid-amide moieties that are due to differences in reactivity of the two carbonyl carbons of the succinimide ring system attributable at least in part to any substituent present in the maleimide ring system of the compounds of Formula II and to the thio substituent introduced by the targeting ligand.

The term "Prodrug" as used herein refers to a less biologically active or inactive compound which is transformed within the body into a more biologically active compound via a chemical or biological process (i.e., a chemical reaction or an enzymatic biotransformation). Typically, a biologically active compound is rendered less biologically active (i.e., is converted to a prodrug) by chemically modifying the compound with a prodrug moiety. In some aspects the prodrug is a Type II prodrug, which are bioactivated outside cells, e.g., in digestive fluids, or in the body's circulation system, e.g., in blood. Exemplary prodrugs are esters and (β-D-glucopyranosides.

In many instances, the assembly of the conjugates, linkers and components described herein will refer to reactive groups. A "reactive group" or RG is a group that contains a reactive site (RS) that is capable of forming a bond with either the components of the linker of camptothecin payload or camptothecin conjugate; or the camptothecin. RS is the reactive site within a Reactive Group (RG). Reactive groups include thiol groups to form disulfide bonds or thioether bonds, aldehyde, ketone, or hydrazine groups to form hydrazone bonds, carboxylic or amino groups to form peptide bonds, carboxylic or hydroxy groups to form ester bonds, sulfonic acids to form sulfonamide bonds, alcohols to form carbamate bonds, and amines to form sulfonamide bonds or carbamate bonds. The following table is illustrative of Reactive Groups, Reactive Sites, and exemplary functional groups that can form after reaction of the reactive site. The table is not limiting. One of skill in the art will appreciate that the noted R' and R" portions in the table are effectively any organic moiety (e.g., an alkyl group, aryl group, heteroaryl group, or substituted alkyl, aryl, or heteroaryl, group) which is compatible with the bond formation provided in converting RG to one of the Exemplary Functional Groups. It will also be appreciated that, as applied to the embodiments of the present invention, R' may represent one or more components of the self-stabilizing linker or optional secondary linker, as the case may be, and R" may represent one or more components of the optional secondary linker, Camptothecin, stabilizing unit, or detection unit, as the case may be.

| RG | RS | Exemplary Functional Groups |
|---|---|---|
| 1) R'—SH | —S— | R'—S—R"<br>R'—S—S—R" |
| 2) R'—C(=O)OH | —C(=O)— | R'—C(=O)NH—R" |
| 3) R'—C(=O)ONHS | —C(=O)— | R'—C(=O)NH—R" |
| 4) R'S(=O)₂—OH | —S(=O)₂— | R'S(=O)₂NH—R" |
| 5) R'—CH₂—X (X is Br, I, Cl) | —CH₂— | R'—CH₂—S—R" |
| 6) R'—NH₂ | —N— | R'—NHC(=O)R" |

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

Compounds of the present invention are, subsequent to their preparation, preferably isolated and purified to obtain a composition containing an amount by weight equal to or greater than 95% ("substantially pure"), which is then used or formulated as described herein.

The term "conjugate" as used herein refers to a compound described herein or a derivative thereof that is linked to a cell binding agent.

The term "linkable to a cell binding agent" as used herein refers to the compounds described herein or derivatives thereof comprising at least one linking group or a precursor thereof suitable to bond these compounds or derivatives thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one of the compounds described herein, or derivative thereof bound to a cell binding agent via a suitable linking group or a precursor thereof.

The terms "abnormal cell growth" and "proliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells, and/or benign or pre-cancerous cells.

A "therapeutic agent" encompasses both a biological agent such as an antibody, a peptide, a protein, an enzyme or a chemotherapeutic agent.

A "chemotherapeutic agent" is a chemical compound useful in the treatment of cancer.

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof.

A "linker", "linker moiety", or "linking group" as defined herein refers to a moiety that connects two groups, such as a cell binding agent and a cytotoxic compound, together. Typically, the linker is substantially inert under conditions for which the two groups it is connecting are linked. A bifunctional crosslinking agent may comprise two reactive groups, one at each ends of a linker moiety, such that one reactive group can be first reacted with the cytotoxic compound to provide a compound bearing the linker moiety and a second reactive group, which can then react with a cell binding agent. Alternatively, one end of the bifunctional crosslinking agent can be first reacted with the cell binding agent to provide a cell binding agent bearing a linker moiety and a second reactive group, which can then react with a cytotoxic compound. The linking moiety may contain a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in US 2009/0274713, US 2010/01293140 and WO 2009/134976, each of which is expressly incorporated herein by reference, each of which is expressly incorporated herein by reference.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, selinocystiene and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. One amino acid that may be used in particular is citrulline, which is a derivative of arginine and is involved in the formation of urea in the liver. Amino acid mimetics refers to chemical compounds that have a structure that is different from the general chemical structure of an amino acid, but functions in a manner similar to a naturally occurring amino acid. The term "unnatural amino acid" is intended to represent the "D" stereochemical form of the twenty naturally occurring amino acids described above. It is further understood that the term unnatural amino acid includes homologues of the natural amino acids or their D isomers, and synthetically modified forms of the natural amino acids. The synthetically modified forms include, but are not limited to, amino acids having side chains shortened or lengthened by up to two carbon atoms, amino acids comprising optionally substituted aryl groups, and amino acids comprised halogenated groups, preferably halogenated alkyl and aryl groups and also N substituted amino acids e.g. N-methyl-alanine. An amino acid or peptide can be attached to a linker/spacer or a cell binding agent through the terminal amine or terminal carboxylic acid of the amino acid or peptide. The amino acid can also be attached to a linker/spacer or a cell-binding agent through a side chain reactive group, such as but not restricted to the thiol group of cysteine, the epsilon amine of lysine or the side chain hydroxyls of serine or threonine.

In embodiments, the amino acid is represented by $NH_2$—$C(R^{aa'}R^{aaa})$—$C(=O)$, wherein $R^{aa}$ and $R^{aa'}$ are each independently H, an optionally substituted linear, branched or cyclic alkyl, alkenyl or alkynyl having 1 to 10 carbon atoms, aryl, heteroaryl or heterocyclyl, or R and the N-terminal nitrogen atom can together form a heterocyclic ring (e.g., as in proline). The term "amino acid residue" refers to the corresponding residue when one hydrogen atom is removed from the amine and/or the hydroxyl group is removed from the carboxy end of the amino acid, such as —NH—C($R^{aa'}R^{aa}$)—C(=O)O—.

As used herein, the amino acid can be L or D isomers. Unless specified otherwise, the when an amino acid is referenced, it can be L or D isomer or a mixture thereof. In embodiments, when a peptide is referenced by its amino acid sequence, each of the amino acid can be L or D isomer unless otherwise specified. If one of the amino acid in a peptide is specified as D isomer, the other amino acid(s) are L isomer unless otherwise specified. For example, the peptide D-Ala-Ala means D-Ala-L-Ala.

Amino acids and peptides may be protected by blocking groups. A blocking group is an atom or a chemical moiety that protects the N-terminus of an amino acid or a peptide from undesired reactions and can be used during the synthesis of a drug-ligand conjugate. It should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, methyl esters, tert-butyl esters, 9-fluorenylmethyl carbamate (Fmoc) and carbobenzoxy (Cbz).

The term "peptide cleavable by a protease" refers to peptides containing a cleavage recognition sequence of a protease. As used herein, a protease is an enzyme that can cleave a peptide bond. A cleavage recognition sequence for a protease is a specific amino acid sequence recognized by the protease during proteolytic cleavage. Many protease cleavage sites are known in the art, and these and other cleavage sites can be included in the linker moiety. See, e.g., Matayoshi et al. *Science* 247: 954 (1990); Dunn et al. *Meth. Enzymol.* 241: 254 (1994); Seidah et al. *Meth. Enzymol.* 244: 175 (1994); Thornberry, *Meth. Enzymol.* 244: 615 (1994); Weber et al. *Meth. Enzymol.* 244: 595 (1994); Smith et al. *Meth. Enzymol.* 244: 412 (1994); Bouvier et al. *Meth. Enzymol.* 248: 614 (1995), Hardy et al, in AMYLOID PROTEIN PRECURSOR IN DEVELOPMENT, AGING, AND ALZHEIMER'S DISEASE, ed. Masters et al. pp. 190-198 (1994).

The peptide sequence is chosen based on its ability to be cleaved by a protease, non-limiting examples of which include cathepsins B, C, D, H, L and S, and furin. Preferably, the peptide sequence is capable of being cleaved by an appropriate isolated protease in vitro, which can be tested using in vitro protease cleavage assays known in the art.

In another embodiment, the peptide sequence is chosen based on its ability to be cleaved by a lysosomal protease. A lysosomal protease is a protease located primarily in the lysosomes, but can also be located in endosomes. Examples of a lysosomal protease include, but are not limited to, cathepsins B, C, D, H, L and S, and furin.

In another embodiment, the peptide sequence is chosen based on its ability to be cleaved by a tumor-associated protease, such as a protease that is found on the surface of a cancerous cell or extracellularly in the vicinity of tumor cells, non-limiting examples of such proteases include thimet oligopeptidase (TOP), CD10 (neprilysin), a matrix metalloprotease (such as MMP2 or MMP9), a type II transmembrane serine protease (such as Hepsin, testisin, TMPRSS4 or matriptase/MT-SP1), legumain and enzymes described in the following reference (Current Topics in Developmental Biology: Cell Surface Proteases, vol. 54 Zucker S. 2003, Boston, MA). The ability of a peptide to be cleaved by tumor-associated protease can be tested using in vitro protease cleavage assays known in the art.

The term "cation" refers to an ion with positive charge. The cation can be monovalent (e.g., $Na^+$, $K^+$, etc.), bi-valent (e.g., $Ca^{2+}$, $Mg^{2+}$, etc.) or multi-valent (e.g., $Al^{3+}$ etc.). In embodiments, the cation is monovalent.

Compounds of Formula (I)

In some aspects, the invention features metabolites comprising a camptothecin derivative. Such metabolites can exhibit desirable cytotoxic properties and can be used to prepare conjugates comprising cell binding agents as described herein.

In one aspect, the invention features a compound of Formula (I), $$D-L_1-L_2-Q \qquad (I),$$

or a pharmaceutically acceptable salt thereof, wherein:
D is represented by the following structural formula:

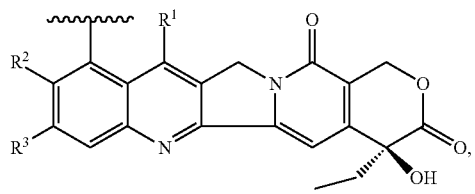

wherein
$R^1$ independently is —H, $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, $C_2$-$C_6$ halogenated alkenyl, or $C_2$-$C_6$ halogenated alkynyl;
$R^2$ independently is —H, —F, —N($R^4$)$_2$, —N($R^4$)($R^5$), —O$R^4$, —S$R^4$, —S(=O)$R^5$, —SO$_2$R', $C_1$-$C_6$ alkyl, or $C_1$-$C_6$ fluoroalkyl; and $R^3$ independently is —H, —F, —CN, —OCH$_3$, —CH$_3$, or —CF$_3$; or $R^2$ and $R^3$ together form a group of the formula —O(CH$_2$)$_n$O— or —O(CF$_2$)$_n$O— wherein n is 1 or 2;
$R^4$ independently is —H or $C_1$-$C_4$ alkyl;
$R^5$ independently is $C_1$-$C_4$ alkyl;
$L_1$ independently is absent or —($C_1$-$C_{10}$ alkylene)-;
$L_2$ independently is absent or is —OCH$_2$-$L_3$-*, —SCH$_2$-$L_3$-*, —S(=O)-$L_3$-*, —SO$_2$-$L_3$-*, —C(=O)-$L_3$-*, —N($R^6$)CH$_2$-$L_3$-*, —N($R^6$)C(=O)-$L_3$-*, —N($R^6$)C(=O)N($R^7$)-$L_3$-*, —C(=O)N($R^6$)CH$_2$-$L_3$-*, —OC(=O)N($R^6$)CH$_2$-$L_3$-*, or —N($R^6$)C(=O)OCH$_2$-$L_3$-*;
wherein * denotes the site covalently linked to Q;
$L_3$ independently is —($C_1$-$C_{10}$ alkylene)-, —CH$_2$OCH$_2$CH$_2$—, or —CH$_2$CH$_2$OCH$_2$CH$_2$—;
each $R^6$ and $R^7$ independently is —H, $C_1$-$C_6$ alkyl, $C_1$-$C_6$ fluoroalkyl, $C_3$-$C_6$ cycloalkyl, aryl, heteroaryl, or benzyl; and
Q is —OH or —SH.

In embodiments, when $R^2$ and $R^3$ combine to form —OCH$_2$O—, $R^1$ is not —CH$_2$CH$_2$CH$_2$CH$_3$.

In embodiments, when $R^1$ is —H or —CH$_2$CH$_3$, $R^2$ is —OH or alkoxy and $R^3$ is —H, then -$L_1$-$L_2$-Q is not —CH(R')CH$_2$OH or —CH(R')(CH$_2$)$_2$OH, where R' is —H or $C_1$-$C_6$ alkyl, alkoxy, substituted alkyl, phenyl or PhCH$_2$—. In embodiments, when $R^1$ is —H or —CH$_2$CH$_3$, $R^2$ is —OH or alkoxy and $R^3$ is —H, then -$L_1$-$L_2$-Q is not —CH(R')CH$_2$OH or —CH(R')(CH$_2$)$_2$ wherein R' is —H or $C_1$-$C_6$ alkyl, alkoxy, substituted alkyl, phenyl or PhCH$_2$—.

In embodiments, at least one of $R^1$, $R^2$ and $R^3$, is not —H.

In embodiments, at least one of $L_1$ and $L_2$ is present.

In embodiments, $R^1$ independently is $C_1$-$C_6$ alkyl, silyl, $C_2$-$C_6$ alkenyl, $C_2$-$C_6$ alkynyl, $C_3$-$C_6$ cycloalkyl, $C_1$-$C_6$ halogenated alkyl, alkene or alkyne.

In embodiments, $R^1$ independently is —H or $C_1$-$C_6$ alkyl.

In embodiments, $R^2$ independently is —H, —F, —N($R^4$)$_2$, —N($R^4$)($R^5$), —O$R^4$, —S$R^4$, —S(=O)$R^5$, —SO$_2$R$^5$, $C_1$-$C_6$ alkyl, or $C_1$-$C_6$ fluoroalkyl; and $R^3$ independently is —H, —F, —CN, —OCH$_3$, —CH$_3$, or —CF$_3$.

In embodiments, $R^2$ independently is $C_1$-$C_6$ alkyl, $C_1$-$C_6$ fluoroalkyl, or —F.

In embodiments, $R^3$ independently is —H, —F, —CN, or —CF$_3$.

In embodiments, $R^3$ independently is —F, —CN, —OCH$_3$, —CH$_3$, or —CF$_3$.

In embodiments, $R^2$ and $R^3$ combine to form —O(CH$_2$)$_n$O— or —O(CF$_2$)$_n$O—, wherein n is 1 or 2.

In embodiments, D is represented by one of the following structures:

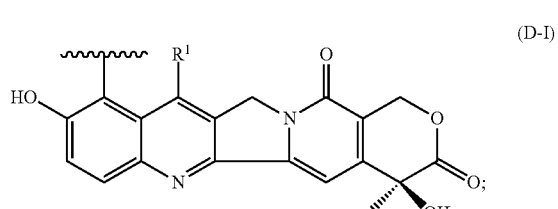

(D-I)

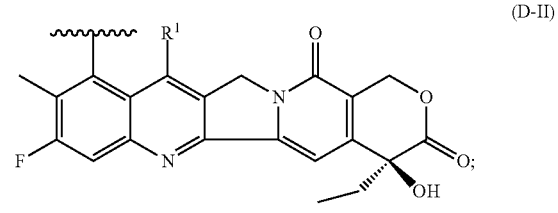

(D-II)

-continued
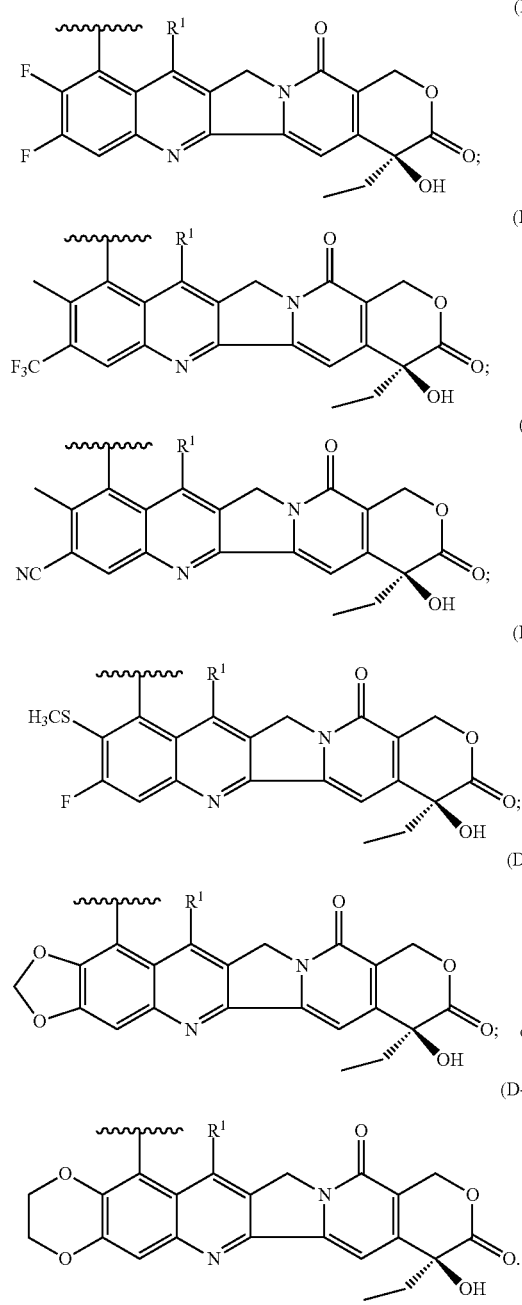
In embodiments, D is
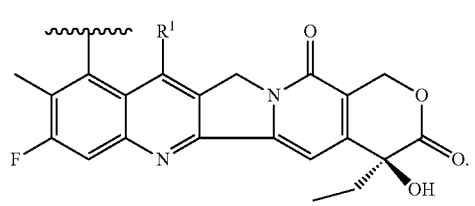
In embodiments, D is (D-I). In embodiments, D is (D-III). In embodiments, D is (D-IV).
In embodiments, D is (D-V). In embodiments, D is (D-VI). In embodiments, D is (D-VII). In embodiments, D is (D-VIII).
In embodiments, $R^1$ is —H or $C_1$-$C_6$ alkyl.
In embodiments, D is represented by one of the following structures:
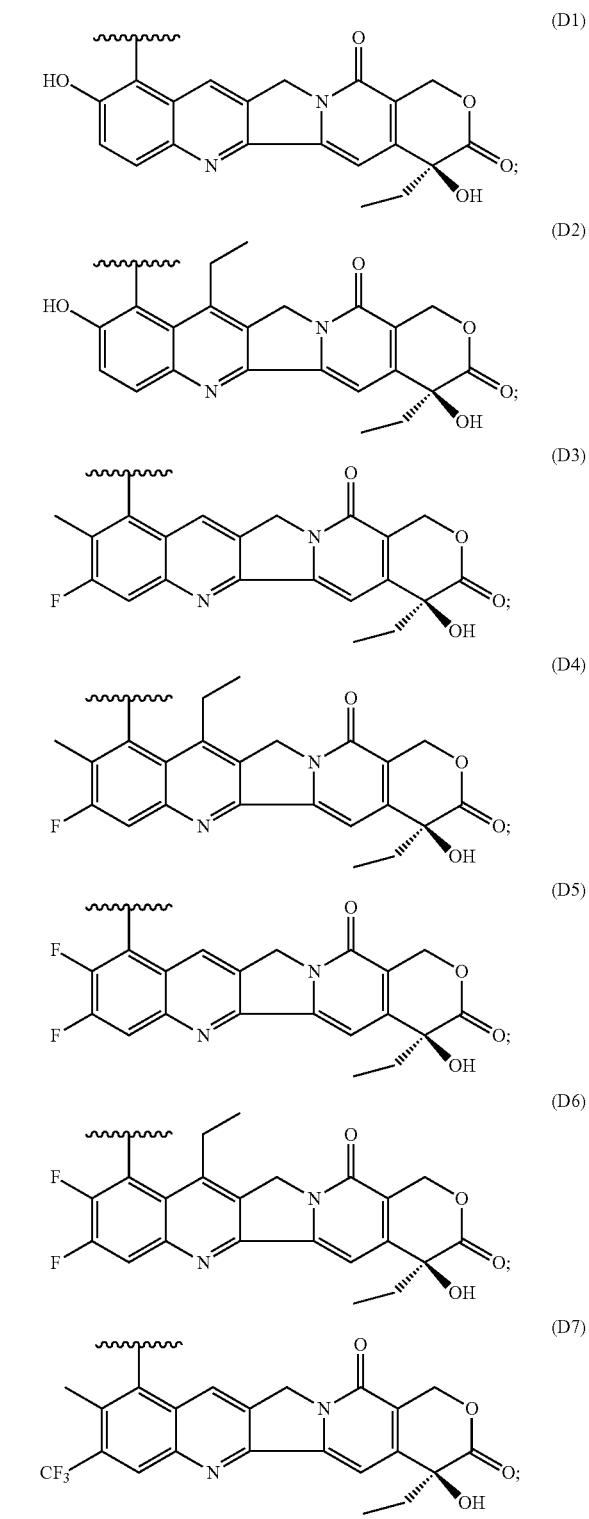

-continued

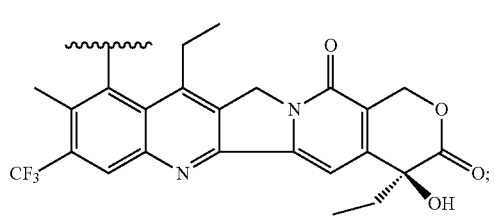
(D8)

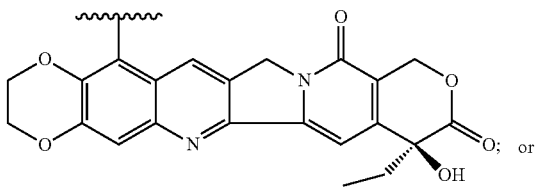
(D15)

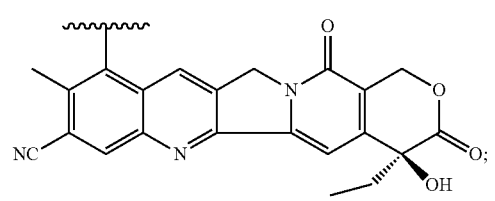
(D9)

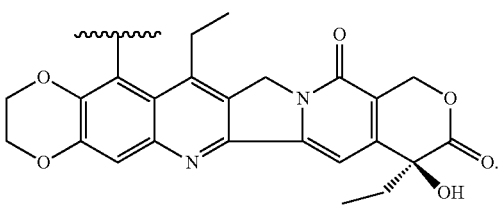
(D16)

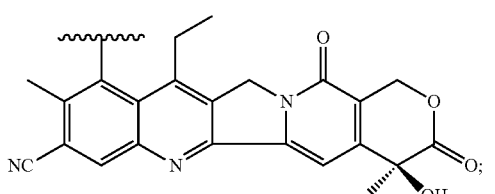
(D10)

In embodiments, D is

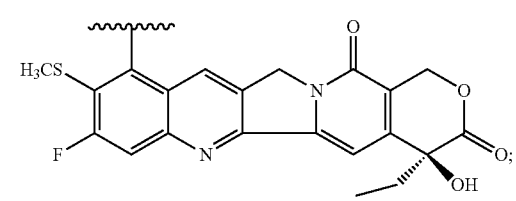
(D11)

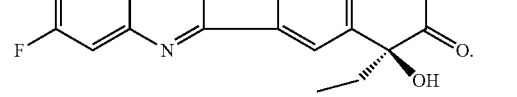
(D3)

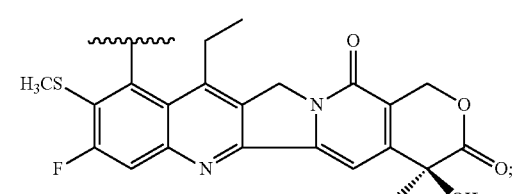
(D12)

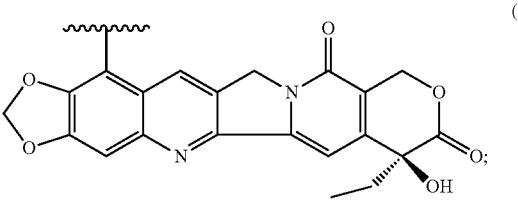
(D13)

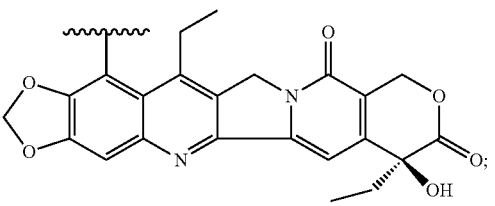
(D14)

In embodiments, D is (D1). In embodiments, D is (D2). In embodiments, D is (D4).

In embodiments, D is (D5). In embodiments, D is (D6). In embodiments, D is (D7). In embodiments, D is (D8).

In embodiments, D is (D9). In embodiments, D is (D10). In embodiments, D is (D11). In embodiments, D is (D12).

In embodiments, D is (D13). In embodiments, D is (D14). In embodiments, D is (D15). In embodiments, D is (D16).

In embodiments, $L_1$ is —($C_1$-$C_{10}$ alkylene)- and $L_2$ is absent.

In embodiments, $L_1$ is —($C_1$-$C_{10}$ alkylene)- and $L_2$ is —N($R^6$)CH$_2$-$L_3$-* or —N($R^6$)C(=O)-$L_3$-*, wherein * denotes the site covalently linked to Q.

In embodiments, $L_1$ is absent and $L_2$ is —N($R^6$)CH$_2$-$L_3$-* or —N($R^6$)C(=O)-$L_3$-*, wherein * denotes the site covalently linked to Q.

In embodiments, $L_3$ is —($C_1$-$C_{10}$ alkylene)-.

In embodiments, $R^6$ is —H or —CH$_3$.

In embodiments, $L_1$-$L_2$ is —CH$_2$—, —CH$_2$CH$_2$—, —CH$_2$CH$_2$CH$_2$—, or —CH$_2$CH$_2$CH$_2$CH$_2$—.

In embodiments, $L_1$-$L_2$ is —OCH$_2$CH$_2$—*, —OCH$_2$CH$_2$OCH$_2$CH$_2$—*, —SCH$_2$CH$_2$—*, —SCH$_2$CH$_2$OCH$_2$CH$_2$—*, —S(=O)CH$_2$—*, —SO$_2$CH$_2$—*, —C(=O)CH$_2$—*, —NHCH$_2$CH$_2$—*, —N(CH$_3$)CH$_2$CH$_2$—*, —N(CF$_3$)CH$_2$CH$_2$—*, —NHC(=O)CH$_2$—*, —CH$_2$NHC(=O)CH$_2$—*, —CH$_2$CH$_2$NHC(=O)CH$_2$—*, CH$_2$N(CH$_3$)C(=O)CH$_2$—*, —N(CH$_3$)C(=O)CH$_2$—*, —N(CH$_3$)C(=O)CH$_2$CH$_2$—*, —C(=O)NHCH$_2$CH$_2$—*, —NHC(=O)NHCH$_2$CH$_2$—*, —NHC(=O)OCH$_2$CH$_2$—*, —CH$_2$OC(=O)NHCH$_2$CH$_2$—*, or —C(=O)N(CH$_3$)CH$_2$CH$_2$—*, wherein * denotes the site covalently linked to Q.

In embodiments, $L_1$-$L_2$-Q is —CH$_2$CH$_2$CH$_2$CH$_2$OH, —CH$_2$CH$_2$CH$_2$OH, —CH$_2$CH$_2$OH, —CH$_2$CH$_2$OCH$_2$CH$_2$OH, —CH$_2$SCH$_2$CH$_2$OH, —CH$_2$NHC(=O)CH$_2$OH, —CH$_2$CH$_2$NHC(=O)CH$_2$OH, —CH$_2$N(CH$_3$)C(=O)CH$_2$OH, —OCH$_2$CH$_2$OH, —OCH$_2$CH$_2$CH$_2$OH, —SCH$_2$CH$_2$CH$_2$OH, —SCH$_2$CH$_2$OH, —NHCH$_2$CH$_2$OH, —NHCH$_2$CH$_2$CH$_2$OH, —N(CH$_3$)CH$_2$CH$_2$OH, —C(=O)NHCH$_2$CH$_2$OH, —NHC(=O)CH$_2$OH, —CH$_2$S(=O)CH$_2$OH, —CH$_2$SO$_2$CH$_2$OH, —CH$_2$CH$_2$CH$_2$CH$_2$SH, —CH$_2$CH$_2$CH$_2$SH, —CH$_2$CH$_2$SH, —CH$_2$CH$_2$OCH$_2$CH$_2$SH, —CH$_2$SCH$_2$CH$_2$SH, —CH$_2$NHC(=O)CH$_2$SH, —OCH$_2$CH$_2$CH$_2$SH, —SCH$_2$CH$_2$CH$_2$SH, —SCH$_2$CH$_2$SH, —NHCH$_2$CH$_2$CH$_2$SH, —N(CH$_3$)CH$_2$CH$_2$SH, —C(=O)NHCH$_2$CH$_2$SH, —NHC(=O)CH$_2$SH, —CH$_2$S(=O)CH$_2$SH, or —CH$_2$SO$_2$CH$_2$SH.

In embodiments, D-$L_1$-$L_2$ is represented by a structure that is

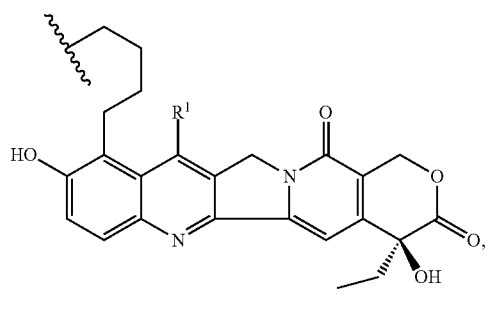

(P-I)

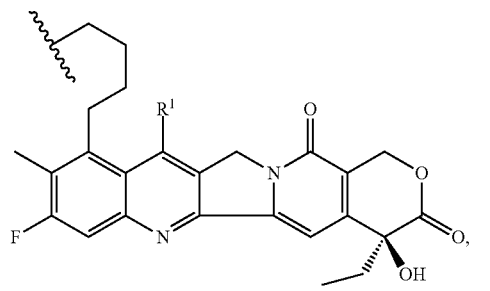

(P-II)

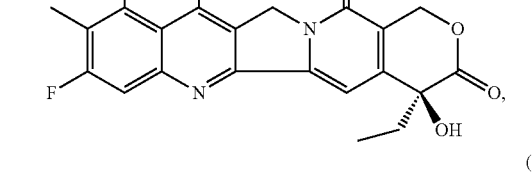

(P-IV)

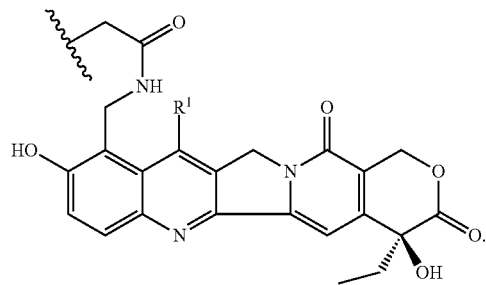

(P-V)

In embodiments, D-$L_1$-$L_2$ is represented by a structure that is:

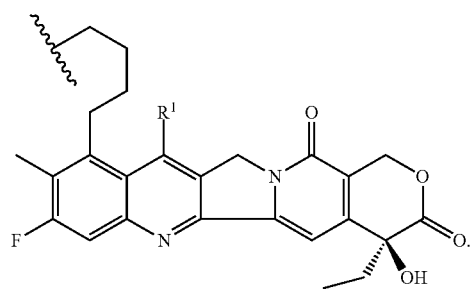

(P-II)

In embodiments, D-$L_1$-$L_2$ is represented by a structure that is (P-I).

In embodiments, D-$L_1$-$L_2$ is represented by a structure that is (P-III).

In embodiments, D-$L_1$-$L_2$ is represented by a structure that is (P-IV).

In embodiments, D-$L_1$-$L_2$ is represented by a structure that is (P-V).

In embodiments, $R^1$ is —H or $C_1$-$C_6$ alkyl.

In embodiments, $R^1$ is —H or —CH$_2$CH$_3$.

In embodiments, Q is —OH.

In embodiments, Q is —SH.

In embodiments, the compound has one of the following structures,

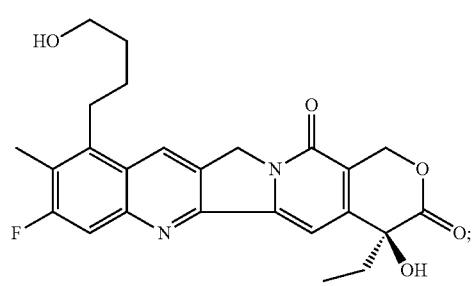

(P1)

-continued

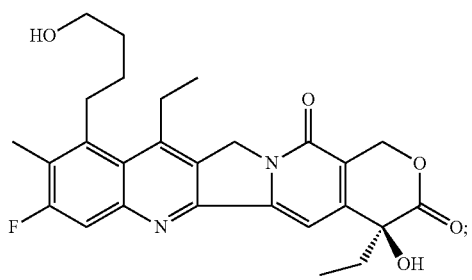
(P2)

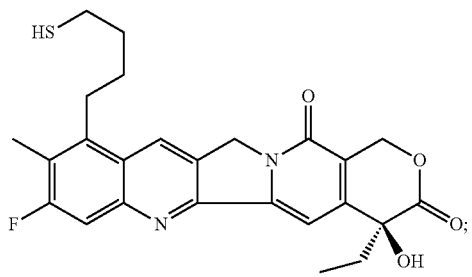
(P3)

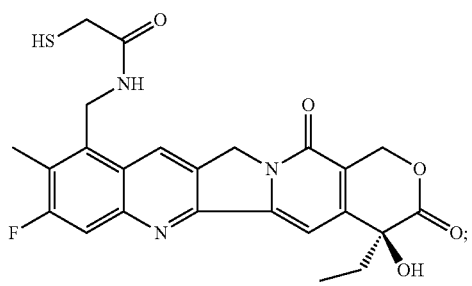
(P4)

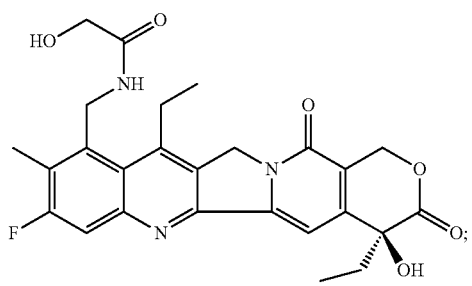
(P5)

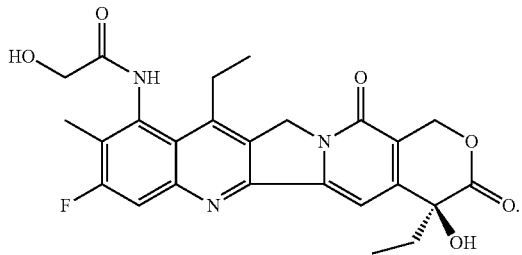
(P6)

or a pharmaceutically acceptable salt thereof.

In embodiments, the compound is

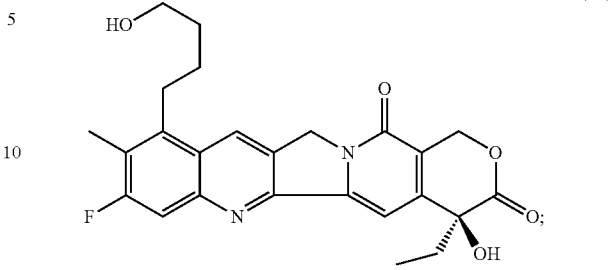
(P1)

or a pharmaceutically acceptable salt thereof.

In embodiments, the compound is Compound P2, or a pharmaceutically acceptable salt thereof.

In embodiments, the compound is Compound P3, or a pharmaceutically acceptable salt thereof.

In embodiments, the compound is Compound P4, or a pharmaceutically acceptable salt thereof.

In embodiments, the compound is Compound P5, or a pharmaceutically acceptable salt thereof.

In embodiments, the compound is Compound P6, or a pharmaceutically acceptable salt thereof.

Compounds of Formula (II)

In some aspects, metabolites comprising a camptothecin derivative can include a peptide linker and a reactive group: such compounds can be useful in preparing conjugates comprising cell binding agents as described herein.

In embodiments, such compounds are formed from or comprise a structure according to any embodiment of Formula (I) as described herein.

In another aspect, the invention features a compound of Formula (II), $$D\text{-}L_1\text{-}L_2\text{-}Q'\text{---}CH_2\text{---}NH\text{-}E\text{-}Z \quad \text{(II)},$$

or a pharmaceutically acceptable salt thereof, wherein:

D is represented by the following structural formula:

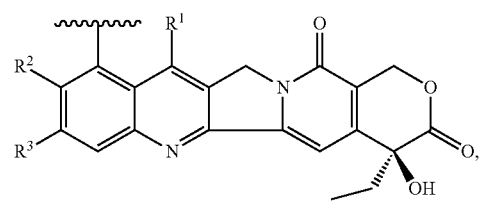

wherein $R^1$ independently is —H, $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, $C_2$-$C_6$ halogenated alkenyl, or $C_2$-$C_6$ halogenated alkynyl;

$R^2$ independently is —H, —F, —N($R^4$)$_2$, —N($R^4$)($R^5$), —O$R^4$, —S$R^4$, —S(=O)$R^5$, —SO$_2$R', $C_1$-$C_6$ alkyl, or $C_1$-$C_6$ fluoroalkyl; and $R^3$ is —H, —F, —CN, —OCH$_3$, —CH$_3$, —CF$_3$; or $R^2$ and $R^3$ together form a group of the formula —O(CH$_2$)$_n$O— or —O(CF$_2$)$_n$O— wherein n is 1 or 2;

$R^4$ independently is —H or $C_1$-$C_4$ alkyl;

$R^5$ independently is $C_1$-$C_4$ alkyl;

$L_1$ independently is absent or —($C_1$-$C_{10}$ alkylene)-;

$L_2$ independently is absent or is —OCH$_2$-$L_3$-*, —SCH$_2$-$L_3$-*, —S(=O)-$L_3$-*, —SO$_2$-$L_3$-*, —C(=O)-$L_3$-*, —N($R^6$)CH$_2$-$L_3$-*, —N($R^6$)C(=O)-$L_3$-*, —N($R^6$)C(=O)N($R^7$)-$L_3$-*, —C(=O)N($R^6$)CH$_2$-$L_3$-*; —OC (=O)N(R⁶)CH₂-L₃-*, or —N(R⁶)C(=O)OCH₂-L₃-* wherein * denotes the site covalently linked to Q';

L₃ independently is —(C₁-C₁₀ alkylene)-, —CH₂OCH₂CH₂—, or —CH₂CH₂OCH₂CH₂—;

each R⁶ and R⁷ independently is —H, C₁-C₆ alkyl, C₁-C₆ fluoroalkyl, C₃-C₆ cycloalkyl, aryl, heteroaryl, or benzyl; and Q' is —O— or —S—;

E is a peptide comprising 2 to 10 amino acids; wherein E is optionally substituted with one or more polyol; and wherein the N terminal of the peptide is covalently attached to Z;

Z is —C(=O)-L₄-Y,

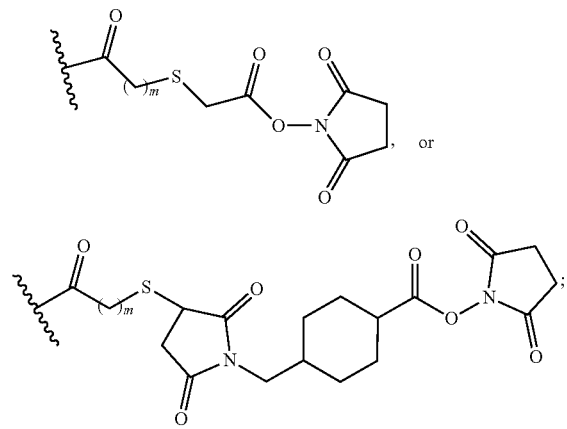

wherein m represents an integer of 1-10;

L₄ is —(C₁-C₁₀ alkylene)-*, —CH₂CH₂(OCH₂CH₂)ₙN(R⁸)C(=O)-L₅-* or —CH₂(OCH₂CH₂)ₙN(R⁸)C(=O)-L₅-*; wherein n represents an integer of 1-10; and wherein * denotes the site covalently linked to Y;

L₅ is —(C₁-C₁₀ alkylene)-;

R⁸ is —H or —CH₃; and

Y is an electrophilic group; and wherein when R² and R³ combine to form —OCH₂O—, R¹ is not —CH₂CH₂CH₂CH₃.

In embodiments, E is a peptide of 2, 3, or 4 amino acids. Each amino acid in said peptide is an L amino acid, or at least one amino acid in said peptide is a D amino acid.

In embodiments, E comprises one or more amino acids selected from glycine, alanine, valine, glutamine, glutamic acid, phenylalanine, and leucine, and wherein said glutamine or glutamic acid is optionally substituted by a polyol.

In embodiments, E comprises amino acids selected from glycine, alanine, valine, glutamine, glutamic acid, phenylalanine, and leucine, and wherein said glutamine or glutamic acid is optionally substituted by a polyol.

In embodiments, E comprises an amino acid having the following structure,

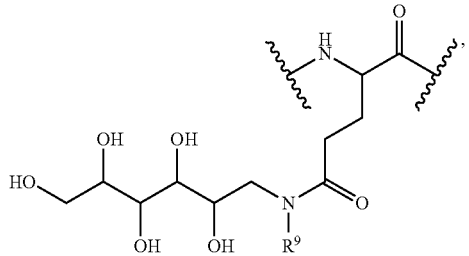

wherein R⁹ is —H or C₁-C₆ alkyl.

In embodiments, E comprises an amino acid having the following structure,

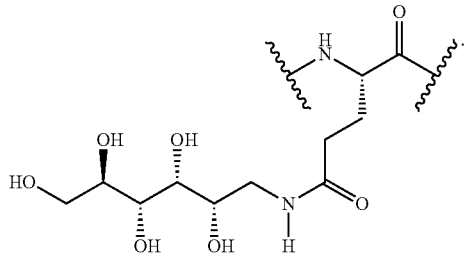

In embodiments, E is selected from the group consisting of -Ala-Val-*, -Val-Ala-*, -Gly-Gly-*, -Val-Cit-*, -Cit-Val-*, -Leu-Ala-*, -Ala-Leu-*, -Leu-Cit-*,-Cit-Leu-*, -Leu-Ala-*, -Ala-Leu-*, -Lys-Lys-*, -Ala-Lys-*, -Lys-Ala-*, -Val-Lys-*, -Lys-Val-*, -Tyr-Arg-*, -Arg-Tyr-*, -Arg-Arg-*, -Ala-Ala-*, -Phe-Lys-*, -Lys-Phe-*, -Thr-Thr-*, -Thr-Met-*, -Met-Thr-*, -Met-Tyr-*, -Tyr-Met-*, -Phe-Gln-*, -Gln-Phe-*, -Gly-Ser-*, -Leu-Gln-*, -Gln-Leu-*, -Ser-Ala-*, -Ser-Gly-*, -Val-Thr-*, -Thr-Val-*, -Val-Gln-*, -Ser-Val-*, -Val-Ser-*, -Ala-Met-*, -Met-Ala-*, -Val-Arg-*, -Arg-Val-*, -Phe-Ala-*,-Ala-Phe-*, -Cit-Val-*, -Gln-Val-*, -Phe-Arg-*, -Arg-Phe-*, -Ala-Ala-Ala-*, -Gly-Gly-Gly-*, -Ala-Val-Ala-*, -Gly-Val-Gly-*, -Ala-Val-Gly-*, -Gly-Phe-Lys-*, -Lys-Phe-Gly-*, -Leu-Ala-Leu-*, -Val-Ala-Leu-*, -Leu-Ala-Val-*, -Val-Ala-Val-*, -Ala-Val-Gly-*, -Gly-Phe-Gly-Gly-*, -Gly-Gly-Phe-Gly-*, -Ala-Val-Gly-Gly-*, -Ala-Ala-Ala-Ala-*, -Ala-Val-Ala-A-*, -Ala-Leu-Ala-Leu-*,-Leu-Ala-Leu-Ala-*, -Gly-Phe-Leu-Gly-* and -Gly-Leu-Phe-Gly-*, wherein * denotes the N-terminal of the peptides covalently attached to Z.

In embodiments, E is selected from the group consisting of -L-Ala-D-Val-*, -L-Val-D-Ala-*, -L-Val-D-Lys-*, -L-Val-D-Arg-*, -L-Val-D-Cit-*, -L-Val-D-Arg-*, -L-Val-D-Cit-*, -L-Val-D-Lys-*, -L-Val-D-Arg-*, -L-Arg-D-Arg-*, -L-Ala-D-Ala-*, -L-Ala-D-Lys-*, -L-Ala-D-Arg-*, -L-Ala-D-Ala-L-Ala-*, -L-Ala-D-Val-L-Ala-*, -L-Ala-D-Ala-Gly-*, and -L-Ala-D-Val-Gly-*, wherein * denotes the N-terminal of the peptides covalently attached to Z.

In embodiments, -E-NH—CH₂— has one of the following structures, wherein * denotes the N-terminal of the peptides covalently attached to Z:

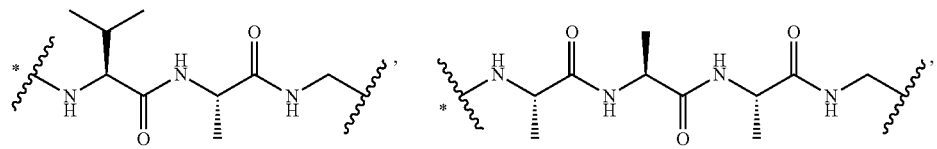

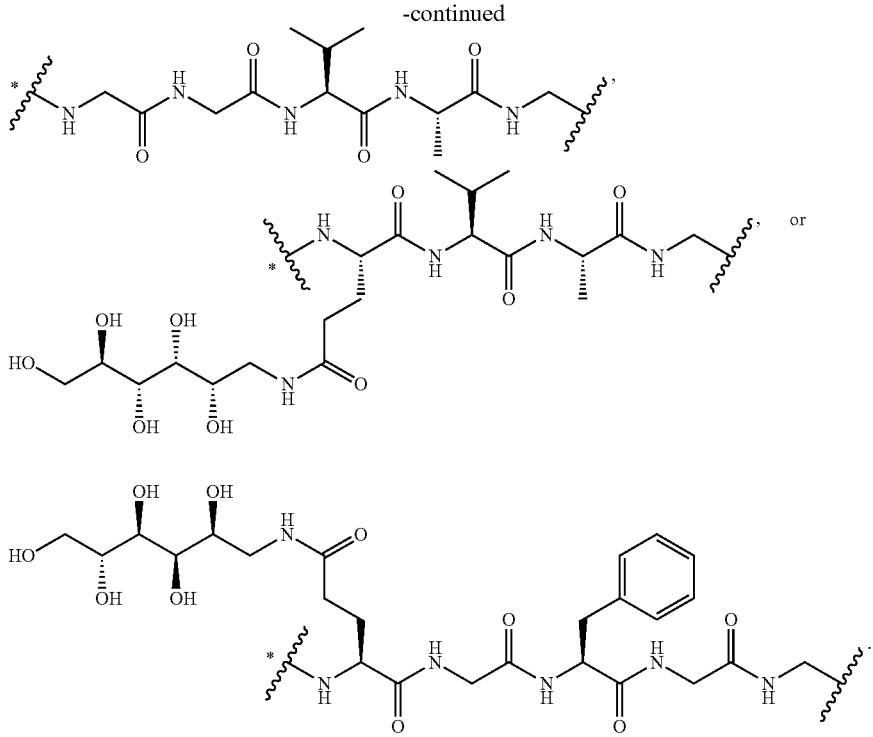

In embodiments, $L_4$ is —($C_1$-$C_{10}$ alkylene)-.

In embodiments, $L_4$ is —$CH_2CH_2(OCH_2CH_2)_nN(R^8)C(=O)$-$L_5$-* or —$CH_2(OCH_2CH_2)_nN(R^8)C(=O)$-$L_5$-*, wherein n represents an integer of 1-10; and wherein * denotes the site covalently linked to Y.

In embodiments, $L_4$ is —$CH_2CH_2CH_2CH_2CH_2$—, —$CH_2CH_2$—, —$CH_2$—, —$CH_2CH_2OCH_2CH_2OCH_2CH_2NHC(=O)CH_2CH_2$—* or —$CH_2OCH_2CH_2OCH_2CH_2NHC(=O)CH_2CH_2$—*, wherein * denotes the site covalently linked to Y.

In embodiments, Y is a Michael acceptor group, a succinimide, an epoxide, or a halogen.

In embodiments, Y is

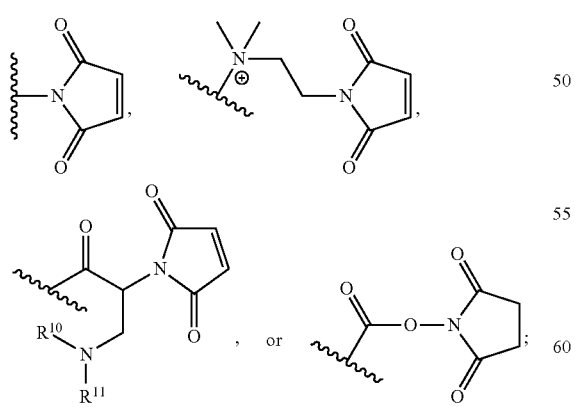

wherein $R^{10}$ and $R^{11}$ are each independently H or $C_1$-$C_3$ alkyl.

In embodiments, Z is —C(=O)-$L_4$-Y.

In embodiments, Z is

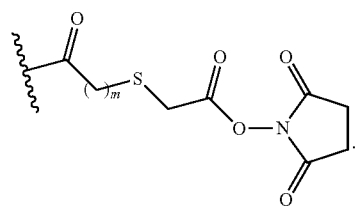

In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z is

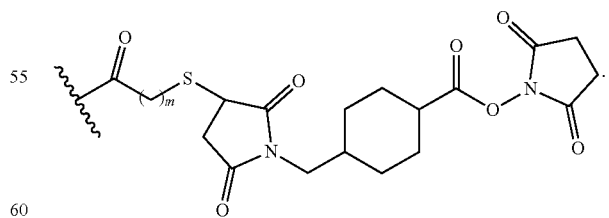

In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z is
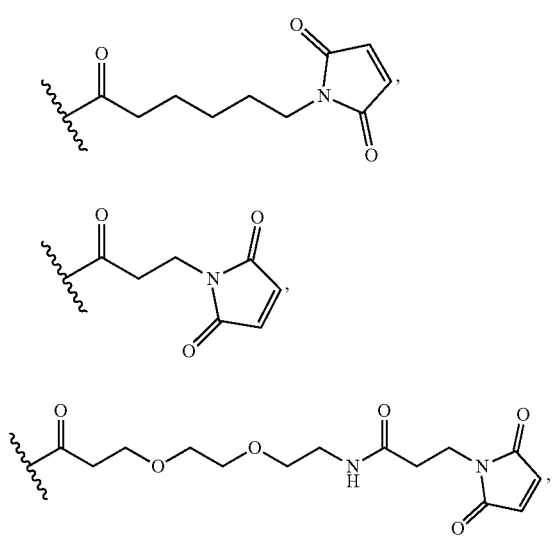
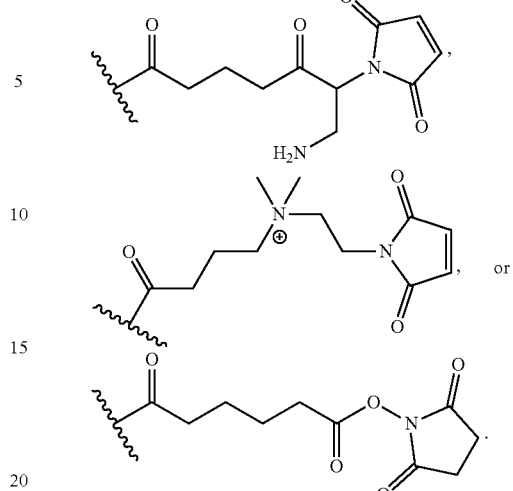
In embodiments, Z-E-NH—CH$_2$— has one of the following structures,
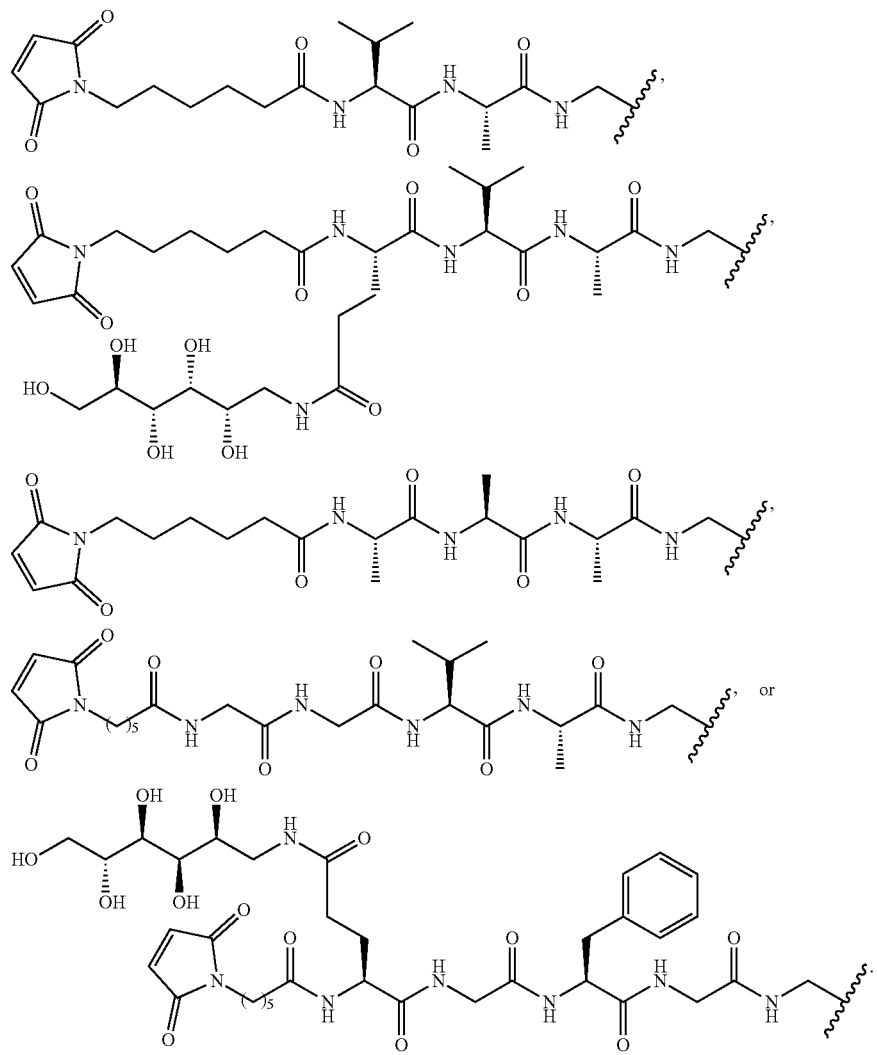

In embodiments, when $R^1$ is —H or —CH$_2$CH$_3$, $R^2$ is —OH or alkoxy and $R^3$ is —H, then -L$_1$-L$_2$-Q'— is not-CH(R')CH$_2$O— or —CH(R')(CH$_2$)$_2$O—, wherein R' is —H or C$_1$-C$_6$ alkyl, alkoxy, substituted alkyl, phenyl or PhCH$_2$—.

In embodiments, when $R^1$ is —H or —CH$_2$CH$_3$, $R^2$ is —OH or alkoxy and $R^3$ is —H, then -L$_1$-L$_2$-Q'— is not-CH(R')CH$_2$O— or —CH(R')(CH$_2$)$_2$O—, wherein R' is —H or C$_1$-C$_6$ alkyl, alkoxy, substituted alkyl, phenyl or PhCH$_2$—.

In embodiments, at least one of L$_1$ and L$_2$ is present.

In embodiments, at least one of $R^1$, $R^2$ and $R^3$, is not —H.

In embodiments, $R^1$ independently is C$_1$-C$_6$ alkyl, C$_2$-C$_6$ alkenyl, C$_2$-C$_6$ alkynyl, silyl, C$_3$-C$_6$ cycloalkyl, C$_1$-C$_6$ halogenated alkyl, alkene or alkyne.

In embodiments, $R^1$ independently is —H or C$_1$-C$_6$ alkyl.

In embodiments, $R^2$ independently is —H, —F, —N(R$^4$)$_2$, —N(R$^4$)(R$^5$), —OR$^4$, —SR$^4$, —S(=O)R$^5$, —SO$_2$R$^5$, C$_1$-C$_6$ alkyl, or C$_1$-C$_6$ fluoroalkyl; and $R^3$ independently is —H, —F, —CN, —OCH$_3$, —CH$_3$, or —CF$_3$.

In embodiments, $R^2$ independently is C$_1$-C$_6$ alkyl, C$_1$-C$_6$ fluoroalkyl, or —F.

In embodiments, $R^3$ independently is —H, —F, —CN, or —CF$_3$.

In embodiments, $R^3$ independently is —F, —CN, —OCH$_3$, —CH$_3$, or —CF$_3$.

In embodiments, $R^2$ and $R^3$ combine to form —O(CH$_2$)$_n$O— or —O(CF$_2$)$_n$O—, wherein n is 1 or 2.

In embodiments, D is represented by one of the following structures:

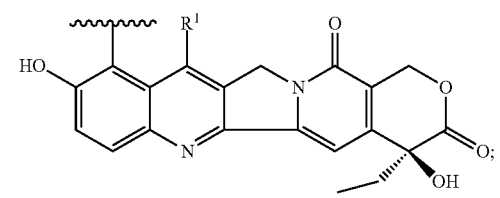
(D-I)

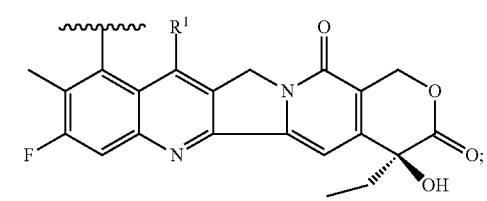
(D-II)

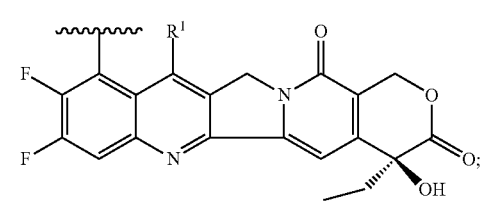
(D-III)

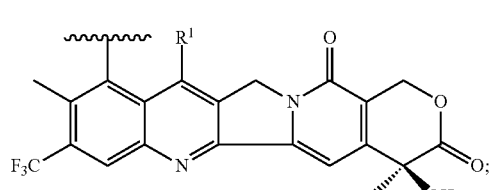
(D-IV)

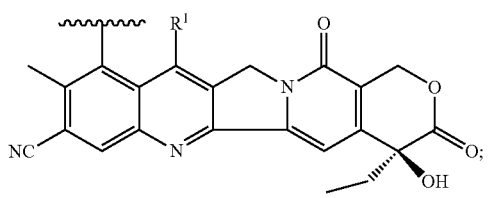
(D-V)

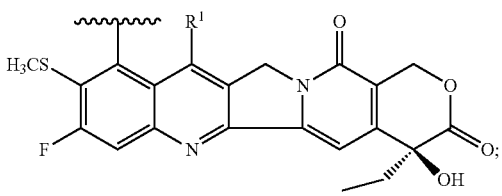
(D-VI)

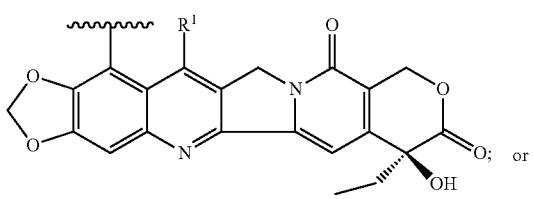
(D-VII)

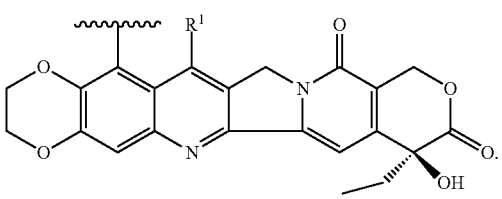
(D-VIII)

In embodiments, D is

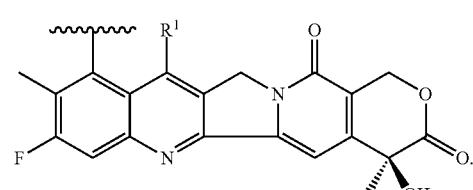
(D-II)

In embodiments, D is (D-I). In embodiments, D is (D-III). In embodiments, D is (D-IV).

In embodiments, D is (D-V). In embodiments, D is (D-VI). In embodiments, D is (D-VII). In embodiments, D is (D-VIII).

In embodiments, $R^1$ is —H or C$_1$-C$_6$ alkyl.

In embodiments, D is represented by one of the following structures:
(D1)
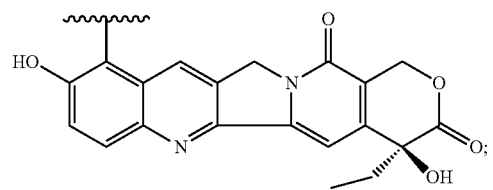
(D2)
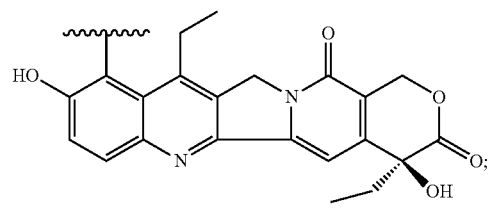
(D3)
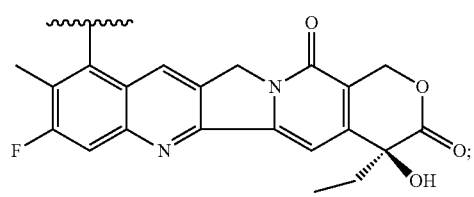
(D4)
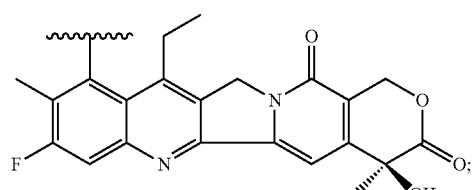
(D5)
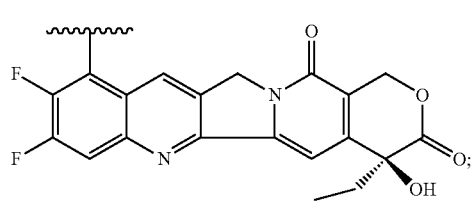
(D6)
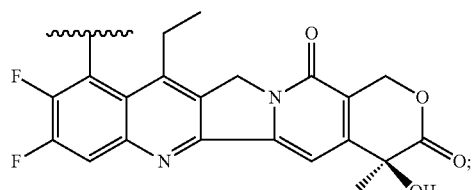
(D7)
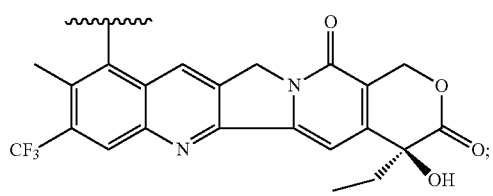
-continued
(D8)
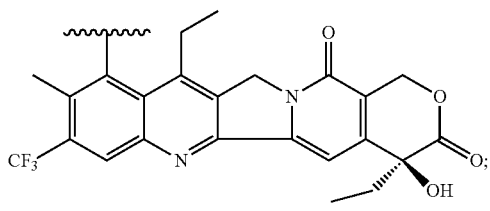
(D9)
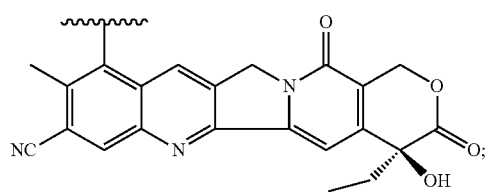
(D10)
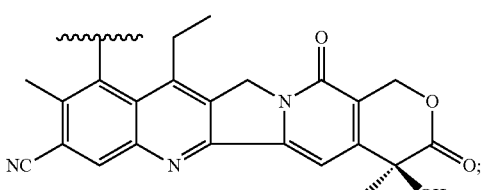
(D11)
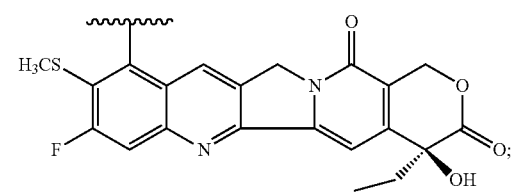
(D12)
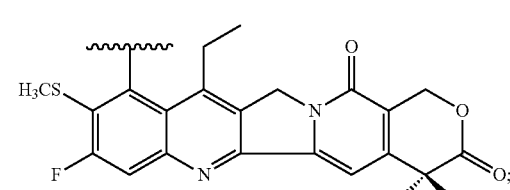
(D13)
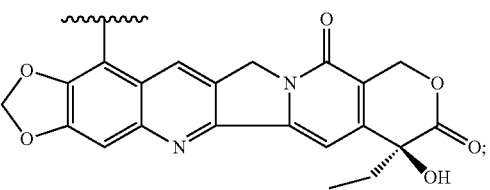
(D14)
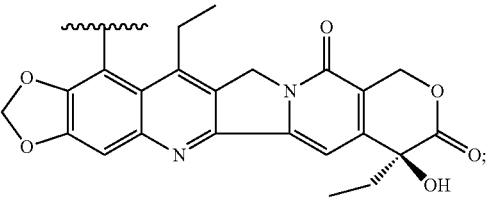

-continued (D15)
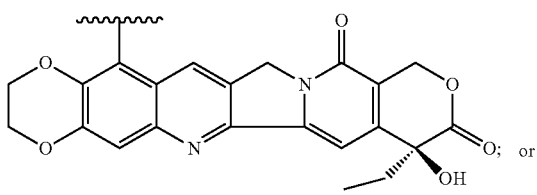

(D16)
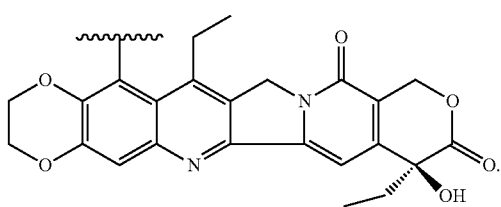

In embodiments, D is (D3)
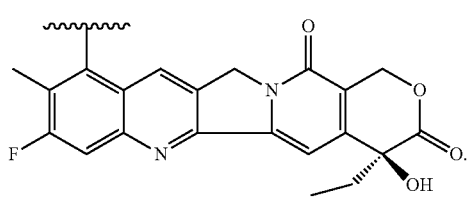

In embodiments, D is (D1). In embodiments, D is (D2). In embodiments, D is (D4).

In embodiments, D is (D5). In embodiments, D is (D6). In embodiments, D is (D7). In embodiments, D is (D8).

In embodiments, D is (D9). In embodiments, D is (D10). In embodiments, D is (D11). In embodiments, D is (D12).

In embodiments, D is (D13). In embodiments, D is (D14). In embodiments, D is (D15). In embodiments, D is (D16).

In embodiments, $L_1$ is —($C_1$-$C_{10}$ alkylene)- and $L_2$ is absent.

In embodiments, $L_1$ is —($C_1$-$C_{10}$ alkylene)- and $L_2$ is —N($R^6$)CH$_2$-$L_3$-* or —NR)(O—$_3$* wherein * denotes the site covalently linked to Q'.

In embodiments, $L_1$ is absent and $L_2$ is —N($R^6$)CH$_2$-$L_3$-* or —N($R^6$)C(=O)-$L_3$-*, wherein * denotes the site covalently linked to Q'.

In embodiments, $L_3$ is —($C_1$-$C_{10}$ alkylene)-.

In embodiments, $R^6$ is —H or —CH$_3$.

In embodiments, $L_1$-$L_2$ is —CH$_2$—, —CH$_2$CH$_2$—, —CH$_2$CH$_2$CH$_2$—, or —CH$_2$CH$_2$CH$_2$CH$_2$—.

In embodiments, $L_1$-$L_2$ is —OCH$_2$CH$_2$—*, —OCH$_2$CH$_2$OCH$_2$CH$_2$—*, —SCH$_2$CH$_2$—*, —SCH$_2$CH$_2$OCH$_2$CH$_2$—*, —S(=O)CH$_2$—*, —SO$_2$CH$_2$—*, —C(=O)CH$_2$—*, —NHCH$_2$CH$_2$—*, —N(CH$_3$)CH$_2$CH$_2$—*, —N(CF$_3$)CH$_2$CH$_2$—*, —NHC(=O)CH$_2$—*, —CH$_2$NHC(=O)CH$_2$—*, —CH$_2$CH$_2$NHC(=O)CH$_2$—*, —CH$_2$N(CH$_3$)C(=O)CH$_2$—*, —N(CH$_3$)C(=O)CH$_2$—*, —N(CH$_3$)C(=O)CH$_2$CH$_2$—*, —C(=O)NHCH$_2$CH$_2$—*, —NHC(=O)NHCH$_2$CH$_2$—*, —NHC(=O)OCH$_2$CH$_2$—*, —CH$_2$OC(=O)NHCH$_2$CH$_2$—*, or —C(=O)N(CH$_3$)CH$_2$CH$_2$—*, wherein * denotes the site covalently linked to Q'.

In embodiments, $L_1$-$L_2$-Q' is —CH$_2$CH$_2$CH$_2$CH$_2$O—, —CH$_2$CH$_2$CH$_2$O—, —CH$_2$CH$_2$O—, —CH$_2$CH$_2$OCH$_2$CH$_2$O—, —CH$_2$SCH$_2$CH$_2$O—, —CH$_2$NHC(=O)CH$_2$O—, —CH$_2$CH$_2$NHC(=O)CH$_2$O—, —CH$_2$N(CH$_3$)C(=O)CH$_2$O—, —OCH$_2$CH$_2$O—, —OCH$_2$CH$_2$CH$_2$O—, —SCH$_2$CH$_2$CH$_2$O—, —SCH$_2$CH$_2$O—, —NHCH$_2$CH$_2$O—, —NHCH$_2$CH$_2$CH$_2$O—, —N(CH$_3$)CH$_2$CH$_2$O—, —C(=O)NHCH$_2$CH$_2$O—, —NHC(=O)CH$_2$O—, —CH$_2$S(=O)CH$_2$O—, —CH$_2$SO$_2$CH$_2$O—, —CH$_2$CH$_2$CH$_2$S—, —CH$_2$CH$_2$CH$_2$S—, —CH$_2$CH$_2$S—, —CH$_2$CH$_2$OCH$_2$CH$_2$S—, —CH$_2$SCH$_2$CH$_2$S—, —CH$_2$NHC(=O)CH$_2$S—, —OCH$_2$CH$_2$CH$_2$S—, —SCH$_2$CH$_2$CH$_2$S—, —SCH$_2$CH$_2$S—, —NHCH$_2$CH$_2$S—, —N(CH$_3$)CH$_2$CH$_2$S—, —C(=O)NHCH$_2$CH$_2$S—, —NHC(=O)CH$_2$S—, —CH$_2$S(=O)CH$_2$S—, or —CH$_2$SO$_2$CH$_2$S—.

In embodiments, D-$L_1$-$L_2$ is represented by a structure that is (P-I)
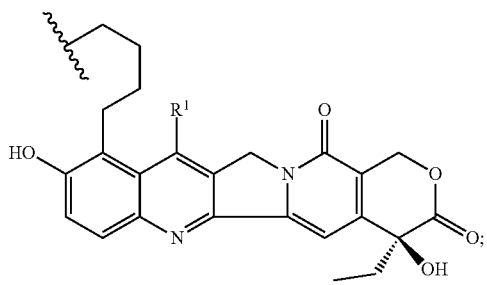

(P-II)
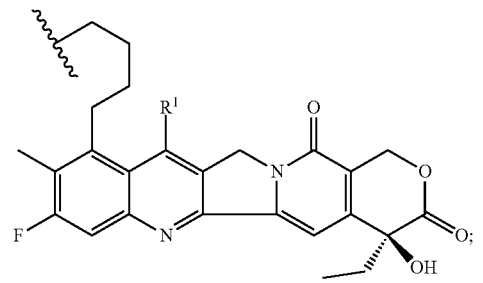

(P-III)
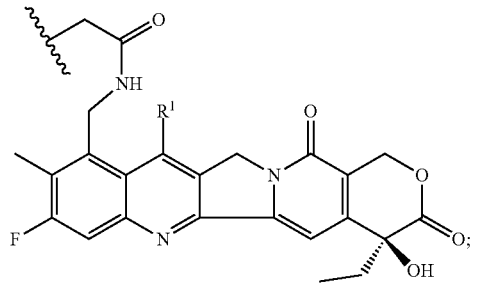

(P-IV)
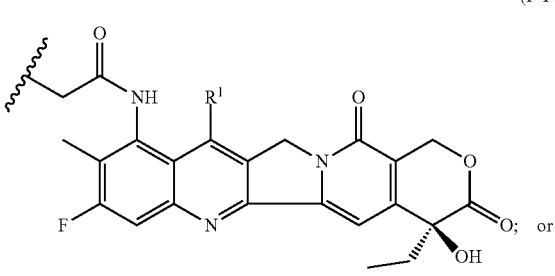

(P-V)

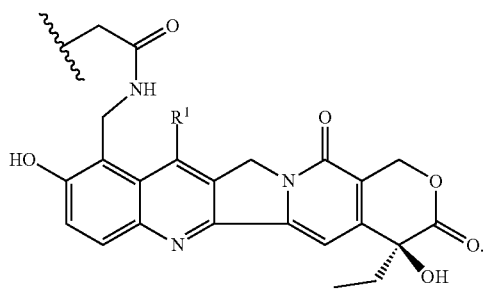

In embodiments, D-L$_1$-L$_2$ is represented by a structure that is:

(P-II)

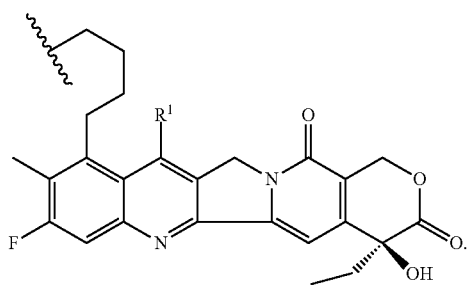

In embodiments, D-L$_1$-L$_2$ is represented by a structure that is (P-I).

In embodiments, D-L$_1$-L$_2$ is represented by a structure that is (P-III).

In embodiments, D-L$_1$-L$_2$ is represented by a structure that is (P-IV).

In embodiments, D-L$_1$-L$_2$ is represented by a structure that is (P-V).

In embodiments, R$^1$ is —H or C$_1$-C$_6$ alkyl.

In embodiments, R$^1$ is —H or —CH$_2$CH$_3$.

In embodiments, Q' is —O—.

In embodiments, Q' is —S—.

In embodiments, D-L$_1$-L$_2$-Q'— has one of the following structures:

(P1')

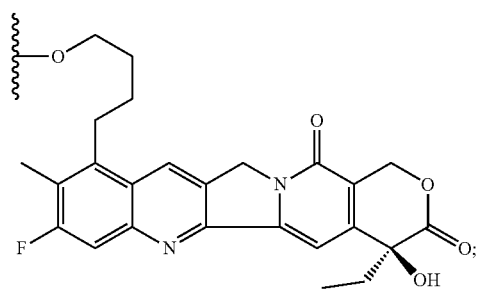

(P2')

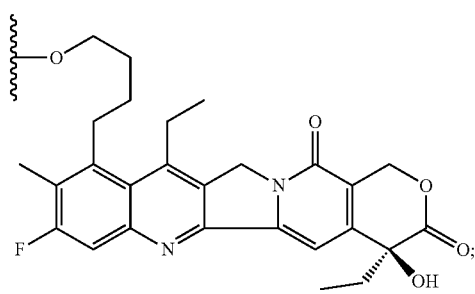

(P3')

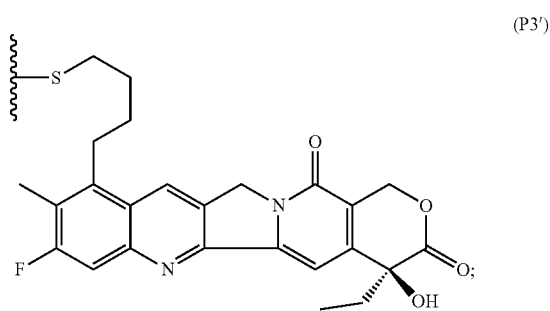

(P4')

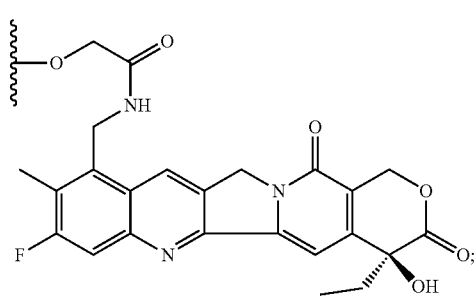

(P5')

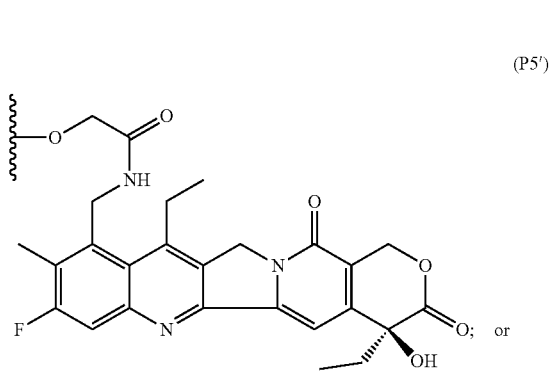

or (P6')

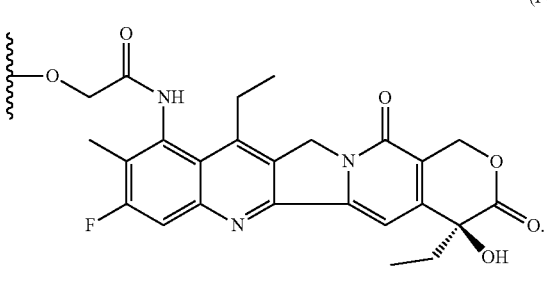

In embodiments, D-L$_1$-L$_2$-Q'— is:
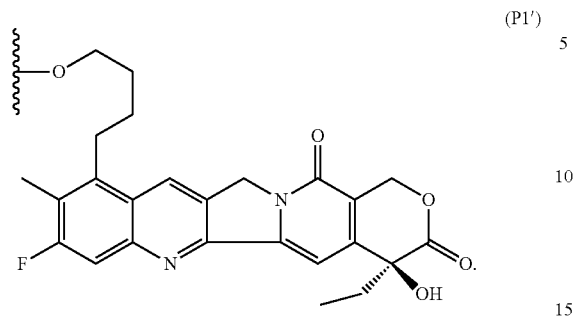
(P1')
In embodiments, D-L$_1$-L$_2$-Q'— is (P2').
In embodiments, D-L$_1$-L$_2$-Q'— is (P3).
In embodiments, D-L$_1$-L$_2$-Q'— is (P4').
In embodiments, D-L$_1$-L$_2$-Q'— is (P5').
In embodiments, D-L$_1$-L$_2$-Q'— is (P6').
In embodiments, the compound has one of the following structures,
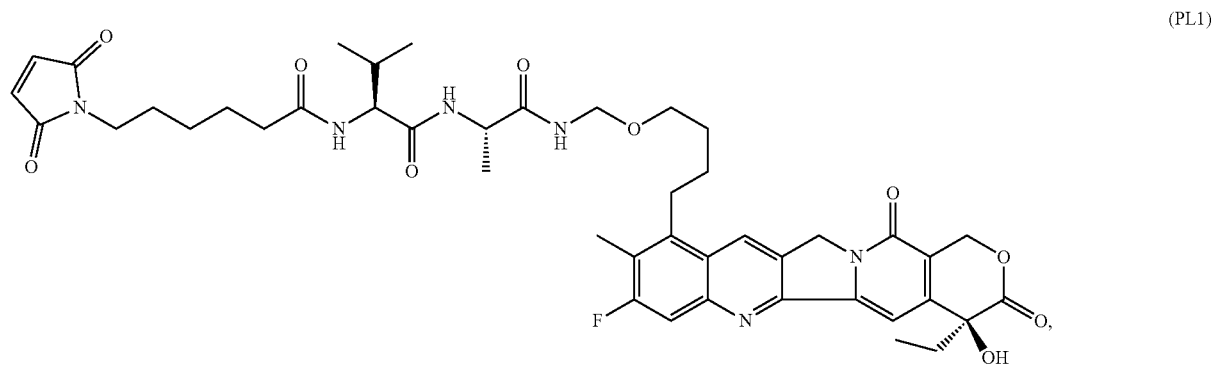
(PL1)
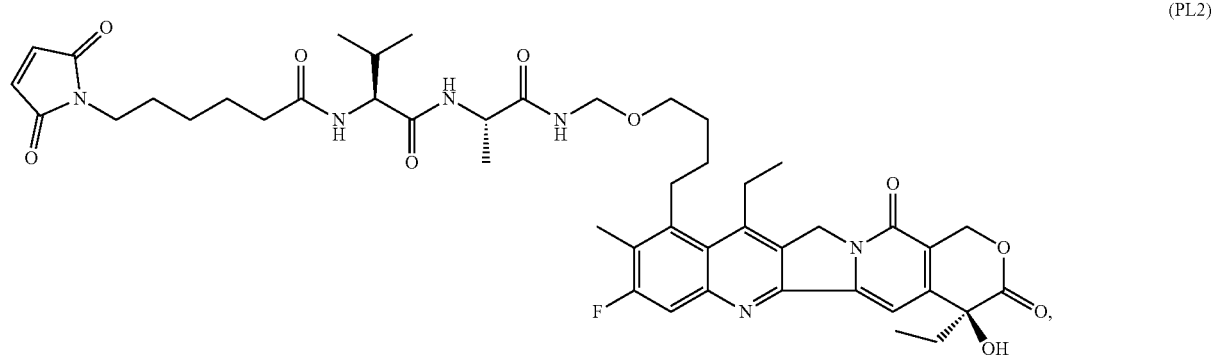
(PL2)
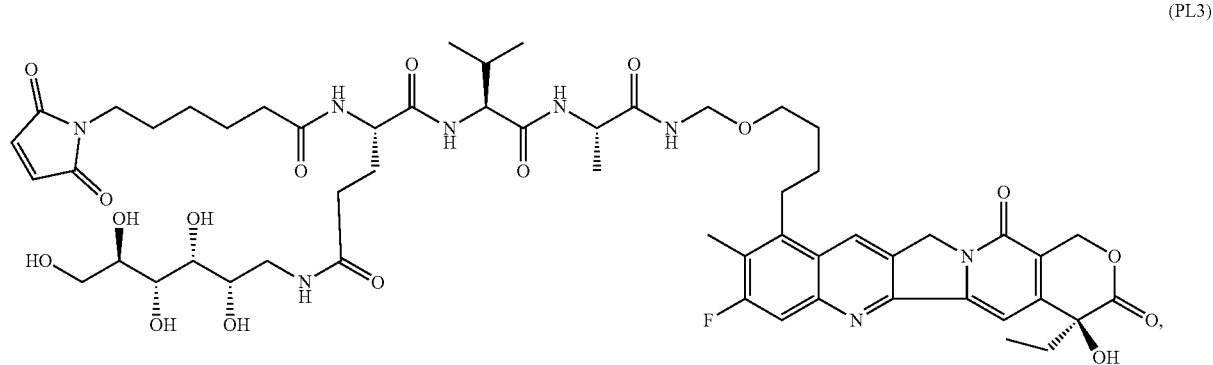
(PL3)

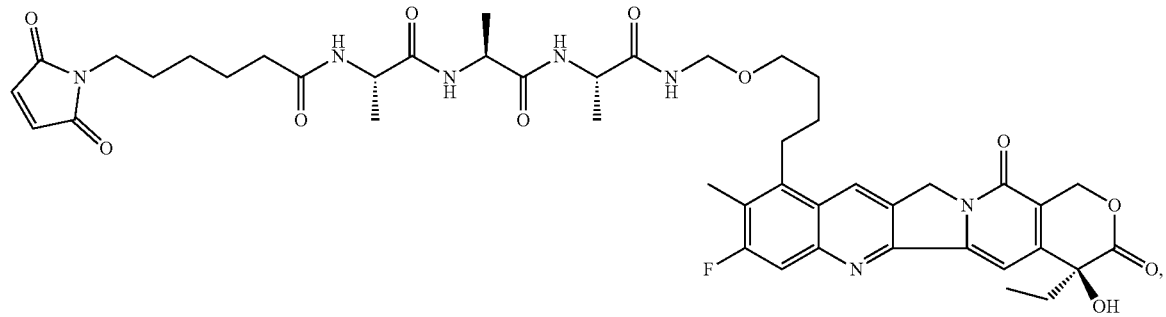
(PL4)
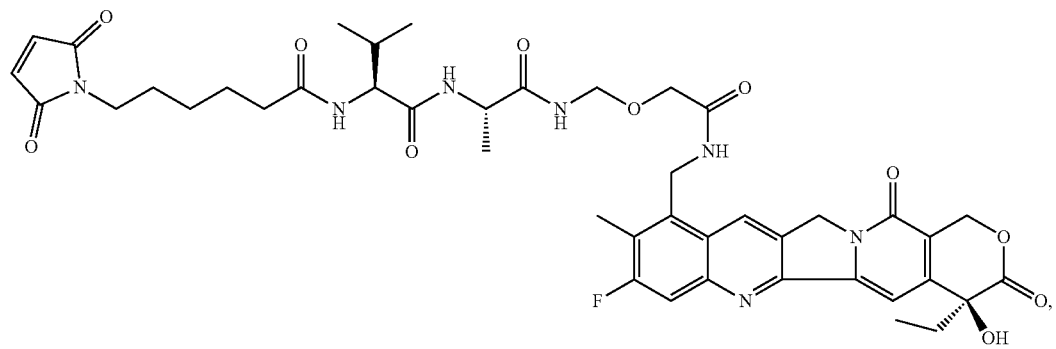
(PL5)
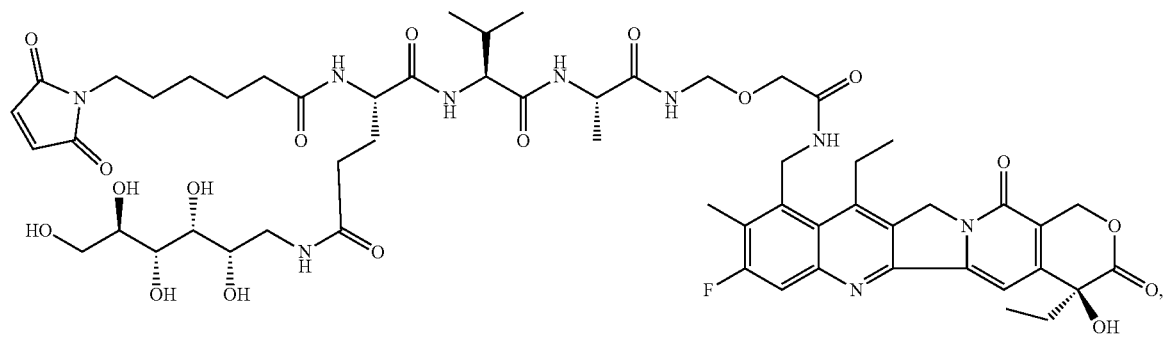
(PL6)
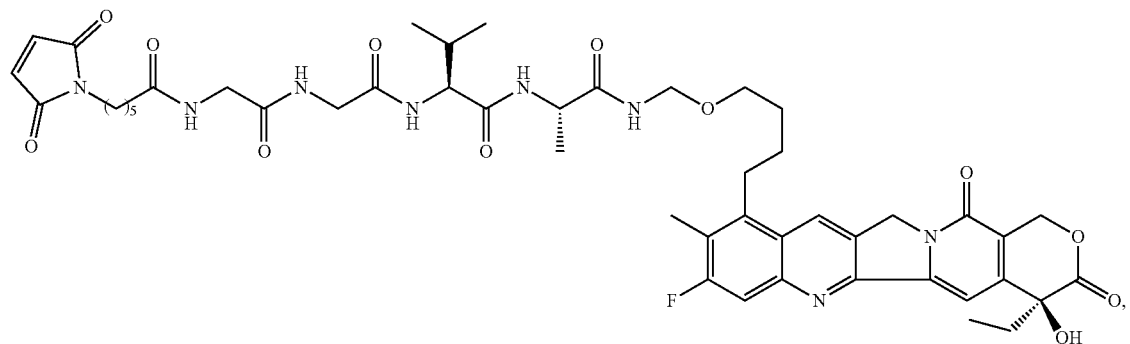
(PL7)

(PL8)
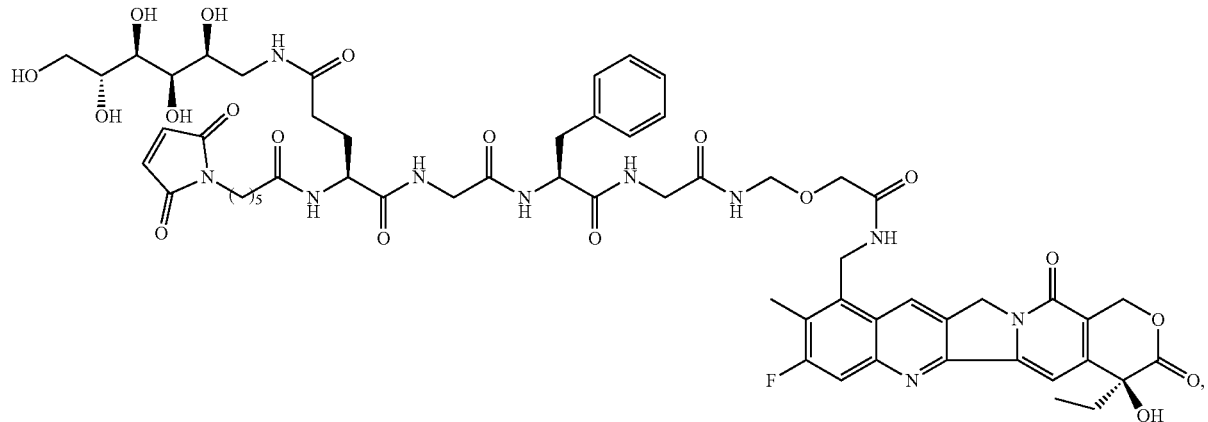
(PL9)
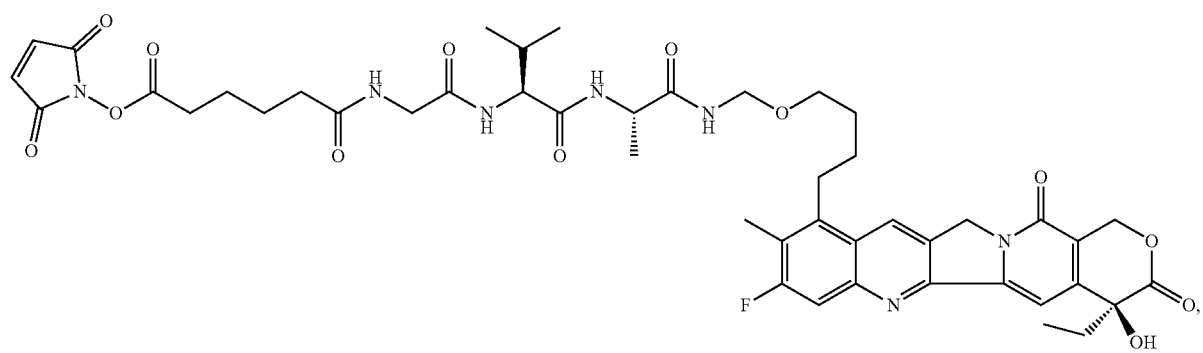
(PL10)
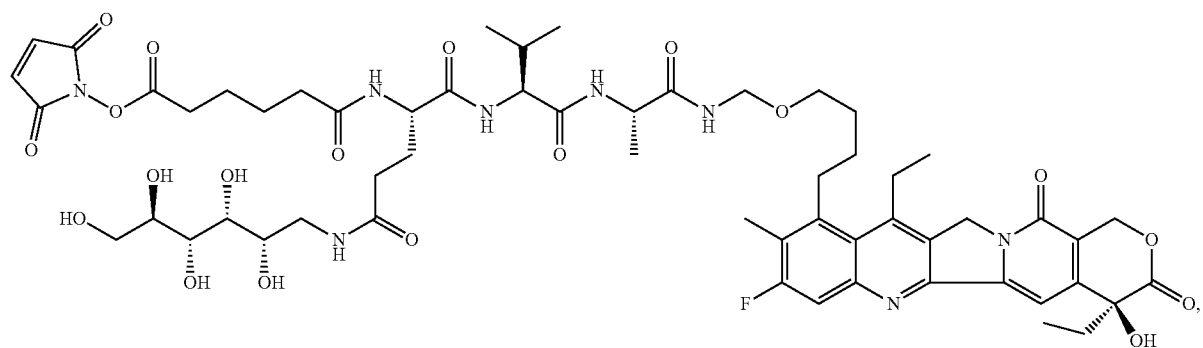
(PL11)
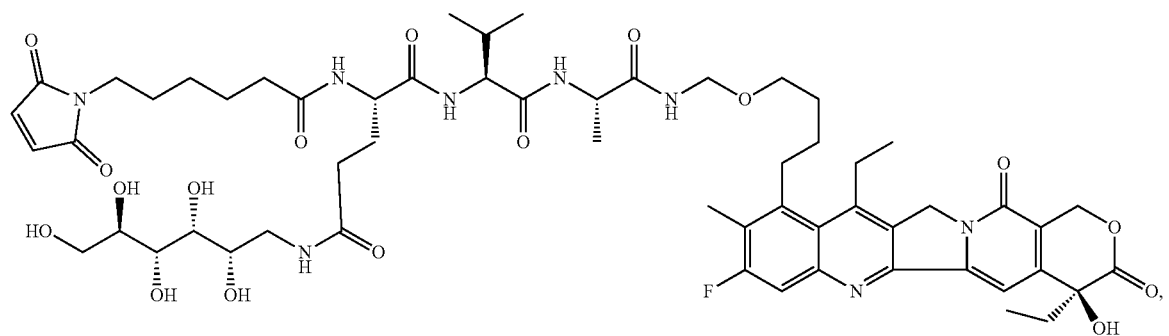

(PL12)
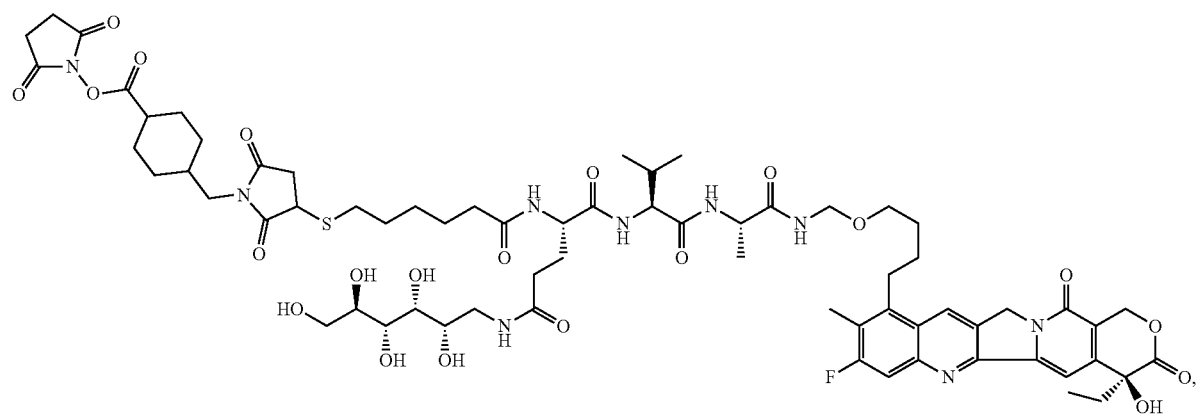
(PL13)
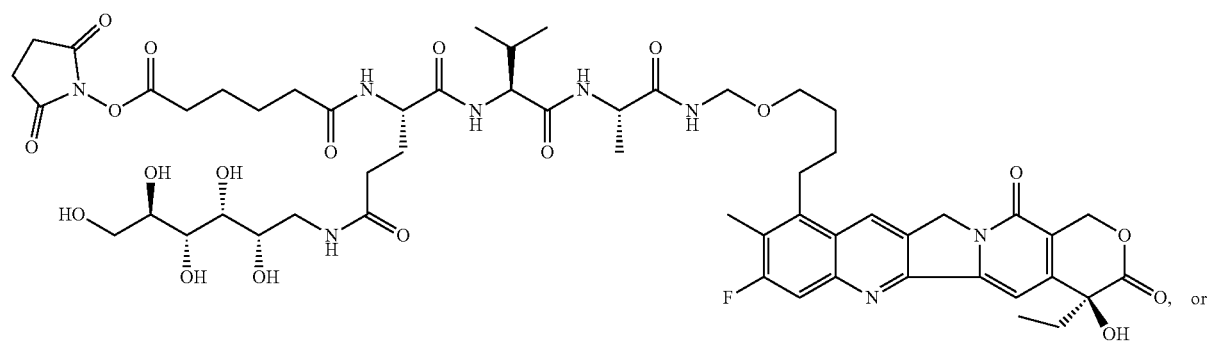
or
(PL14)
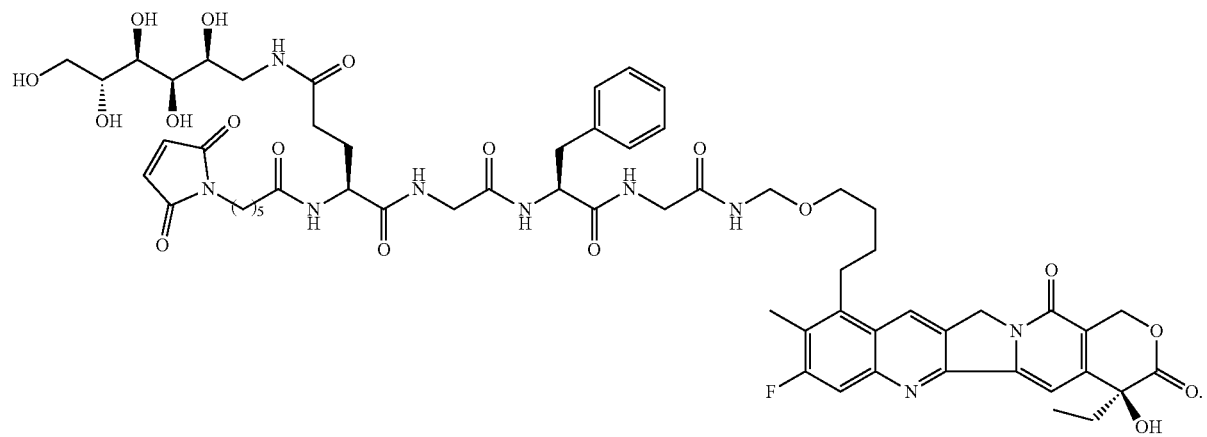
or a pharmaceutically acceptable salt thereof.

In embodiments, the compound is

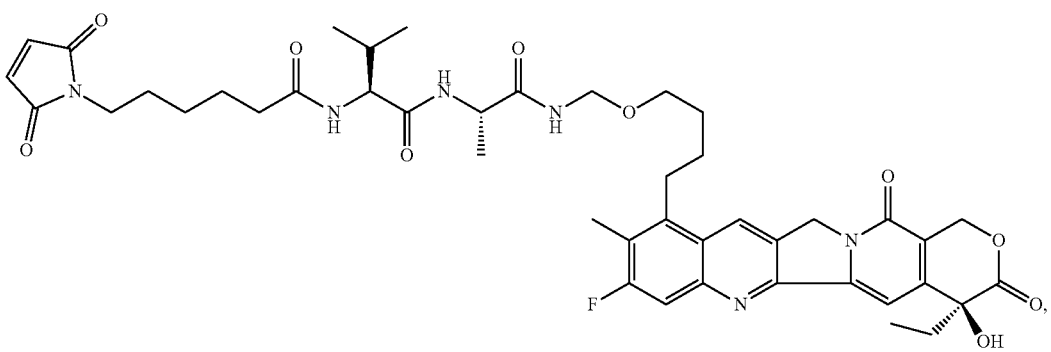

(PL1)

or a pharmaceutically acceptable salt thereof.

In embodiments, the compound is

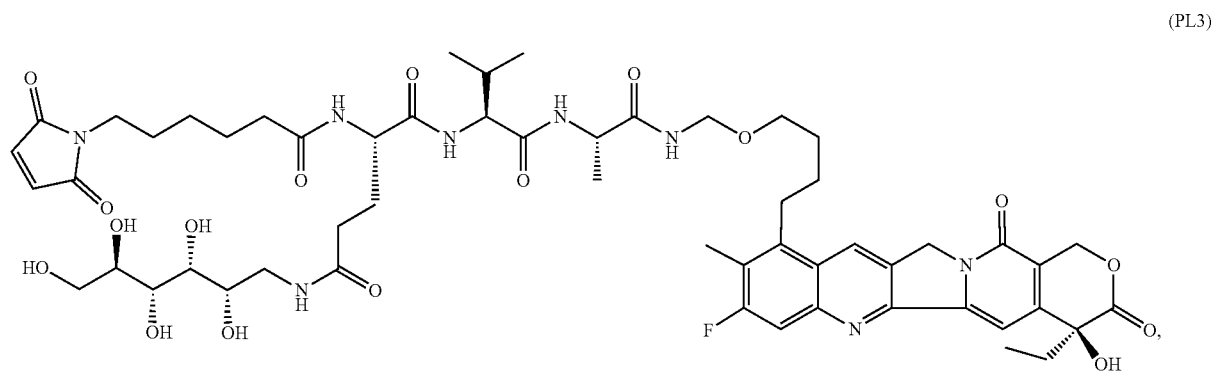 [SMILES: CC[C@@]1(O)C(=O)OCc2c1cc1n(c2=O)Cc2cc3c(CCCCOCNC(=O)[C@H](C)NC(=O)[C@@H](NC(=O)[C@H](CCC(=O)NC[C@H](O)[C@@H](O)[C@H](O)[C@H](O)CO)NC(=O)CCCCCN4C(=O)C=CC4=O)C(C)C)c(C)c(F)cc3nc2-1]

(PL3)

or a pharmaceutically acceptable salt thereof.

In embodiments, the compound is (PL2), or a pharmaceutically acceptable salt thereof.

In embodiments, the compound is (PL4), or a pharmaceutically acceptable salt thereof.

In embodiments, the compound is (PL5), or a pharmaceutically acceptable salt thereof.

In embodiments, the compound is (PL6), or a pharmaceutically acceptable salt thereof.

In embodiments, the compound is (PL7), or a pharmaceutically acceptable salt thereof.

In embodiments, the compound is (PL8), or a pharmaceutically acceptable salt thereof.

In embodiments, the compound is (PL9), or a pharmaceutically acceptable salt thereof.

In embodiments, the compound is (PL10), or a pharmaceutically acceptable salt thereof.

In embodiments, the compound is (PL11), or a pharmaceutically acceptable salt thereof.

In embodiments, the compound is (PL12), or a pharmaceutically acceptable salt thereof.

In embodiments, the compound is (PL13), or a pharmaceutically acceptable salt thereof.

In embodiments, the compound is (PL14), or a pharmaceutically acceptable salt thereof.

In another aspect, the invention features a method of preparing a conjugate comprising a cell binding agent and a drug, said method comprising contacting a cell binding agent with a compound of Formula (II), such that a covalent bond forms between said cell binding agent and said compound of Formula (II). In embodiments, said conjugate has a structure according to Formula (III) as described herein.

In embodiments, a cell binding agent is an antibody or an antigen-binding fragment thereof.

In embodiments, a cell binding agent is a monoclonal antibody or an antigen-binding fragment thereof.

In another aspect, the invention features a conjugate comprising a cell binding agent and a drug. In embodiments, the conjugate is prepared according to any method described herein.

In embodiments, a conjugate comprises a cell binding agent that is an antibody or an antigen-binding fragment thereof.

In embodiments, a conjugate comprises a cell binding agent that is a monoclonal antibody or an antigen-binding fragment thereof.

In another aspect, the invention features a pharmaceutical composition comprising any conjugate described herein.

In still another aspect, the invention features a method of treating a cell proliferative disease or disorder or inhibiting abnormal cell growth, where the method comprises administering any conjugate described herein or any pharmaceutical composition comprising any conjugate described herein.

In embodiments, a method is for treating cancer.

In embodiments, a cancer is adenocarcinoma, brain cancer, bladder cancer, breast cancer, cervical cancer, choriocarcinoma, a CNS tumor, colon or colorectal cancer, diffuse intrinsic pontine glioma (DIPG), endometrial cancer, esophageal cancer, Ewing's sarcoma, fallopian tube cancer, gall bladder cancer, gastric cancer, glioblastoma, head and neck cancer, hematological cancer, Hodgkin's lymphoma, kidney cancer, laryngeal cancer, leukemia, liver cancer, lung cancer, lymphoma, melanoma, Merkel cell carcinoma, mesothelioma, multiple myeloma, myelodysplastic syndrome (MDS), neuroblastoma, non-Hodgkin's lymphoma, osteosarcoma, pancreatic cancer, peritoneal cancer, prostate cancer, ovarian cancer, renal cancer, rhabdomyosarcoma salivary gland cancer, sarcoma, skin cancer, small intestine cancer, squamous cell carcinoma, testicular cancer, thyroid cancer, uterine cancer, or Wilms tumor.

In embodiments, a cancer is breast cancer.

Compounds of Formula (III)

In some aspects, the invention features a conjugate comprising a cell-binding agent and a camptothecin derivative. In embodiments, the portion of the conjugate comprising a camptothecin derive is formed from or includes a structure according to any embodiment of Formula (I) or Formula (II) as described herein.

In a still further aspect, the invention features a compound of Formula (III),

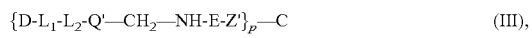   (III), or a pharmaceutically acceptable salt thereof, wherein:

D is represented by the following structural formula:

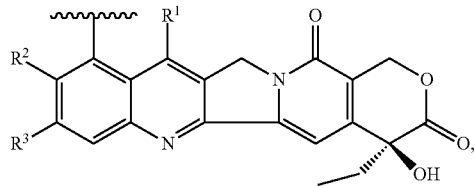

wherein
- $R^1$ independently is —H, $C_1$-$C_6$ alkyl, $C_2$-$C_6$ alkenyl, $C_2$-$C_6$ alkynyl, silyl, $C_3$-$C_6$ cycloalkyl, $C_1$-$C_6$ halogenated alkyl, $C_2$-$C_6$ halogenated alkenyl, or $C_2$-$C_6$ halogenated alkynyl;
- $R^2$ independently is —H, —F, —N($R^4$)$_2$, —N($R^4$)($R^5$), —O$R^4$, —S$R^4$, —S(=O)$R^5$, —SO$_2R^5$, $C_1$-$C_6$ alkyl, or $C_1$-$C_6$ fluoroalkyl; and $R^3$ is —H, —F, —CN, —OCH$_3$, —CH$_3$, or —CF$_3$; or $R^2$ and $R^3$ together form a group of the formula —O(CH$_2$)$_n$O— or —O(CF$_2$)$_n$O— wherein n is 1 or 2;
- $R^4$ independently is —H or $C_1$-$C_4$ alkyl;
- $R^5$ independently is $C_1$-$C_4$ alkyl;
- $L_1$ independently is absent or —($C_1$-$C_{10}$ alkylene)-;
- $L_2$ independently is absent or is —OCH$_2$-L$_3$-*, —SCH$_2$-L$_3$-*, —S(=O)-L$_3$-*, —SO$_2$-L$_3$-*, —C(=O)-L$_3$-*, —N(R$^6$)CH$_2$-L$_3$-*, —N(R$^6$)C(=O)-L$_3$-*, —N(R$^6$)C(=O)N(R$^7$)-L$_3$-*, —C(=O)N(R$^6$)CH$_2$-L$_3$-*, —OC(=O)N(R$^6$)CH$_2$-L$_3$-*, or —N(R$^6$)C(=O)OCH$_2$-L$_3$-*; wherein * denotes the site covalently linked to Q';
- $L_3$ independently is —($C_1$-$C_{10}$ alkylene)-, —CH$_2$OCH$_2$CH$_2$—, or —CH$_2$CH$_2$OCH$_2$CH$_2$—;
- each $R^6$ and $R^7$ independently is —H, $C_1$-$C_6$ alkyl, $C_1$-$C_6$ fluoroalkyl, $C_3$-$C_6$ cycloalkyl, aryl, heteroaryl, or benzyl;

Q' is —O— or —S—;

E is a peptide comprising 2 to 10 amino acids; wherein E is optionally substituted with one or more polyol; and wherein the N terminal of the peptide is covalently attached to Z';

Z' is —C(=O)-L$_4$-Y',

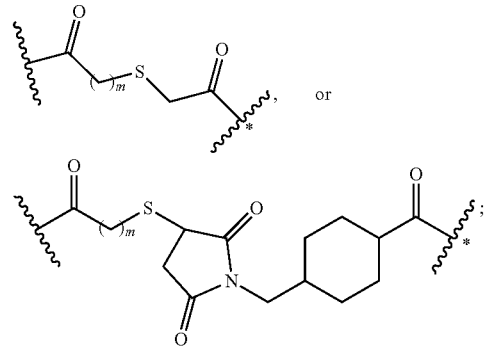

wherein m represents an integer of 1-10 and * denotes the site covalently linked to said C;

- $L_4$ is —($C_1$-$C_{10}$ alkylene)-, —CH$_2$CH$_2$(OCH$_2$CH$_2$)$_n$N(R$^8$)C(=O)-L$_5$-*, or —CH$_2$(OCH$_2$CH$_2$)$_n$N(R$^8$)C(=O)-L$_5$-*; wherein n represents an integer of 1-10; and wherein * denotes the site covalently linked to Y';
- $L_5$ is —($C_1$-$C_{10}$ alkylene)-;
- $R^8$ is —H or —CH$_3$;
- C represents a cell binding agent;
- Y' is a group formed by the reaction of an electrophilic group with a reactive nucleophilic group present on said cell binding agent; and
- wherein when $R^2$ and $R^3$ combine to form —OCH$_2$O—, $R^1$ is not —CH$_2$CH$_2$CH$_3$; and
- p has an value between 1 to 18.

In embodiments, $L_4$ is —($C_1$-$C_{10}$ alkylene)-.

In embodiments, $L_4$ is —CH$_2$CH$_2$(OCH$_2$CH$_2$)$_n$N(R$^8$)C(=O)-L$_5$-* or —CH$_2$(OCH$_2$CH$_2$)$_n$N(R$^8$)C(=O)-L$_5$-*, wherein n represents an integer of 1-10; and wherein * denotes the site covalently linked to Y'.

In embodiments, $L_4$ is —CH$_2$CH$_2$CH$_2$CH$_2$CH$_2$—, —CH$_2$CH$_2$—, —CH$_2$—, —CH$_2$CH$_2$OCH$_2$CH$_2$ OCH$_2$CH$_2$ NHC(=O)CH$_2$CH$_2$—* or —CH$_2$OCH$_2$CH$_2$OCH$_2$CH$_2$ NHC(=O)CH$_2$CH$_2$—*, wherein * denotes the site covalently linked to Y'.

In embodiments, Y' is formed from a Michael acceptor group, a succinimide, an epoxide, or a halogen.

In embodiments, Y' is formed from

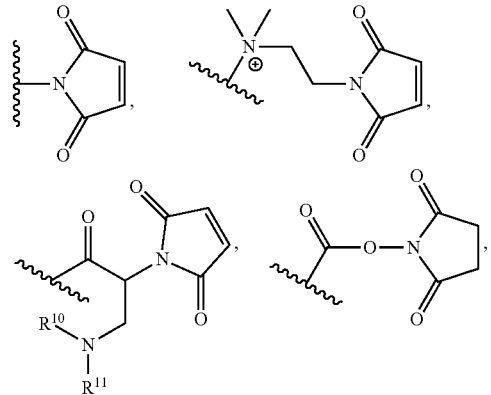

wherein $R^{10}$ and $R^{11}$ are each independently —H or $C_1$-$C_3$ alkyl.

In embodiments, Y' is

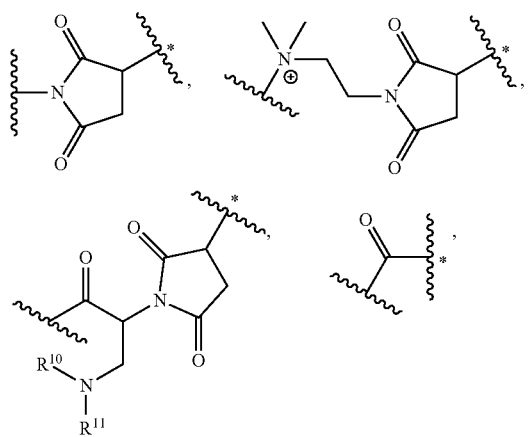

wherein $R^{10}$ and $R^{11}$ are each independently —H or $C_1$-$C_3$ alkyl and * denotes the site covalently linked to said C.

In embodiments, Z' is formed from:

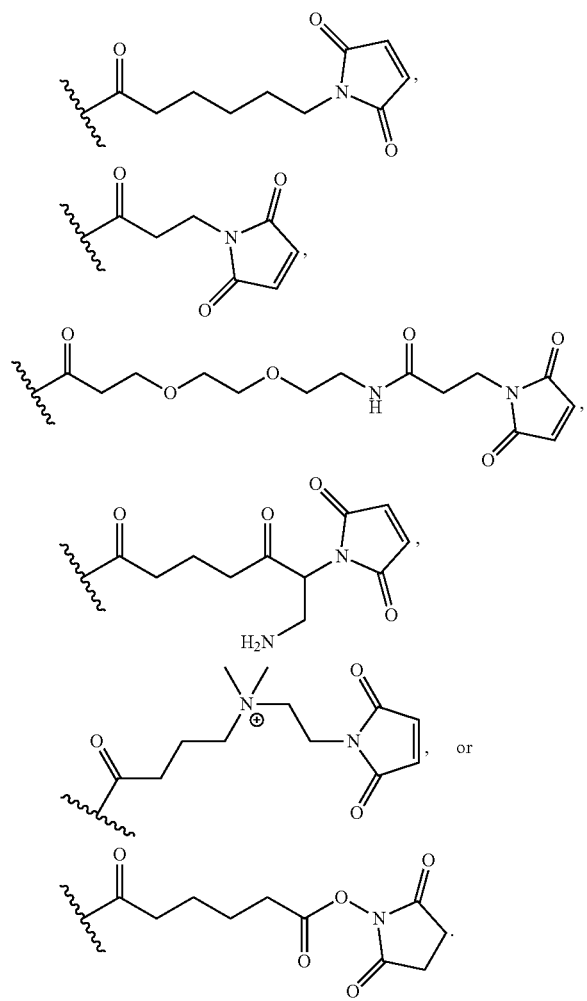

In embodiments, Z' is —C(=O)-$L_4$-Y'.

In embodiments, Z' is

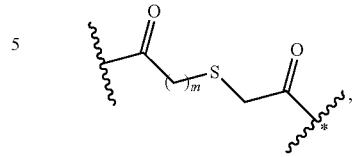

and * denotes the site covalently linked to said C. In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z' is

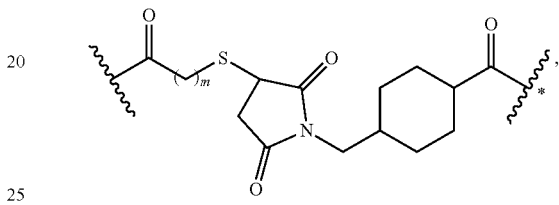

and * denotes the site covalently linked to said C. In embodiments, m is 1. In embodiments, m is 2. In embodiments, m is 3. In embodiments, m is 4. In embodiments, m is 5. In embodiments, m is 6. In embodiments, m is 7. In embodiments, m is 8. In embodiments, m is 9. In embodiments, m is 10.

In embodiments, Z' is:

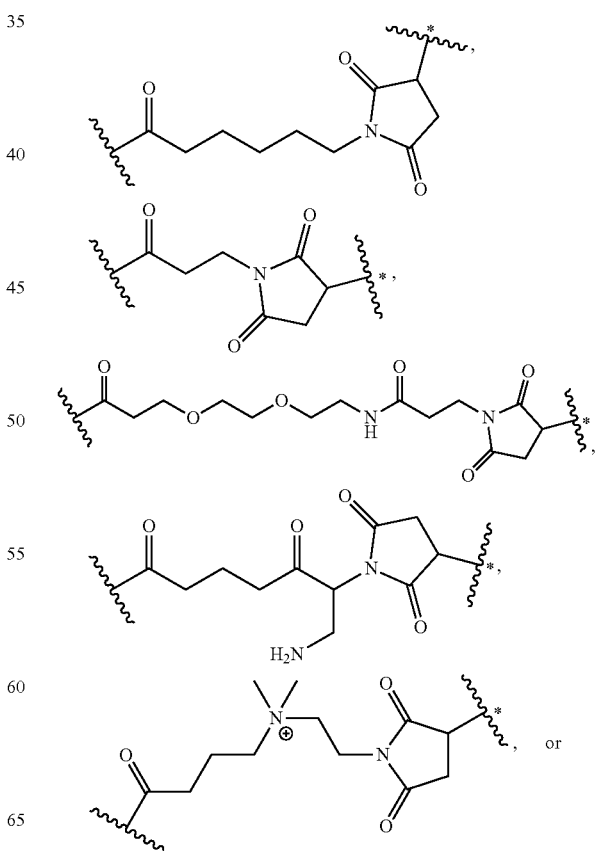

-continued

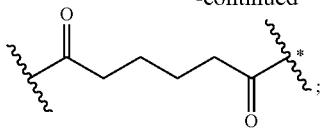

wherein * denotes the site covalently linked to C.

In embodiments, E is a peptide of 2, 3, or 4 amino acids. Each amino acid in said peptide is an L amino acid, or at least one amino acid in said peptide is a D amino acid.

In embodiments, E comprises one or more amino acids selected from glycine, alanine, valine, glutamine, glutamic acid, phenylalanine, and leucine, and wherein said glutamine or glutamic acid is optionally substituted by a polyol.

In embodiments, E comprises amino acids selected from glycine, alanine, valine, glutamine, glutamic acid, phenylalanine, and leucine, and wherein said glutamine or glutamic acid is optionally substituted by a polyol.

In embodiments, E comprises an amino acid having the following structure,

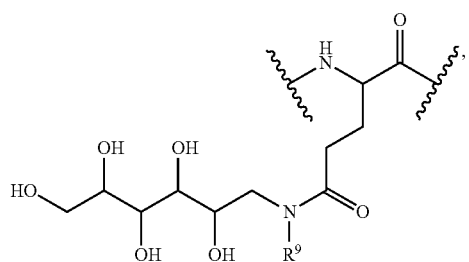

wherein $R^9$ is —H or $C_1$-$C_6$ alkyl.

In embodiments, E comprises an amino acid having the following structure,

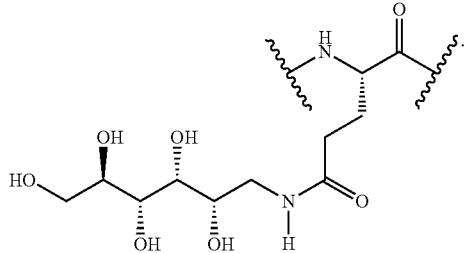 [SMILES: *N[C@@H](CCC(=O)NC[C@H](O)[C@@H](O)[C@H](O)[C@H](O)CO)C(*)=O]

In embodiments, E is selected from the group consisting of -Ala-Val-*, -Val-Ala-*, -Gly-Gly-*, -Val-Cit-*, -Cit-Val-*, -Leu-Ala-*, -Ala-Leu-*, -Leu-Cit-*,-Cit-Leu-*, -Leu-Ala-*, -Ala-Leu-*, -Lys-Lys-*, -Ala-Lys-*, -Lys-Ala-*, -Val-Lys-*, -Lys-Val-*, -Tyr-Arg-*, -Arg-Tyr-*, -Arg-Arg-*, -Ala-Ala-*, -Phe-Lys-*, -Lys-Phe-*, -Thr-Thr-*, -Thr-Met-*, -Met-Thr-*, -Met-Tyr-*, -Tyr-Met-*, -Phe-Gln-*, -Gln-Phe-*, -Gly-Ser-*, -Leu-Gln-*, -Gln-Leu-*, -Ser-Ala-*, -Ser-Gly-*, -Val-Thr-*, -Thr-Val-*, -Val-Gln-*, -Ser-Val-*, -Val-Ser-*, -Ala-Met-*, -Met-Ala-*, -Val-Arg-*, -Arg-Val-*, -Phe-Ala-*,-Ala-Phe-*, -Cit-Val-*, -Gln-Val-*, -Phe-Arg-*, -Arg-Phe-*, -Ala-Ala-Ala-*, -Gly-Gly-Gly-*, -Ala-Val-Ala-*, -Gly-Val-Gly-*, -Ala-Val-Gly-*, -Gly-Phe-Lys-*, -Lys-Phe-Gly-*, -Leu-Ala-Leu-*, -Val-Ala-Leu-*, -Leu-Ala-Val-*, -Val-Ala-Val-*, -Ala-Val-Ala-Gly-*, -Gly-Phe-Gly-Gly-*, -Gly-Gly-Phe-Gly-*, -Ala-Val-Gly-Gly-*, -Ala-Ala-Ala-Ala-*, -Ala-Val-Ala-Ala-*, -Ala-Leu-Ala-Leu-*,-Leu-Ala-Leu-Ala-*, -Gly-Phe-Leu-Gly-* and -Gly-Leu-Phe-Gly-*, wherein * denotes the N-terminal of the peptides covalently attached to Z'.

In embodiments, E is selected from the group consisting of -L-Ala-D-Val-*, -L-Val-D-Ala-*, -L-Val-D-Lys-*, -L-Val-D-Arg-*, -L-Val-D-Cit-*, -L-Val-D-Arg-*, -L-Val-D-Cit-*, -L-Val-D-Lys-*, -L-Val-D-Arg-*, -L-Arg-D-Arg-*, -L-Ala-D-Ala-*, -L-Ala-D-Lys-*, -L-Ala-D-Arg-*, -L-Ala-D-Ala-L-Ala-*, -L-Ala-D-Val-L-Ala-*, -L-Ala-D-Ala-Gly-*, and -L-Ala-D-Val-Gly-*, wherein * denotes the N-terminal of the peptides covalently attached to Z'.

In embodiments, -E-NH—$CH_2$— has one of the following structures, wherein * denotes the N-terminal of the peptides covalently attached to Z':

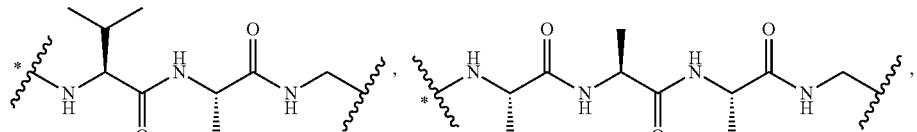

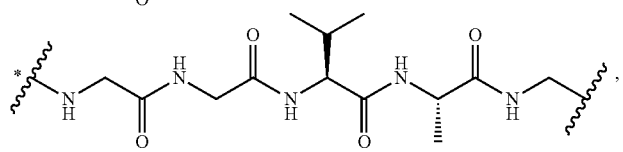

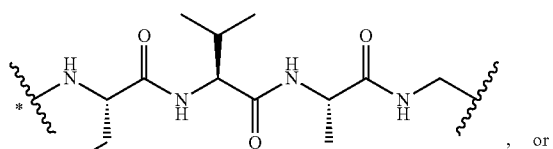, or

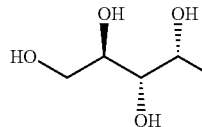

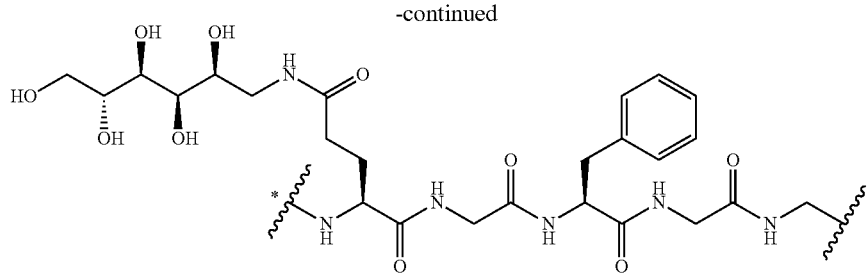
In embodiments, Z'-E-NH—CH$_2$ is formed from one of the following structures:
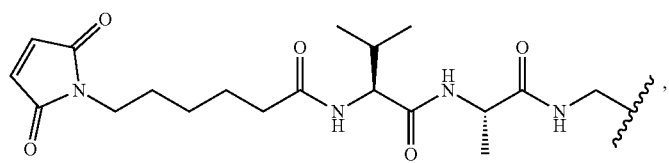,
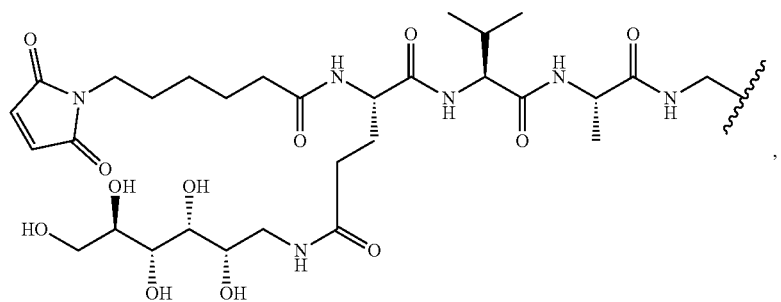,
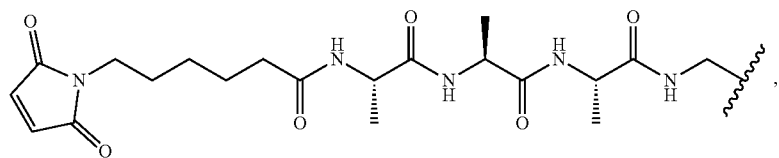,
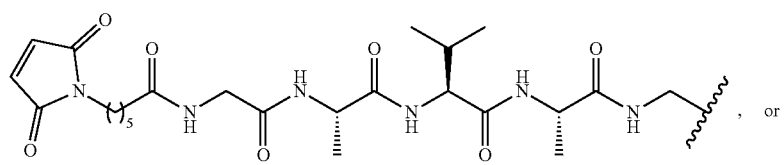, or
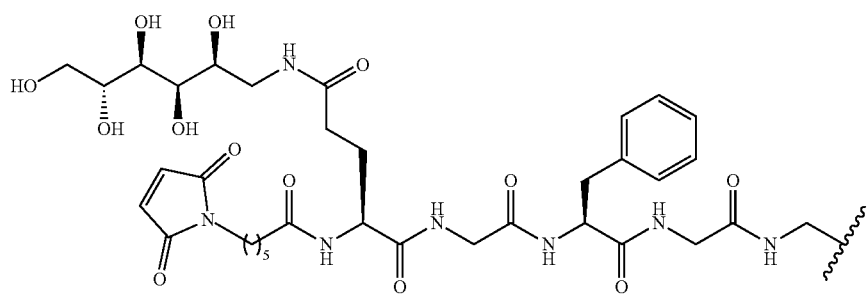.

In embodiments, Z'-E-NH—CH₂ is one of the following structures, wherein * denotes the point of attachment to the C:

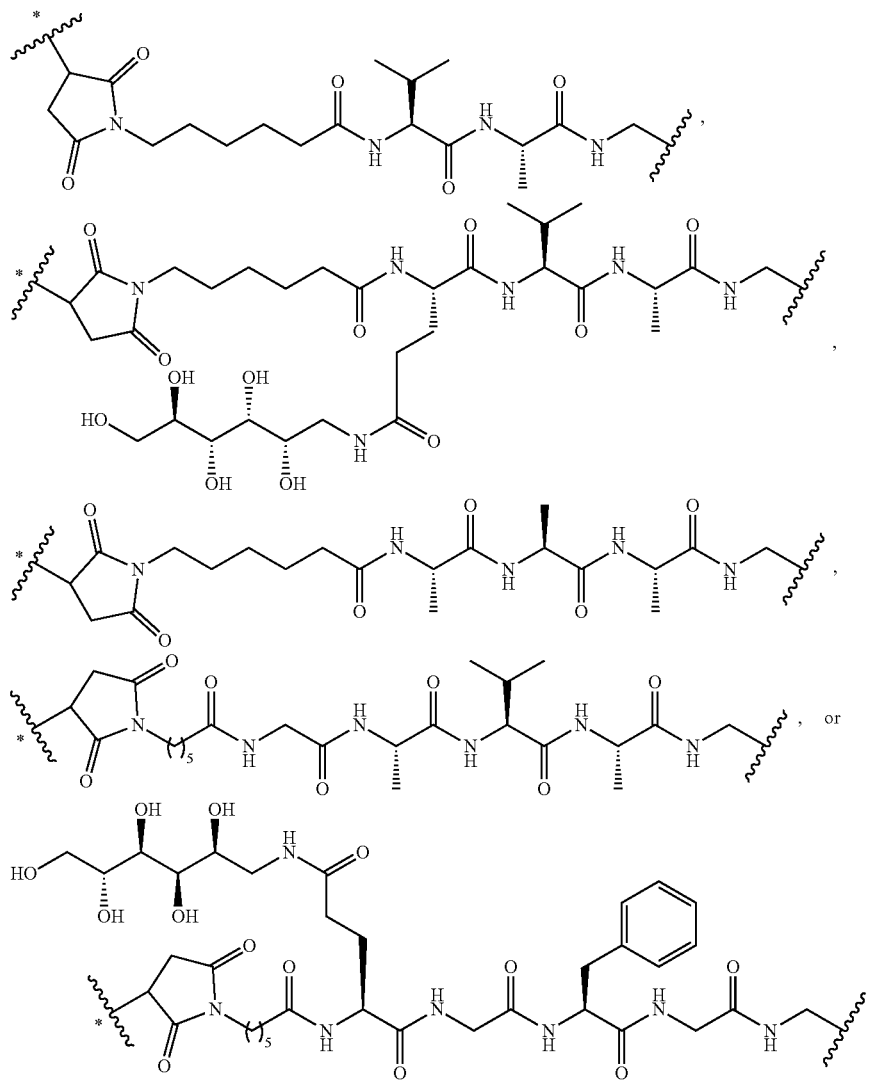

In embodiments, when $R^1$ is —H or —CH₂CH₃, $R^2$ is —OH or alkoxy and $R^3$ is —H, then -L-L₂-Q'— is not —CH(R')CH₂O— or —CH(R')(CH₂)₂O—, wherein R' is —H or $C_1$-$C_6$ alkyl, alkoxy, substituted alkyl, phenyl or PhCH₂—. In embodiments, when $R^1$ is —H or —CH₂CH₃, $R^2$ is —OH or alkoxy and $R^3$ is —H, then -L₈-L₂-Q'— is not —CH(R')CH₂O— or —CH(R')(CH₂)₂—, wherein R' is —H or $C_1$-$C_6$ alkyl, alkoxy, substituted alkyl, phenyl or PhCH₂—.

In embodiments, at least one of $L_1$ and $L_2$ is present.

In embodiments, at least one of $R^1$, $R^2$ and $R^3$, is not —H.

In embodiments, $R^2$ independently is $C_1$-$C_6$ alkyl, $C_2$-$C_6$ alkenyl, $C_2$-$C_6$ alkynyl, silyl, $C_3$-$C_6$ cycloalkyl, $C_1$-$C_6$halogenated alkyl, alkene or alkyne.

In embodiments, $R^1$ independently is —H or $C_1$-$C_6$ alkyl.

In embodiments, $R^2$ independently is —H, —F, —N($R^4$)₂, —N($R^4$)($R^5$), —OR', —SR', —S(=O)$R^5$, —SO₂$R^5$, $C_1$-$C_6$ alkyl, or $C_1$-$C_6$ fluoroalkyl; and $R^3$ independently is —H, —F, —CN, —OCH₃, —CH₃, or —CF₃.

In embodiments, $R^2$ independently is $C_1$-$C_6$ alkyl, $C_1$-$C_6$ fluoroalkyl, or —F.

In embodiments, $R^3$ independently is —H, —F, —CN, or —CF₃.

In embodiments, $R^3$ independently is —F, —CN, —OCH₃, —CH₃, or —CF₃.

In embodiments, $R^2$ and $R^3$ combine to form —O(CH₂)ₙO— or —O(CF₂)ₙO—, wherein n is 1 or 2.

In embodiments, D is represented by one of the following structures:

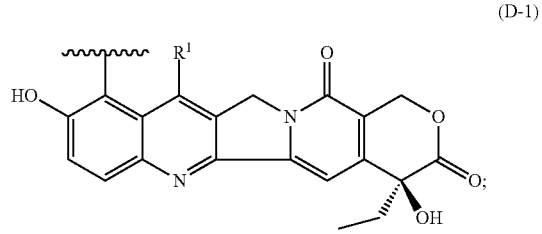

(D-1)

(D-II)
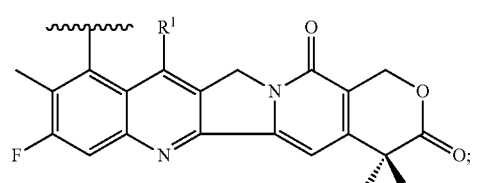
(D-III)
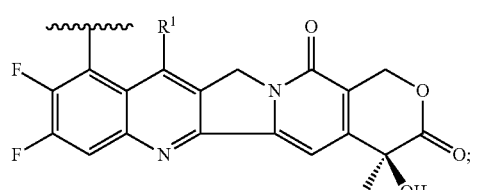
(D-IV)
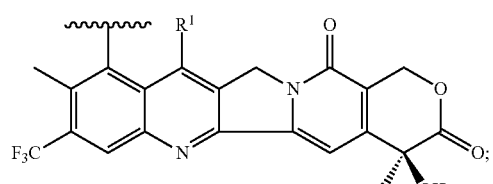
(D-V)
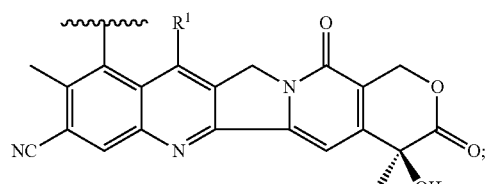
(D-VI)
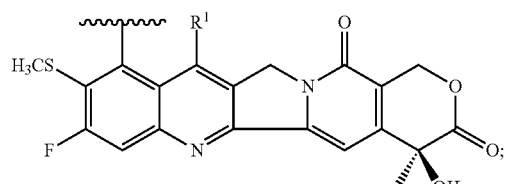
(D-VII)
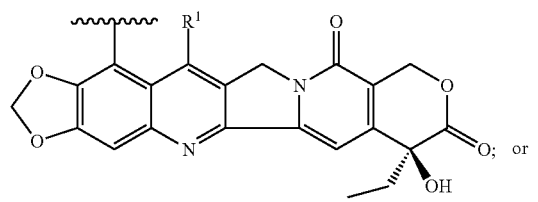; or
(D-VIII)
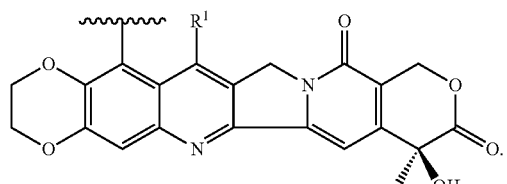
In embodiments, D is
(D-II)
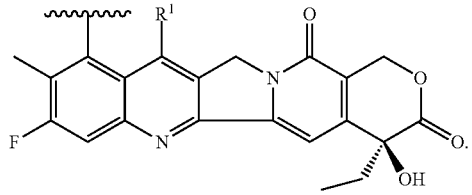
In embodiments, D is (D-I). In embodiments, D is (D-III). In embodiments, D is (D-IV).
In embodiments, D is (D-V). In embodiments, D is (D-VI). In embodiments, D is (D-VII). In embodiments, D is (D-VIII).
In embodiments, $R^1$ is —H or $C_1$-$C_6$ alkyl.
In embodiments, D is represented by one of the following structures:
(D1)
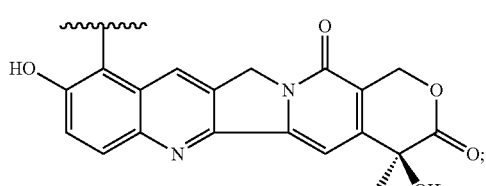
(D2)
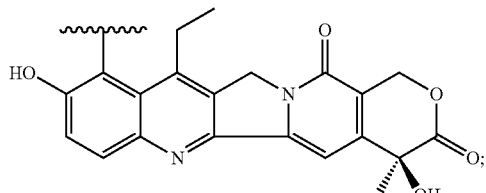
(D3)
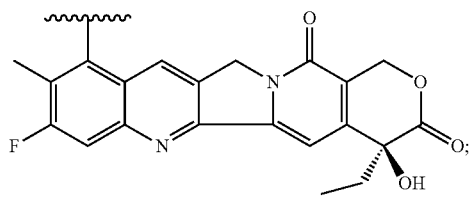
(D4)
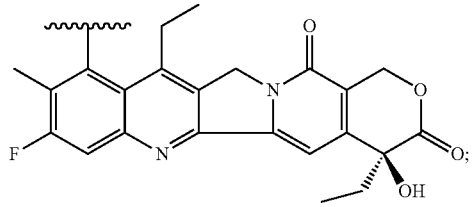
(D5)
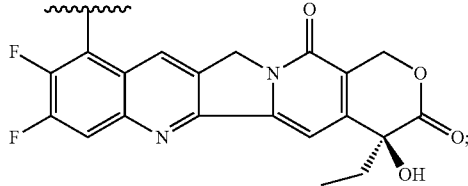

-continued (D6) 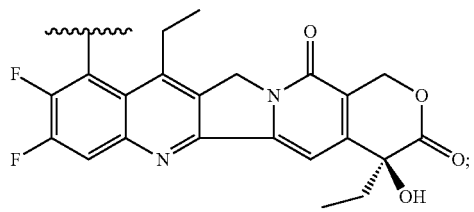

(D7) 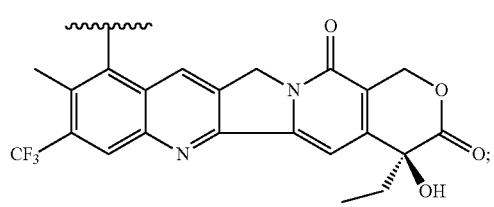

(D8) 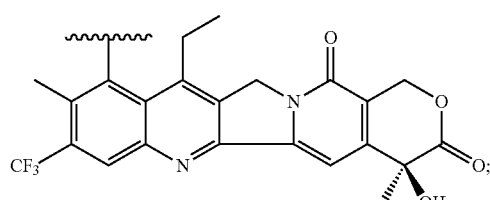

(D9) 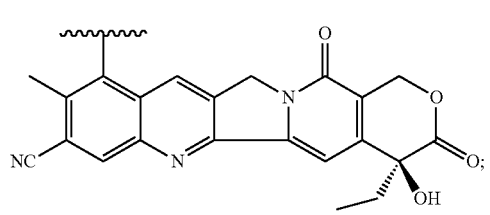

(D10) 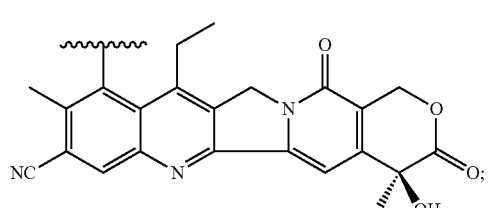

(D11) 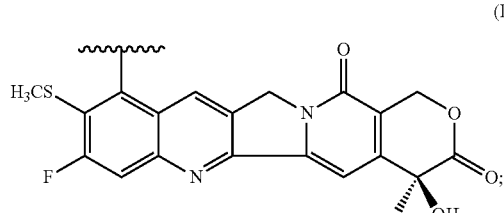

(D12) 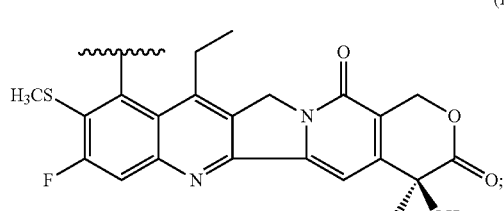

-continued (D13) 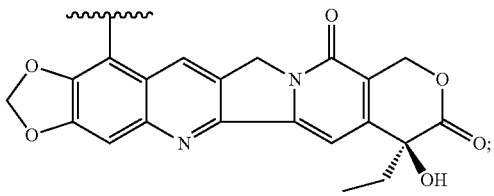

(D14) 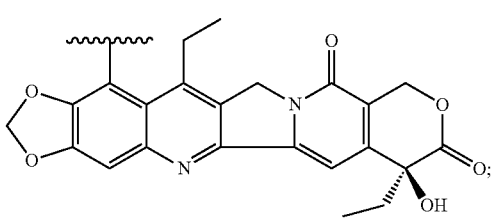

(D15) 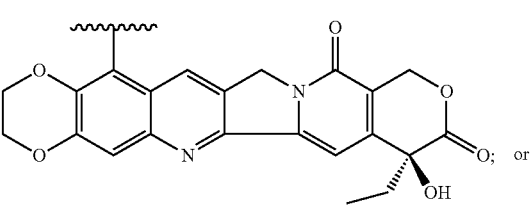

or (D16) 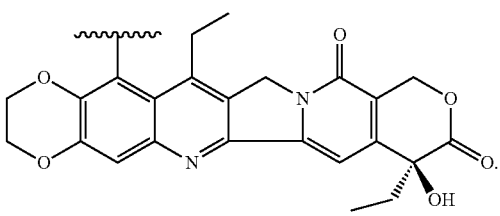

In embodiments, D is (D3) 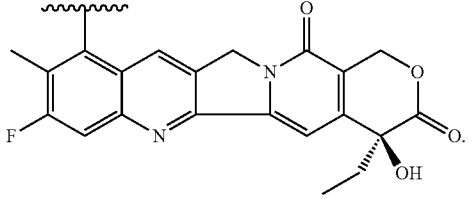

In embodiments, D is (D1). In embodiments, D is (D2). In embodiments, D is (D4).
In embodiments, D is (D5). In embodiments, D is (D6). In embodiments, D is (D7). In embodiments, D is (D8).
In embodiments, D is (D9). In embodiments, D is (D10). In embodiments, D is (D11). In embodiments, D is (D12).
In embodiments, D is (D13). In embodiments, D is (D14). In embodiments, D is (D15). In embodiments, D is (D16).
In embodiments, $L_1$ is —($C_1$-$C_{10}$ alkylene)- and $L_2$ is absent.
In embodiments, $L_1$ is —($C_1$-$C_{10}$ alkylene)- and $L_2$ is —N($R^6$)CH$_2$-$L_3$-* or —N($R^6$)C(=O)-$L_3$-*, wherein * denotes the site covalently linked to Q'.
In embodiments, $L_1$ is absent and $L_2$ is —N($R^6$)CH$_2$-$L_3$-* or —N($R^6$)C(=O)-$L_3$-*, wherein * denotes the site covalently linked to Q'.

In embodiments, $L_3$ is —($C_1$-$C_{10}$ alkylene)-.

In embodiments, $R^6$ is —H or —$CH_3$.

In embodiments, $L_1$-$L_2$ is —$CH_2$—, —$CH_2CH_2$—, —$CH_2CH_2CH_2$—, or —$CH_2CH_2CH_2CH_2$—.

In embodiments, $L_1$-$L_2$ is —O$CH_2CH_2$—*, —O$CH_2CH_2$O$CH_2CH_2$—*, —S$CH_2CH_2$—*, —S$CH_2CH_2$O$CH_2CH_2$—*, —S(=O)$CH_2$—*, —S$O_2CH_2$—*, —C(=O)$CH_2$—*, —NH$CH_2CH_2$—*, —N($CH_3$)$CH_2CH_2$—*, —N($CF_3$)$CH_2CH_2$—*, —NHC(=O)$CH_2$—*, —$CH_2$NHC(=O)$CH_2$—*, —$CH_2CH_2$NHC(=O)$CH_2$—*, —$CH_2$N($CH_3$)C(=O)$CH_2$—* —N($CH_3$)C(=O)$CH_2$—*, —N($CH_3$)C(=O)$CH_2CH_2$—*, —C(=O)NH$CH_2CH_2$—*, —NHC(=O)NH$CH_2CH_2$—*, —NHC(=O)O$CH_2CH_2$—*, —$CH_2$OC(=O)NH$CH_2CH_2$—*, or —C(=O)N($CH_3$)$CH_2CH_2$—*, wherein * denotes the site covalently linked to Q'.

In embodiments, $L_1$-$L_2$-Q' is —$CH_2CH_2CH_2CH_2$O—, —$CH_2CH_2CH_2$O—, —$CH_2CH_2$O—, —$CH_2CH_2$O$CH_2CH_2$O—, —$CH_2$S$CH_2CH_2$O—, —$CH_2$NHC(=O)$CH_2$O—, —$CH_2CH_2$NHC(=O)$CH_2$O—, —$CH_2$N($CH_3$)C(=O)$CH_2$O—, —O$CH_2CH_2$O—, —O$CH_2CH_2CH_2$O—, —S$CH_2CH_2CH_2$O—, —S$CH_2CH_2$O—, —NH$CH_2CH_2$O—, —NH$CH_2CH_2CH_2$O—, —N($CH_3$)$CH_2CH_2$O—, —C(=O)NH$CH_2$O—, —NHC(=O)$CH_2$O—, —$CH_2$S(=O)$CH_2$O—, —$CH_2$S$O_2CH_2$O—, —$CH_2CH_2CH_2$S—, —$CH_2CH_2CH_2$S—, —$CH_2CH_2$S—, —$CH_2CH_2$O$CH_2CH_2$S—, —$CH_2$S$CH_2CH_2$S—, —$CH_2$NHC(=O)$CH_2$S—, —O$CH_2CH_2$S—, —S$CH_2CH_2CH_2$S—, —S$CH_2CH_2$S—, —NH$CH_2CH_2CH_2$S—, —N($CH_3$)$CH_2CH_2$S—, —C(=O)NH$CH_2CH_2$S—, —NHC(=O)$CH_2$S—, —$CH_2$S(=O)$CH_2$S—, or —$CH_2$S$O_2CH_2$S—.

In embodiments, D-$L_1$-$L_2$ is represented by a structure that is

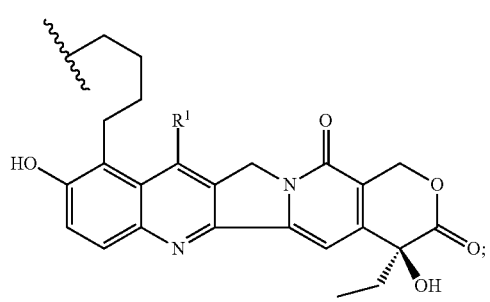

(P-I)

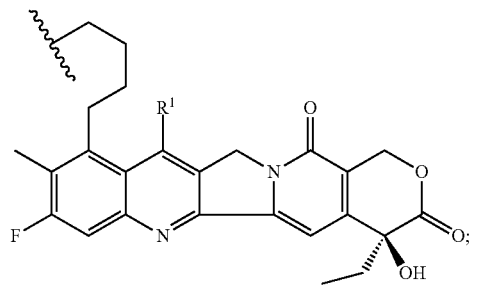

(P-II)

-continued

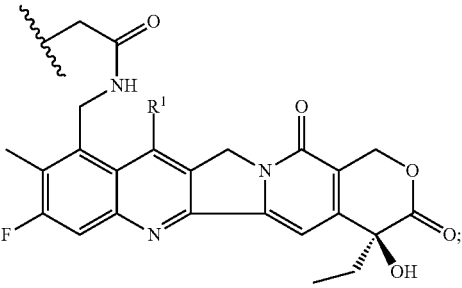

(P-III)

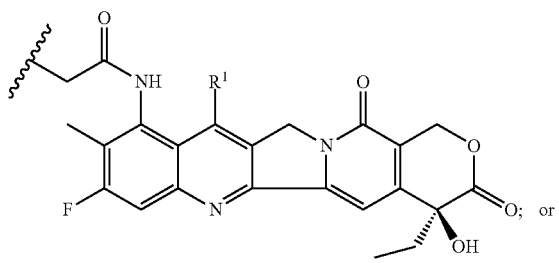

(P-IV)

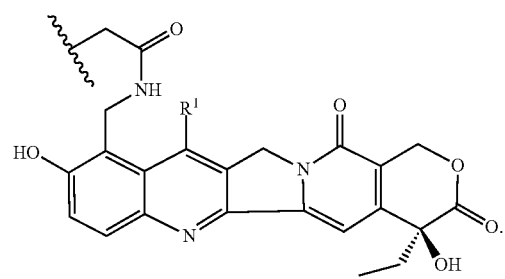

(P-V)

In embodiments, D-$L_1$-$L_2$ is represented by a structure that is:

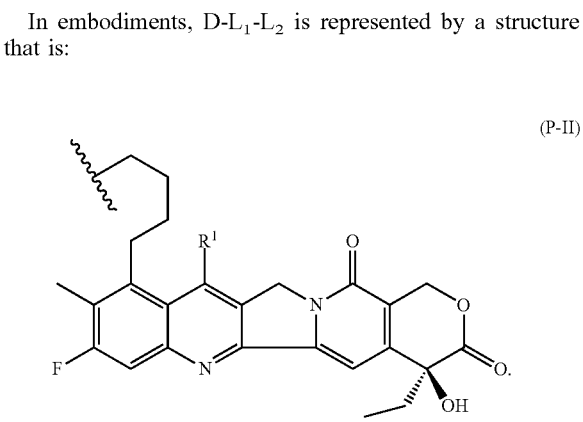

In embodiments, D-$L_1$-$L_2$ is represented by a structure that is (P-I).

In embodiments, D-$L_1$-$L_2$ is represented by a structure that is (P-II).

In embodiments, D-$L_1$-$L_2$ is represented by a structure that is (P-IV).

In embodiments, D-$L_1$-$L_2$ is represented by a structure that is (P-V).

In embodiments, $R^1$ is —H or $C_1$-$C_6$ alkyl.

In embodiments, $R^1$ is —H or —$CH_2CH_3$.

In embodiments, Q' is —O—.

In embodiments, Q' is —S—.

In embodiments, D-L₁-L₂-Q'— has one of the following structures:
(P1')
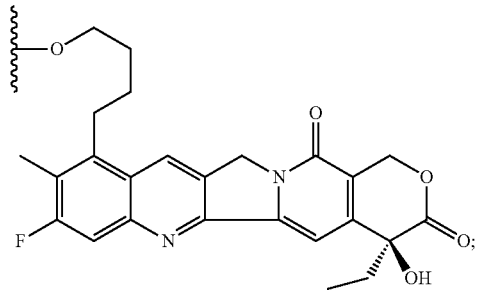
(P2')
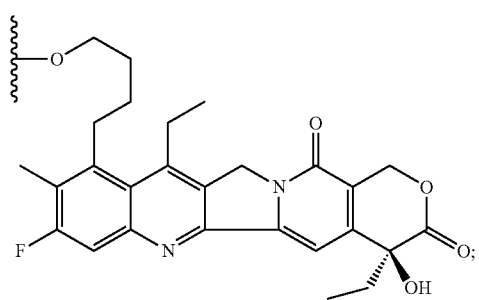
(P3')
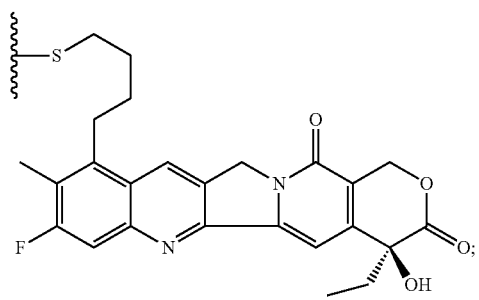
(P4')
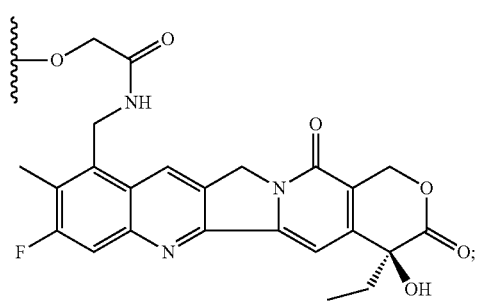
(P5')
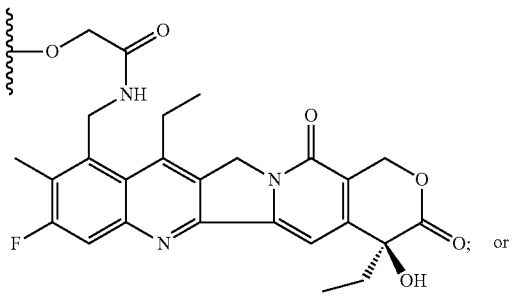
(P6')
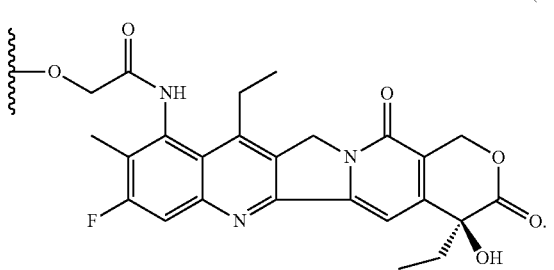
In embodiments, D-L₁-L₂-Q'— is:
(P1')
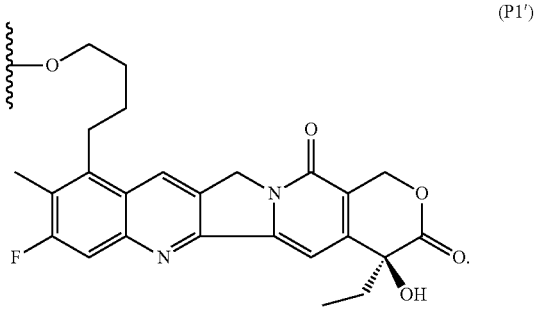 [SMILES: *OCCCCc1c(C)c(F)cc2nc3c(cc12)Cn1c-3cc2c(c1=O)COC(=O)[C@]2(O)CC]
In embodiments, D-L₁-L₂-Q'— is (P2').
In embodiments, D-L₁-L₂-Q'— is (P4').
In embodiments, D-L₁-L₂-Q'— is (P4').
In embodiments, D-L₁-L₂-Q'— is (P5').
In embodiments, D-L₁-L₂-Q'— is (P6').

In embodiments, D-L$_1$-L$_2$-Q'—CH$_2$—NH-E-Z'— is formed from one of the following structures,
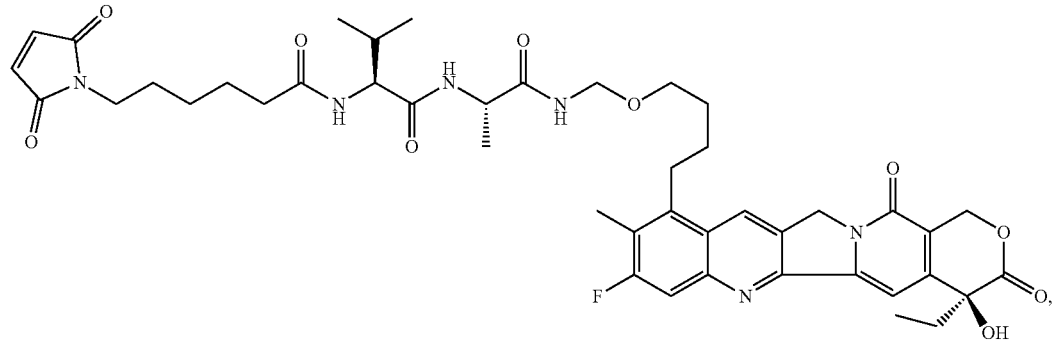
(PL1)
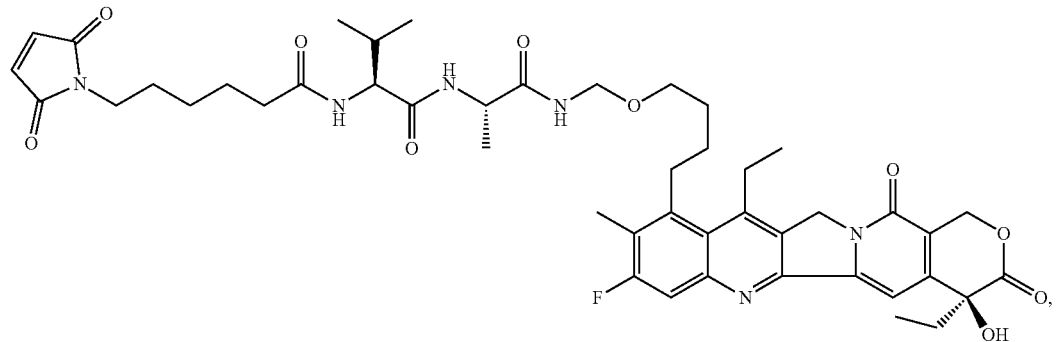
(PL2)
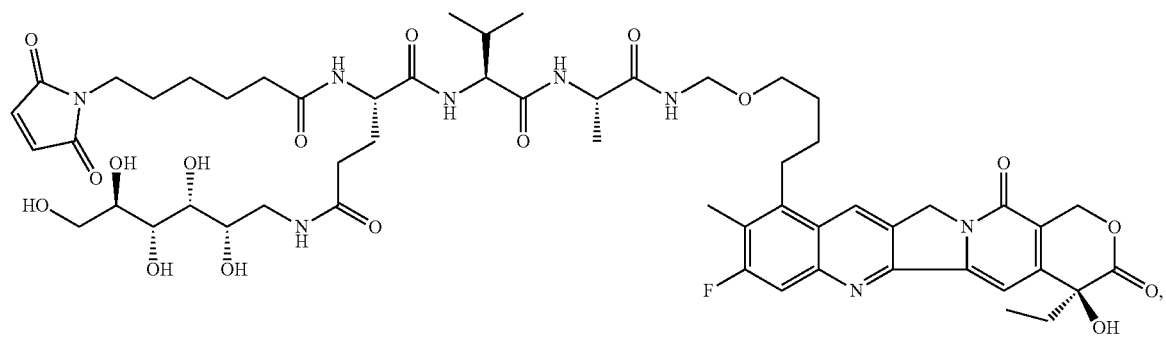
(PL3)
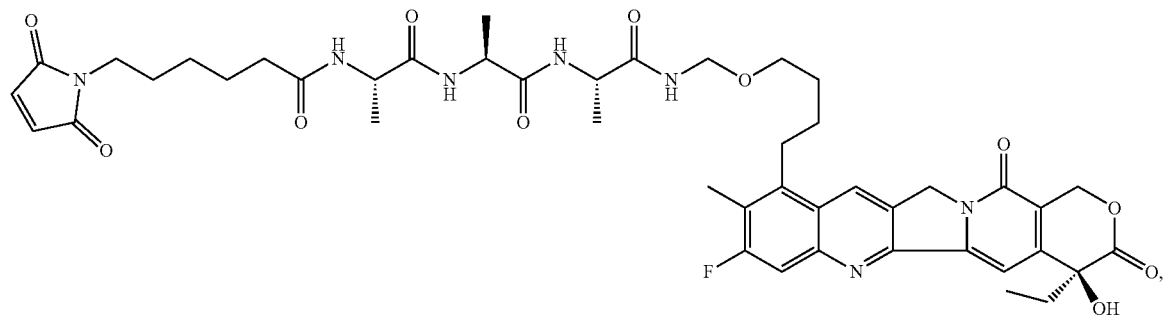
(PL4)

(PL5)
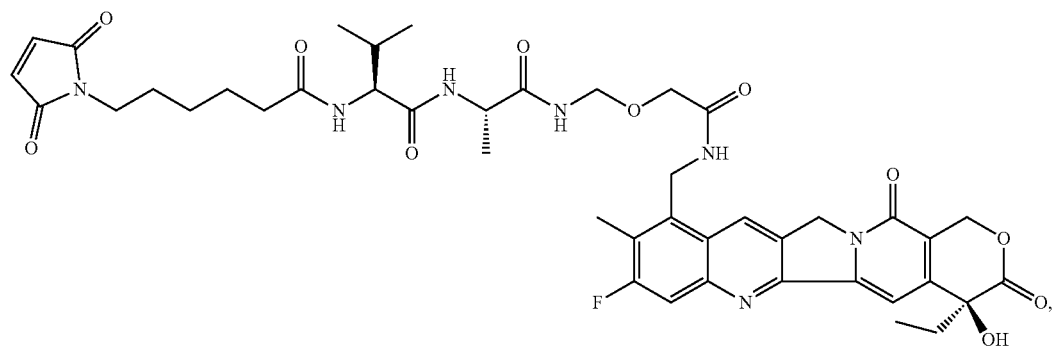
(PL6)
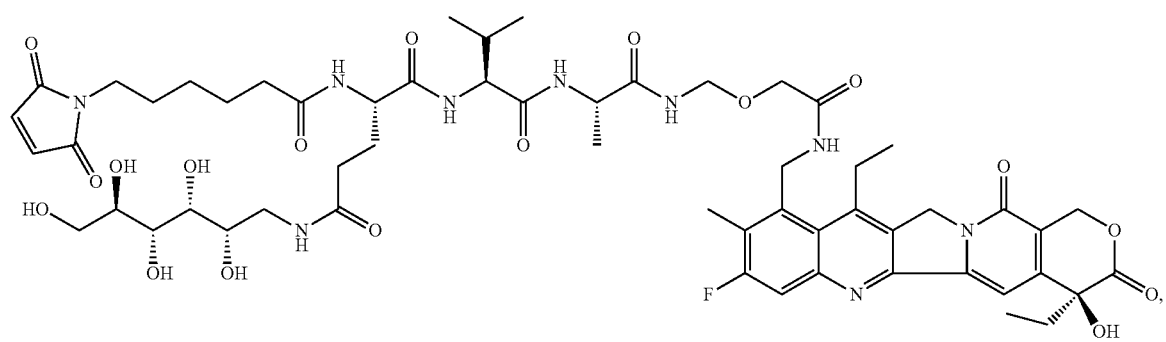
(PL7)
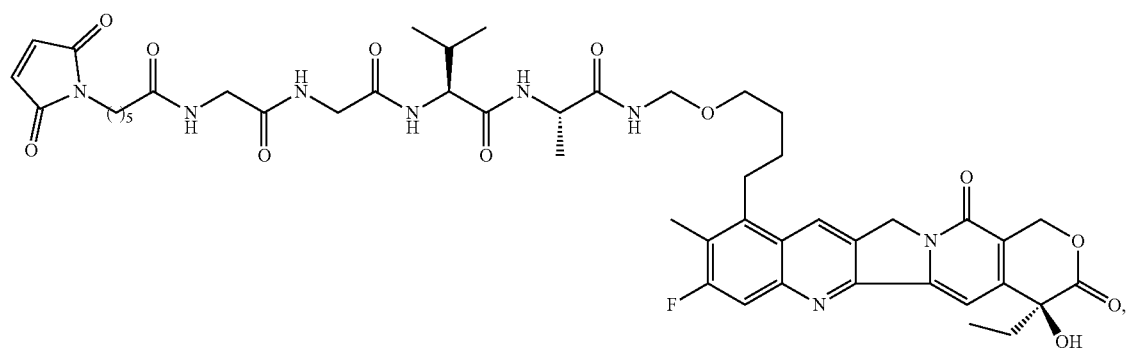
(PL8)
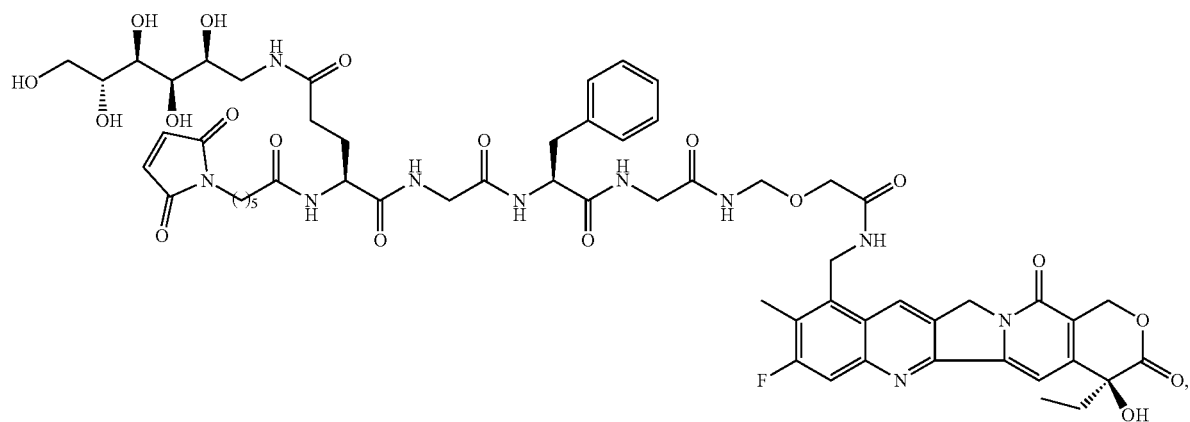

-continued
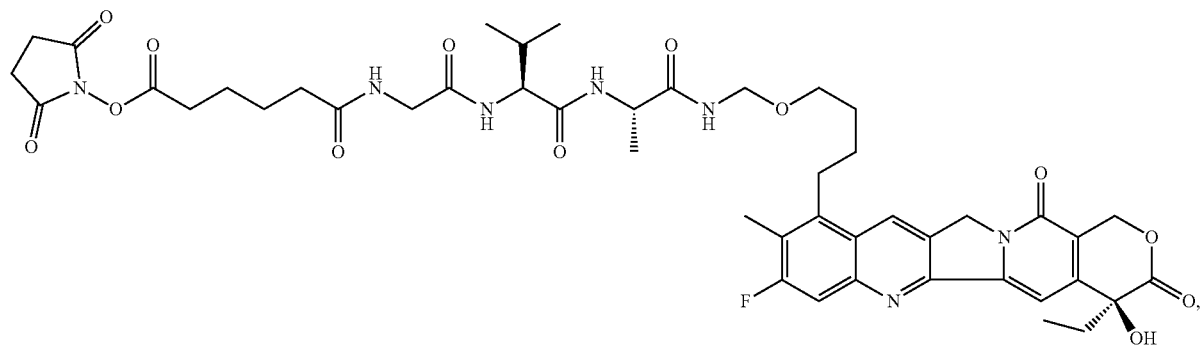
(PL9)
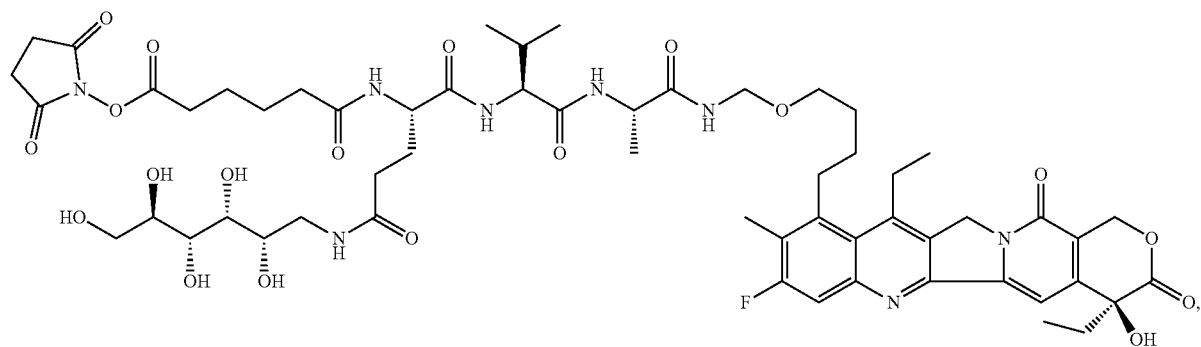
(PL10)
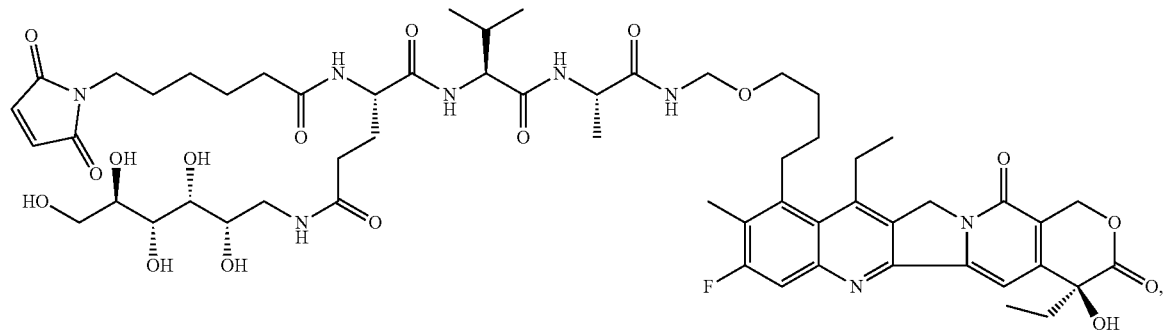
(PL11)
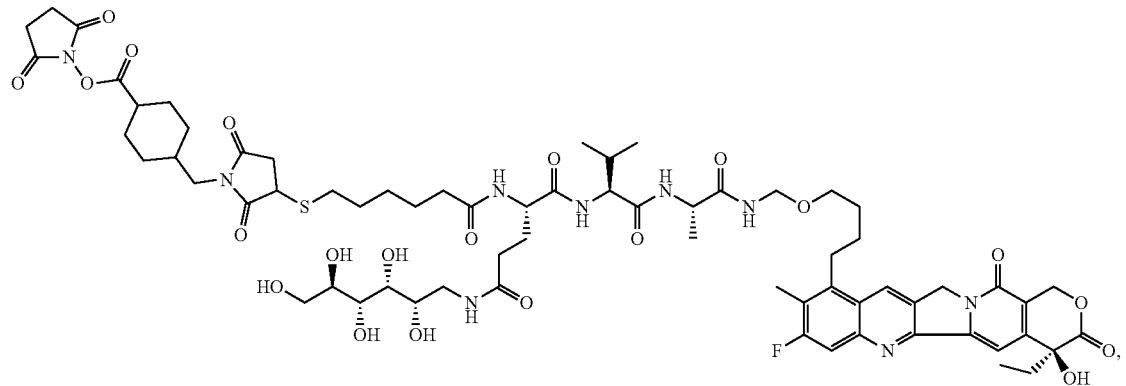
(PL12)

(PL13)
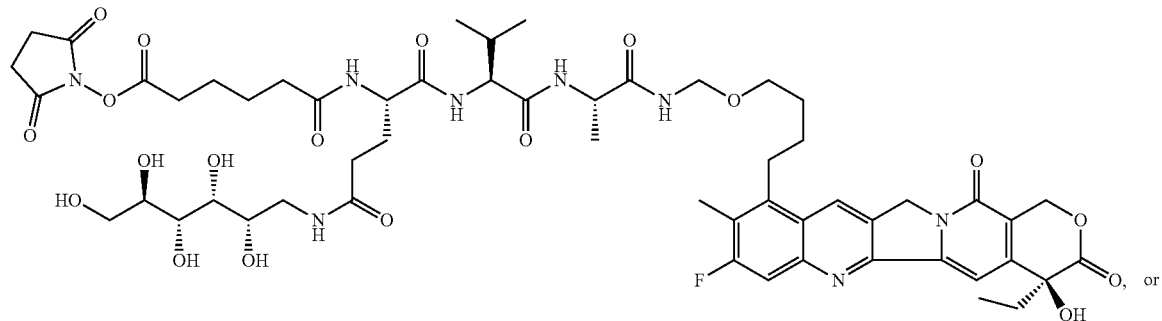
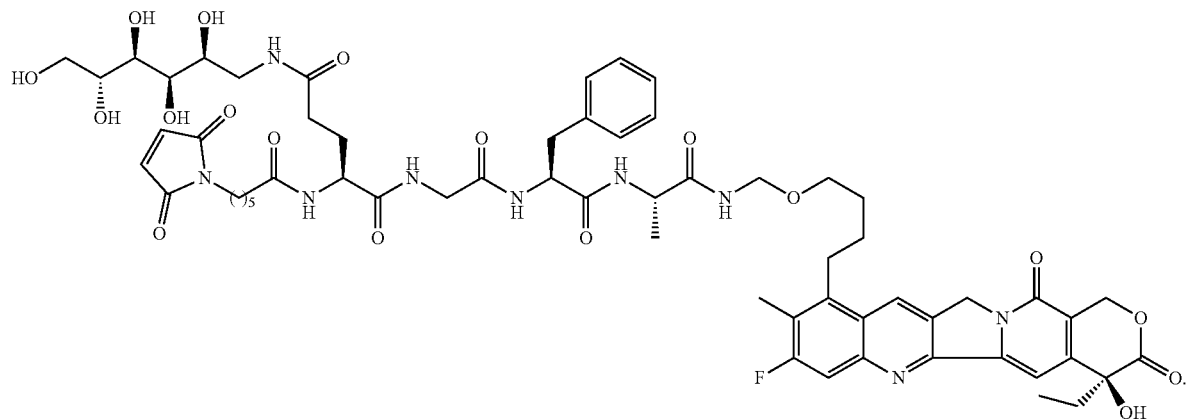
(PL14)
In embodiments, the compound is
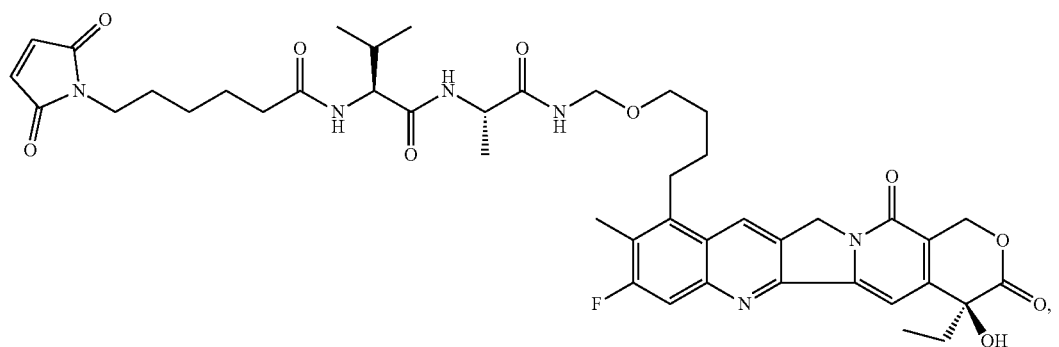
(PL1)
or a pharmaceutically acceptable salt thereof.

In embodiments, the compound is

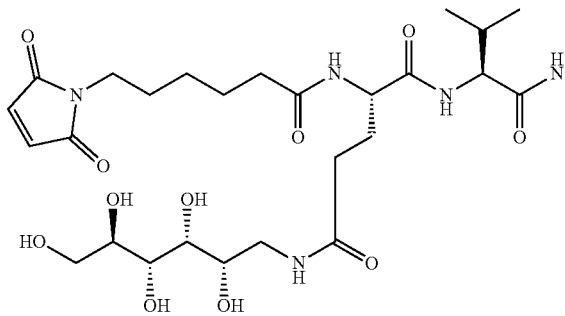

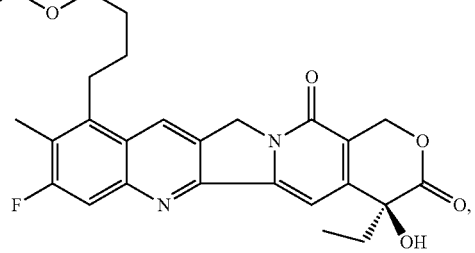

(PL3)

or a pharmaceutically acceptable salt thereof.

In embodiments, the compound is (PL2), or a pharmaceutically acceptable salt thereof.

In embodiments, the compound is (PL4), or a pharmaceutically acceptable salt thereof.

In embodiments, the compound is (PL5), or a pharmaceutically acceptable salt thereof.

In embodiments, the compound is (PL6), or a pharmaceutically acceptable salt thereof.

In embodiments, the compound is (PL7), or a pharmaceutically acceptable salt thereof.

In embodiments, the compound is (PL8), or a pharmaceutically acceptable salt thereof.

In embodiments, the compound is (PL9), or a pharmaceutically acceptable salt thereof.

In embodiments, the compound is (PL10), or a pharmaceutically acceptable salt thereof.

In embodiments, the compound is (PL11), or a pharmaceutically acceptable salt thereof.

In embodiments, the compound is (PL12), or a pharmaceutically acceptable salt thereof.

In embodiments, the compound is (PL13), or a pharmaceutically acceptable salt thereof.

In embodiments, the compound is (PL14), or a pharmaceutically acceptable salt thereof.

In embodiments, $\{D-L_1-L_2-Q'—CH_2—NH-E-Z'\}_p—C$ is one of the following structures, wherein C is a monoclonal antibody and p is the drug to antibody ratio (DAR) and p is a average number ranging from about 2-10, 4-8, or 7-8 (e.g., 3.2 to 8.0),

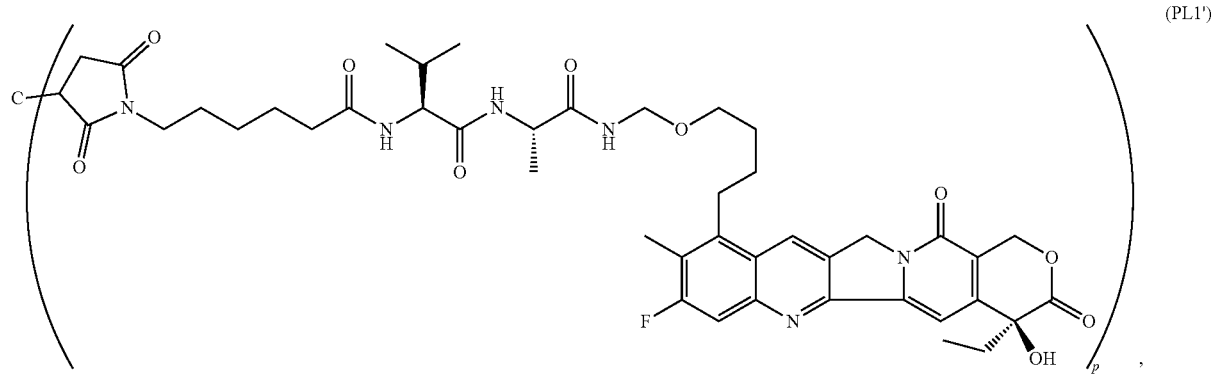

(PL1')

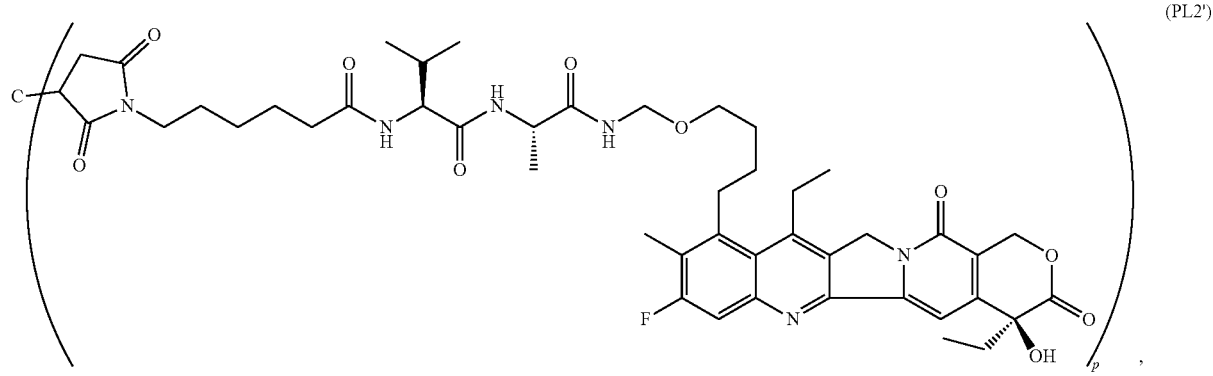

(PL2')

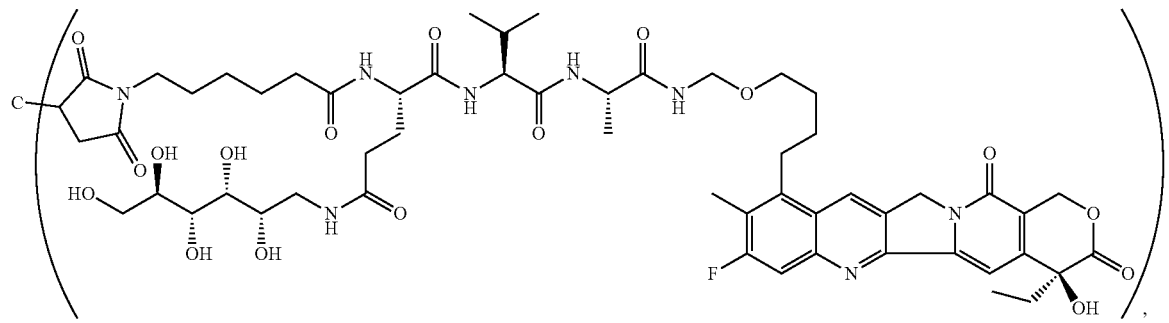
(PL3')
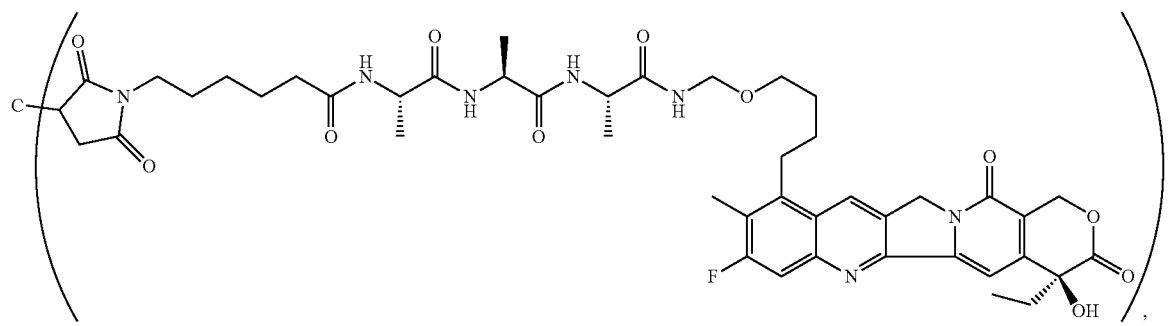
(PL4')
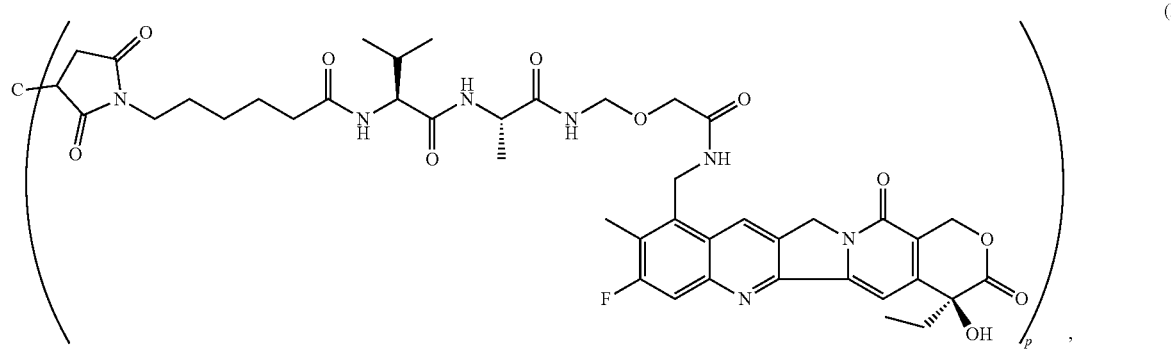
(PL5')
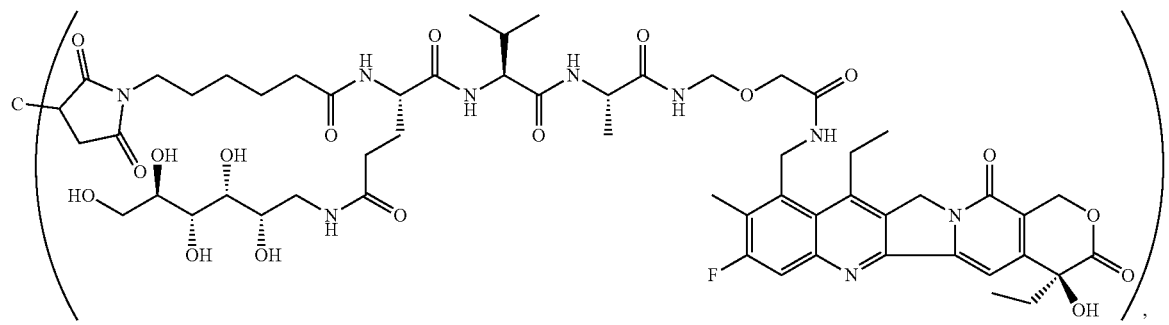
(PL6')

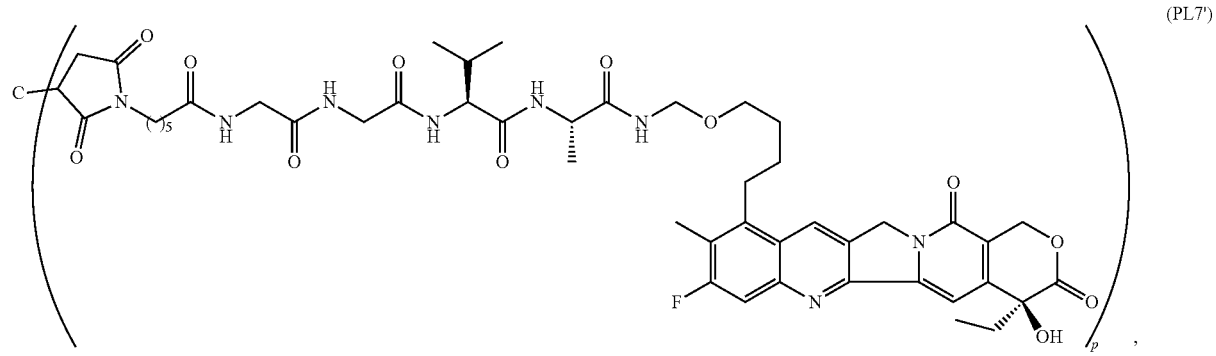
(PL7')
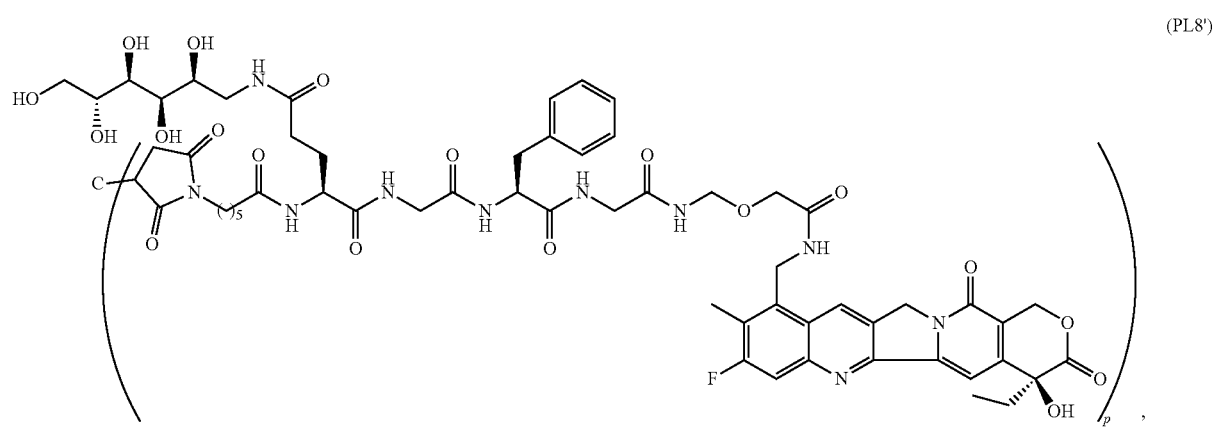
(PL8')
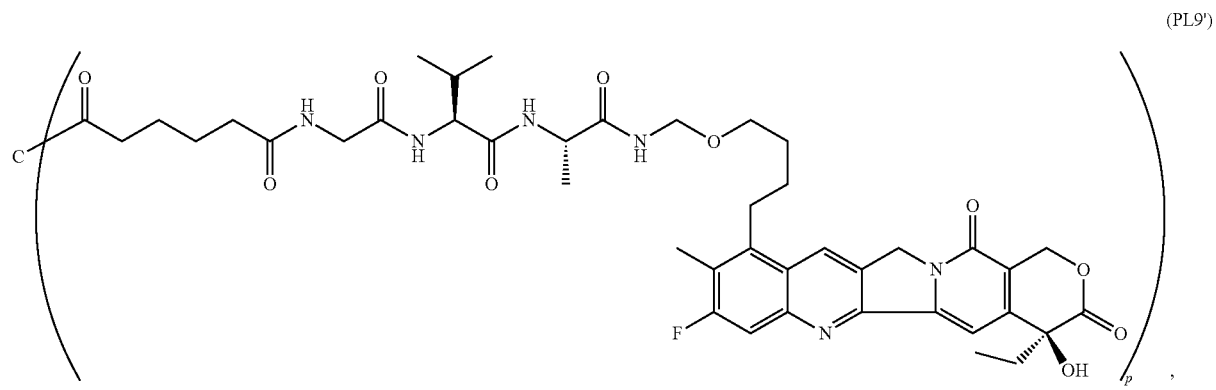
(PL9')
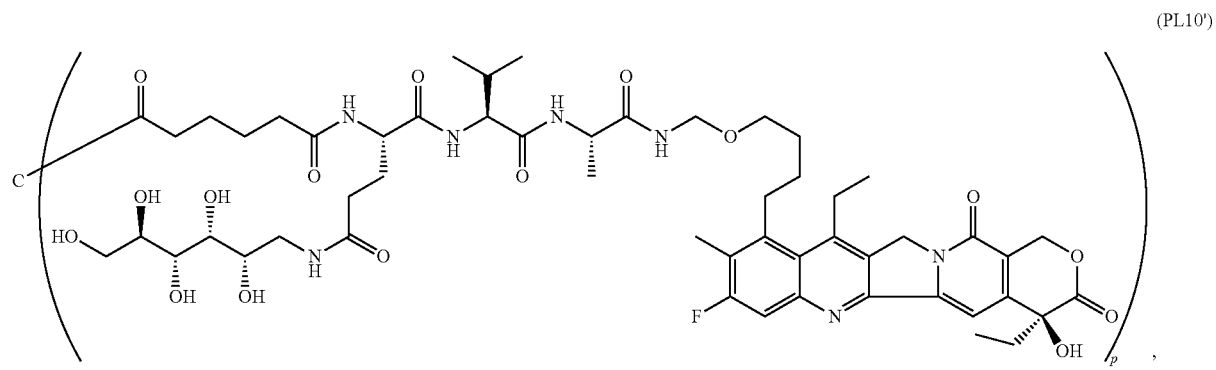
(PL10')

-continued
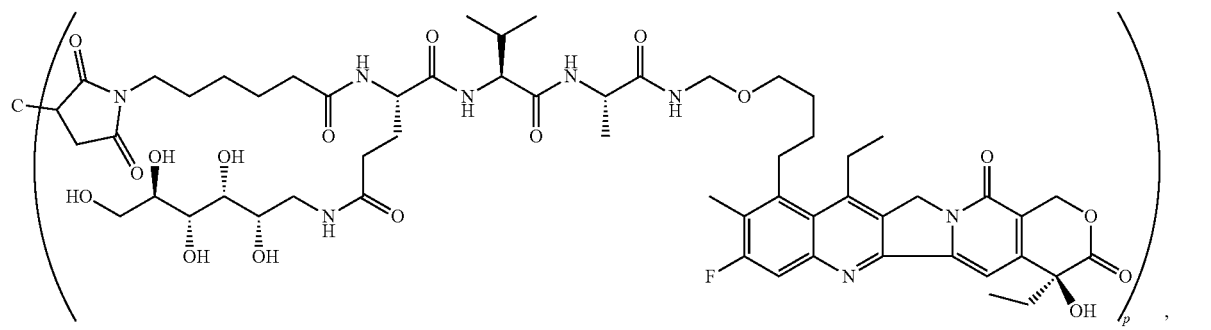
(PL11')
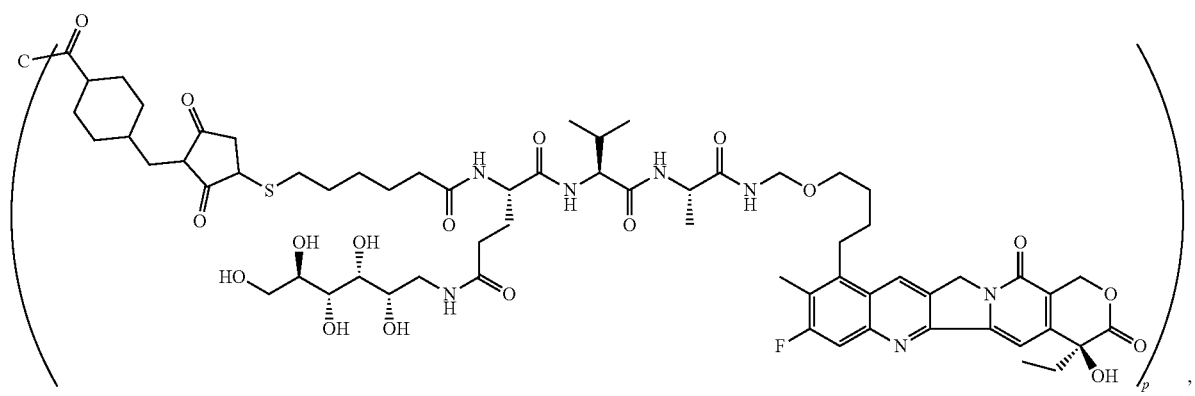
(PL12')
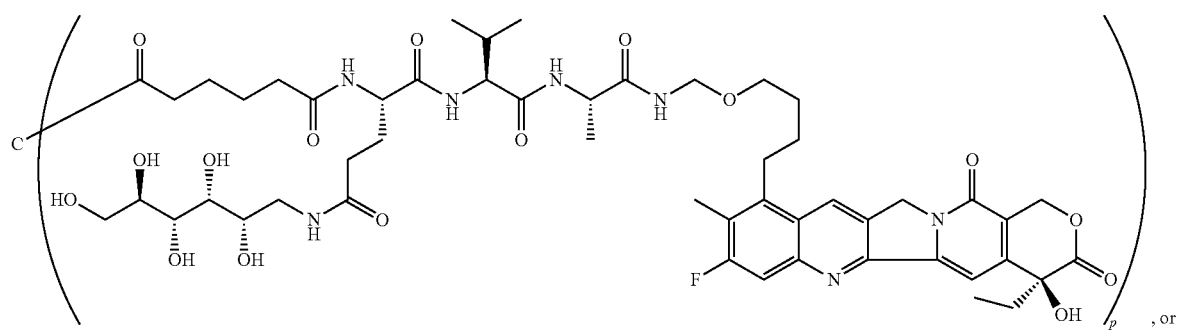
(PL13'), or
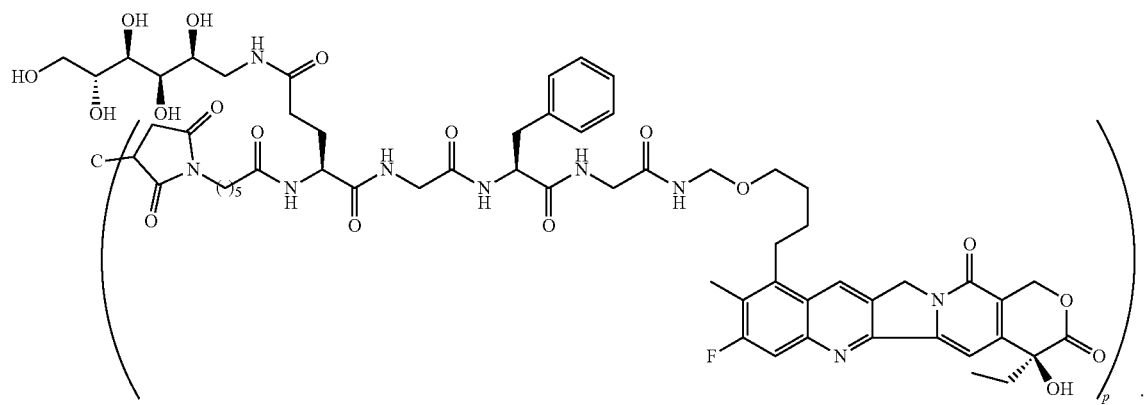
(PL14').

In embodiments, {D-L$_1$-L$_2$-Q'—CH$_2$—NH-E-Z'}$_p$—C is

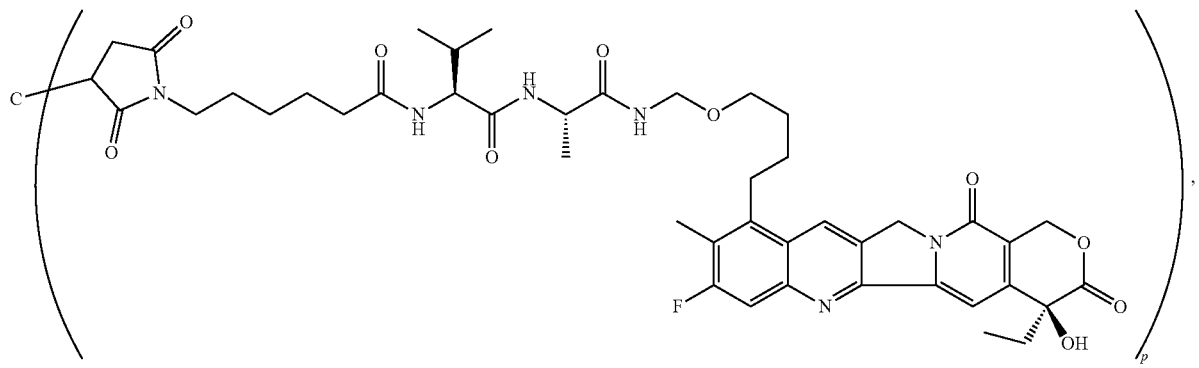

(PL1')

wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is

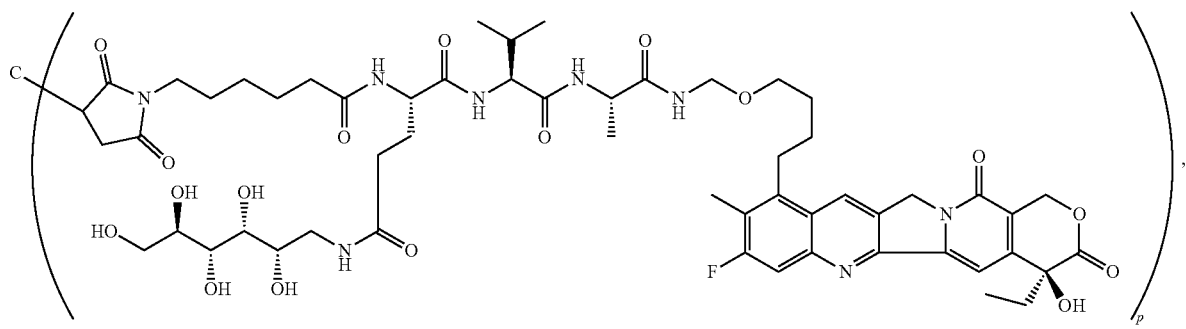

(PL3')

wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL2'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL4'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL5'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL6'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL7'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL8'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL9'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL10'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-L$_1$-L$_2$-Q'—CH$_2$—NH-E-Z'}$_p$—C is (PL11'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-$L_1$-$L_2$-Q'—$CH_2$—NH-E-Z'}$_p$—C is (PL12'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-$L_1$-$L_2$-Q'—$CH_2$—NH-E-Z'}$_p$—C is (PL13'), wherein C is a monoclonal antibody and p is the drug to antibody ratio (DAR). In embodiments, p is a average number ranging from about 2-10, 4-8, or 7-8 (e.g., 3.2 to 8.0).

In embodiments, {D-$L_1$-$L_2$-Q'—$CH_2$—NH-E-Z'}$_p$—C is (PL14'), wherein C is a monoclonal antibody and p is the drug to antibody ratio (DAR). In embodiments, p is a average number ranging from about 2-10, 4-8, or 7-8 (e.g., 3.2 to 8.0).

In another aspect, the invention features a method of preparing a conjugate of Formula (III) which comprises a cell binding agent and a drug and, said method comprising contacting a cell binding agent with a compound of Formula (II), such that a covalent bond forms between said cell binding agent and said compound of Formula (II).

In still another aspect, the invention features a conjugate comprising a cell binding agent and a drug. In embodiments, the conjugate is prepared according to any method described herein.

In embodiments, a conjugate comprises a cell binding agent that is an antibody or an antigen-binding fragment thereof.

In embodiments, a conjugate comprises a cell binding agent that is a monoclonal antibody or an antigen-binding fragment thereof.

In embodiments, the cell binding agent is an antibody or an antigen-binding fragment thereof; p is the drug to antibody ratio (DAR) and has a value between 1 to 18. In embodiments, p is a average number ranging from about 2-10, 4-8, or 7-8 (e.g., 3.2 to 8.0).

In embodiments, the cell binding agent is a monoclonal antibody or an antigen-binding fragment thereof; p is the drug to antibody ratio (DAR) and has a value between 1 to 18. In embodiments, p is a average number ranging from about 2-10, 4-8, or 7-8 (e.g., 3.2 to 8.0).

In another aspect, the invention features a pharmaceutical composition comprising any conjugate described herein.

In still another aspect, the invention features a method of treating a cell proliferative disease or disorder or inhibiting abnormal cell growth, where the method comprises administering any conjugate described herein or any pharmaceutical composition comprising any conjugate described herein.

In another aspect, the invention features a pharmaceutical composition comprising any compound of Formula (III), or a pharmaceutically acceptable salt thereof, as described herein.

In another aspect, the invention features a method of treating a cell proliferative disease or disorder or inhibiting abnormal cell growth, said method comprising administering any compound of Formula (III), or a pharmaceutically acceptable salt thereof, as described herein, or a pharmaceutical composition comprising any compound of Formula (III), or a pharmaceutically acceptable salt thereof, as described herein.

In embodiments, the method is for treating cancer.

In embodiments, a cancer is adenocarcinoma, brain cancer, bladder cancer, breast cancer, cervical cancer, choriocarcinoma, a CNS tumor, colon or colorectal cancer, diffuse intrinsic pontine glioma (DIPG), endometrial cancer, esophageal cancer, Ewing's sarcoma, fallopian tube cancer, gall bladder cancer, gastric cancer, glioblastoma, head and neck cancer, hematological cancer, Hodgkin's lymphoma, kidney cancer, laryngeal cancer, leukemia, liver cancer, lung cancer, lymphoma, melanoma, Merkel cell carcinoma, mesothelioma, multiple myeloma, myelodysplastic syndrome (MDS), neuroblastoma, non-Hodgkin's lymphoma, osteosarcoma, pancreatic cancer, peritoneal cancer, prostate cancer, ovarian cancer, renal cancer, rhabdomyosarcoma salivary gland cancer, sarcoma, skin cancer, small intestine cancer, squamous cell carcinoma, testicular cancer, thyroid cancer, uterine cancer, or Wilms tumor.

In embodiments, a cancer is breast cancer.

The Subscript "p"

Conjugates described herein (e.g., any compound according to Formula (III)) can comprise covalent attachments at least camptothecin derivative (e.g., any compound according to Formula (II) as described herein such as those formed from any compound according to Formula (I) as described herein).

In embodiments, the subscript p represents the number of camptothecin payload moieties (e.g., as formed from a compound according to Formula (II)) on a cell binding agent and has a value from 1 to 18, 1 to 12, or 1 to 8. Individual camptothecin conjugates can be also be referred to as a camptothecin conjugate compound. In embodiments herein, there can be 1, 2, 3, 4, 5, 6, 7, 8, 9, 10, 11, 12, 13, 14, 15, 16, 17, or 18 camptothecin payload moieties conjugated to a cell binding agent of an individual camptothecin conjugate.

In embodiments, a population of individual camptothecin conjugates substantially identical except for the number of camptothecin payload moieties bound to each cell binding agent (i.e., a camptothecin conjugate composition) so that p represents the average number of camptothecin payload moieties bound to the cell binding agents of the camptothecin conjugate composition. In that group of embodiments, p is a average number ranging from 1 to about 18, 1 to about 10, or 1 to about 8, from 2 to about 6, 3 to about 5, or 6 to about 8. In embodiments, p is a average number ranging from about 2-10, 4-8, or 7-8 (e.g., 3.2 to 8.0). In embodiments, p is about 2. In embodiments, p is about 4. In embodiments, p is about 6. In embodiments, p is about 8. In embodiments, p is about 10. In embodiments, p is about 12. In embodiments, p is 2. In embodiments, p is 4. In embodiments, p is 8. In embodiments, p has a value from 3 to 4. In embodiments, p has a value from 4 to 5. In embodiments, p has a value from 5 to 6. In embodiments, p has a value from 6 to 7. In embodiments, p has a value from 7 to 8. In embodiments, p has a value from 7.4 to 8. In embodiments, the p value refers to the average drug loading as well as the drug loading of the predominate ADC in the composition.

In embodiments, conjugation (e.g., as found in any compound according to Formula (III) as described herein) will be via the reduced interchain disulfides and can be from about 1 to about 8, or from 3 to 5, or from 6 to 8 camptothecin payload compounds (e.g., any compound according to Formula (II) described herein or formed from a compound of Formula (I) as described herein) conjugated to a cell binding agent.

In embodiments, conjugation (e.g., as found in any compound according to Formula (III) as described herein) will be via an introduced cysteine residue as well as the reduced interchain disulfides and there can be from 1 to 8, or 1 to 10, or 1 to 12, or 1 to 18 camptothecin payload compounds (e.g., any compound according to Formula (II) described herein or formed from a compound of Formula (I) as described herein) conjugated to a cell binding agent.

In embodiments, conjugation (e.g., as found in any compound according to Formula (III) as described herein) will be via an introduced cysteine residue and there will be 2, or 4, or 6, or 8 camptothecin payload compounds (e.g., any compound according to Formula (II) described herein or formed from a compound of Formula (I) as described herein) conjugated to a cell binding agent.

In embodiments, conjugation (e.g., as found in any compound according to Formula (III) as described herein) will be via an lysine residue and there can be from 1 to 10, or 1 to 12, or 1 to 14, or 1 to 18 camptothecin payload compounds (e.g., any compound according to Formula (II) described herein or formed from a compound of Formula (I) as described herein) conjugated to a cell binding agent.

Reactive Groups on Cell Binding Agent for Covalent Attachment

In embodiments a cell binding agent is bonded to a peptide releasable linker in compound of Formula (II) to form conjugates such as those according to Formula (III). As noted above, still other linking components in Formula (II) can be present in the conjugates described herein to serve the purpose of providing additional space between the camptothecin compound and the cell binding agent. In embodiments, the cell binding agent is bonded to the linker unit in Formula (II) via a heteroatom of the cell binding agent.

Heteroatoms that may be present on a cell binding agent for that bonding include sulfur (in one embodiment, from a thiol group of a targeting ligand), oxygen (in one embodiment, from a carboxyl or hydroxyl group of a targeting ligand) and nitrogen, optionally substituted (in one embodiment, from a primary or secondary amine functional group of a targeting ligand or in another embodiment from an optionally substituted amide nitrogen). Those heteroatoms can be present on the targeting ligand in the cell binding agent's natural state, for example in a naturally-occurring antibody, or can be introduced into the targeting ligand via chemical modification or biological engineering.

In one embodiment, a cell binding agent has a thiol functional group so that the cell binding agent is bonded to a camptothecin payload compound (e.g., any compound according to Formula (II) described herein or formed from a compound of Formula (I) as described herein) via the sulfur atom of the thiol functional group.

In another embodiment, a cell binding agent has one or more lysine residues that are capable of reacting with activated esters (such esters include, but are not limited to, N-hydroxysuccimide, pentafluorophenyl, and p-nitrophenyl esters) of a camptothecin payload compound (e.g., any compound according to Formula (II) described herein or formed from a compound of Formula (I) as described herein) and thus provides an amide bond consisting of the nitrogen atom of the cell binding agent and the C=O group of the compound of Formula (II).

In yet another aspect, a cell binding agent has one or more lysine residues capable of chemical modification to introduce one or more thiol groups. In those embodiments, the cell binding agent is covalently attached to the camptothecin payload compound (e.g., any compound according to Formula (II) described herein or formed from a compound of Formula (I) as described herein) via the thiol functional group's sulfur atom. The reagents that can be used to modify lysines in that manner include, but are not limited to, N-succinimidyl S-acetylthioacetate (SATA) and 2-iminothiolane hydrochloride (Traut's Reagent).

In another embodiment, a cell binding agent has one or more carbohydrate groups capable of modification to provide one or more thiol functional groups. The chemically modified cell binding agent in a camptothecin conjugate is bonded to a camptothecin payload compound (e.g., any compound according to Formula (II) described herein or formed from a compound of Formula (I) as described herein) via the sulfur atom of the thiol functional group.

In yet another embodiment, the cell binding agent has one or more carbohydrate groups that can be oxidized to provide an aldehyde (—CHO) functional group (see, e.g., Laguzza, et al., 1989, *J. Med. Chem.* 32(3):548-55). In these embodiments, the corresponding aldehyde interacts with a reactive site on a camptothecin payload compound (e.g., in any compound according to Formula (II) described herein or formed from a compound of Formula (I) as described herein) to form a bond between the camptothecin payload compound (e.g., in any compound according to Formula (II) described herein or formed from a compound of Formula (I) as described herein) and the cell binding agent. Reactive sites on a camptothecin payload compound (e.g., in any compound according to Formula (II) described herein or formed from a compound of Formula (I) as described herein) that capable of interacting with a reactive carbonyl-containing functional group on a targeting ligand include, but are not limited to, hydrazine and hydroxylamine.

In some aspects, a cell binding agent is capable of forming a bond by interacting with a reactive functional group Y in (e.g., in any compound according to Formula (II)) to form a covalent bond between the Y' in Formula (III) and the cell binding agent corresponding to the targeting ligand. The functional group Y having that capability for interacting with a targeting ligand will depend on the nature of the cell binding agent. In embodiments, the reactive group is a maleimide that is present on a camptothecin payload compound prior to its attachment to form a cell binding agent. Covalent attachment of a cell binding agent to a camptothecin payload compound is accomplished through a thiol functional group of a cell binding agent interacting with the maleimide functional group Y of a payload compound (e.g., in any compound according to Formula (II) described herein or formed from a compound of Formula (I) as described herein) to form a thio-substituted succinimide. The thiol functional group can be present on the cell binding agent in the cell binding agent's natural state, for example, in a naturally-occurring residue, or can be introduced into the cell binding agent via chemical modification or by biological engineering.

In still another embodiment, the cell binding agent is an antibody and the thiol group is generated by reduction of an interchain disulfide of the antibody. Accordingly, In embodiments, the camptothecin payload compound is conjugated to a cysteine residue from reduced interchain disulfide(s).

In yet another embodiment, the cell binding agent is an antibody and the thiol functional group is chemically introduced into the antibody, for example, by introduction of a cysteine residue. Accordingly, in embodiments, the camptothecin payload compound is conjugated to a cell binding agent through an introduced cysteine residue of a cell binding agent.

It has been observed for bioconjugates that the site of drug conjugation can affect a number of parameters including ease of conjugation, drug-linker stability, effects on biophysical properties of the resulting bioconjugates, and in-vitro cytotoxicity. With respect to drug-linker stability, the site of conjugation of a drug-linker moiety to a cell binding agent can affect the ability of the conjugated drug-linker moiety to undergo an elimination reaction, in some instances, to cause premature release of free drug. Sites for conjugation on a targeting ligand include, for example, a reduced interchain disulfide as well as selected cysteine residues at engineered sites. In embodiments conjugation methods to form camptothecin conjugates as described herein use thiol residues at genetically engineered sites that are less susceptible to the elimination reaction (e.g., positions 239 according to the EU index as set forth in Kabat) in comparison to conjugation methods that use thiol residues from a reduced disulfide bond. In other embodiments conjugation methods to form camptothecin conjugates as described herein use thiol residues at sites that are more susceptible to the elimination reaction (e.g. resulting from interchain disulfide reduction).

Cell Binding Agent (C)

In embodiments of the invention, a cell binding agent is present. The cell binding agent acts to target and present the camptothecin or a drug component containing camptothecin to the particular target cell population with which the cell binding agent interacts due to the presence of its targeted component or molecule and allows for subsequent release of free drug within (i.e., intracellularly) or within the vicinity of the target cells (i.e., extracellularly).

In embodiments, a cell-binding agent can be a ligand that binds to a moiety on the target cell, such as a cell-surface receptor. In embodiments, a ligand can be a growth factor or a fragment thereof that binds to a growth factor receptor. In embodiments, a ligand can be a cytokine or a fragment thereof that binds to a cytokine receptor. In embodiments, a growth factor receptor or cytokine receptor is a cell-surface receptor.

Accordingly, the therapeutic use of a camptothecin conjugate (e.g., a compound according to Formula (III) as described herein) can be tailed by appropriate selection of a cell binding agents.

Cell binding agents, include, but are not limited to, proteins, polypeptides and peptides. Suitable cell binding agents include, for example, antibodies (e.g., full-length antibodies and antigen binding fragments thereof, including polyclonal antibodies and monoclonal antibodies), interferons, lymphokines, hormones, growth factors, colony-stimulating factors, vitamins (e.g., folate), nutrient-transport molecules (such as, but not limited to, transferrin), or any other cell binding molecule or substance. In embodiments, the cell binding agent is an antibody or a non-antibody protein targeting agent.

Antigens Targeted by Cell Binding Agents

In embodiments, exemplary antigens or ligands include renin; a growth hormone (e.g., human growth hormone and bovine growth hormone); a growth hormone releasing factor; a parathyroid hormone; or a thyroid stimulating hormone, or fragments thereof.

In embodiments, exemplary antigens or ligands include a lipoprotein; alpha-1-antitrypsin; insulin A-chain; insulin B-chain; proinsulin; a follicle stimulating hormone; calcitonin; a luteinizing hormone; or glucagon, or fragments thereof.

In embodiments, exemplary antigens or ligands include a clotting factor (e.g., factor vmc, factor IX, tissue factor, and von Willebrands factor); an anti-clotting factor (e.g., Protein C); an atrial natriuretic factor; a lung surfactant; a plasminogen activator (e.g., a urokinase, a human urine or tissue-type plasminogen activator); bombesin; a thrombin; or hemopoietic growth factor, or fragments thereof.

In embodiments, exemplary antigens or ligands include tumor necrosis factor-alpha and -beta, or fragments thereof.

In embodiments, exemplary antigens or ligands include an enkephalinase; RANTES (i.e., the regulated on activation normally T-cell expressed and secreted); human macrophage inflammatory protein-1-alpha; a serum albumin (human serum albumin); Muellerian-inhibiting substance; relaxin A-chain; relaxin B-chain; prorelaxin; a mouse gonadotropin-associated peptide; a microbial protein (beta-lactamase); DNase; IgE; inhibin; or activin; or fragments thereof.

In embodiments, exemplary antigens or ligands include a cytotoxic T-lymphocyte associated antigen (e.g., CTLA-4), or fragments thereof.

In embodiments, exemplary antigens or ligands include a vascular endothelial growth factor, or fragments thereof.

In embodiments, exemplary antigens or ligands include a receptor for hormones or growth factors; protein A or D; a rheumatoid factor; a neurotrophic factor (e.g., bone-derived neurotrophic factor, neurotrophin-3, -4, -5, or -6), a nerve growth factor (e.g., NGF-b); a platelet-derived growth factor; a fibroblast growth factor (e.g., aFGF and bFGF); fibroblast growth factor receptor 2; an epidermal growth factor; a transforming growth factor (e.g., TGF-alpha, TGF-bI, TGF-p2, TGF-p3, TGF-p4, and TGF-p5); insulin-like growth factor-I and —II; des(1-3)-IGF-I (brain IGF-I); or an insulin-like growth factor binding protein, or fragments thereof.

In embodiments, exemplary antigens or ligands include melanotransferrin; CA6, CAK1, CALLA, CAECAM5, GD3; FLT3; PSMA; PSCA; MUC1; STEAP; CEA; TENB2; an EphA receptor; an EphB receptor; a folate receptor; FOLR1; mesothelin; cripto; an $alpha_v beta_6$; or integrins, or fragments thereof.

In embodiments, exemplary antigens or ligands include VEGF or VEGFR, or fragments thereof.

In embodiments, exemplary antigens or ligands include EGFR, or fragments thereof.

In embodiments, exemplary antigens or ligands include FGFR3; LAMP1, p-cadherin, or transferrin receptor, or fragments thereof.

In embodiments, exemplary antigens or ligands include IRTA1; IRTA2; IRTA3; IRTA4; IRTA5, or fragments thereof.

In embodiments, exemplary antigens or ligands include Tyrosine-protein kinase transmembrane receptor (e.g., ROR1 and ROR2), or fragments thereof.

In embodiments, exemplary antigens or ligands include CD proteins (e.g., CD2, CD3, CD4, CD6, CD8, CD11, CD14, CD19, CD20, CD21, CD22, CD26, CD28, CD30, CD33, CD36, CD37, CD38, CD40, CD44, CD52, CD55, CD56, CD59, CD70, CD79, CD80. CD81, CD103, CD105, CD123, CD134, CD137, CD138, CD152, and CD276), or fragments thereof.

In embodiments, exemplary antigens or ligands include one or more tumor-associated antigens or cell-surface receptors (see US Publication No. 2008/0171040 or US Publication No. 2008/0305044, incorporated in their entirety by reference), or fragments thereof.

In embodiments, exemplary antigens or ligands include erythropoietin, or fragments thereof.

In embodiments, exemplary antigens or ligands include an osteoinductive factor, or fragments thereof.

In embodiments, exemplary antigens or ligands include an immunotoxin, or fragments thereof.

In embodiments, exemplary antigens or ligands include a bone morphogenetic protein, or fragments thereof.

In embodiments, exemplary antigens or ligands include an interferon (e.g., interferon-alpha, -beta, and -gamma).

In embodiments, exemplary antigens or ligands include a colony stimulating factor (e.g., M-CSF, GM-CSF, and G-CSF), or fragments thereof.

In embodiments, exemplary antigens or ligands include interleukins (e.g., IL-1 to IL-10), or fragments thereof.

In embodiments, exemplary antigens or ligands include a superoxide dismutase, or fragments thereof.

In embodiments, exemplary antigens or ligands include a T-cell receptor, or fragments thereof.

In embodiments, exemplary antigens or ligands include a surface membrane protein, or fragments thereof.

In embodiments, exemplary antigens or ligands include a decay accelerating factor, or fragments thereof.

In embodiments, exemplary antigens or ligands include a viral antigen (e.g., a portion of the HIV envelope), or fragments thereof.

In embodiments, exemplary antigens or ligands include a transport protein, or fragments thereof.

In embodiments, exemplary antigens or ligands include a homing receptor, or fragments thereof.

In embodiments, exemplary antigens or ligands include an addressin, or fragments thereof.

In embodiments, exemplary antigens or ligands include a regulatory protein, or fragments thereof.

In embodiments, exemplary antigens or ligands include an integrin (e.g., CDlla, CDllb, CDllc, CD18, an ICAM, VLA-4, and VCAM), or fragments thereof.

In embodiments, exemplary antigens or ligands include a tumor associated antigen (e.g., HER2, HER3 and HER4 receptor), or fragments thereof.

In embodiments, exemplary antigens or ligands include endoglin; c-Met; c-kit; 1GF1R; PSGR; NGEP; PSMA; PSCA; TMEFF2; LGR5; B7H4; TROP-2, DLL-3, CDH6, AXL, SLITRK6, ENPP3, BCMA, tissue factor, or CD352, or fragments thereof.

In embodiments, a cell binding agent targets Apo2, BAFF-R, bone morphogenetic protein receptor, IGF-IR, CA125, CanAg, E16, ErbB2, MUC1, MUC16, Napi3b, TF, EpCAM, FcRH2, C242, CD2, CD3, CD4, CD5, CD6, CD11, CD18, CD19, CD20, CD21, CD22, CD26, CD30, CD33, CD37, CD38, CD40, CD44, CD56, CD70, CD72, CD79, CD90, CD138, CRIPTO, CXCR5, LY64, TDGF1, endothelin B receptor, EphA receptors, EphB receptors, Endothelin, FCRH1, HER2, HER2/neu, HER3, MHC class II molecule Ia antigen, integrins, IRTA2, LIV-1, MPF, NaPi2b, PDL1, FLJ10372, KIAA1445, Mm42015, SEMA5B, SEMAG, six transmembrane epithelial antigen of prostate 1, IPCA-1, PCANP1, STMP, prostate antigens; insulin growth factor receptor, or folate receptor.

In embodiments, a cell binding agent targets GPNMB, NCAM (CD56), TACSTD2 (TROP-2), folate receptor alpha, tissue factor, ENPP3, CD70, P-cadherin, mesothelin, STEA1, CEACAM5, mucin 1, nectin 4, guanylyl cyclase C, SLC44A4, PSMA, LIV1 (ZIP6), SLITRK6, 5T4, or SC-16.

In embodiments, a cell binding agent targets HER2 or EGFR.

In embodiments, a cell binding agent targets fibronectin extra-domain B (EDB), endothelium receptor ETB, PSMA, VEGFR2 (CD309), tissue factor, or ROBO4.

In embodiments, a cell binding agent targets collagen IV, periostin, or tenascin c.

In embodiments, a cell binding agent targets CD30, CD22, CD79b, CD19, CD138, CD74, CD37, CD33, CD19, or CD98.

In embodiments, a cell binding agent targets HER2.
In embodiments, a cell binding agent targets EGFR.
In embodiments, a cell binding agent targets CD70.
In embodiments, a cell binding agent targets CD33.
In embodiments, a cell binding agent targets CD30.
In embodiments, a cell binding agent targets CD22.
In embodiments, a cell binding agent targets CD19.
In embodiments, a cell binding agent targets Mucl.
In embodiments, a cell binding agent targets CD37.
In embodiments, a cell binding agent targets CD123.

Non-Protein Cell Binding Agents

In embodiments, the cell-binding agent is not a protein. For example, in embodiments, the cell binding agent may be a vitamin that binds to a vitamin receptor, such as a cell-surface receptor. In this regard, vitamin A binds to retinol-binding protein (RBP) to form a complex, which complex in turn binds the STRA6 receptor with high affinity and increases vitamin A in-take. In another example, folic acid/folate/vitamin $B_9$ binds the cell-surface folate receptor (FR), for example, FRa, with high affinity. Folic acid or antibodies that bind to FRa can be used to target the folate receptor expressed on ovarian and other tumors. In addition, vitamin D and its analog bind to vitamin D receptor.

Protein and Polypeptide Cell Binding Agents

In other embodiments, the cell-binding agent is a protein or a polypeptide, or a compound comprising a protein or polypeptide, including antibody, non-antibody protein, or polypeptide.

In embodiments, the cell-binding agent can be a lymphokine, a hormone, a growth factor, a colony stimulating factor, or a nutrient-transport molecule.

In embodiments, GM-CSF, a ligand/growth factor which binds to myeloid cells can be used as a cell-binding agent to diseased cells from acute myelogenous leukemia.

In embodiments, IL-2 which binds to activated T-cells can be used for prevention of transplant graft rejection, for therapy and prevention of graft-versus-host disease, and for treatment of acute T-cell leukemia.

In embodiments, MSH, which binds to melanocytes, can be used for the treatment of melanoma, as can antibodies directed towards melanomas.

In embodiments, epidermal growth factor can be used to target squamous cancers, such as lung and head and neck and gingival squamous cell carcinoma.

In embodiments, somatostatin can be used to target neuroblastomas and other tumor types.

In embodiments, estrogen (or estrogen analogues) can be used to target breast cancer.

In embodiments, androgen (or androgen analogues) can be used to target testes.

In embodiments, the cell-binding agent is an antibody mimetic, such as an ankyrin repeat protein, a Centyrin, or an adnectin/monobody.

In embodiments, a camptothecin conjugate comprises a non-immunoreactive protein, polypeptide, or peptide, as its cell binding agent. Accordingly, in embodiments, the cell binding agent is a non-immunoreactive protein, polypeptide, or peptide. Examples include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, somatostatin, lectins and apoprotein from low density lipoprotein.

Antibodies and Related Cell Binding Agents

In embodiments, the cell binding agent is an antibody or an antigen-binding fragment thereof. In any of the embodiments described herein, a cell binding agent can be an antibody.

In embodiments, where a cell-binding agent is an antibody or an antigen-binding portion thereof (including antibody derivatives), or certain antibody mimetics, a cell binding agent can bind to a ligand on the target cell, such as a cell-surface ligand, including cell-surface receptors.

Suitable antibodies also include, but are not limited to, human antibodies, primatized antibodies, chimeric antibodies, bispecific antibodies, humanized antibodies, conjugated antibodies (i.e., antibodies conjugated or fused to other proteins, radiolabels, cytotoxins), Small Modular Immuno-Pharmaceuticals ("SMIPs™"), and antibody fragments.

For example, antibodies include immunoglobulins (Ig) and fragments thereof which are specifically reactive to the designated protein or peptide, or fragments thereof. In embodiments, antibodies include intact monoclonal antibodies, polyclonal antibodies, single domain antibodies (e.g., shark single domain antibodies (e.g., IgNAR or fragments thereof)), and antibody fragments so long as they exhibit the desired biological activity. In embodiments, an antibody is IgG, IgA, IgE, IgD, or IgM. In embodiments, an antibody is IgG1, IgG2, IgG3, or IgG4. In embodiments, an antibody is IgA1 or IgA2.

In embodiments, the cell-binding agent is a resurfaced antibody, a resurfaced single chain antibody, a resurfaced antibody fragment (or "antigen-binding portion"), or a bispecific antibody.

In embodiments, the cell-binding agent is a minibody, an avibody, a diabody, a tribody, a tetrabody, a nanobody, a probody, a domain antibody, or a unibody.

An antibody fragment can include a portion of an intact antibody, such as, for example, the antigen-binding or variable region of an antibody. Examples of antibody fragments include Fab, Fab', F(ab')2, and Fv fragments; triabodies; tetrabodies; linear antibodies; single-chain antibody molecules. An antibody fragment also can be any synthetic or genetically engineered protein that acts like an antibody by binding to a specific antigen to form a complex. For example, antibody fragments can include isolated fragments, "Fv" fragments, consisting of the variable regions of the heavy and light chains, recombinant single chain polypeptide molecules in which light and heavy chain variable regions are connected by a peptide linker ("ScFv proteins"), and minimal recognition units consisting of the amino acid residues that mimic the hypervariable region.

Useful polyclonal antibodies are heterogeneous populations of antibody molecules derived from the sera of immunized animals. Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art, which provides for the production of antibody molecules by continuous cell lines in culture.

In embodiments, the cell binding agent is a monoclonal antibody or an antigen-binding fragment thereof.

Useful monoclonal antibodies include, but are not limited to, human monoclonal antibodies, humanized monoclonal antibodies, or chimeric human-mouse (or other species) monoclonal antibodies. The antibodies include full-length antibodies and antigen binding fragments thereof. Human monoclonal antibodies can be made by any of numerous techniques known in the art (e.g., Teng et ah, 1983, *Proc. Natl. Acad. Sci. USA.* 80:7308-7312; Kozbor et al., 1983, *Immunology Today* 4:72-79; and Olsson et al., 1982, *Meth. Enzymol.* 92:3-16).

In embodiments, antibodies suitable for the invention may include humanized or human antibodies. Humanized forms of non-human antibodies are chimeric Igs, Ig chains or fragments (such as Fv, Fab, Fab', F(ab')$_2$ or other antigen-binding subsequences of Abs) that contain minimal sequence derived from non-human Ig. Generally, a humanized antibody has one or more amino acid residues introduced from a non-human source. These non-human amino acid residues are often referred to as "import" residues, which are typically taken from an "import" variable domain. Humanization is accomplished by substituting rodent complementarity determining regions (CDRs) or CDR sequences for the corresponding sequences of a human antibody (Riechmann et al., *Nature* 332(6162):323-7, 1988; Verhoeyen et al., *Science.* 239(4847):1534-6, 1988.). Such "humanized" antibodies are chimeric Abs (U.S. Pat. No. 4,816,567, 1989), wherein substantially less than an intact human variable domain has been substituted by the corresponding sequence from a non-human species. In embodiments, the CDRs of a non-human antibody (e.g., mouse) targeting a human antigen are grafted onto the framework regions of the variable domains of a human Ig. Various techniques known in the art are suitable for CDR-grafting, including, for example site directed mutagenesis. In embodiments, humanized antibodies are typically human antibodies in which some CDR residues and possibly some FR residues are substituted by residues from analogous sites in rodent Abs. Humanized antibodies include human Igs (recipient antibody) in which residues from a CDR of the recipient are replaced by residues from a CDR of a non-human species (donor antibody) such as mouse, rat or rabbit, having the desired specificity, affinity and capacity. In embodiments, the monospecific and bispecific antibodies described herein have cross-reactivity with non-human primate common antigens. In some instances, corresponding non-human residues replace Fv framework residues of the human Ig. Humanized antibodies may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region (Fc), typically that of a human Ig (Riechmann et al., Nature 332(6162):323-7, 1988; Verhoeyen et al., Science. 239 (4847):1534-6, 1988.).

Human antibodies can also be produced using various techniques, including phage display libraries (Hoogenboom et al., *Mol Immunol.* (1991) 28(9):1027-37; Marks et al., *J Mol Biol.* (1991) 222(3):581-97) and the preparation of human monoclonal antibodies (Reisfeld and Sell, 1985, *Cancer Surv.* 4(1):271-90). Similarly, introducing human Ig genes into transgenic animals in which the endogenous Ig genes have been partially or completely inactivated can be exploited to synthesize human antibodies. Upon challenge, human antibody production is observed, which closely resembles that seen in humans in all respects, including gene rearrangement, assembly, and antibody repertoire (Fishwild et al., High-avidity human IgG kappa monoclonal antibodies from a novel strain of minilocus transgenic mice, *Nat Biotechnol.* 1996 July; 14(7):845-51; Lonberg et al., Antigen-specific human antibodies from mice comprising four distinct genetic modifications, *Nature* 1994 Apr. 28;368 (6474):856-9; Lonberg and Huszar, Human antibodies from transgenic mice, *Int. Rev. Immunol.* 1995; 13(1):65-93; Marks et al., By-passing immunization: building high affinity human antibodies by chain shuffling. *Biotechnology* (N Y). 1992 July; 10(7):779-83).

The antibody can be a functionally active fragment, derivative or analog of an antibody that immunospecifically binds to target cells (e.g., cancer cell antigens, viral antigens, or microbial antigens) or other antibodies bound to tumor cells or matrix. In this regard, "functionally active" means that the fragment, derivative or analog is able to immunospecifically binds to target cells. To determine which CDR sequences bind the antigen, synthetic peptides containing the CDR sequences can be used in binding assays with the antigen by any binding assay method known in the art (e.g., the BIAcore assay) (See, e.g., Kabat et al., 1991, Sequences of Proteins of Immunological Interest, Fifth Edition, National Institute of Health, Bethesda, Md.; Kabat E et ah, 1980, J. Immunology 125(3):961-969).

Other useful antibodies include fragments of antibodies such as, but not limited to, F(ab')$_2$ fragments, Fab fragments, Fvs, single chain antibodies, diabodies, triabodies, tetrabodies, scFv, scFv-FV, or any other molecule with the same specificity as the antibody.

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., Methods: A Companion to Methods in Enzymology 2:106 (1991); Courtenay-Luck, "Genetic Manipulation of Monoclonal Antibodies," in *Monoclonal Antibodies: Production, Engineering And Clinical Application*, Ritter et al. (eds.), pages 166 179 (Cambridge University Press 1995); and Ward et al., "Genetic Manipulation and Expression of Antibodies," in *Monoclonal Antibodies: Principles And Applications*, Birch et al., (eds.), pages 137 185 (Wiley-Liss, Inc. 1995).

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as for example, those having a variable region derived from a murine monoclonal and human immunoglobulin constant regions. (See, e.g., U.S. Pat. Nos. 4,816,567; and 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., U.S. Pat. No. 5,585,089, which is incorporated herein by reference in its entirety.) Such chimeric and humanized monoclonal antibodies can be produced by recombinant DNA techniques known in the art, for example using methods described in International Publication No. WO 87/02671; European Patent Publication No. 0 184 187; European Patent Publication No. 0 171 496; European Patent Publication No. 0 173 494; International Publication No. WO 86/01533; U.S. Pat. No. 4,816,567; European Patent Publication No. 012 023; Berter et al., 1988, *Science* 240:1041-1043; Liu et al., 1987, *Proc. Natl. Acad. Sci. USA* 84:3439-3443; Liu et al., 1987, *J. Immunol.* 139:3521-3526; Sun et al, 1987, *Proc. Natl. Acad. Sci. USA* 84:214-218; Nishimura et al, 1987, *Cancer. Res.* 47:999-1005; Wood et al, 1985, *Nature* 314:446-449; and Shaw et al, 1988, *J. Natl. Cancer Inst.* 80:1553-1559; Morrison, 1985, *Science* 229: 1202-1207; Oi et al, 1986, *BioTechniques* 4:214; U.S. Pat. No. 5,225,539; Jones et al, 1986, *Nature* 321:552-525; Verhoeyan et al, 1988, *Science* 239: 1534; and Beidler et al, 1988, *J. Immunol.* 141:4053-4060; each of which is incorporated herein by reference in its entirety.

Completely human antibodies in some instances (e.g., when immunogenicity to a non-human or chimeric antibody may occur) are more desirable and can be produced using transgenic mice that are incapable of expressing endogenous immunoglobulin heavy and light chains genes, but which can express human heavy and light chain genes.

Antibodies include analogs and derivatives that are either modified, i.e., by the covalent attachment of any type of molecule as long as such covalent attachment permits the antibody to retain its antigen binding immunospecificity. For example, but not by way of limitation, derivatives and analogs of the antibodies include those that have been further modified, e.g., by glycosylation, acetylation, PEGylation, phosphorylation, amidation, derivatization by known protecting/blocking groups, proteolytic cleavage, linkage to a cellular antibody unit or other protein, etc. Any of numerous chemical modifications can be carried out by known techniques including, but not limited to, specific chemical cleavage, acetylation, formylation, metabolic synthesis in the presence of tunicamycin, etc. Additionally, the analog or derivative can contain one or more unnatural amino acids.

Antibodies can have modifications (e.g., substitutions, deletions or additions) in amino acid residues that interact with Fc receptors. In particular, antibodies can have modifications in amino acid residues identified as involved in the interaction between the anti-Fc domain and the FcRn receptor (see, e.g., International Publication No. WO 97/34631, which is incorporated herein by reference in its entirety).

Antibodies can be generated using methods well known in the art. For example, protocols for antibody production are described by Harlow and Lane, *Antibodies: A Laboratory Manual*, (1988). Typically, antibodies can be generated in mouse, rat, guinea pig, hamster, camel, llama, shark, or other appropriate host. Alternatively, antibodies may be made in chickens, producing IgY molecules (Schade et al., (1996) *ALTEX* 13(5):80-85). In embodiments, antibodies suitable for the present invention are subhuman primate antibodies. For example, general techniques for raising therapeutically useful antibodies in baboons may be found, for example, in Goldenberg et al., international patent publication No. WO 91/11465 (1991), and in Losman et al., *Int. J. Cancer* 46: 310 (1990). In embodiments, monoclonal antibodies may be prepared using hybridoma methods (Milstein and Cuello, (1983) *Nature* 305(5934):537-40.). In embodiments, monoclonal antibodies may also be made by recombinant methods (U.S. Pat. No. 4,166,452, 1979).

Many of the difficulties associated with generating monoclonal antibodies by B-cell immortalization can be overcome by engineering and expressing antibody fragments in *E. coli*, using phage display. To ensure the recovery of high affinity, monoclonal antibodies a combinatorial immunoglobulin library must typically contain a large repertoire size. A typical strategy utilizes mRNA obtained from lymphocytes or spleen cells of immunized mice to synthesize cDNA using reverse transcriptase. The heavy- and light-chain genes are amplified separately by PCR and ligated into phage cloning vectors. Two different libraries are produced, one containing the heavy-chain genes and one containing the light-chain genes. Phage DNA is isolated from each library, and the heavy- and light-chain sequences are ligated together and packaged to form a combinatorial library. Each phage contains a random pair of heavy- and light-chain cDNAs and upon infection of *E. coli* directs the expression of the antibody chains in infected cells. To identify an antibody that recognizes the antigen of interest, the phage library is plated, and the antibody molecules present in the plaques are transferred to filters. The filters are incubated with radioactively labeled antigen and then washed to remove excess unbound ligand. A radioactive spot on the autoradiogram identifies a plaque that contains an antibody that binds the antigen. Cloning and expression vectors that are useful for producing a human immunoglobulin phage library can be obtained, for example, from STRATAGENE Cloning Systems (La Jolla, Calif.).

A similar strategy can be employed to obtain high-affinity scFv. See, e.g., Vaughn et al., Nat. Biotechnol., 14: 309 314 (1996). An scFv library with a large repertoire can be constructed by isolating V-genes from non-immunized human donors using PCR primers corresponding to all known $V_H$, $V_k$ and $V_\lambda$ gene families. Following amplification, the $V_k$ and $V_\lambda$ pools are combined to form one pool. These fragments are ligated into a phagemid vector. The scFv linker, $(Gly_4, Ser)_3$, is then ligated into the phagemid upstream of the $V_L$ fragment. The $V_H$ and linker-$V_L$ fragments are amplified and assembled on the JH region. The resulting $V_H$-linker-$V_L$ fragments are ligated into a phagemid vector. The phagemid library can be panned using filters, as described above, or using immunotubes (Nunc; Maxisorp™). Similar results can be achieved by constructing a combinatorial immunoglobulin library from lymphocytes or spleen cells of immunized rabbits and by expressing the scFv constructs in *P. pastoris*. See, e.g., Ridder et al., Biotechnology, 13: 255 260 (1995). Additionally, following isolation of an appropriate scFv, antibody fragments with higher binding affinities and slower dissociation rates can be obtained through affinity maturation processes such as CDR3 mutagenesis and chain shuffling. See, e.g., Jackson et al., Br. J. Cancer, 78: 181 188 (1998); Osbourn et al., Immunotechnology, 2: 181 196 (1996).

In embodiments, a conjugate described herein (e.g., any compound according to Formula (III)) comprises a cell binding agent is an antibody that targets an antigen that is overexpressed in a cancer cell.

In embodiments, a conjugate described herein (e.g., any compound according to Formula (III)) comprises a cell binding agent is an antibody that recognizes a specific tumor associated antigen (TAA).

Antibodies immunospecific for a cancer cell antigen can be obtained commercially or produced by any method known to one of skill in the art such as, recombinant expression techniques. The nucleotide sequence encoding antibodies immunospecific for a cancer cell antigen can be obtained, e.g., from the GenBank database or a database like it, the literature publications, or by routine cloning and sequencing.

In a specific embodiment, a known antibody for the treatment of cancer can be used.

In another specific embodiment, antibodies for the treatment of an autoimmune disease are used in accordance with the compositions and methods of the invention.

In embodiments, useful antibodies can bind to a receptor or a receptor complex expressed on an activated lymphocyte. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein.

In embodiments, a conjugate described herein (e.g., any compound according to Formula (III)) comprises a cell binding agent (e.g., an antibody or fragment thereof) that targets Apo2, BAFF-R, bone morphogenetic protein receptor, IGF-IR, CA125, CanAg, E16, ErbB2, MUC1, MUC16, Napi3b, TF, EpCAM, FcRH2, $C_{242}$, CD2, CD3, CD4, CD5, CD6, CD11, CD18, CD19, CD20, CD21, CD22, CD26, CD30, CD33, CD37, CD38, CD40, CD44, CD56, CD70, CD72, CD79, CD90, CD138, CRIPTO, CXCR5, LY64, TDGF1, endothelin B receptor, EphA receptors, EphB receptors, Endothelin, FCRH1, HER2, HER2/neu, HER3, MHC class II molecule Ia antigen, integrins, IRTA2, LIV-1, MPF, NaPi2b, PDL1, FLJ10372, KIAA1445, Mm42015, SEMA5B, SEMAG, six transmembrane epithelial antigen of prostate 1, IPCA-1, PCANP1, STMP, prostate antigens; insulin growth factor receptor, or folate receptor.

In embodiments, a conjugate described herein (e.g., any compound according to Formula (III)) comprises a cell binding agent (e.g., an antibody or fragment thereof) that targets GPNMB, NCAM (CD56), TACSTD2 (TROP-2), folate receptor alpha, tissue factor, ENPP3, CD70, P-cadherin, mesothelin, STEA1, CEACAM5, mucin 1, nectin 4, guanylyl cyclase C, SLC44A4, PSMA, LIV1 (ZIP6), SLITRK6, 5T4, or SC-16.

In embodiments, a conjugate described herein (e.g., any compound according to Formula (III)) comprises a cell binding agent (e.g., an antibody or fragment thereof) that targets HER2 or EGFR.

In embodiments, a conjugate described herein (e.g., any compound according to Formula (III)) comprises a cell binding agent (e.g., an antibody or fragment thereof) that targets fibronectin extra-domain B (EDB), endothelium receptor ETB, PSMA, VEGFR2 (CD309), tissue factor, or ROBO4.

In embodiments, a conjugate described herein (e.g., any compound according to Formula (III)) comprises a cell binding agent (e.g., an antibody or fragment thereof) that targets collagen IV, periostin, or tenascin c.

In embodiments, a conjugate described herein (e.g., any compound according to Formula (III)) comprises a cell binding agent (e.g., an antibody or fragment thereof) that targets CD30, CD22, CD79b, CD19, CD138, CD74, CD37, CD33, CD19, or CD98.

In embodiments, a conjugate described herein (e.g., any compound according to Formula (III)) comprises a cell binding agent (e.g., an antibody or fragment thereof) that targets HER2.

In embodiments, a conjugate described herein (e.g., any compound according to Formula (III)) comprises a cell binding agent (e.g., an antibody or fragment thereof) that targets EGFR.

In embodiments, a conjugate described herein (e.g., any compound according to Formula (III)) comprises a cell binding agent (e.g., an antibody or fragment thereof) that targets CD70.

In embodiments, a conjugate described herein (e.g., any compound according to Formula (III)) comprises a cell binding agent (e.g., an antibody or fragment thereof) that targets CD33.

In embodiments, a conjugate described herein (e.g., any compound according to Formula (III)) comprises a cell binding agent (e.g., an antibody or fragment thereof) that targets CD30.

In embodiments, a conjugate described herein (e.g., any compound according to Formula (III)) comprises a cell binding agent (e.g., an antibody or fragment thereof) that targets CD22.

In embodiments, a conjugate described herein (e.g., any compound according to Formula (III)) comprises a cell binding agent (e.g., an antibody or fragment thereof) that targets CD19.

In embodiments, a conjugate described herein (e.g., any compound according to Formula (III)) comprises a cell binding agent (e.g., an antibody or fragment thereof) that targets Muc1.

In embodiments, a conjugate described herein (e.g., any compound according to Formula (III)) comprises a cell binding agent (e.g., an antibody or fragment thereof) that targets CD37.

In embodiments, a conjugate described herein (e.g., any compound according to Formula (III)) comprises a cell binding agent (e.g., an antibody or fragment thereof) that targets CD123.

Methods of Synthesis

Compounds described herein (e.g., a compound according to any one of Formula (I), Formula (II), or Formula (III) can be prepared according to methods known in the art. Exemplary methods are described herein.

In embodiments, Scheme 1 provides an exemplary synthetic method for described compound MB-1 (P1).

In embodiments, Scheme 2 provides an alternative synthetic method for described compound MB-1 (P1):

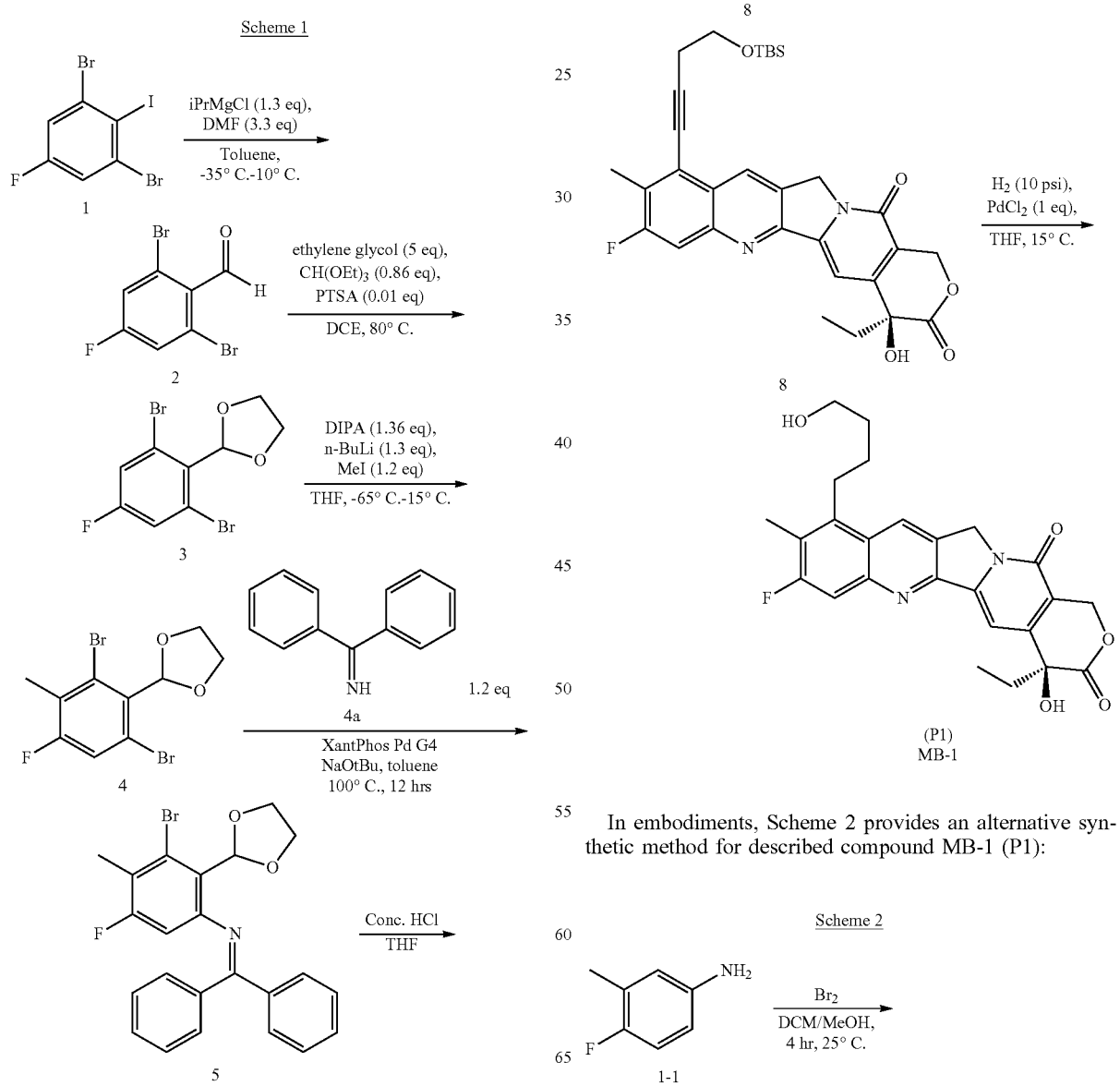

-continued
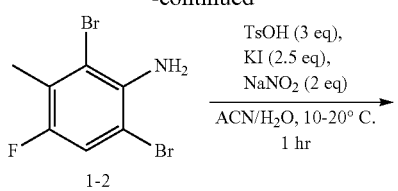
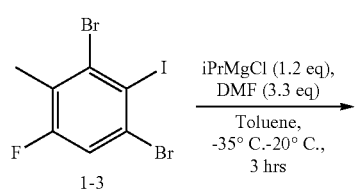
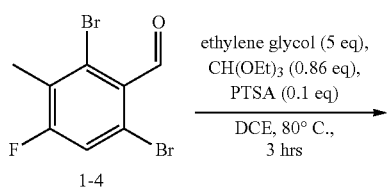
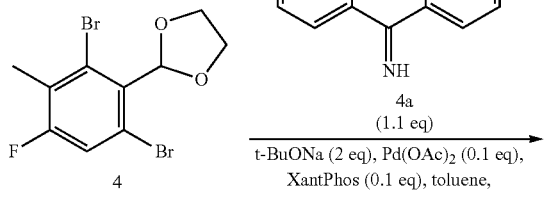
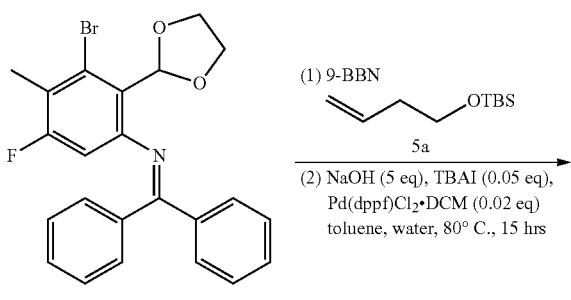
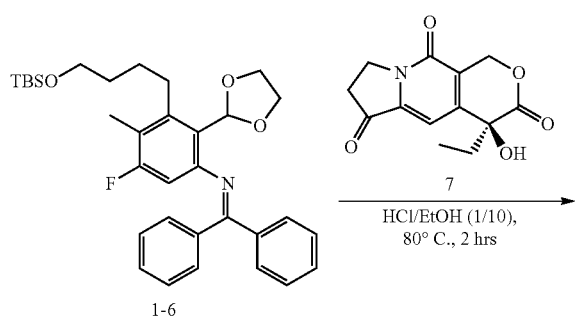
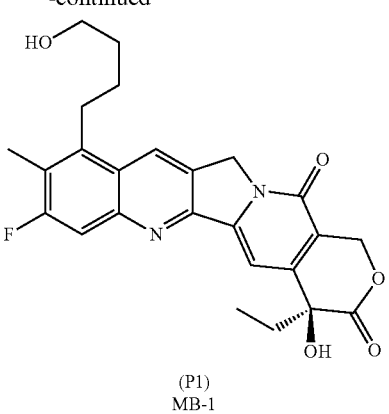
(P1)
MB-1
In embodiments, Scheme 3 provides an exemplary synthetic method for described compound (P2):
Scheme 3
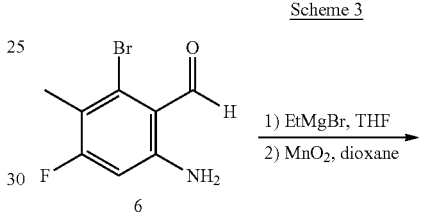
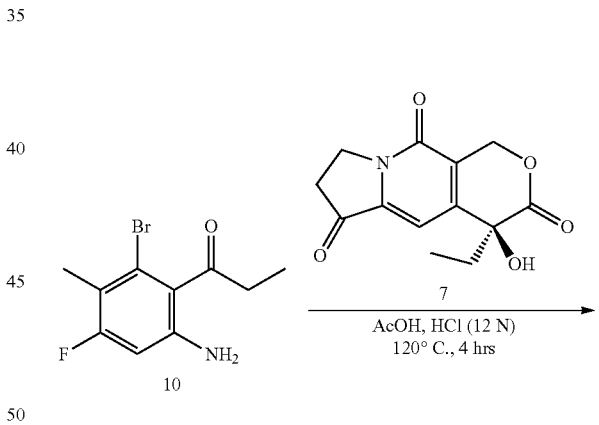
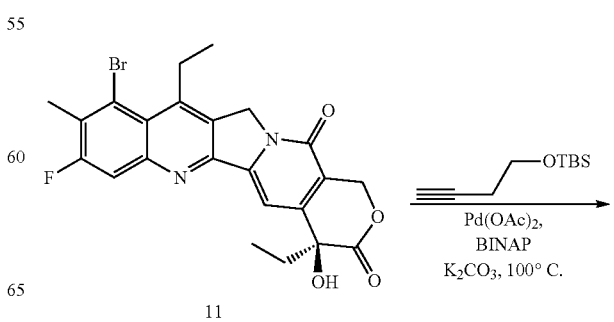

In embodiments, Scheme 4 provides an exemplary synthetic method for described compound (P3):

In embodiments, Scheme 5 provides an exemplary synthetic method for described compound (P4):

169
-continued
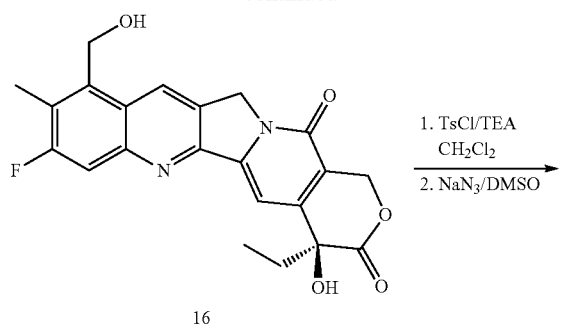
170
In embodiments, Scheme 6 provides an exemplary synthetic method for described compound (P5):
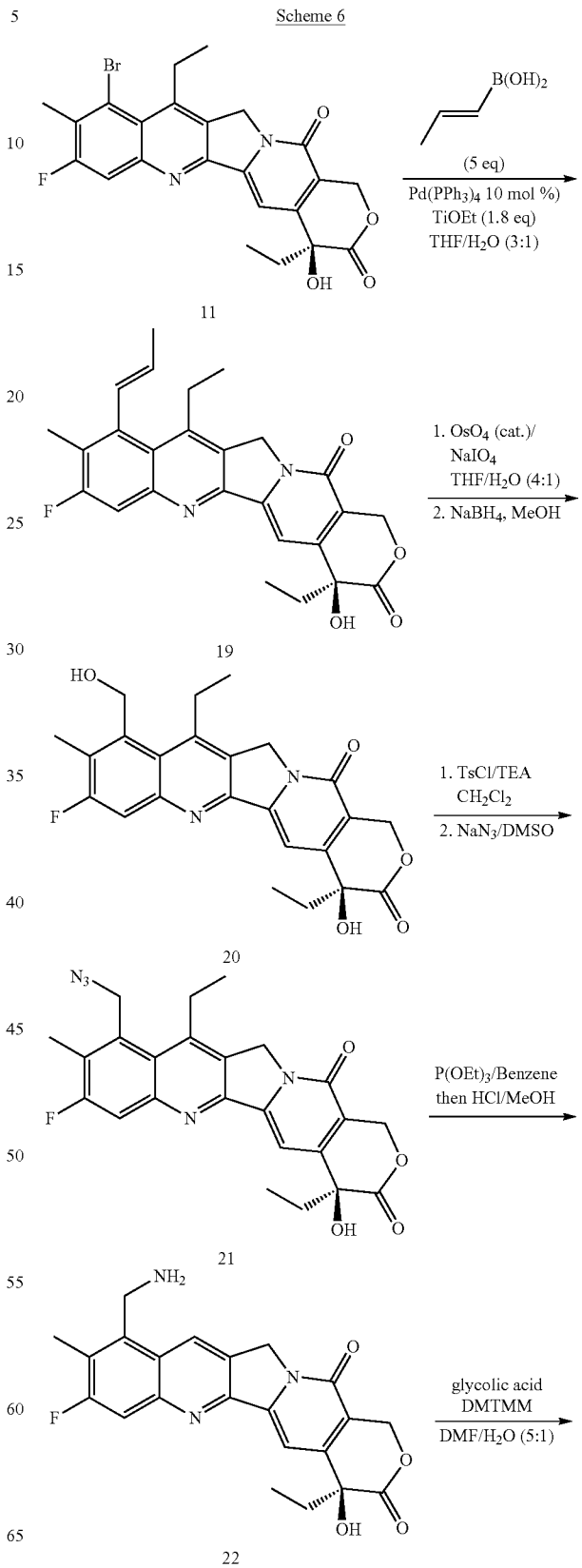

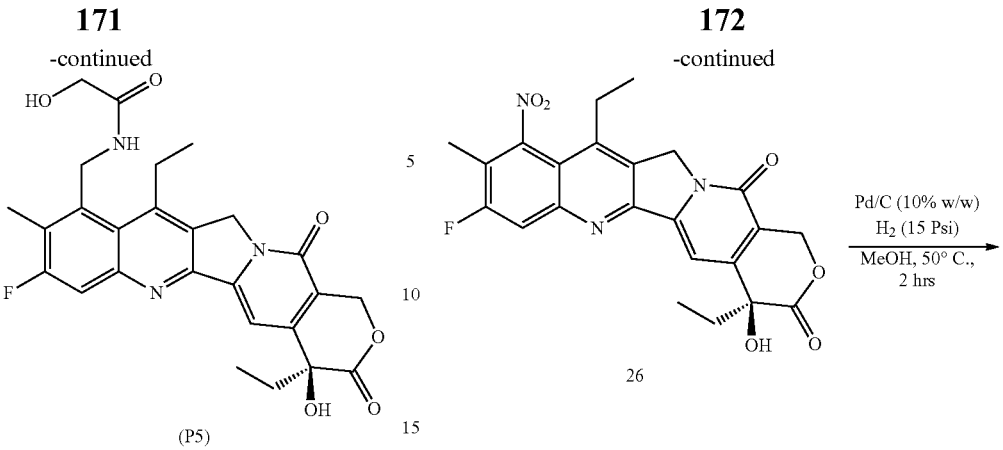
In embodiments, Scheme 7 provides an exemplary synthetic method for described compound (P6):
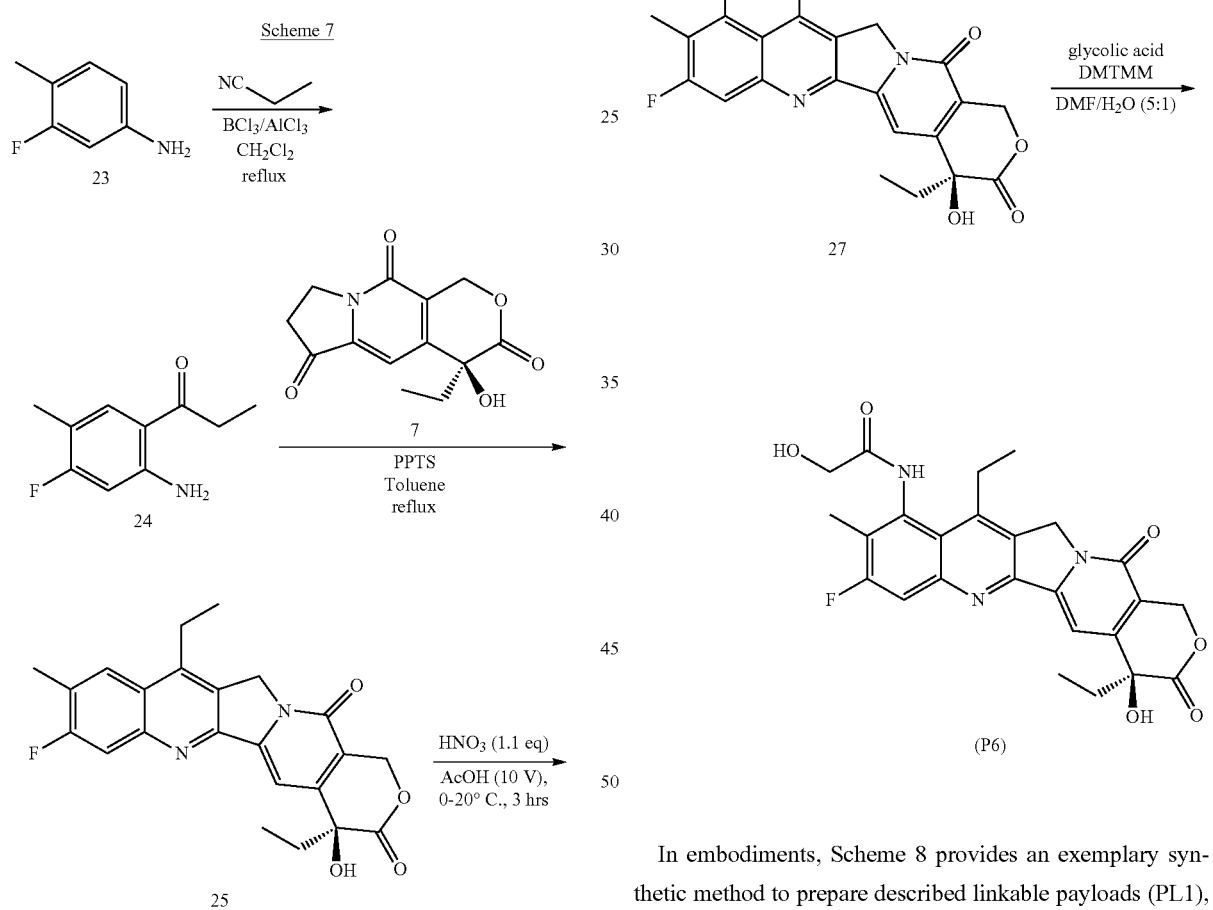
In embodiments, Scheme 8 provides an exemplary synthetic method to prepare described linkable payloads (PL1), (PL2), (PL4) and (PL7):
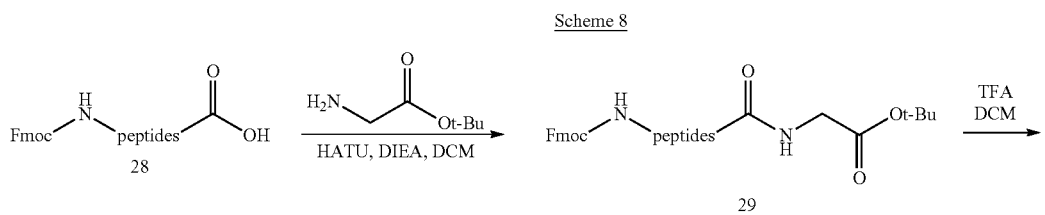

-continued
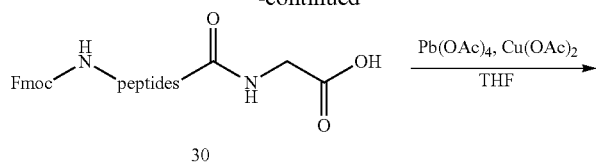
30
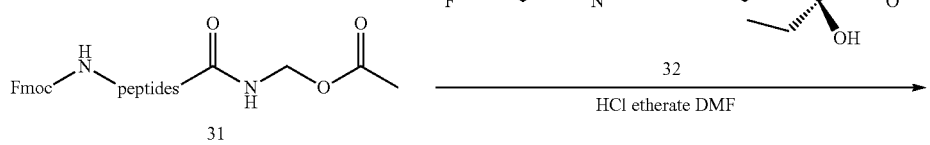
31
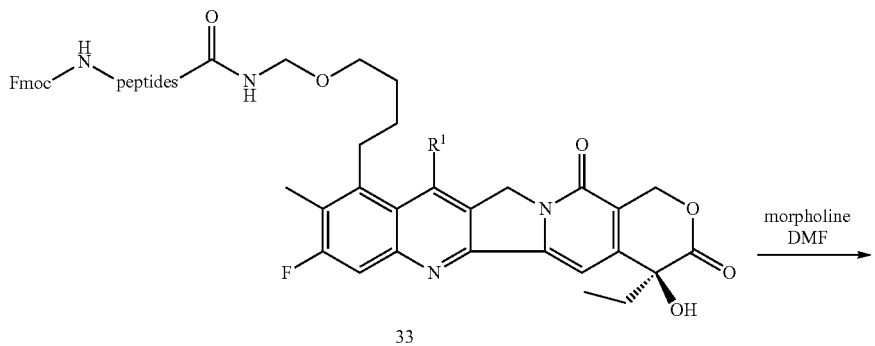
32
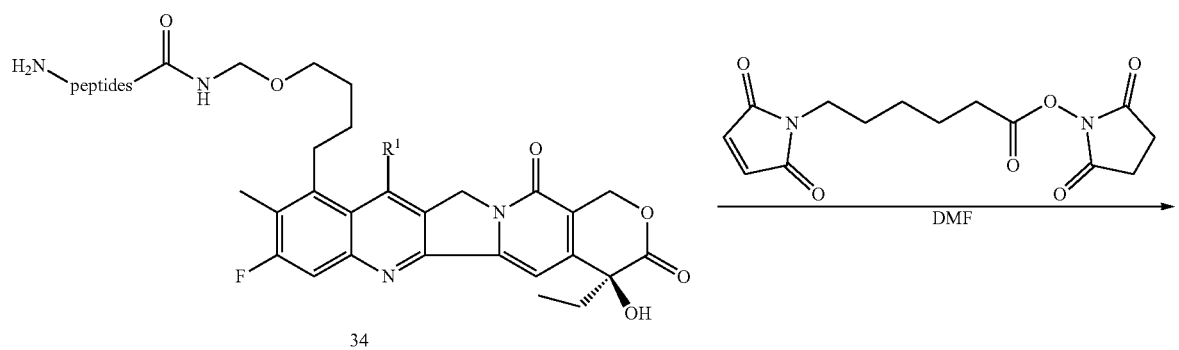
33
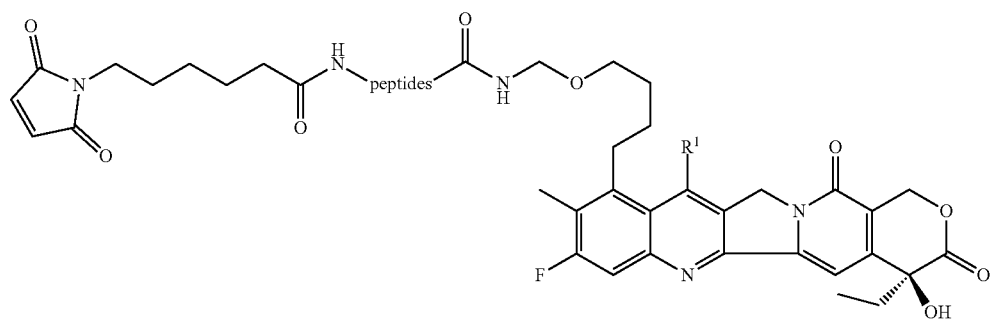
34
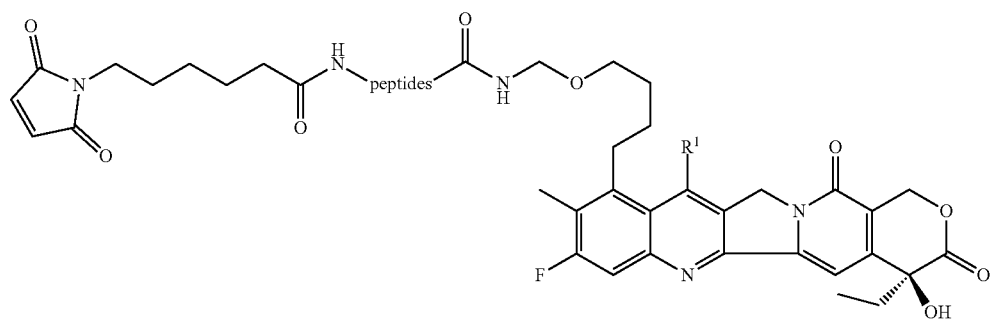
(PL1), (PL2), (PL4) and (PL7)

In embodiments, Scheme 9 provides an exemplary synthetic method for described compound MB-2 (PL1):
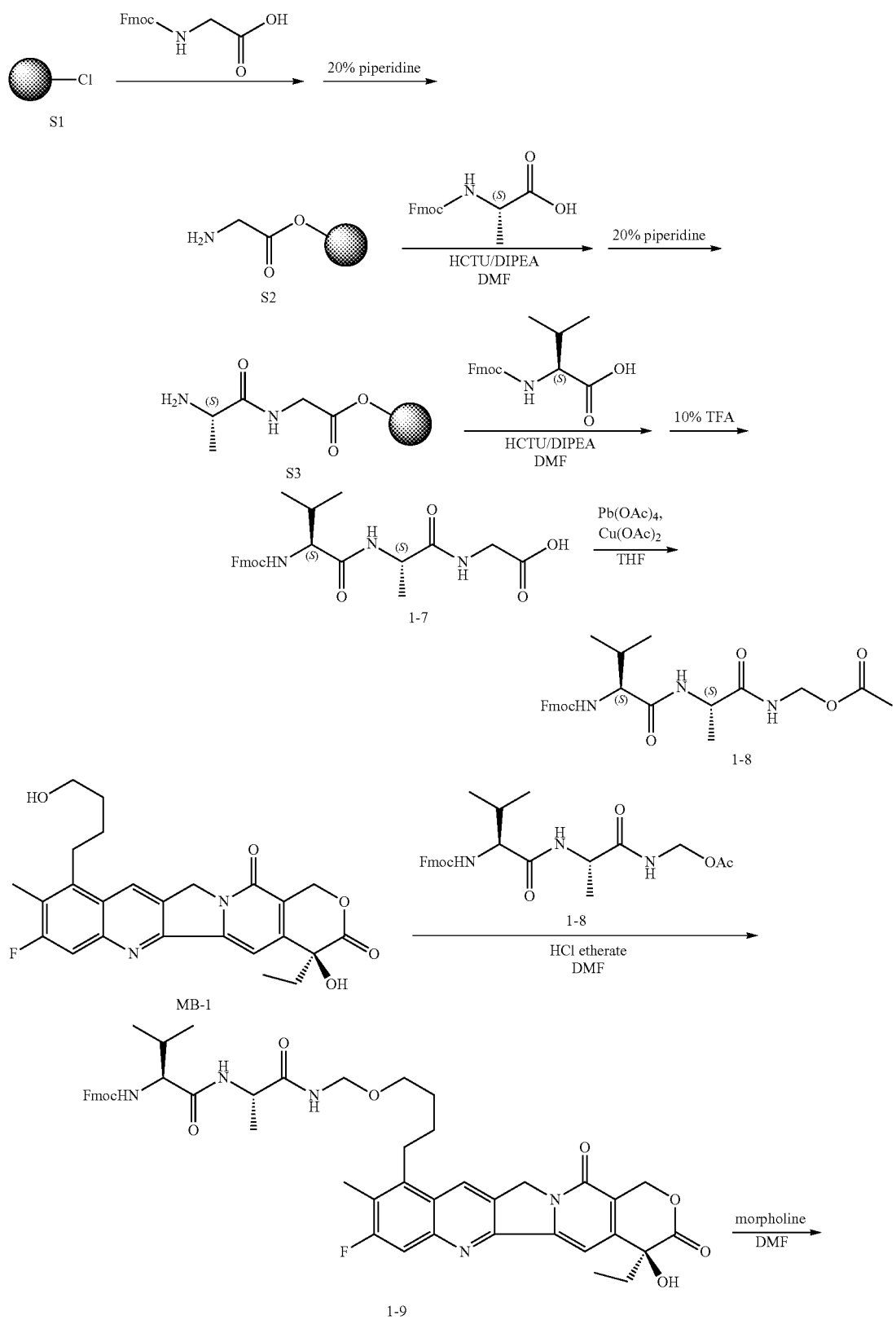

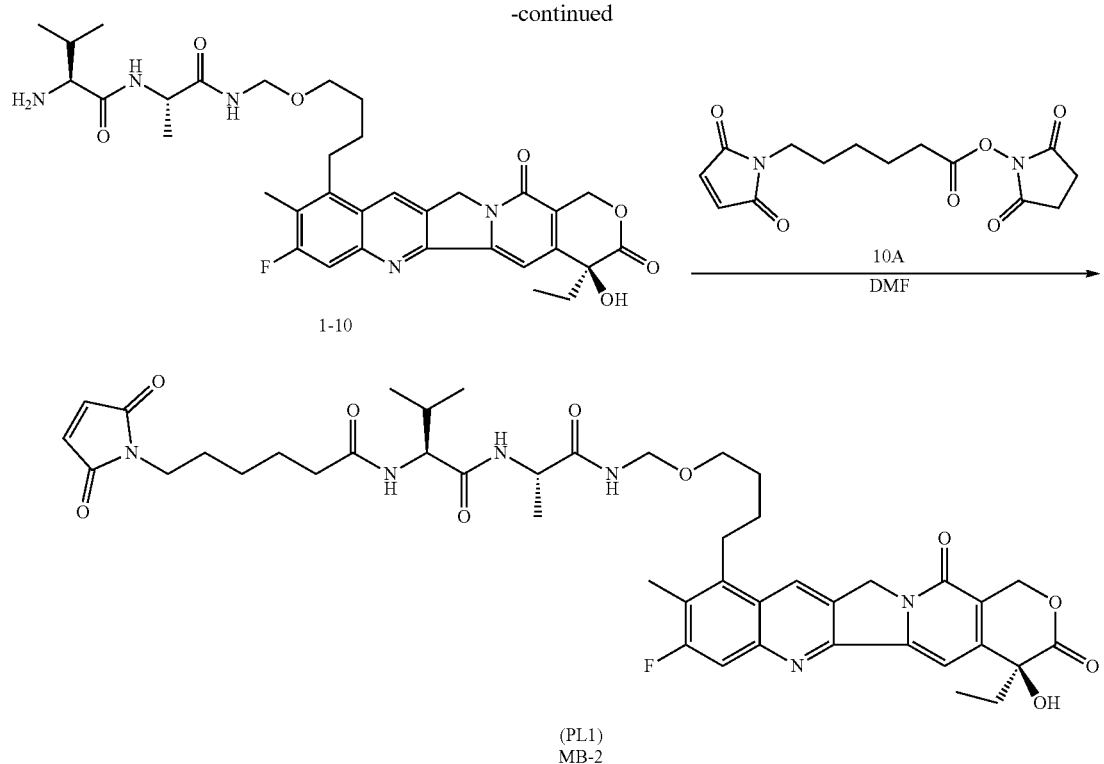
1-10
(PL1)
MB-2
In embodiments, Scheme 10 provides an exemplary synthetic method for described compound MB-3 (meditecan) (PL3):
Scheme 10
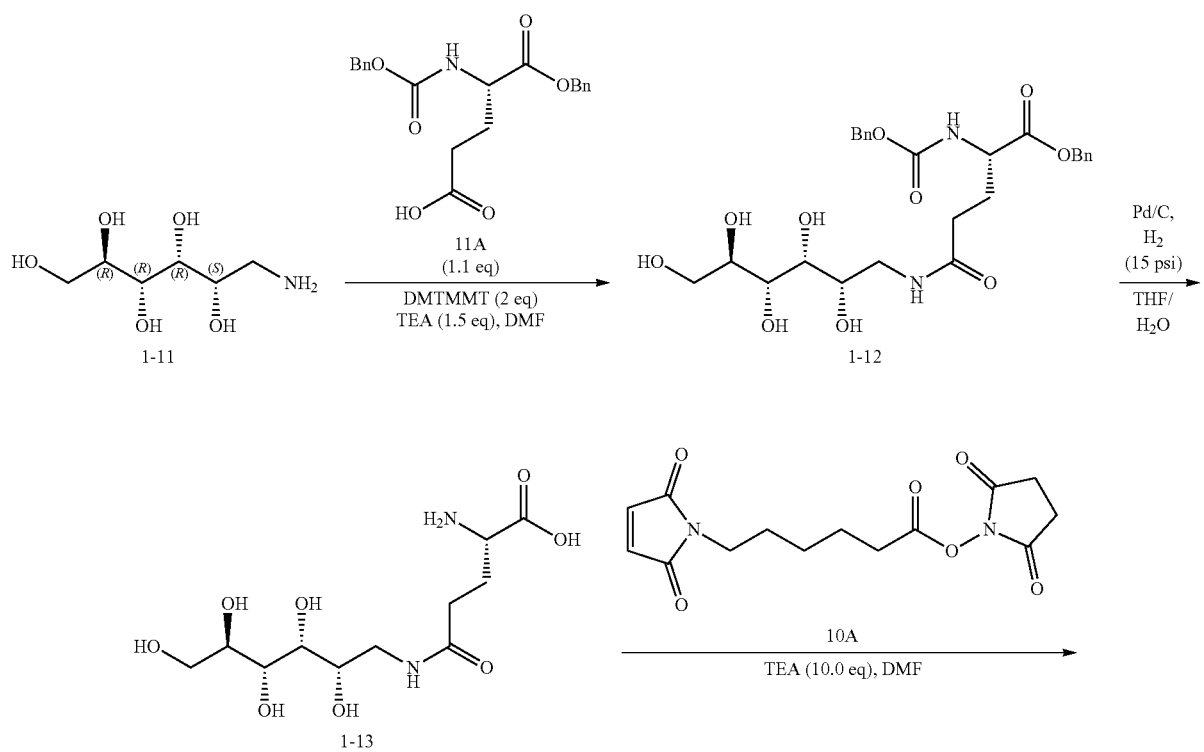

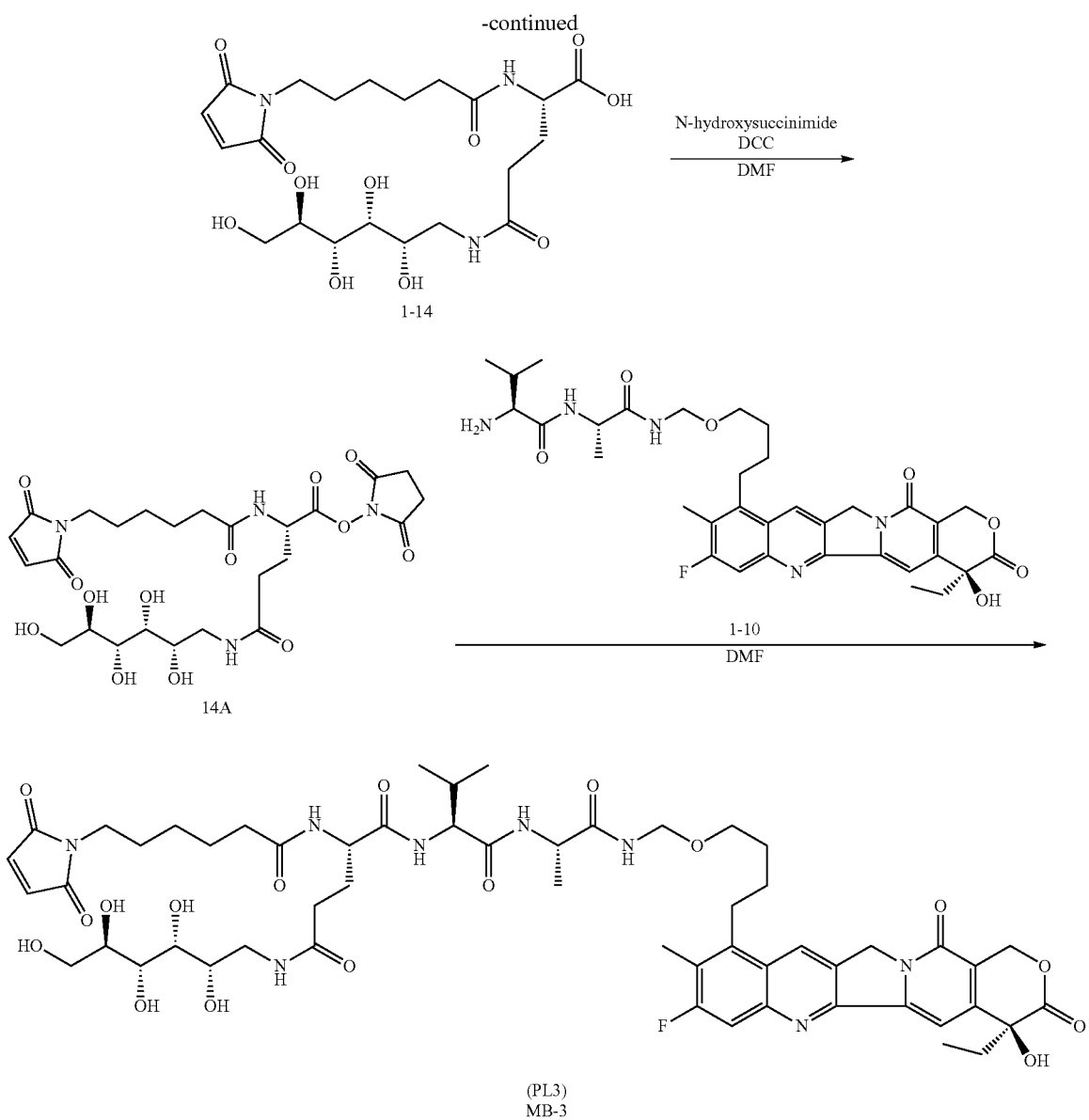
In embodiments, Scheme 11 provides an alternative synthetic method for described linkable payload MB-3 (meditecan) (PL3):
Scheme 11
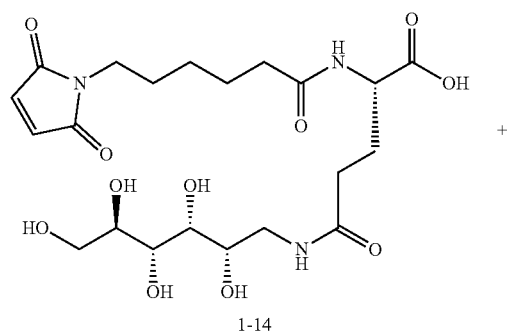

181
182
-continued
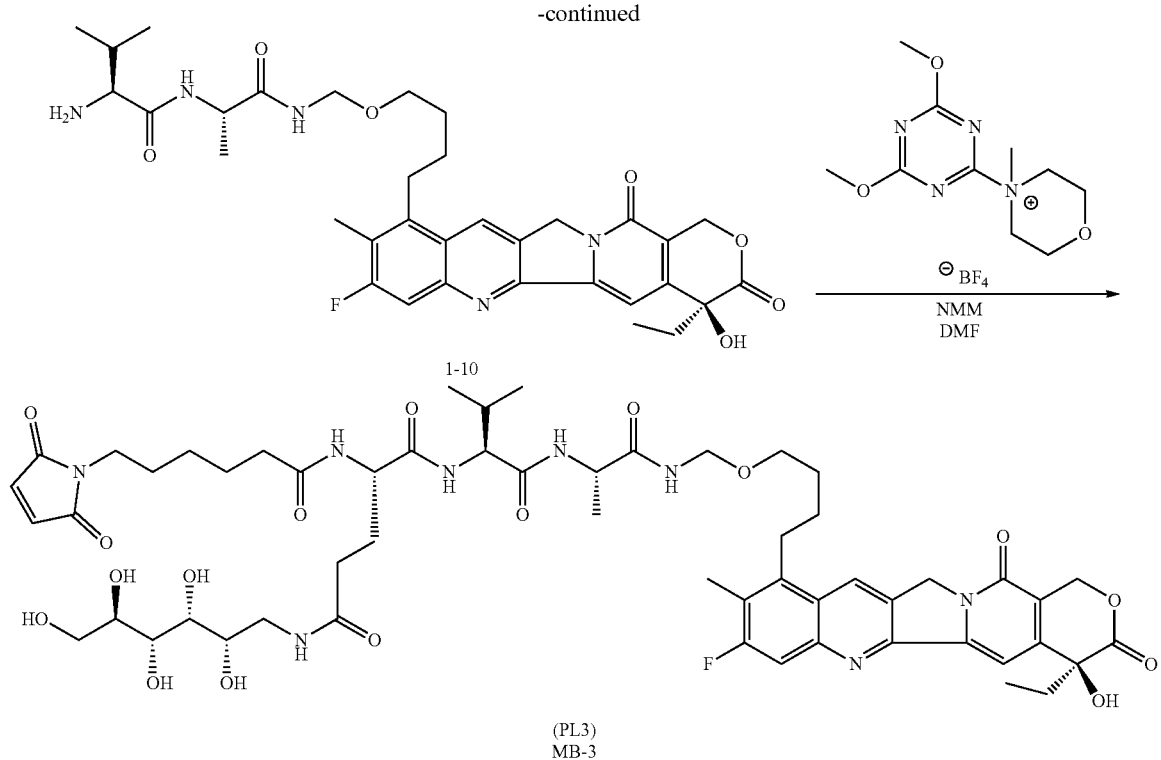
(PL3)
MB-3
In embodiments, Scheme 12 provides an exemplary synthetic method for described linkable payload (PL9):
Scheme 12
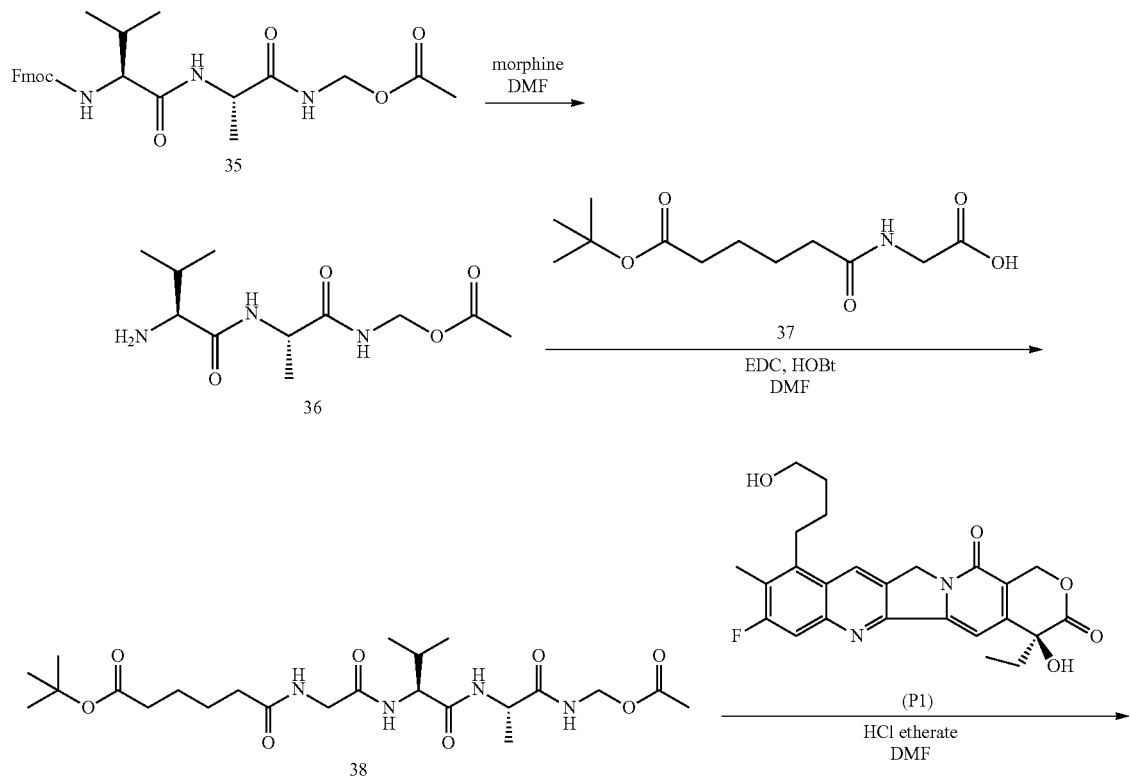

-continued
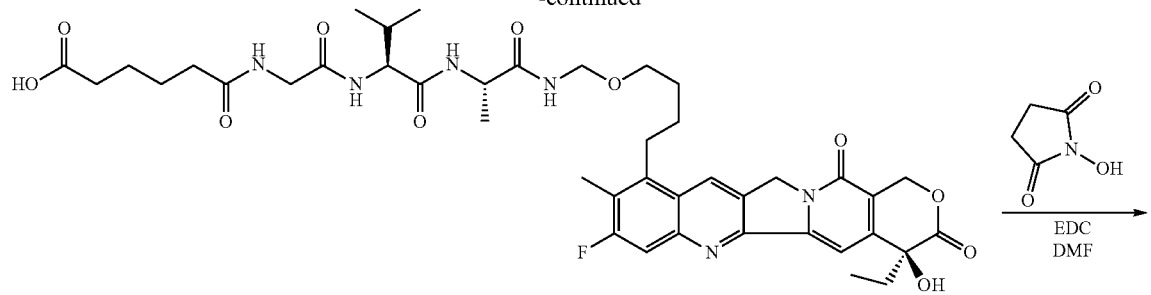
39
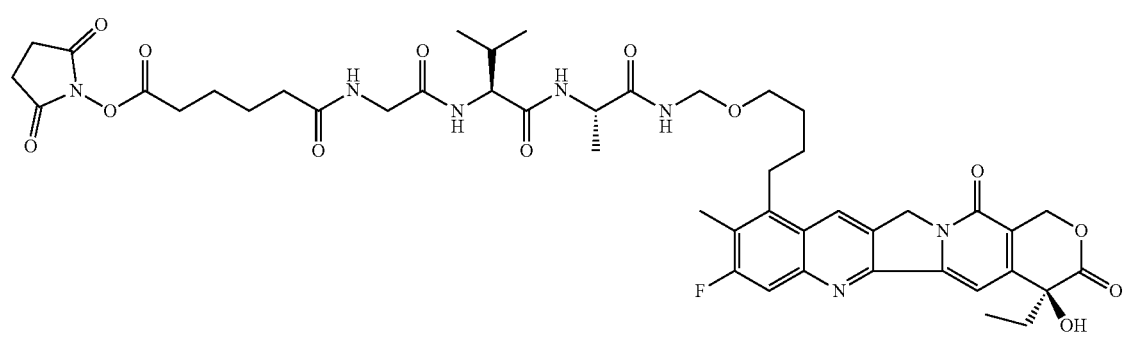
(PL9)
In embodiments, Scheme 13 provides an exemplary synthetic method for described compound PL12:
Scheme 13
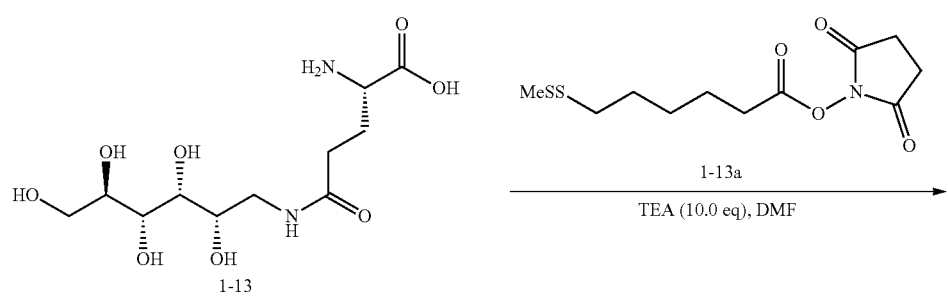
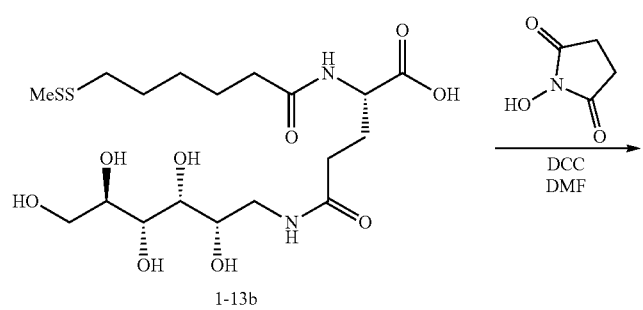

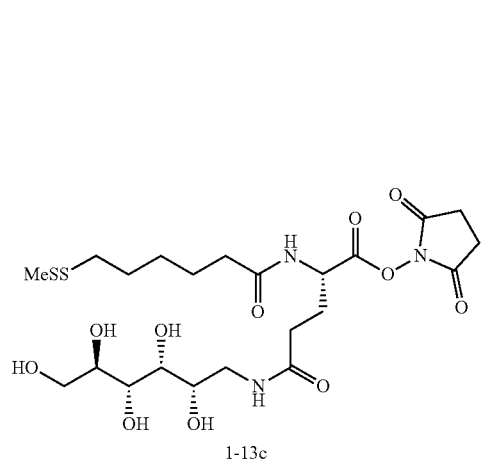
1-13c
-continued
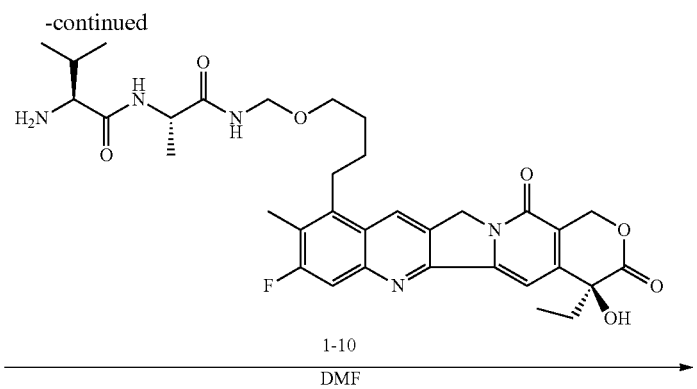
1-10
DMF
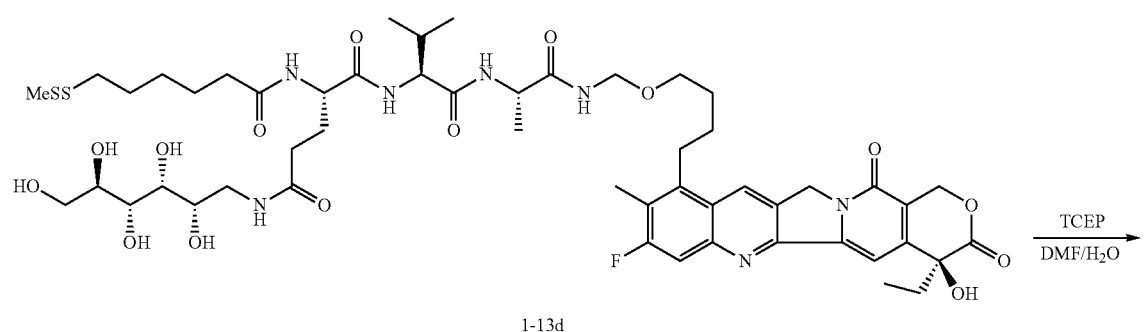
1-13d
TCEP
DMF/H$_2$O
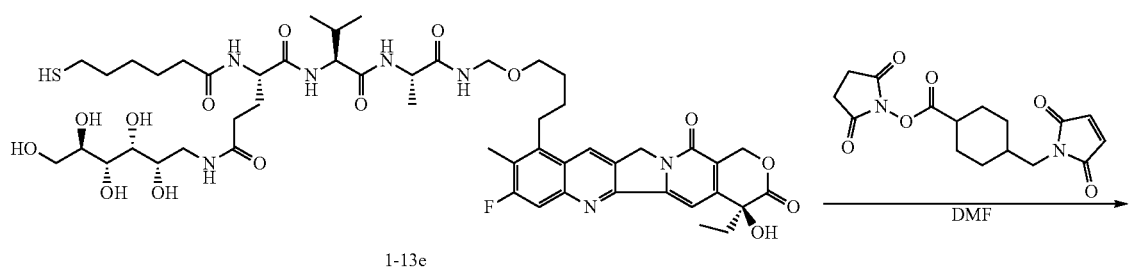
1-13e
DMF
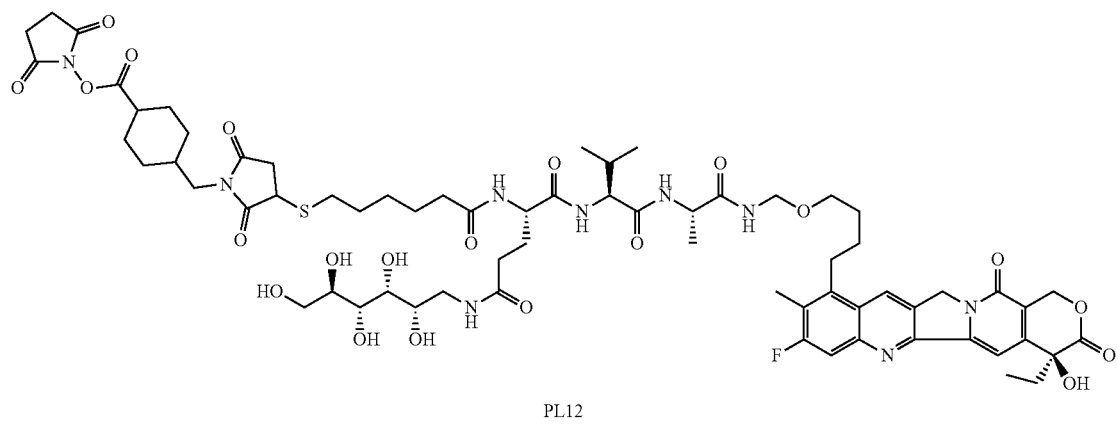
PL12

In embodiments, Scheme 14 provides an exemplary synthetic method for described compound PL13:
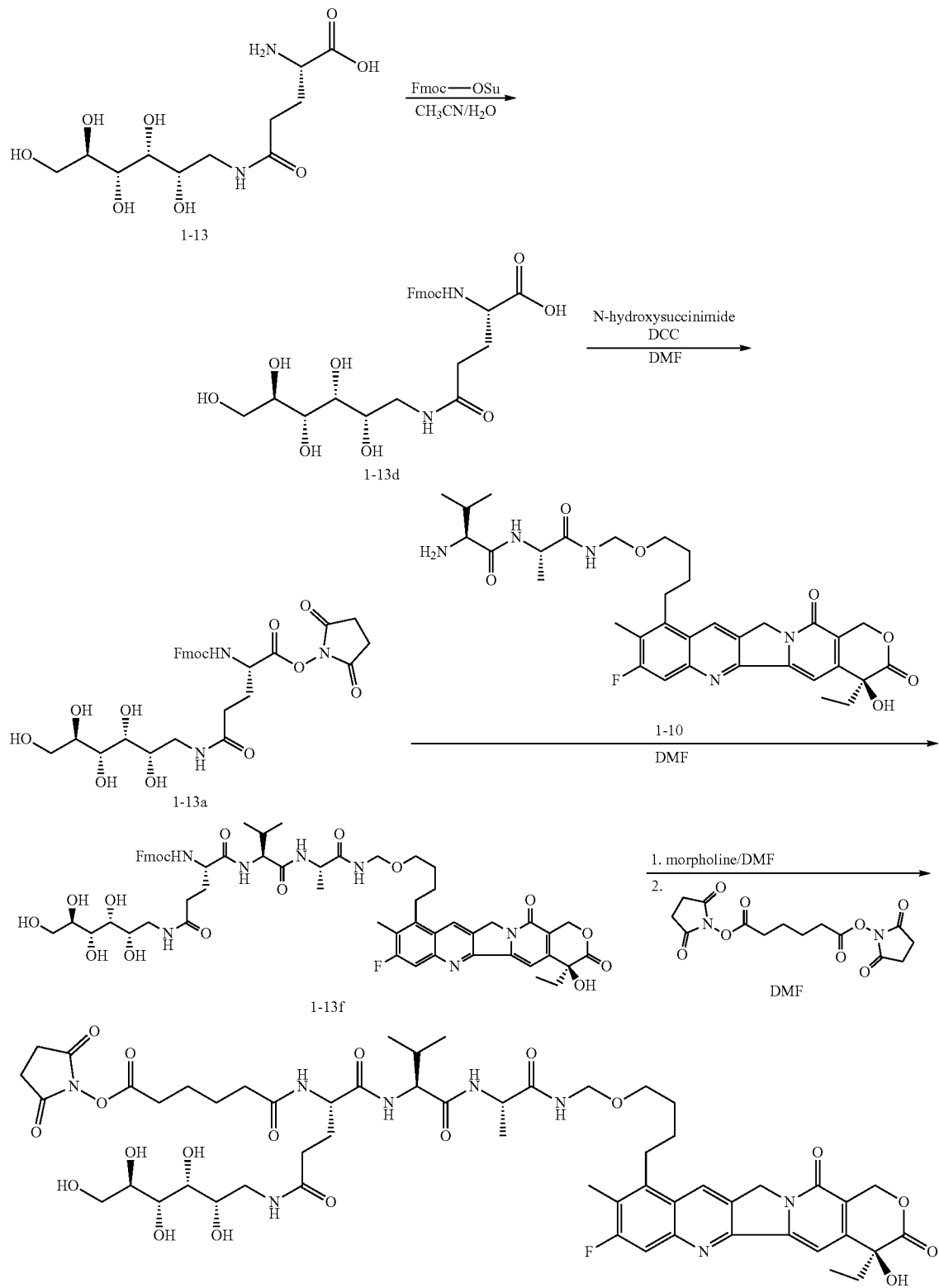

In embodiments, Scheme 15 provides an exemplary general method to prepare the conjugate (PL'):

Scheme 15

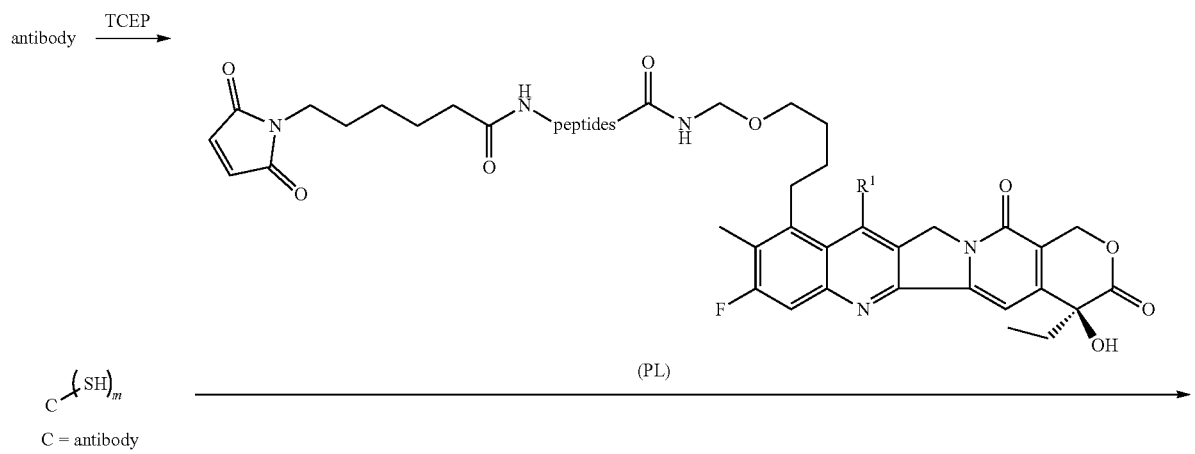

C = antibody
m = number of thiols

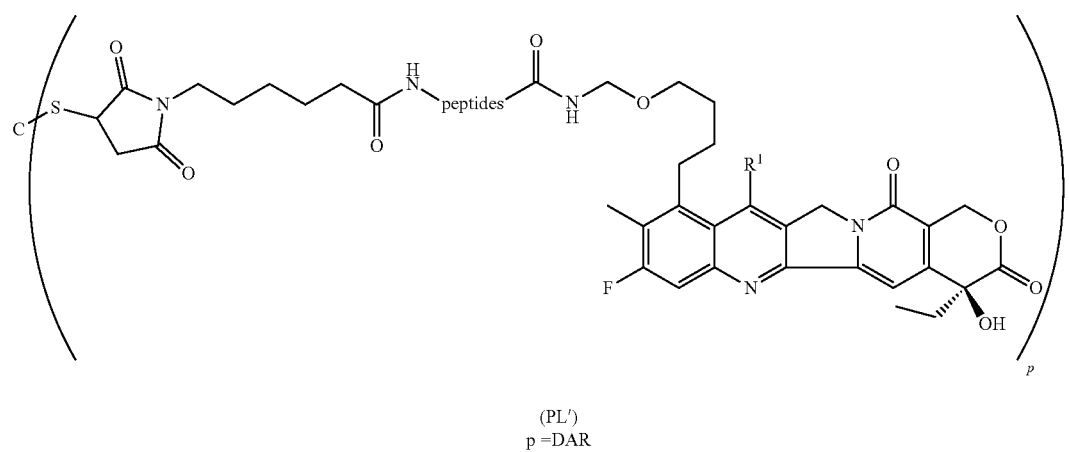

(PL')
p =DAR

In embodiments, an exemplary experimental procedure to prepare the conjugate (PL') with a drug to antibody ratio (DAR) between 7-8 or 8:

Antibody C is treated with 8 equivalents (2 equivalents per disulfide bond) of tris(2-carboxyethyl)phosphine hydrochloride (TCEP) in 50 mM pH7.4 phosphate buffer and 10 mM DTPA (diethylenetriaminepentaacetic acid) at 25° C. for 2 hours, followed by the addition of 12 equivalents of payload (PL) in DMSO (volume of DMSO is about 12-15% of the volume of the phosphate buffer). The obtained reaction solution is spinning on a tube rotator for 1 hour at 25° C. The reaction mixture is immediately purified using ultrafiltration tube (30 KD) for a few cycles with the formulation buffer. The resulting conjugate (PL') usually has a drug to antibody ratio (DAR) between 7-8 or 8, and is >95% monomeric measured by size exclusion chromatography.

In embodiments, an antibody-drug conjugate is MB-2a. In embodiments, Scheme 16 provides an exemplary synthetic method for described antibody-drug conjugate MB-2a:

Scheme 16
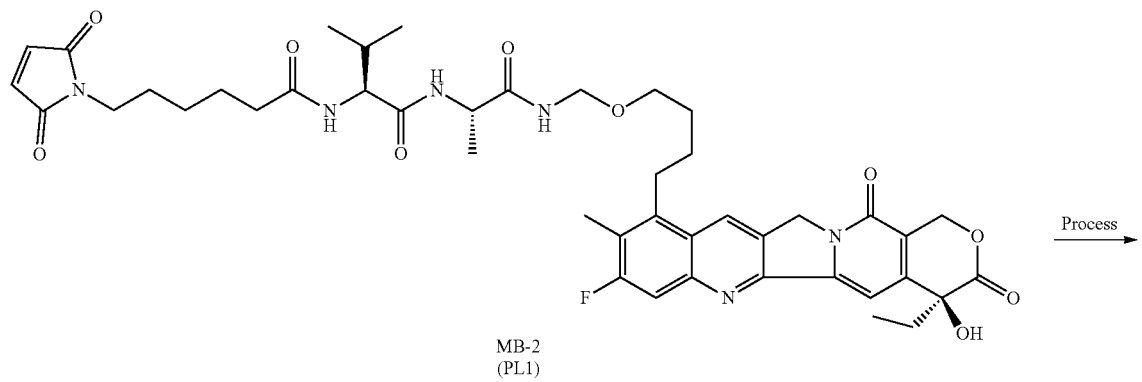
MB-2
(PL1)
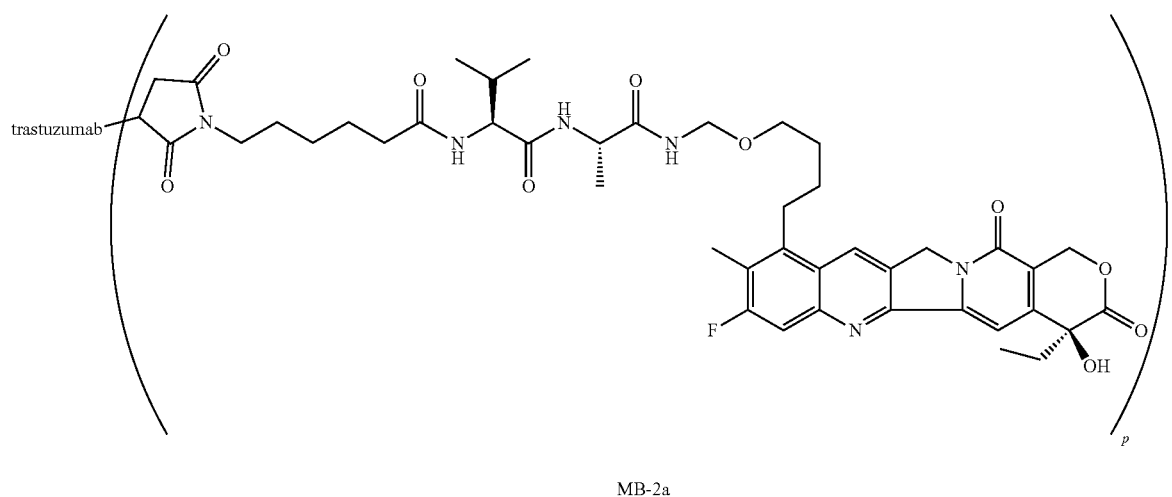
MB-2a
In embodiments, an antibody-drug conjugate is MB-3a (trastuzumab meditecan). In embodiments, Scheme 17 provides an exemplary synthetic method for described antibody-drug conjugate MB-3a (trastuzumab meditecan):
Scheme 17
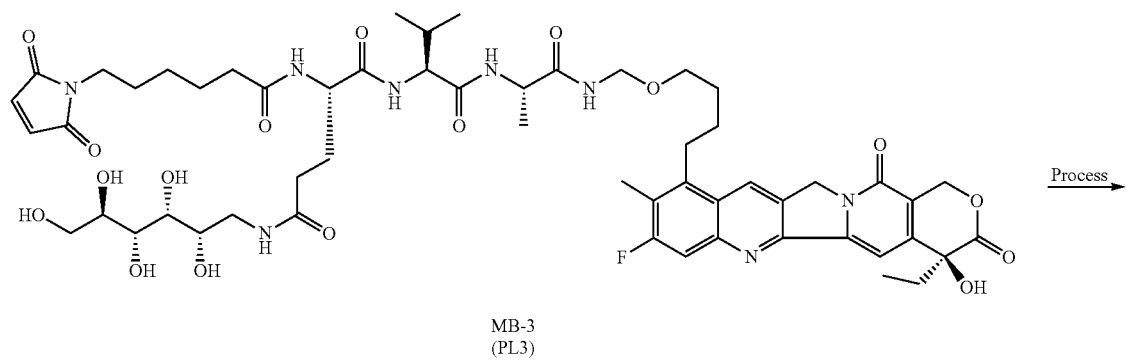
MB-3
(PL3)

-continued

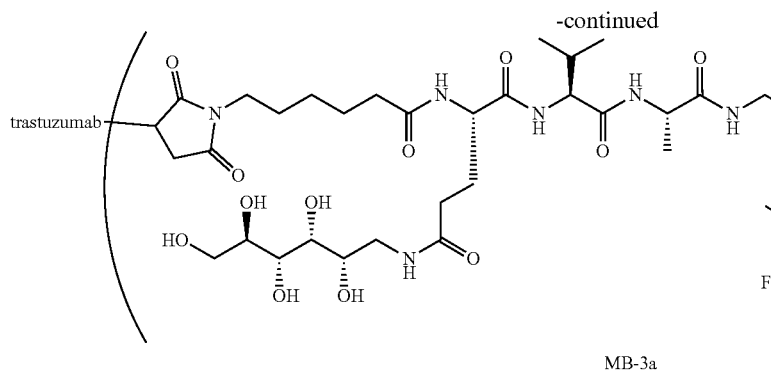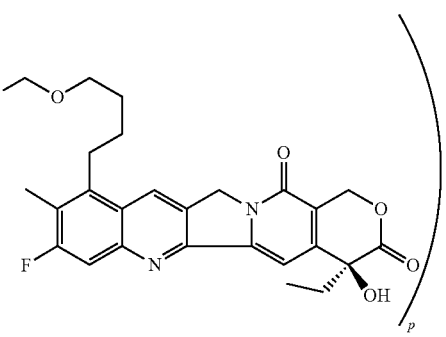

MB-3a

Camptothecin Conjugate Mixtures and Compositions

The present invention provides camptothecin conjugate mixtures and pharmaceutical compositions comprising any of the camptothecin conjugates (Formula III) described herein. The mixtures and pharmaceutical compositions comprise a plurality of conjugates. In some aspects, each of the conjugates in the mixture or composition is identical or substantially identical; however, the distribution of drug-linkers on the cell binding agent in the mixture or compositions may vary as well as the drug loading. For example, the conjugation technology used to conjugate drug-linkers to antibodies as the targeting ligand can result in a composition or mixture that is heterogeneous with respect to the distribution of camptothecin payload compounds on the antibody (cell binding agent) within the mixture and/or composition. In some aspects, the loading of camptothecin payload compounds on each of the antibody molecules in a mixture or composition of such molecules is an integer that ranges from 1 to 18.

In those aspects, when referring to the composition as a whole the loading of drug-linkers is a number ranging from 1 to about 18. Within the composition or mixture, there may also be a small percentage of unconjugated antibodies. The average number of drug-linkers per cell binding agent in the mixture or composition (i.e., average drug-load) is an important attribute as it determines the maximum amount of drug that can be delivered to the target cell. The average drug load can be about 1, 2 or about 2, 3 or about 3, 4 or about 4, 5 or about 5, 6 or about 6, 7 or about 7, 8 or about 8, 9 or about 9, 10 or about 10, 11 or about 11, 12 or about 12, 13 or about 13, 14 or about 14, 15 or about 15, 16 or about 16, 17 or about 17, 18 or about 18.

In some aspects, the mixtures and pharmaceutical compositions comprise a plurality (i.e., population) of conjugates; however, the conjugates are identical or substantially identical and are substantially homogenous with respect to the distribution of drug-linkers on the ligand molecules within the mixture and/or composition and with respect to loading of drug-linkers on the cell binding agent molecules within the mixture and/or composition. In some such aspects, the loading of drug-linkers on an antibody is 2 or 4. Within the composition or mixture, there may also be a small percentage of unconjugated antibodies. The average drug load in such embodiments is about 2 or about 4. Typically, such compositions and mixtures result from the use of site-specific conjugation techniques and conjugation is due to an introduced cysteine residue.

The average number of camptothecins (Formula I) or camptothecin payload compounds (Formula II) per cell binding agent in a preparation from a conjugation reaction may be characterized by conventional means such as HIC, UV, LC-MS, ELISA assay. The quantitative distribution of camptothecin conjugates in terms of p may also be determined. In some instances, separation, purification, and characterization of homogeneous Camptothecin Conjugates may be achieved by means such as reverse phase HPLC or electrophoresis.

In some aspects, the compositions are pharmaceutical compositions comprising the camptothecin conjugates described herein and a pharmaceutically acceptable carrier. In some aspects, the pharmaceutical composition is in liquid form. In some aspects, the pharmaceutical composition is a solid. In some aspects, the pharmaceutical composition is a lyophilized powder.

The compositions, including pharmaceutical compositions, can be provided in purified form. As used herein, "purified" means that when isolated, the isolate contains at least 95%, and in another aspect at least 98%, of Conjugate by weight of the isolate.

Methods of Use
Compositions and Methods of Administration

In another aspect, the invention features a pharmaceutical composition comprising any compound described herein (e.g., any compound of Formula (I), Formula (II), or Formula (III), or a pharmaceutically acceptable salt thereof, as described herein. In embodiments, a pharmaceutical composition comprises a pharmaceutically acceptable carrier.

In embodiments, a pharmaceutical composition comprises a conjugate according to Formula (III).

In embodiments, the invention provides pharmaceutical compositions comprising the camptothecin conjugates described herein and a pharmaceutically acceptable carrier. The camptothecin conjugates can be in any form that allows the compound to be administered to a patient for treatment of a disorder associated with expression of the antigen to which the cell binding agent binds. For example, the conjugates can be in the form of a liquid or solid. The preferred route of administration is parenteral. Parenteral administration includes subcutaneous injections, intravenous, intramuscular, intrasternal injection or infusion techniques. In one aspect, the compositions are administered parenterally. In one aspect, the conjugates are administered intravenously. Administration can be by any convenient route, for example by infusion or bolus injection.

Pharmaceutical compositions can be formulated to allow a compound to be bioavailable upon administration of the composition to a patient. Compositions can take the form of one or more dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of animal (e.g., human), the particular form of the compound, the manner of administration, and the composition employed.

The composition can be, for example, in the form of a liquid. The liquid can be useful for delivery by injection. In a composition for administration by injection, one or more of a surfactant, preservative, wetting agent, dispersing agent, suspending agent, buffer, stabilizer and isotonic agent can also be included.

The liquid compositions, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as amino acids, acetates, citrates or phosphates; detergents, such as nonionic surfactants, polyols; and agents for the adjustment of tonicity such as sodium chloride or dextrose. A parenteral composition can be enclosed in ampoule, a disposable syringe or a multiple-dose vial made of glass, plastic or other material. Physiological saline is an exemplary adjuvant. An injectable composition is preferably sterile.

The amount of the conjugate that is effective in the treatment of a particular disorder or condition will depend on the nature of the disorder or condition, and can be determined by standard clinical techniques. In addition, in vitro or in vivo assays can optionally be employed to help identify optimal dosage ranges. The precise dose to be employed in the compositions will also depend on the route of administration, and the seriousness of the disease or disorder, and should be decided according to the judgment of the practitioner and each patient's circumstances.

The compositions comprise an effective amount of a compound such that a suitable dosage will be obtained. Typically, this amount is at least about 0.01% of a compound by weight of the composition.

For intravenous administration, the composition can comprise from about 0.01 to about 100 mg of a camptothecin conjugate per kg of the animal's body weight. In one aspect, the composition can include from about 1 to about 100 mg of a Camptothecin Conjugate per kg of the animal's body weight. In another aspect, the amount administered will be in the range from about 0.1 to about 25 mg/kg of body weight of a compound. Depending on the drug used, the dosage can be even lower, for example, 1.0 µg/kg to 5.0 mg/kg, 4.0 mg/kg, 3.0 mg/kg, 2.0 mg/kg or 1.0 µg/kg, or 1.0 µg/kg to 500.0 µg/kg of the subject's body weight.

Generally, the dosage of a conjugate administered to a patient is typically about 0.01 mg/kg to about 100 mg/kg of the subject's body weight or from 1.0 µg/kg to 5.0 mg/kg of the subject's body weight. In embodiments, the dosage administered to a patient is between about 0.01 mg/kg to about 15 mg/kg of the subject's body weight. In embodiments, the dosage administered to a patient is between about 0.1 mg/kg and about 15 mg/kg of the subject's body weight. In embodiments, the dosage administered to a patient is between about 0.1 mg/kg and about 20 mg/kg of the subject's body weight. In embodiments, the dosage administered is between about 0.1 mg/kg to about 5 mg/kg or about 0.1 mg/kg to about 10 mg/kg of the subject's body weight. In embodiments, the dosage administered is between about 1 mg/kg to about 15 mg/kg of the subject's body weight. In embodiments, the dosage administered is between about 1 mg/kg to about 10 mg/kg of the subject's body weight. In embodiments, the dosage administered is between about 0.1 to 4 mg/kg, even more preferably 0.1 to 3.2 mg/kg, or even more preferably 0.1 to 2.7 mg/kg of the subject's body weight over a treatment cycle.

The term "carrier" refers to a diluent, adjuvant or excipient, with which a compound is administered. Such pharmaceutical carriers can be liquids, such as water and oils, including those of petroleum, animal, vegetable or synthetic origin, such as peanut oil, soybean oil, mineral oil, sesame oil. The carriers can be saline, gum acacia, gelatin, starch paste, talc, keratin, colloidal silica, urea. In addition, auxiliary, stabilizing, thickening, lubricating and coloring agents can be used. In one embodiment, when administered to a patient, the compound or compositions and pharmaceutically acceptable carriers are sterile.

Water is an exemplary carrier when the compounds are administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol. The present compositions, if desired, can also contain minor amounts of wetting or emulsifying agents, or pH buffering agents.

In an embodiment, the conjugates are formulated in accordance with routine procedures as a pharmaceutical composition adapted for intravenous administration to animals, particularly human beings. Typically, the carriers or vehicles for intravenous administration are sterile isotonic aqueous buffer solutions. Where necessary, the compositions can also include a solubilizing agent. Compositions for intravenous administration can optionally comprise a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachets indicating the quantity of active agent. Where a conjugate is to be administered by infusion, it can be dispensed, for example, with an infusion bottle containing sterile pharmaceutical grade water or saline. Where the conjugate is administered by injection, an ampoule of sterile water for injection or saline can be provided so that the ingredients can be mixed prior to administration.

The pharmaceutical compositions are generally formulated as sterile, substantially isotonic and in full compliance with all Good Manufacturing Practice (GMP) regulations of the U.S. Food and Drug Administration.

Treatment of Cancer

Compounds described herein (e.g., any compound according to any one of Formula (I), Formula (II), or Formula (III) can be effective for selectively inducing cell death in certain populations (e.g., cells overexpressing certain antigens including those described herein such as tumor associated antigens).

In vitro cytotoxicity assay:

Cytotoxic potencies of the compounds are assessed in flat-bottomed 96-well cell culture plates (Corning Costar) using cell counting Kit-8 (CCK-8) assay (Shanghai Life Lab Biotech Co., Ltd.). Briefly, human tumor cells (2,000-10,000 cells/well, depending on the cell line), in the appropriate culture medium are incubated, with the compounds, or with conjugates in the presence or absence of an excess of the corresponding unconjugated antibodies, for 120 hours, at 37° C., 5% $CO_2$.

For example, for any compound according to Formula (III), appropriate selection of a cell binding agent can afford effective, highly selective targeting of cancer cells, which would be useful The camptothecin conjugates (e.g., any compound according to Formula (III)) described herein are useful for inhibiting abnormal cell proliferation (e.g., of a tumor cell or cancer cell, causing apoptosis in a tumor or cancer cell), or for treating cancer in a patient. Accordingly, provided herein are methods of treating cancer in a subject in need thereof, the method includes administering to the subject one or more camptothecin conjugates described herein.

In embodiments, the invention features a method of treating a cell proliferative disease or disorder or inhibiting abnormal cell growth, said method comprising administering any compound of Formula (III), or a pharmaceutically acceptable salt thereof, as described herein, or a pharmaceutical composition comprising any compound of Formula (III), or a pharmaceutically acceptable salt thereof, as described herein.

Accordingly, compounds described herein (e.g., any compound according to Formula (III)) can be used accordingly for the treatment of various cancers. In embodiments, a camptothecin conjugate can be used to deliver a drug to a tumor cell or cancer cell. Without being bound by theory, in one embodiment, the cell binding agent of a camptothecin conjugate binds to or associates with a cancer-cell or a tumor-cell-associated antigen, and the camptothecin conjugate can be taken up (internalized) inside the tumor cell or cancer cell through receptor-mediated endocytosis or other internalization mechanism. The antigen can be attached to a tumor cell or cancer cell or can be an extracellular matrix protein associated with the tumor cell or cancer cell. Once inside the cell, the drug is released via peptide cleavage within the cell. In an alternative embodiment, the free drug is released from the camptothecin conjugate outside the tumor cell or cancer cell, and the free drug subsequently penetrates the cell.

In one embodiment, the cell binding agent binds to the tumor cell or cancer cell.

In another embodiment, the cell binding agent binds to a tumor cell or cancer cell antigen which is on the surface of the tumor cell or cancer cell.

In another embodiment, the cell binding agent binds to a tumor cell or cancer cell antigen which is an extracellular matrix protein associated with the tumor cell or cancer cell.

The specificity of the cell binding agent for a particular tumor cell or cancer cell can be important for determining the tumors or cancers that are most effectively treated.

Cancers that can be treated with a camptothecin conjugate include, but are not limited to, hematopoietic cancers such as, for example, lymphomas (Hodgkin Lymphoma and Non-Hodgkin Lymphomas) and leukemias and solid tumors. Examples of hematopoietic cancers include follicular lymphoma, anaplastic large cell lymphoma, mantle cell lymphoma, acute myeloblastic leukemia, chronic myelocytic leukemia, chronic lymphocytic leukemia, diffuse large B cell lymphoma, and multiple myeloma. Examples of solid tumors include fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

In embodiments, a cancer is adenocarcinoma, brain cancer, bladder cancer, breast cancer, cervical cancer, choriocarcinoma, a CNS tumor, colon or colorectal cancer, diffuse intrinsic pontine glioma (DIPG), endometrial cancer, esophageal cancer, Ewing's sarcoma, fallopian tube cancer, gall bladder cancer, gastric cancer, glioblastoma, head and neck cancer, hematological cancer, Hodgkin's lymphoma, kidney cancer, laryngeal cancer, leukemia, liver cancer, lung cancer, lymphoma, melanoma, Merkel cell carcinoma, mesothelioma, multiple myeloma, myelodysplastic syndrome (MDS), neuroblastoma, non-Hodgkin's lymphoma, osteosarcoma, pancreatic cancer, peritoneal cancer, prostate cancer, ovarian cancer, renal cancer, rhabdomyosarcoma salivary gland cancer, sarcoma, skin cancer, small intestine cancer, squamous cell carcinoma, testicular cancer, thyroid cancer, uterine cancer, or Wilms tumor.

In embodiments, a cancer is breast cancer.

Multi-Modality Therapy for Cancer

Cancers, including, but not limited to, a tumor, metastasis, or other disease or disorder characterized by uncontrolled cell growth, can be treated or inhibited by administration of a camptothecin conjugate.

In other embodiments, methods for treating cancer are provided, including administering to a patient in need thereof an effective amount of a camptothecin conjugate and a chemotherapeutic agent. In one embodiment, the chemotherapeutic agent is that with which treatment of the cancer has not been found to be refractory. In another embodiment, the chemotherapeutic agent is that with which the treatment of cancer has been found to be refractory. The camptothecin conjugates can be administered to a patient that has also undergone surgery as treatment for the cancer.

In embodiments, the patient also receives an additional treatment, such as radiation therapy. In a specific embodiment, the camptothecin conjugate is administered concurrently with the chemotherapeutic agent or with radiation therapy. In another specific embodiment, the chemotherapeutic agent or radiation therapy is administered prior or subsequent to administration of a camptothecin conjugate.

A chemotherapeutic agent can be administered over a series of sessions. Any one or a combination of the chemotherapeutic agents, such a standard of care chemotherapeutic agent(s), can be administered.

Additionally, methods of treatment of cancer with a camptothecin conjugate are provided as an alternative to chemotherapy or radiation therapy where the chemotherapy or the radiation therapy has proven or can prove too toxic, e.g., results in unacceptable or unbearable side effects, for the subject being treated. The patient being treated can, optionally, be treated with another cancer treatment such as surgery, radiation therapy or chemotherapy, depending on which treatment is found to be acceptable or bearable.

Treatment of Autoimmune Diseases

The camptothecin conjugates are useful for killing or inhibiting the unwanted replication of cells that produces an autoimmune disease or for treating an autoimmune disease.

The camptothecin conjugates can be used accordingly in a variety of settings for the treatment of an autoimmune disease in a patient. The camptothecin conjugates can be used to deliver a drug to a target cell. Without being bound by theory, in one embodiment, the camptothecin conjugate associates with an antigen on the surface of a pro-inflammatory or inappropriately-stimulated immune cell, and the camptothecin conjugate is then taken up inside the targeted cell through receptor-mediated endocytosis. Once inside the cell, the cell binding agent is cleaved, resulting in release of the camptothecin. The released camptothecin is then free to migrate in the cytosol and induce cytotoxic or cytostatic activities. In an alternative embodiment, the drug is cleaved from the camptothecin conjugate outside the target cell, and the camptothecin subsequently penetrates the cell.

In one embodiment, the cell binding agent binds to an autoimmune antigen. In one aspect, the antigen is on the surface of a cell involved in an autoimmune condition.

In one embodiment, the cell binding agent binds to activated lymphocytes that are associated with the autoimmune disease state.

In a further embodiment, the camptothecin conjugate kills or inhibits the multiplication of cells that produce an autoimmune antibody associated with a particular autoimmune disease.

Particular types of autoimmune diseases that can be treated with the camptothecin conjugates include, but are not limited to, Th2 lymphocyte related disorders (e.g., atopic dermatitis, atopic asthma, rhinoconjunctivitis, allergic rhinitis, Omenn's syndrome, systemic sclerosis, and graft versus host disease); Th1 lymphocyte-related disorders (e.g., rheumatoid arthritis, multiple sclerosis, psoriasis, Sjorgren's syndrome, Hashimoto's thyroiditis, Grave's disease, primary biliary cirrhosis, Wegener's granulomatosis, and tuberculosis); and activated B lymphocyte-related disorders (e.g., systemic lupus erythematosus, Goodpasture's syndrome, rheumatoid arthritis, and type I diabetes).

Multi-Drug Therapy of Autoimmune Diseases

Methods for treating an autoimmune disease are also disclosed including administering to a patient in need thereof an effective amount of a camptothecin conjugate and another therapeutic agent known for the treatment of an autoimmune disease.

Methods of Preparing Camptothecin Conjugates

The camptothecin conjugates described herein can be prepared in either a serial construction of antibodies, linkers, and drug units, or in a convergent fashion by assembling portions followed by a completed assembly step.

In one group of embodiments, camptothecin payload compounds as provided herein, are combined with a suitable cell binding agent to facilitate covalent attachment of the camptothecin payload compounds to the cell binding agent. In embodiments, the cell binding agent is an antibody that has at least 2, at least 4, at least 6 or 8 thiols available for attachment of the camptothecin payload compounds as a result of reducing interchain disulfide linkages. In embodiments, the camptothecin payload compounds are attached to the cell binding agnet through an introduced cysteine moiety on the antibody.

Kits for Therapeutic Use

In some aspects, kits for use in cancer treatment and the treatment of autoimmune diseases are provided. Such kits can include a pharmaceutical composition that comprises a camptothecin conjugate described herein.

In embodiments, the kit can include instructions for use in any of the therapeutic methods described herein. The included instructions can provide a description of administration of the pharmaceutical compositions to a subject to achieve the intended activity, e.g., treatment of a disease or condition such as cancer, in a subject. In embodiments, the instructions relating to the use of the pharmaceutical compositions described herein can include information as to dosage, dosing schedule, and route of administration for the intended treatment. The containers can be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

In embodiments, the kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. In embodiments, a kit can have a sterile access port (for example, the container can be an intravenous solution bag or a vial having a stopper pierceable by a hypodermic injection needle).

In embodiments, the kits provided herein include an additional therapeutic agent useful in treating a cancer of autoimmune disease as described herein.

EXAMPLES

The following abbreviations are used for the following terms:
ADCs Antibody-drug conjugates
ACN Acetonitrile
DAR Drug to antibody ratio
DCC N,N'-Dicyclohexylcarbodiimide
DCM Dichloromethane
DIPA Diisopropylamine
DIPEA Diisopropylethylamine
DMF Dimethylformamide
DMSO Dimethylsulfoxide
DMTMM 4-(4,6-Dimethoxy-1,3,5-triazin-2-yl)-4-methylmorpholinium chloride
DMTMMT 4-(4,6-Dimethoxy-1,3,5-triazin-2-yl)-4-methylmorpholinium tetrafluoroborate
DTPA Diethylenetriaminepentaacetic acid
HIC Hidrophobic interaction chromatography
i.v. Intravenous
LC-MS Liquid chromatography-mass spectrometry
M molar
nM nanomolar
NMM N-methylmorpholine
PPTS Pyridinium p-toluenesulfonate
PTSA 4-methylbenzenesulfonic acid
SEC Size exclusion chromatography
TBS tert-Butyldimethylsilyl
TCEP 3,3',3"-phosphinetriyltripropanoic acid hydrochloride TEA Triethylamine
TFA Trifluoroacetic acid
THF Tetrahydrofuran
TLC Thin layer chromatography
p-TsOH p-Toluenesulfonic acid Example 1. Exemplary Syntheses of Compound MB-1 (P1)

General procedure for preparation of 2,6-dibromo-4-fluorobenzaldehyde (2)

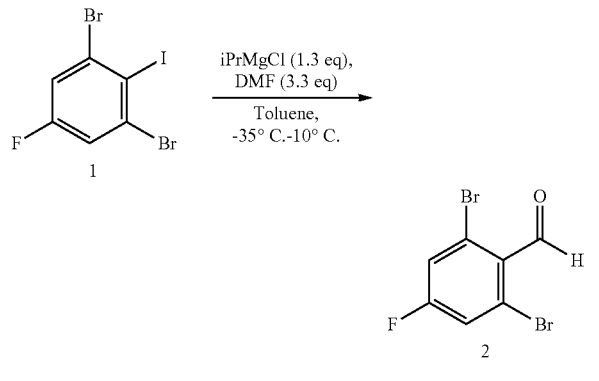

A solution of compound 1 (30 g, 79.0 mmol, 1 eq) in anhydrous toluene (180 mL) was cooled to −35° C. and i-PrMgCl (2 M in anhydrous THF, 51.3 mL, 1.3 eq) was added over a period of 5 minutes while maintaining the internal temperature below −25° C. A clear brown solution was obtained. The reaction mixture was stirred at −30° C. to −25° C. for 1.5 hrs. Then anhydrous DMF (17.32 g, 236.97 mmol, 18.2 mL, 3.3 eq) was added dropwise over a period of 5 minutes. The reaction mixture was warmed to 10° C. and stirred at this temperature for 1.5 hrs. TLC (petroleum ether/ethyl acetate=10/1, Rf=0.7) showed no starting materials left. The reaction was quenched with saturated aqueous NH$_4$Cl (60 mL) and then filtered. The filtrate was dried over Na$_2$SO$_4$, evaporated under reduced pressure to give a residue which was purified by silica-gel column chromatography (petroleum ether/ethyl acetate=50/1 to 10/1) to give 2,6-dibromo-4-fluoro-benzaldehyde (14.8 g, 47.3 mmol, yield 59.8%) as a yellow solid. $^1$H NMR (400 MHz, CHLOROFORM-d) δ 10.23 (s, 1H), 7.44 (d, J=7.7 Hz, 2H).

General procedure for preparation of 2-(2,6-dibromo-4-fluorophenyl)-1,3-dioxolane (3)

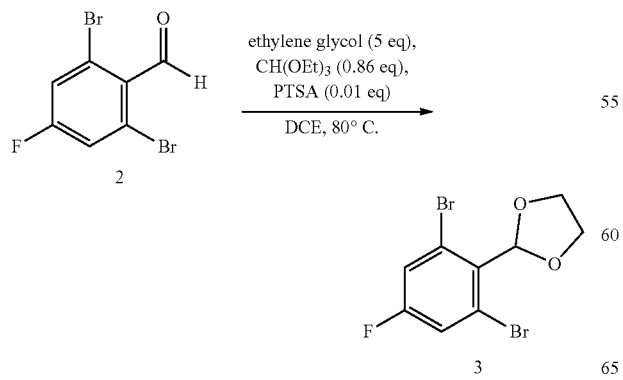

To a solution of compound 2 (14.8 g, 47.3 mmol, 1 eq) in 1,2-dichloro-ethane (240 mL) was added ethylene glycol (14.66 g, 236.25 mmol, 13.2 mL, 5 eq), diethoxymethoxyethane (6.02 g, 40.64 mmol, 6.76 mL, 0.86 eq) and 4-methylbenzenesulfonic acid (81.37 mg, 472.50 umol, 0.01 eq) at 25° C. The reaction mixture was stirred at 80° C. for 10 hrs. TLC (petroleum ether/ethyl acetate=10/1, Rf=0.45, UV and I$_2$) showed that the starting material was consumed. The reaction mixture was cooled to 20° C., washed successively with saturated NaHCO$_3$ (100 mL), H$_2$O (2×100 mL) and brine (2×100 mL), dried over Na$_2$SO$_4$ and concentrated under reduced pressure to give 2-(2,6-dibromo-4-fluorophenyl)-1,3-dioxolane (15.4 g, 44.9 mmol, yield 100%) as a yellow solid. $^1$H NMR (400 MHz, CHLOROFORM-d) δ 7.36 (d, J=7.7 Hz, 2H), 6.36 (s, 1H), 4.36-4.31 (m, 2H), 4.11-4.06 (m, 2H).

General procedure for preparation of 2-(2,6-dibromo-4-fluoro-3-methylphenyl)-1,3-dioxolane (4)

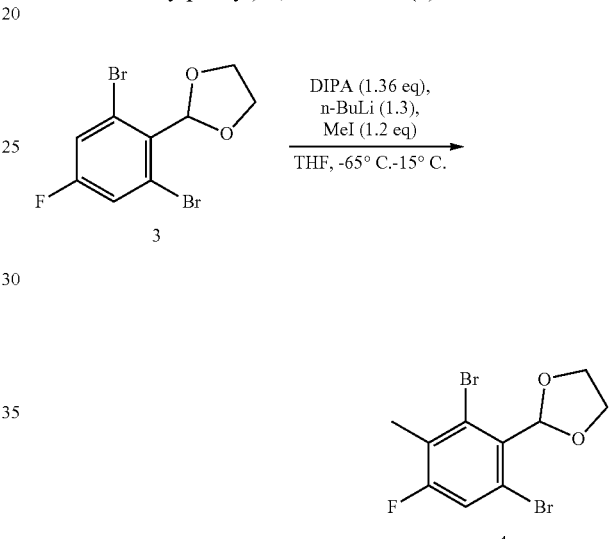

To a solution of diisopropylamine (6.50 g, 64.25 mmol, 9.08 mL, 1.36 eq) in anhydrous THF (26 mL) was added n-butyllithium (2.5 M, 24.6 mL, 1.3 eq) dropwise at −65° C. The reaction mixture was warmed to 0° C. and stirred for 20 min. Then the reaction was cooled to −65° C. again. A solution of compound 3 (15.4 g, 47.3 mmol, 1 eq) in anhydrous THF (42 mL) was added dropwise and the mixture was stirred at −65° C. for additional 1 hr. Iodomethane (8.05 g, 56.7 mmol, 3.5 mL, 1.2 eq) was added dropwise at −65° C. The mixture was stirred at −65° C. for 2 hrs and then warmed to 15° C. and stirred for 12 hrs. TLC (petroleum ether/ethyl acetate, 10/1, Rf=0.48) showed that the starting material was consumed. The reaction was quenched by addition of water (50 mL) and extracted with ethyl acetate (2×80 mL). The combined organic phase was washed with saturated brine (2×50 mL), dried over anhydrous Na$_2$SO$_4$, filtered and concentrated in vacuo to give a residue which was purified by silica gel chromatography (petroleum ether/ethyl acetate, 50/1 to 10/1) to give 2-(2,6-dibromo-4-fluoro-3-methyl-phenyl)-1,3-dioxolane (6.5 g, 19.1 mmol, yield 40.5%) as a yellow solid. $^1$H NMR (400 MHz, CHLOROFORM-d) δ 7.34 (d, J=8.8 Hz, 1H), 6.44 (s, 1H), 4.37-4.32 (m, 2H), 4.11-4.07 (m, 2H), 2.33 (d, J=2.4 Hz, 3H).

General procedure for preparation of N-[3-bromo-2-(1,3-dioxolan-2-yl)-5-fluoro-4-methyl-phenyl]-1,1-diphenyl-methanimine (5)

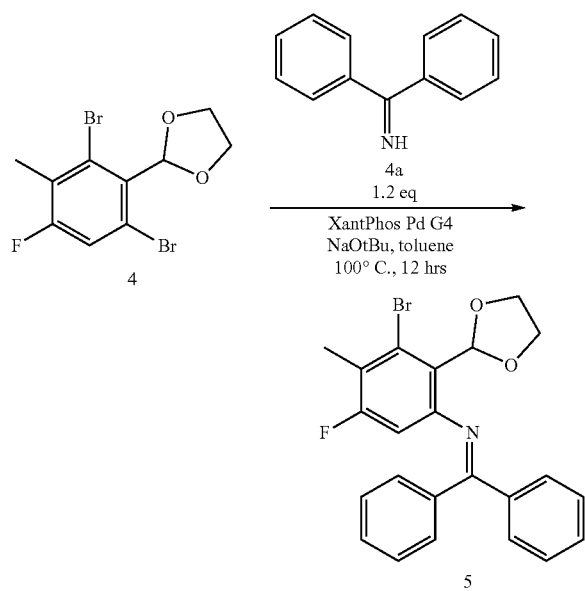

To a solution of compound 4 (0.1 g, 294.13 umol, 1 eq) in toluene (6 mL) was added compound 4a (63.97 mg, 352.96 umol, 59.23 uL, 1.2 eq), Sodium tert-butoxide (56.53 mg, 588.26 umol, 2 eq) and Xantphos-Pd-G4 (14.14 mg, 14.71 umol, 0.05 eq) under $N_2$ protection. The reaction mixture was stirred at 100° C. for 12 hrs under $N_2$ protection. TLC (petroleum ether/ethyl acetate=10/1, Rf=0.32) showed the starting material was consumed. Nine additional vials were set up as described above and all ten reaction mixtures were combined. The combined reaction mixture was filtered through a Celite pad and the filter cake was washed with ethyl acetate (100 mL). The combined filtrate was concentrated under reduced pressure to give a residue which was purified by silica gel chromatography (petroleum ether/ethyl acetate=100/1 to 10/1) to give N-[3-bromo-2-(1,3-dioxolan-2-yl)-5-fluoro-4-methyl-phenyl]-1,1-diphenyl-methanimine (0.7 g, 1.27 mmol, yield 43.24%) as a yellow solid.

$^1$H NMR (400 MHz, CHLOROFORM-d) δ 7.77 (br d, J=7.5 Hz, 2H), 7.48 (br d, J=7.1 Hz, 1H), 7.45-7.37 (m, 3H), 7.31 (br d, J=4.3 Hz, 4H), 6.48 (s, 1H), 5.93 (d, J=10.1 Hz, 1H), 4.11-4.06 (m, 2H), 3.96-3.91 (m, 2H), 2.23 (d, J=2.3 Hz, 3H).

General procedure for preparation of 6-amino-2-bromo-4-fluoro-3-methylbenzaldehyde (6)

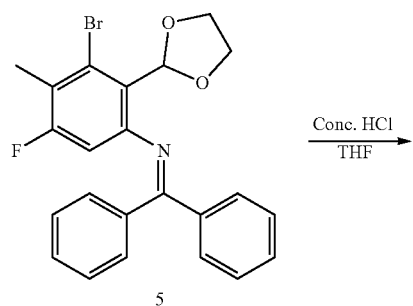

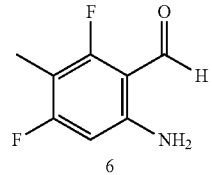

To a solution of compound 5 (0.5 g, 1.14 mmol, 1 eq) in tetrahydrofuran (2 mL) was added HCl (12 M, 6.66 mL, 70.39 eq) at 0° C. The reaction mixture was stirred at 0° C. for 10 min. TLC (petroleum ether/ethyl acetate=10/1, Rf=0.35) showed that all starting materials were consumed. The reaction mixture was neutralized by addition of solid $NaHCO_3$. The resulting solution was extracted with ethyl acetate (3×2 mL). Four additional reaction vials were set up as described above. The reaction mixtures were combined and neutralized by addition of solid $NaHCO_3$. The resulting solution was extracted with ethyl acetate. All of the organic layers were combined, dried over $Na_2SO_4$, filtered and concentrated under reduced pressure to give a residue which was purified by prep-TLC (petroleum ether/ethyl acetate=10/1) to give 6-amino-2-bromo-4-fluoro-3-methyl-benzaldehyde (0.12 g, 439.6 umol, yield 38.7%) as a yellow solid. $^1$H NMR (400 MHz, CHLOROFORM-d) δ 10.40 (s, 1H), 6.52 (br s, 2H), 6.32 (d, J=11.2 Hz, 1H), 2.26 (d, J=2.2 Hz, 3H).

General procedure for preparation (S)-10-bromo-4-ethyl-8-fluoro-4-hydroxy-9-methyl-1H-pyrano[3',4':6,7]indolizino[1,2-b]quinoline-3,14(4H,12H)-dione (8)

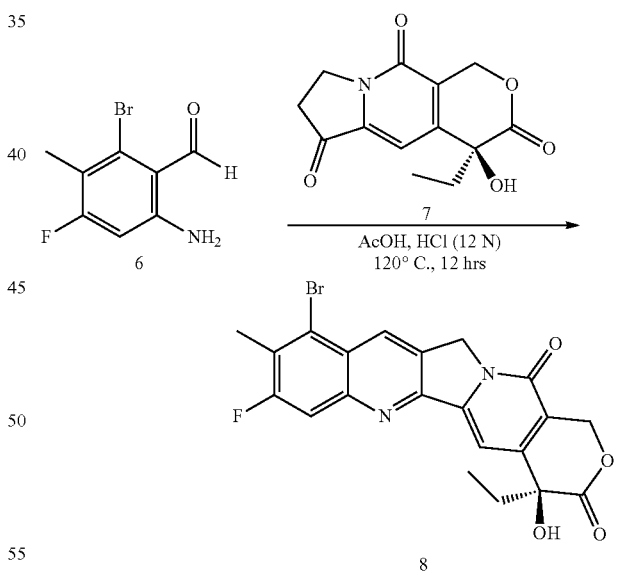

A mixture of compound 6 (120 mg, 517.13 umol, 1 eq) and compound 7 (122.52 mg, 465.42 umol, 0.9 eq) in acetic acid (2 mL) was heated to 120° C. Then HCl (12 N, 100 uL, 2.32 eq) was added to the mixture. The reaction mixture was stirred at 120° C. for 12 hrs. TLC (petroleum ether/ethyl acetate=2/1, Rf=0.2) showed that all starting materials were consumed. Six additional reaction vials were set up as described above and all seven reaction mixtures were combined. The combined reaction mixture was concentrated under reduced pressure to give a residue. The residue was triturated with methanol (6 mL) and filtered to give (S)-10-bromo-4-ethyl-8-fluoro-4-hydroxy-9-methyl-1H-pyrano[3',4':6,7]indolizino[1,2-b]quinoline-3,14(4H,12H)-dione (600 mg, 1.18 mmol, yield 45.47%) as a brown solid. $^1$H NMR (400 MHz, DMSO-$d_6$) δ 8.90 (s, 1H), 8.01 (d, J=10.6 Hz, 1H), 7.33 (s, 1H), 6.55 (br s, 1H), 5.43 (s, 2H), 5.29 (s, 2H), 2.57 (d, J=1.8 Hz, 3H), 1.87 (tt, J=7.1, 14.6 Hz, 2H), 0.88 (t, J=7.3 Hz, 3H).

General procedure for preparation of (S)-10-(4-((tert-butyldimethylsilyl)oxy)but-1-yn-1-yl)-4-ethyl-8-fluoro-4-hydroxy-9-methyl-1H-pyrano[3',4':6,7]indolizino[1,2-b]quinoline-3,14(4H,12H)-dione

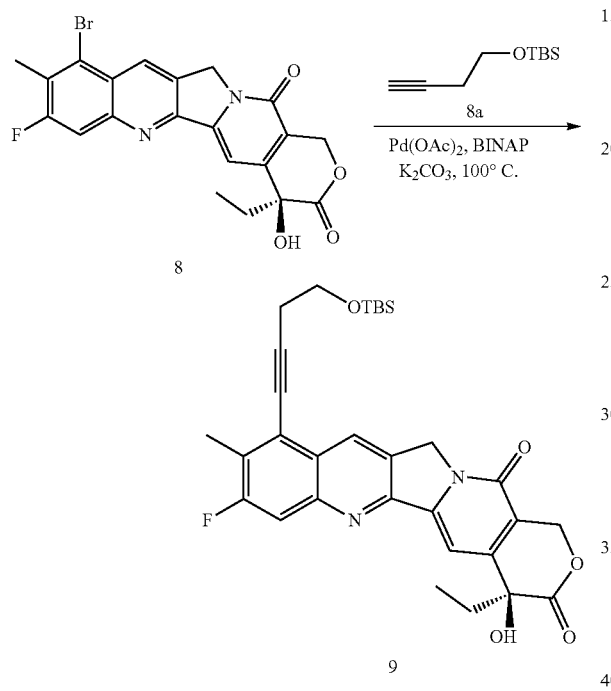

To a solution of compound 8 (50 mg, 108.87 umol, 1 eq) in toluene (1.5 mL) was added compound 8a (100.35 mg, 544.35 umol, 5 eq), K$_2$CO$_3$ (75.23 mg, 544.35 umol, 5 eq), (±)-2,2'-bis(diphenylphosphino)-1,1'-binaphthalene (BINAP, 13.56 mg, 21.77 umol, 0.2 eq) and diacetoxypalladium (4.89 mg, 21.77 umol, 0.2 eq) under N$_2$ protection. The reaction mixture was stirred at 100° C. for 12 hrs. TLC (petroleum ether/ethyl acetate=1/2, Rf=0.35) showed that all starting materials were consumed. Three additional reaction vials were set up as described above and all four reaction mixtures were combined. The combined reaction mixture was diluted with water (6 mL) and ethyl acetate (6 mL). The organic layer was separated and the aqueous phase was extracted with ethyl acetate (2×6 mL). The combined organic layers were concentrated under reduced pressure to give a residue which was purified by prep-TLC (petroleum ether/ethyl acetate=1/2) to give (S)-10-(4-((tert-butyldimethylsilyl)oxy)but-1-yn-1-yl)-4-ethyl-8-fluoro-4-hydroxy-9-methyl-1H-pyrano[3',4':6,7]indolizino[1,2-b]quinoline-3,14(4H,12H)-dione (60 mg, 90.6 umol, yield 27.8%) as a light brown solid. $^1$H NMR (400 MHz, CHLOROFORM-d) δ 8.87-8.82 (m, 1H), 7.77 (d, J=10.3 Hz, 1H), 7.68-7.64 (m, 1H), 5.76 (d, J=16.4 Hz, 1H), 5.30 (s, 3H), 3.99-3.91 (m, 2H), 2.91-2.81 (m, 2H), 2.69-2.55 (m, 3H), 1.98-1.81 (m, 2H), 1.06 (s, 3H), 0.96-0.93 (m, 9H), 0.16-0.11 (m, 6H).

General procedure for preparation of (S)-4-ethyl-8-fluoro-4-hydroxy-10-(4-hydroxybutyl)-9-methyl-1H-pyrano[3',4':6,7]indolizino[1,2-b]quinoline-3,14(4H,12H)-dione MB-1 (P1)

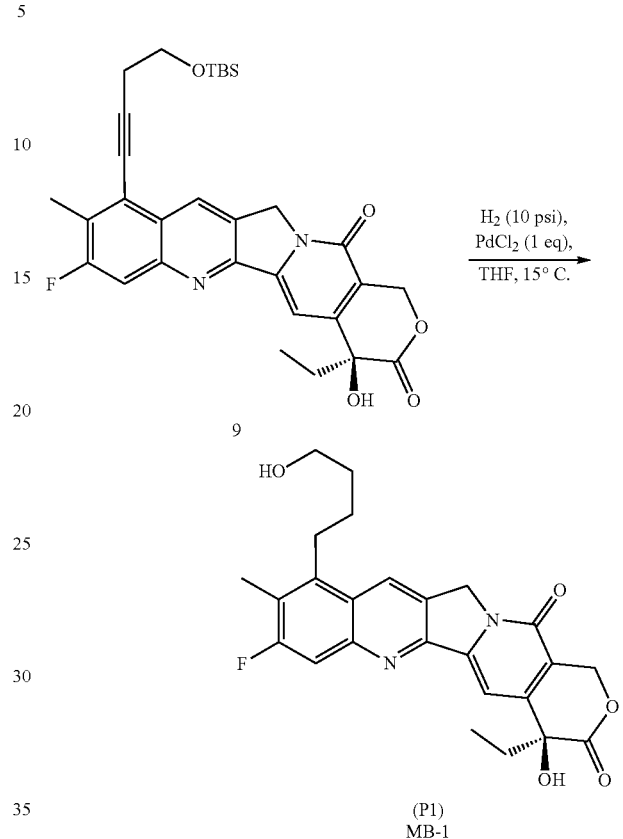

To a solution of compound 9 (30 mg, 53.31 umol, 1 eq) in tetrahydrofuran (5 mL) was added PdCl$_2$ (9.45 mg, 53.31 umol, 1 eq). The reaction mixture was stirred at 15° C. for 15 min under H$_2$ (10 psi). TLC (petroleum ether/ethyl acetate=1/2, Rf=0.45) showed that the starting material was consumed. The desired product MB-1 (P1) and the TBS protected product were detected. Then the reaction mixture was stirred at 25° C. for additional 1 hr. TLC (ethyl acetate/methanol=8/1, Rf=0.45) showed that the TBS protected product was consumed and the major product was compound MB-1 (P1). One additional reaction vial was set up as described above and the two reaction mixtures were combined. The combined reaction mixture was filtered and the filtrate was concentrated under reduced pressure to give a residue which was purified by prep-HPLC under neutral condition to give (S)-4-ethyl-8-fluoro-4-hydroxy-10-(4-hydro-xybutyl)-9-methyl-1H-pyrano[3',4':6,7]indolizino[1,2-b]quinoline-3,14(4H,12H)-dione (5 mg, yield 10.4%) as a yellow solid. $^1$H NMR (400 MHz, DMSO-$d_6$) δ 8.87 (s, 1H), 7.75 (d, J=10.8 Hz, 1H), 7.31 (s, 1H), 6.52 (br s, 1H), 5.42 (s, 2H), 5.25 (s, 2H), 3.49 (br t, J=5.8 Hz, 2H), 3.16 (br s, 1H), 3.14 (br s, 2H), 2.43 (d, J=1.5 Hz, 3H), 1.87 (tt, J=7.0, 14.4 Hz, 2H), 1.62 (br s, 4H), 0.88 (t, J=7.3 Hz, 3H); $^{13}$C NMR (101 MHz, DMSO-$d_6$) δ 172.93, 161.00, 157.28, 152.78, 150.42, 148.38 (d, J=14.5 Hz, 1C), 145.80, 140.76 (d, J=5.1 Hz, 1C), 129.70, 128.78, 125.53 (d, J=18.9 Hz, 1C), 124.48, 119.49, 110.64 (br d, J=23.3 Hz, 1C), 97.15, 72.84, 65.72, 60.88, 50.88, 32.84, 30.75, 28.31, 27.07, 11.91, 8.23; HRMS (ESI-TOF) m/z: [M−H$^-$] calcd 451.1650; found 451.1650;

Prep-HPLC Method (Gilson 281 semi-preparative HPLC system):

Mobile phase: A: H$_2$O; B: acetonitrile; Column: Welch Xtimate C18 150×25 mm×5 um Flow rate: 25 mL/min; Monitor wavelength: 220&254 nm; Gradient: B from 20% to 45% in 8 min, then B from 45% to 100% in 0.2 min, then B 100% for 2 min, B from 100% to 20% in 0.2 min, then B 20% for 1.5 min.

Example 2. Exemplary Alternative Synthesis of Compound MB-1 (P1)

General procedure for preparation of 2,6-dibromo-4-fluoro-3-methyl-aniline (1-2)

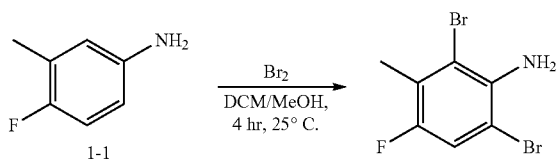

To a stirred solution of compound 1-1 (70 g, 559.36 mmol, 1 eq) in CH$_2$Cl$_2$/methanol (1:1, 1.2 L) was added a solution of Br$_2$ (223.48 g, 1.40 mol, 72.09 mL, 2.5 eq) in CH$_2$Cl$_2$/methanol (1:1, 200 mL) dropwise at 15° C. over 1.5 hrs using an addition funnel. The reaction mixture was stirred at 25° C. for 4 hrs and TLC (petroleum ether/ethyl acetate=6/1, Rf=0.6) showed that the starting material was consumed. Three additional vials were set up as describe above and the mixtures from the four reactions were combined and concentrated. To the resulting residue was added 1 N Na$_2$S$_2$O$_3$ (1.5 L) and ethyl acetate (1.5 L). The solution was stirred for 10 min and then carefully basified with 1 N Na$_2$CO$_3$ (150 mL). It was transferred into a separatory funnel and the organic layer was isolated. The aqueous layer was extracted with ethyl acetate (2×1 L). The combined organic layers were washed with 1 N Na$_2$S$_2$O$_3$ (1 L), followed by brine (1 L), then dried over Na$_2$SO$_4$. It was filtered and concentrated under reduced pressure to give a residue. The residue was triturated with petroleum ether (1 L) and filtered to afford product 1-2 (574 g, 1.93 mol, yield 86%, purity 95%) as a light purple solid. $^1$H NMR (400 MHz, CHLOROFORM-d) δ 7.18 (d, J=8.6 Hz, 1H), 4.52-4.30 (m, 2H), 2.29 (d, J=2.4 Hz, 3H).

General procedure for preparation of 1,3-dibromo-5-fluoro-2-iodo-4-methyl-benzene (1-3)

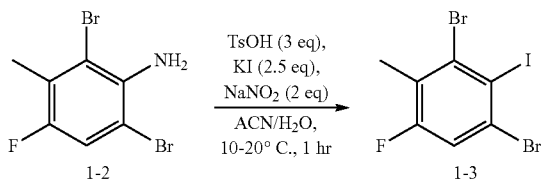

To a solution of p-TsOH (90 g, 522.2 mmol, 3 eq) in acetonitrile (700 mL) was added compound 1-2 (49.25 g, 174.07 mmol, 1 eq). The resulting white suspension was cooled to 10$^{-15°}$ C. and then a solution of NaNO$_2$ (24.02 g, 348.14 mmol, 2 eq) and KI (73.22 g, 435.13 mmol, 2.5 eq) in water (105 mL) was added gradually. The suspension became dark brown and there was gas released. The thick mixture was stirred for 10 min at 10° C., then at 20° C. for additional 1 hr. TLC (petroleum ether/ethyl acetate=6/1, Rf=0.6) showed that the starting material was consumed. The reaction mixture was poured into water (400 mL). 1 N sodium hydrogen carbonate solution (200 mL) was added to adjust the pH to 9-10 followed by the addition of 2 N solution of sodium thiosulfate (200 mL). The obtained mixture was extracted with ethyl acetate (3×500 mL). Eleven additional vials were set up as described above. The combined organic layers from the 12 reactions were combined, dried over Na$_2$SO$_4$ and concentrated under reduced pressure. The obtained residue was purified by silica gel chromatography and eluted with petroleum ether to afford product 1-3 (504 g, 1.09 mol, yield 56%, purity 85%) as a yellow solid. $^1$H NMR (400 MHz, CHLOROFORM-d) δ 7.41 (d, J=8.8 Hz, 1H), 2.43 (d, J=2.4 Hz, 3H).

General procedure for preparation of 2,6-dibromo-4-fluoro-3-methyl-benzaldehyde (1-4)

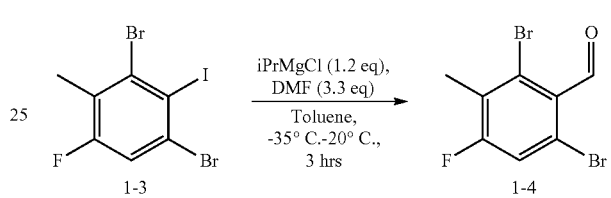

To a solution of compound 1-3 (50.4 g, 127.98 mmol, 1 eq) in anhydrous toluene (300 mL) was added a solution of chloro(isopropyl)magnesium (2 M in tetrahydrofuran, 76.80 mL, 1.2 eq) over a period of 10 min while maintaining the internal temperature below −25° C. A clear brown solution was obtained and the mixture was stirred for 1.5 hrs. followed by the addition of N,N-dimethylformamide (30.86 g, 422.33 mmol, 3.3 eq) in 10 min. The temperature of the reaction mixture increased to −19° C. after the addition. The reaction mixture was warmed to 20° C. over 0.5 hr and stirred for 1.5 hrs. TLC (petroleum ether/ethyl acetate=10/1, Rf=0.45) showed the reaction completed. The reaction mixture was quenched with saturated aqueous NH$_4$Cl (50 mL). Ten additional vials were set up as described above and all eleven reaction mixture were combined. The combined mixture was filtered and the filtrate was evaporated under reduced pressure to give a residue. The residue was purified by silica-gel column chromatography and eluted with petroleum ether to give product 1-4 (253 g, 812.18 mmol, yield 60%, purity 95%) as a yellow solid. $^1$H NMR (400 MHz, CHLOROFORM-d) δ 10.22 (s, 1H), 7.40 (d, J=8.6 Hz, 1H), 2.37 (d, J=2.4 Hz, 3H).

General procedure for preparation of 2-(2,6-dibromo-4-fluoro-3-methyl-phenyl)-1,3-dioxolane (4).

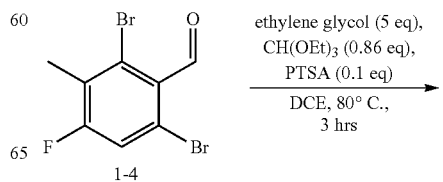

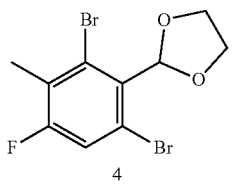

To a solution of compound 1-4 (50.6 g, 170.99 mmol, 1 eq) in 1,2-dichloroethane (430 mL) was added ethylene glycol (53.06 g, 878.58 mmol, 47.80 mL, 5 eq), triethyl orthoformate (25.34 g, 170.99 mmol, 28.44 mL, 1 eq) and p-toluene sulphonic acid (1.47 g, 8.55 mmol, 0.05 eq). The reaction mixture was stirred at 80° C. for 3 hrs and TLC (petroleum ether/ethyl acetate=10/1, Rf=0.59) showed that the reaction completed. Four additional vials were set up as described above and the reaction mixtures from the five reactions were combined. The combined reaction mixture was washed subsequently with saturated aqueous Na₂CO₃ (1 L), saturated aqueous NH₄Cl (1 L) and water (1 L). The organic layer was dried over Na₂SO₄, filtered and evaporated under reduced pressure to give crude product. The crude product was triturated with petroleum ether at 20° C. for 15 min and filtered to give product 4 (280 g, 741.21 mmol, yield 84%, purity 90%) as a light yellow solid. ¹H NMR (400 MHz, CHLOROFORM-d) δ 7.34 (d, J=8.6 Hz, 1H), 6.44 (s, 1H), 4.37-4.31 (m, 2H), 4.11-4.06 (m, 2H), 2.34 (d, J=2.4 Hz, 3H).

General procedure for preparation of N-[3-bromo-2-(1,3-dioxolan-2-yl)-5-fluoro-4-methyl-phenyl]-1,1-diphenyl-methanimine (5)

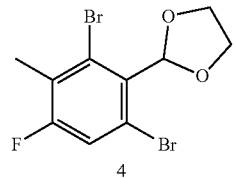
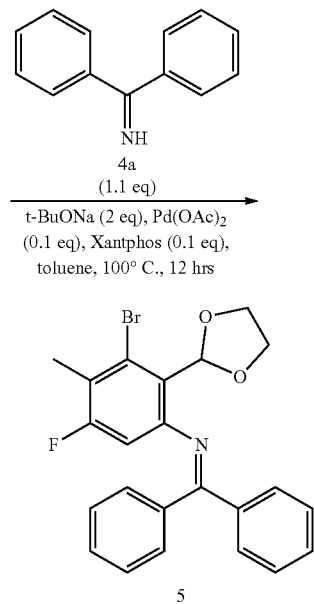

To a solution of compound 4 (53 g, 155.89 mmol, 1 eq) in toluene (100 mL) was added compound 4a (29.67 g, 163.69 mmol, 27.46 mL, 1.05 eq), sodium tert-butoxide (29.97 g, 311.78 mmol, 2 eq), palladium(II) acetate (3.5 g, 15.59 mmol, 0.1 eq) and 4,5-bis(diphenylphosphino)-9,9-dimethylxanthene (9.02 g, 15.59 mmol, 0.1 eq) under N₂ protection. The reaction mixture was stirred at 100° C. for 12 hrs under N₂ protection and TLC (petroleum ether/ethyl acetate=10/1, Rf=0.32) showed the reaction completed. Two additional vials were set up as described above and all three reaction mixtures were combined and filtered via a celite pad. The filter cake was washed with ethyl acetate (500 mL). The combined filtrate was concentrated under reduced pressure to give a residue. The residue was purified by column chromatography and eluted with petroleum ether/ethyl acetate=10/1 to give product 5 (105 g, 214.62 mmol, yield 45.61%, 80% purity) as a yellow solid. The product was used in the next step without further purification. ¹H NMR (400 MHz, CHLOROFORM-d) δ 7.77 (br d, J=7.3 Hz, 2H), 7.54-7.37 (m, 4H), 7.31 (br d, J=4.5 Hz, 3H), 7.26-7.22 (m, 1H), 6.48 (s, 1H), 5.93 (d, J=10.3 Hz, 1H), 4.11-4.05 (m, 2H), 3.96-3.91 (m, 2H), 2.23 (d, J=2.3 Hz, 3H).

General procedure for preparation of N-[3-[4-[tert-butyl(dimethyl)silyl]oxybutyl]-2-(1,3-dioxolan-2-yl)-5-fluoro-4-methyl-phenyl]-1,1-diphenyl-methanimine (1-6)

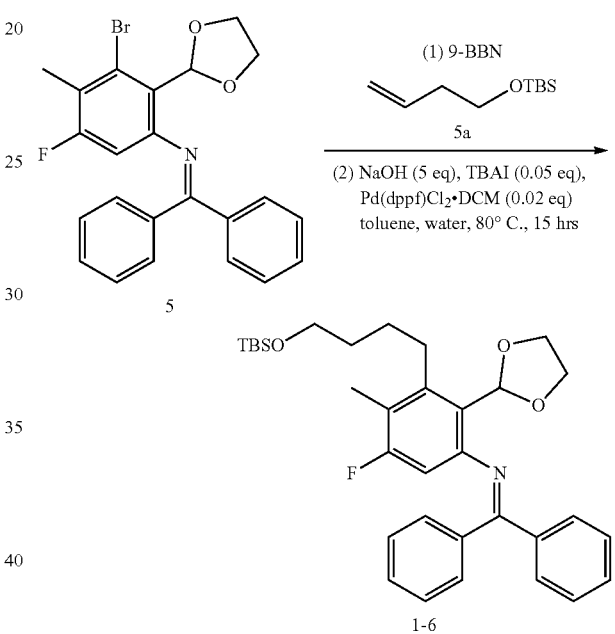

To a stirred mixture of compound 5a (5.3 g, 28.44 mmol, 1 eq) in toluene (80 mL) was added 9-BBN (0.5 M in tetrahydrofuran, 68.13 mL, 1.2 eq) at 10° C. under nitrogen atmosphere. The resulting mixture was stirred at 80° C. for 20 min under nitrogen protection and TLC (petroleum ether/ethyl acetate=1/1, Product Rf=0.2, I₂) showed the reaction completed. A solution of NaOH (2.27 g, 56.78 mmol, 2 eq) in water (20 mL) was added to the above mixture at 10° C. under nitrogen atmosphere. The resulting mixture was stirred at 10° C. for 10 min followed by the addition of compound 5 (10.00 g, 22.71 mmol, 0.8 eq), tetrabutylammonium iodide (524.31 mg, 1.42 mmol, 0.05 eq) and [1,1-Bis(diphenyl-phosphino)ferrocene]palladium (II) dichloride dichloromethane adduct (463.7 mg, 568.8 μmol, 0.02 eq) at 10° C. under nitrogen atmosphere. The resulting mixture was stirred at 80° C. for 15 hrs under nitrogen atmosphere and LCMS (retention time=3.620) showed reaction completed. Seven additional vials were set up as described above and all eight reaction mixtures were combined. The combined reaction mixture was washed with water (500 mL×3), dried over Na₂SO₄, filtered and concentrated under reduced pressure. The obtained residue was purified by column chromatography (SiO₂, petroleum ether/ ethyl acetate=10/1 to 5/1) to give the crude product which was further purified by reversed-phase HPLC to give product 1-6 (45 g, 82.15 mmol, yield 50%, purity 80%) as a yellow gum. $^1$H NMR (400 MHz, DMSO-d6) δ 7.72-7.61 (m, 2H), 7.59-7.51 (m, 1H), 7.50-7.42 (m, 2H), 7.37-7.22 (m, 4H), 7.19 (br d, J=3.5 Hz, 1H), 6.03 (s, 1H), 5.89 (s, 1H), 4.07-3.99 (m, 2H), 3.93-3.78 (m, 2H), 3.65-3.56 (m, 2H), 2.75-2.64 (m, 2H), 2.01 (s, 2H), 1.64 (s, 1H), 1.59-1.44 (m, 4H), 0.87 (s, 9H), 0.03 (s, 6H).

General procedure for preparation of (19S)-19-ethyl-6-fluoro-19-hydroxy-8-(4-hydroxybutyl)-7-methyl-17-oxa-3,13-diazapentacyclo[11.8.0.0$^{2,11}$.0$^{4,9}$.0$^{15,20}$]henicosa-1(21),2,4,6,8,10,15(20)-heptaene-14,18-dione (MB-1) (P1)

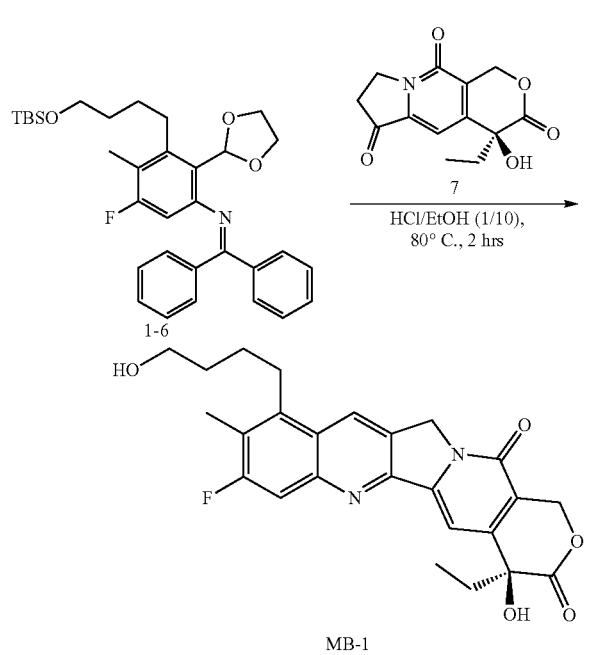

To a solution of compound 1-6 (500 mg, 912.79 umol, 1 eq) in ethanol (5 mL) was added compound 7 (144.17 mg, 547.67 umol, 0.6 eq) and concentrated hydrochloric acid (12 M, 0.5 mL, 6.57 eq) at 20° C. The reaction mixture was stirred at 80° C. for 2 hrs. TLC (petroleum ether/ethyl acetate=10/1, product Rf=0; ethyl acetate/methanol=10/1, product Rf=0.2) showed that most of compound 7 was consumed and new spots were generated. Twenty-nine additional vials were set up as described above and all thirty reaction mixtures were combined. The combined reaction mixture was concentrated under reduced pressure. The obtained residue was purified by silica gel chromatography (ethyl acetate/methanol=1/0 to 7/3) to give the crude product. Compound 7 (1.7 g, 4.52 mmol, 22.5% yield, 70% purity) was recovered as a brown solid after purified by column chromatography (SiO$_2$, ethyl acetate/methanol=1/0 to 7/3) and reversed-phase HPLC. The recovered compound 7 was subjected to the same reaction conditions in another twenty reactions. The reactions were worked up and purified as detailed above. The combined crude product was further triturated with ethyl acetate/methanol (1/1, 1 mL) to give product MB-1 (P1) (3.7 g, 8.18 mmol, yield 10%, 90% purity) as a black brown solid. $^1$H NMR (400 MHz, DMSO-d6) δ 8.89 (s, 1H), 7.77 (d, J=11.0 Hz, 1H), 7.31 (s, 1H), 6.54 (br s, 1H), 5.53-5.33 (m, 2H), 5.26 (s, 2H), 4.80-4.06 (m, 1H), 3.49 (br t, J=5.9 Hz, 2H), 3.19-3.11 (m, 2H), 2.43 (d, J=1.8 Hz, 3H), 1.86 (tt, J=7.2, 14.5 Hz, 2H), 1.62 (br s, 4H), 0.88 (t, J=7.3 Hz, 3H).

Example 3. Exemplary Synthesis of Compound MB-2 (PL1)

General procedure for preparation of C$_{17}$H$_{14}$NO$_4$ (S2).

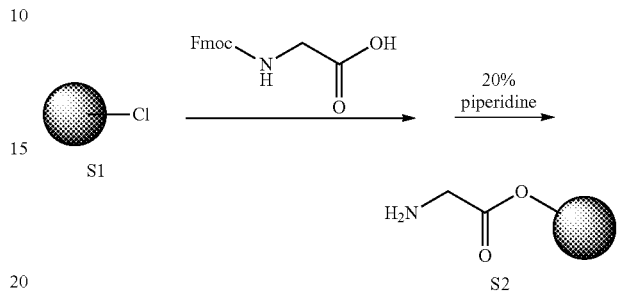

A column charged with 2-(9H-fluoren-9-ylmethoxycarbonylamino)acetic acid (74.92 g, 252.10 mmol, 2 eq), Trt-resin Si (120.00 g, 126.05 mmol, 1 eq) and N,N-Diisopropylethylamine (162.85 g, 1.26 mol, 219.47 mL, 10 eq) in dichloromethane (1500 mL) was bubbled with nitrogen at 20° C. for 12 hrs. After filtration, the residue was washed with dichloromethane (3×300 mL), dimethyl formamide dichloromethane/methanol=1/1 (3×300 mL) and dimethyl formamide (3×300 mL) subsequently. The residue was further dried on high vacuum to give crude resin-C$_{17}$H$_{14}$NO$_4$ (150 g, 123.66 mmol, 98.10% yield, crude purity) as a yellow solid. The product was used in the next step directly without purification. A column charged with resin-C$_{17}$H$_{14}$NO$_4$ (150 g, 123.66 mmol, 1 eq) in DMF (1200 mL) was added piperidine (105.30 g, 1.24 mol, 122.13 mL, 10 eq). The mixture was bubbled with N$_2$ at 20° C. for 1 hrs. The resulting resin was filtered out and washed subsequently with dimethyl formamide (2×500 mL) and dichloromethane (2×500 mL). The resin was dried to afford resin-C$_2$H$_4$NO$_2$ (S2) (120 g, 121.21 mmol, 98.02% yield) as a yellow solid and used in next step directly.

General procedure for preparation of resin-C$_5$H$_9$N$_2$O$_3$ (S3)

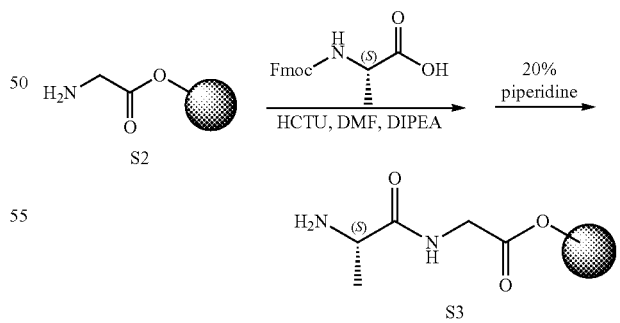

A column charged with (2S)-2-(9H-fluoren-9-ylmethoxycarbonylamino)propanoic acid (75.47 g, 242.42 mmol, 2 eq) and resin-C$_2$H$_4$NO$_2$ (S2) (120 g, 121.21 mmol, 1 eq) in dimethyl formamide (1200 mL) was added HCTU (O—(6-Chloro-1-hydrocibenzotriazol-1-yl) -1,1,3,3-tetramethyluroniumhexafluorophosphate) (100.29 g, 242.42 mmol, 2 eq) and N,N-Diisopropylethylamine (78.33 g, 606.06 mmol, 105.56 mL, 5 eq). The mixture was bubbled with $N_2$ at 20° C. for 1 hr. The resulting resin was filtered out and washed with dimethyl formamide (2×500 mL) and dichloromethane (2×500 mL) successively. It was dried to afford resin-$C_2OH_{19}N_2O_5$ (150 g, crude) as a yellow solid which was directly used in next step. A column charged with the resin-$C_2OH_{19}N_2O_5$ (150 g, 116.91 mmol, 1 eq) in dimethyl formamide (1200 mL) was added piperidine (99.55 g, 1.17 mol, 115.46 mL, 10 eq). The mixture was bubbled with $N_2$ at 20° C. for 1 hr. The resulting resin was filtered out and washed with dimethyl formamide (2×500 mL) and dichloromethane (2×500 mL) successively. It was dried to afford resin $C_5H_9N_2O_3$(S3) (120 g, crude) as a yellow solid and used in next step directly.

General procedure for preparation of 2-[[(2S)-2-[[(2S)-2-(9H-fluoren-9-ylmethoxy-carbonylamino)-3-methyl-butanoyl]amino]propanoyl]amino]acetic acid (1-7)

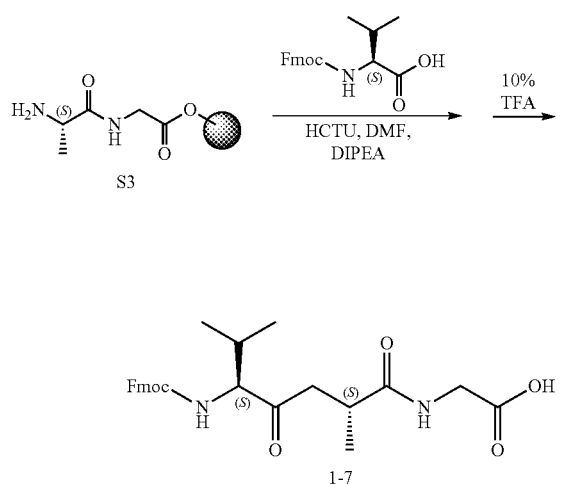

To a column charged with resin $C_5H_9N_2O_3$(S3) (120 g, 112.99 mmol, 1 eq) and (2S)-2-(9H-fluoren-9-ylmethoxycarbonylamino)-3-methyl-butanoic acid (76.70 g, 225.99 mmol, 2 eq) in dimethyl formamide (200 mL) was added O—(6-Chloro-1-hydrocibenzotriazol-1-yl)-1,1,3,3-tetramethyluroniumhexafluorophosphate (93.49 g, 225.99 mmol, 2 eq) and N,N-Diisopropyl-ethylamine (73.02 g, 564.97 mmol, 98.41 mL, 5 eq). The mixture was bubbled with $N_2$ at 20° C. for 12 hrs. The resulting resin was filtered out and washed with dimethyl formamide (2×500 mL) and dichloromethane (2×500 mL) successively. The resin was quenched with trifluoroacetic acid/dichloromethane (10%, 3×500 mL). The organic layers were combined and concentrated under reduced pressure to give a residue. The residue was triturated with n-hexane at 20° C. for 12 hrs. It was filtered to give product 1-7 (60 g, 39.05 mmol, yield 34.56%, purity 90%) as a white solid. $^1$H NMR (400 MHz, DMSO-d6) δ 8.17 (br t, J=5.7 Hz, 1H), 7.99 (d, J=7.5 Hz, 1H), 7.89 (d, J=7.3 Hz, 2H), 7.74 (t, J=6.6 Hz, 2H), 7.45-7.38 (m, 3H), 7.37-7.29 (m, 2H), 4.39-4.19 (m, 4H), 3.93-3.66 (m, 3H), 2.03-1.92 (m, 1H), 1.22 (d, J=7.1 Hz, 3H), 0.85 (dd, J=6.9, 9.8 Hz, 6H).

General procedure for preparation of [[(2S)-2-[[(2S)-2-(9H-fluoren-9-ylmethoxycarbonyl amino)-3-methyl-butanoyl]amino]propanoyl]amino]methyl acetate (1-8).

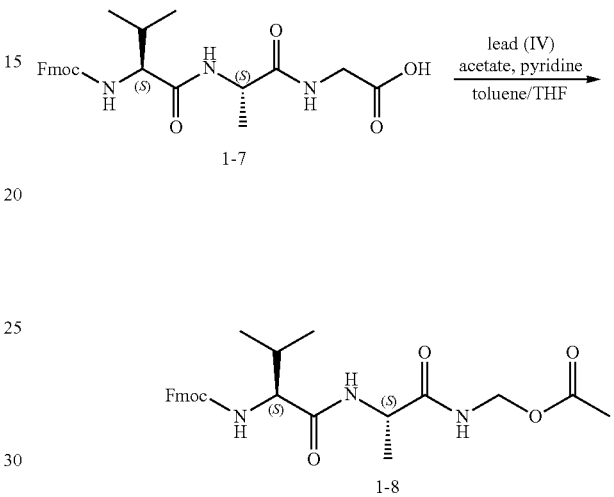

A solution of compound 1-7 (15 g, 32.08 mmol, 1 eq), pyridine (3.04 g, 38.51 mmol, 1.2 eq) and lead (IV) acetate (17.07 g, 38.51 mmol, 1.2 eq) in tetrahydrofuran (192 mL) and toluene (38.4 mL) was stirred at 80° C. for 12 hrs and LCMS (retention time of product=1.157) showed the reaction completed. The reaction mixture was concentrated under reduced pressure to give a residue, which was triturated with ethanol (15 mL) and filtered to give product 1-8 (5 g, 8.31 mmol, yield 38.83%, purity 80%) as a brown solid. $^1$H NMR (400 MHz, DMSO-d6) δ 8.03-7.93 (m, 1H), 7.89 (d, J=7.5 Hz, 2H), 7.74 (br t, J=6.3 Hz, 2H), 7.47-7.36 (m, 3H), 7.36-7.28 (m, 2H), 5.16-5.02 (m, 1H), 4.39-4.26 (m, 2H), 4.22 (br d, J=3.9 Hz, 2H), 3.93-3.82 (m, 1H), 1.98 (s, 2H), 1.78 (s, 1H), 1.27-1.13 (m, 3H), 0.92-0.75 (m, 6H).

General procedure for preparation of 9H-fluoren-9-ylmethyl N-[(1S)-1-[[(1S)-2-[4-[(19S)-19-ethyl-6-fluoro-19-hydroxy-7-methyl-14,18-dioxo-17-oxa-3,13-diazapentacyclo[11.8.0.0$^{2,11}$.0$^{4,9}$.0$^{15,20}$]henicosa-1(21),2,4,6,8,10,15(20)-heptaen-8-yl]butoxymethylamino]-1-methyl-2-oxo-ethyl]carbamoyl]-2-methyl-propyl]carbamate (1-9).

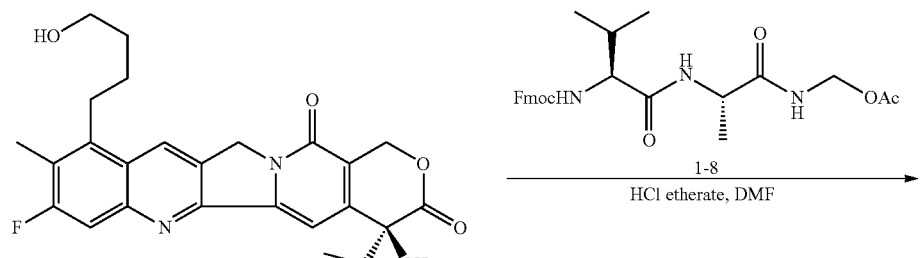

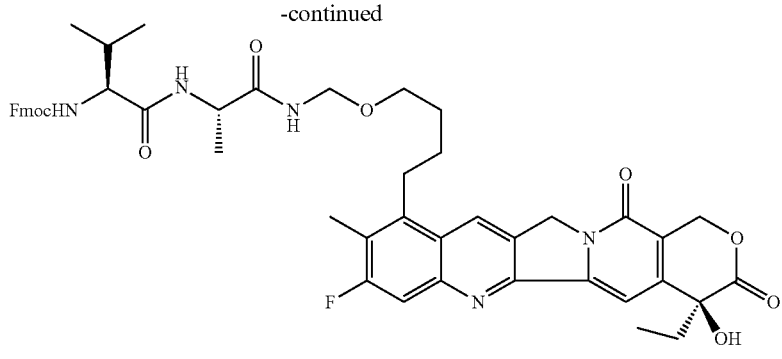

1-9

To a stirring solution of MB-1 (411 mg, 0.908 mmol, 1 eq) and compound 1-8 (555 mg, 1.15 mmol, 1.27 eq) in anhydrous N,N-dimethylformamide (6 mL) was added HCl/etherate (1.5 M HCl diethyl ether solution, 1.18 mL, 2 eq). The reaction mixture was stirred at 20° C. for 15 hrs. LCMS (retention time of product=2.415) showed that most of starting material was consumed and new peak with desired MS was detected. Eight additional vials were set up as described above and all nine reaction mixtures were combined. The combined reaction mixture was concentrated under reduced pressure (35° C. heating bath) to give a residue. The residue was redissolved in N,N-dimethylformamide (20 mL) and purified by prep-HPLC to give product 1-9 (2 g, 2.29 mmol, yield 25.19%, purity 90%) as a light yellow solid. $^1$H NMR (400 MHz, DMSO-d6) δ 8.85 (br s, 1H), 8.62 (br s, 1H), 8.02 (br d, J=6.8 Hz, 1H), 7.85 (br d, J=6.8 Hz, 2H), 7.77 (br d, J=11.0 Hz, 1H), 7.70 (br s, 2H), 7.37 (br d, J=7.3 Hz, 3H), 7.33-7.22 (m, 3H), 6.52 (s, 1H), 5.49-5.35 (m, 2H), 5.27 (br s, 2H), 4.55 (br d, J=4.9 Hz, 2H), 4.31-4.12 (m, 4H), 3.90-3.79 (m, 1H), 3.58 (br s, 2H), 3.13 (br s, 2H), 2.42 (br s, 3H), 1.88 (td, J=7.0, 13.8 Hz, 3H), 1.68 (br s, 2H), 1.57 (br s, 2H), 1.19 (br d, J=6.6 Hz, 3H), 0.94-0.72 (m, 9H).

Prep-HPLC Method:
Column: Kromasil $C_{18}$ (250×50 mm×10 um); Mobile phase: A for $H_2O$ and B for acetonitrile;
Gradient: B from 40% to 70% in 20 min; Flow rate: 80 mL/min; Wavelength: 220&254 nm.

General procedure for preparation of (2S)-2-amino-N-[(1S)-2-[4-[(19S)-19-ethyl-6-fluoro-19-hydroxy-7-methyl-14,18-dioxo-17-oxa-3,13-diazapentacyclo[11.8.0.0$^{2.11}$.0$^{4.9}$.0$^{15,20}$]henicosa-1(21),2,4,6,8,10,15(20)-heptaen-8-yl]butoxymethylamino]-1-methyl-2-oxo-ethyl]-3-methyl-butanamide (1-10)

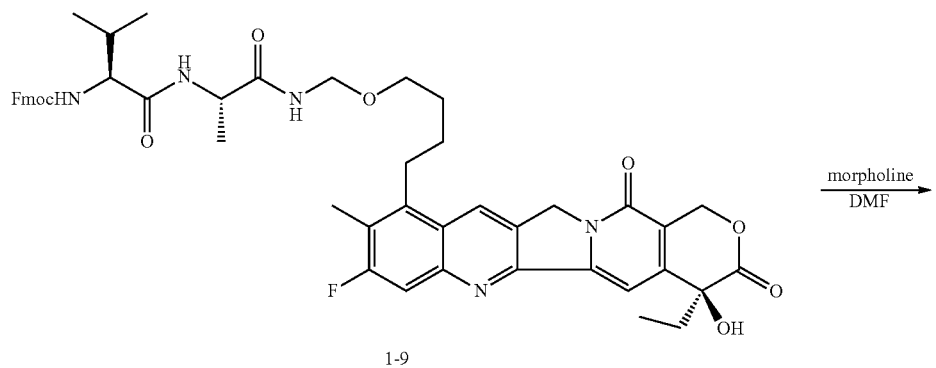

1-9

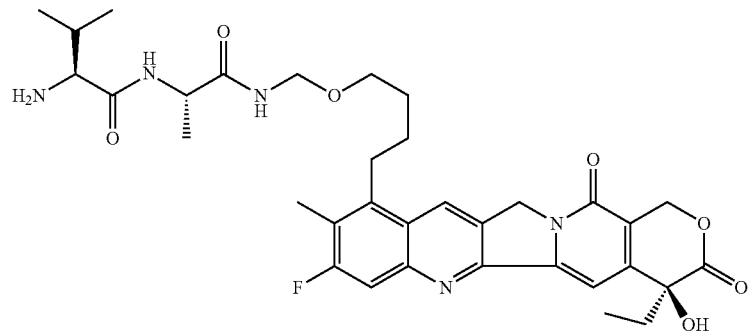

1-10

To the stirring solution of compound 1-9 (400 mg, 0.458 mmol, 1 eq) in anhydrous N,N-dimethylformamide (4 mL) was added morpholine (199.37 mg, 2.29 mmol, 200 µL, 5 eq). The reaction mixture was stirred at 15° C. for 4 hrs. LCMS (retention time of product=1.812) showed that all starting material was consumed and new peak with desired MS was detected. Four additional vials were set up as described above. The five reaction mixtures were combined after the reactions were completed. The combined reaction mixture was concentrated under reduced pressure to give a residue. The residue was re-dissolved in N,N-dimethylformamide and purified by prep-HPLC to give product 1-10 (990 mg, 1.47 mmol, yield 77.10%, purity 90%) as a white solid. $^1$H NMR (400 MHz, DMSO-d6) δ 8.87 (s, 1H), 8.68 (br s, 1H), 8.09 (br s, 1H), 7.77 (br d, J=10.6 Hz, 1H), 7.32 (s, 1H), 6.51 (s, 1H), 5.43 (s, 2H), 5.29 (br s, 2H), 4.55 (br s, 2H), 4.28 (br s, 1H), 3.46 (br s, 1H), 3.45-3.42 (m, 1H), 3.14 (br s, 2H), 3.02 (br s, 1H), 2.43 (br s, 3H), 1.88 (br dd, J=7.9, 14.8 Hz, 3H), 1.70 (br s, 2H), 1.58 (br s, 2H), 1.19 (br d, J=6.8 Hz, 3H), 0.88 (br t, J=7.2 Hz, 3H), 0.82 (br d, J=6.6 Hz, 3H), 0.73 (br d, J=6.6 Hz, 3H).

Prep-HPLC Method:
Column: Kromasil $C_{18}$ (250×50 mm×10 um); Mobile phase: A for $H_2O$ and B for acetonitrile;
Gradient: B from 10% to 45% in 20 min; Flow rate: 80 mL/min; Wavelength: 220&254 nm.

General procedure for preparation of 6-(2,5-dioxopyrrol-1-yl)-N-[(1S)-1-[[(1S)-2-[4-[(19S)-19-ethyl-6-fluoro-19-hydroxy-7-methyl-14,18-dioxo-17-oxa-3,13-diazapentacyclo[11.8.0.0$^2$,1.0$^4$,9.0$^{15}$r]henicosa-1(21),2,4,6,8,10,15(20)-heptaen-8-yl]butoxymethylamino]-1-methyl-2-oxo-ethyl]carbamoyl]-2-methyl-propyl]hexanamide (MB-2) (PL1)

To a solution of compound 1-10 (400 mg, 613.8 µmol, 1 eq) in N,N-dimethylformamide (10 mL) was added compound 10A (283.8 mg, 920.6 µmol, 1.5 eq). The reaction mixture was stirred at 15° C. for 12 hrs. LCMS (retention time of product=2.080) showed that all of compound 1-10 was consumed and new peak with desired MS was detected. The reaction mixture was filtered and the filtrate was purified by prep-HPLC using acetonitrile and deionized water as mobile phase to give product MB-2 (PL1) (173 mg, 203.9 µmol, yield 33.36%, purity 95.74%) as a white solid. $^1$H NMR (400 MHz, DMSO-d6) δ 8.87 (s, 1H), 8.57 (t, J=6.4 Hz, 1H), 7.97 (d, J=7.2 Hz, 1H), 7.81-7.71 (m, 2H), 7.32 (s, 1H), 6.99 (s, 2H), 6.52 (s, 1H), 5.43 (s, 1H), 5.49-5.37 (m, 1H), 5.30 (s, 2H), 4.54 (dq, J=6.6, 10.1 Hz, 2H), 4.21 (quin, J=7.1 Hz, 1H), 4.10 (dd, J=6.8, 8.4 Hz, 1H), 3.48-3.41 (m, 2H), 3.37-3.34 (m, 2H), 3.20-3.08 (m, 2H), 2.43 (d, J=2.0 Hz, 3H), 2.18-2.01 (m, 2H), 1.95-1.79 (m, 3H), 1.68 (br d, J=7.0 Hz, 2H), 1.58 (br s, 2H), 1.51-1.38 (m, 4H), 1.20-1.10 (m, 5H), 0.88 (t, J=7.3 Hz, 3H), 0.76 (dd, J=6.8, 9.3 Hz, 6H). $^{13}$C NMR (101 MHz, DMSO-d6) δ 173.09, 172.54, 172.26, 171.09, 170.85, 160.54, 156.86, 152.36, 150.00, 147.85, 145.38, 140.13, 134.46, 129.33, 128.33, 125.02, 124.04, 119.05, 110.14, 96.73, 72.40, 69.18, 66.72, 65.27 (br s, 1C), 57.44, 50.49 (br s, 1C), 48.29, 37.02, 34.88, 30.31 (br s, 1C), 29.00, 27.78, 27.62 (br s, 1C), 26.73 (br s, 1C), 25.78, 24.89, 19.18, 18.03 (br d, J=5.8 Hz, 1C), 11.46, 7.80. HRMS (ESI-TOF) m/z: [M+H]$^+$ calcd 845.39; found 845.3859.

Prep-HPLC Method:
Gilson 281 semi-preparative HPLC system and Phenomenex Gemini $C_{18}$ column (75×40 mm×3 um); Mobile phase: acetonitrile and water; Flow rate: 25 mL/min; Monitor wavelength: 220&254 nm. Gradient: 30% to 50% acetonitrile in 8 minutes, 50% to 100% acetonitrile in 0.2 minutes, 100% acetonitrile for 2 minutes,

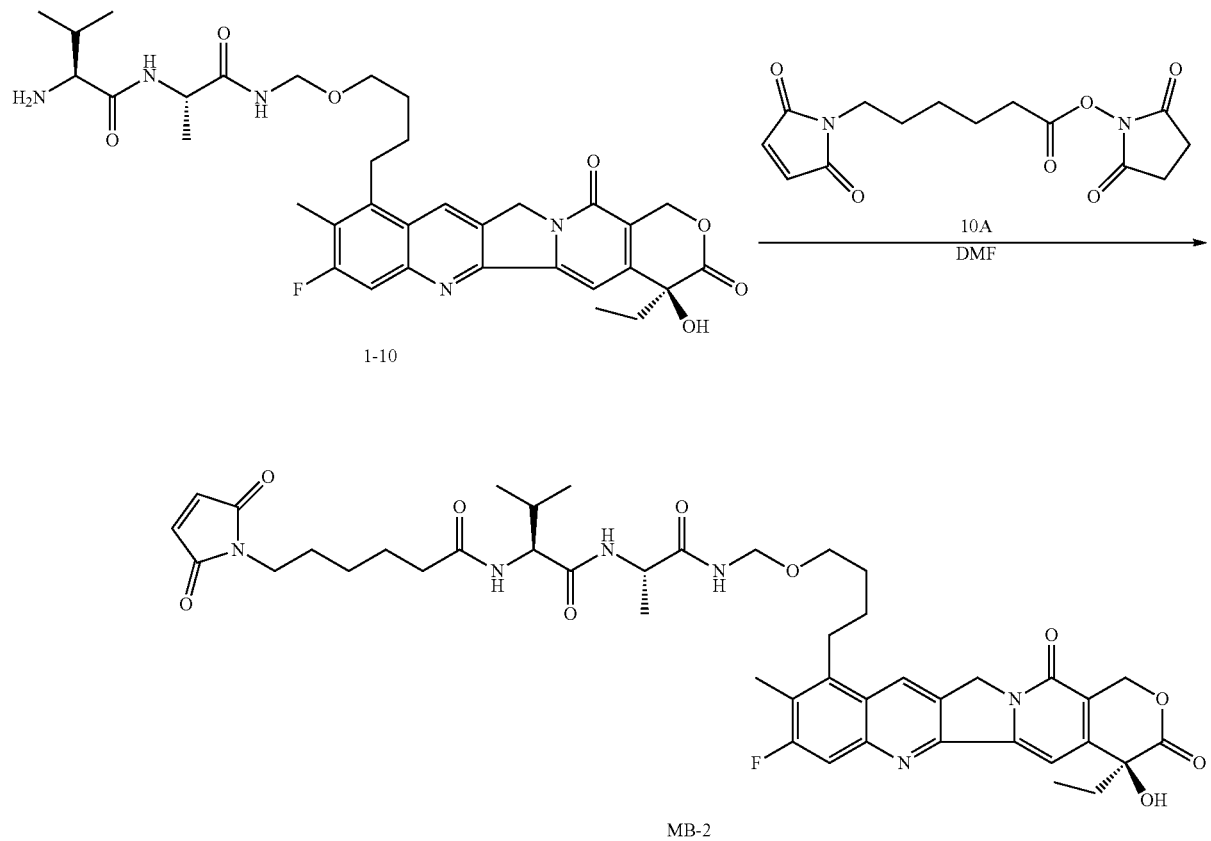

100% to 30% acetonitrile in 0.1 minute then 30% acetonitrile for 1.2 minutes.

Example 4. Exemplary Synthesis of MB-3 (meditecan) (PL3)

General procedure for preparation of benzyl (2S)-2-(benzyloxycarbonylamino)-5-oxo-5-[[(2S,3R,4R,5R)-2,3,4,5,6-pentahydroxyhexyl]amino]pentanoate (1-12).

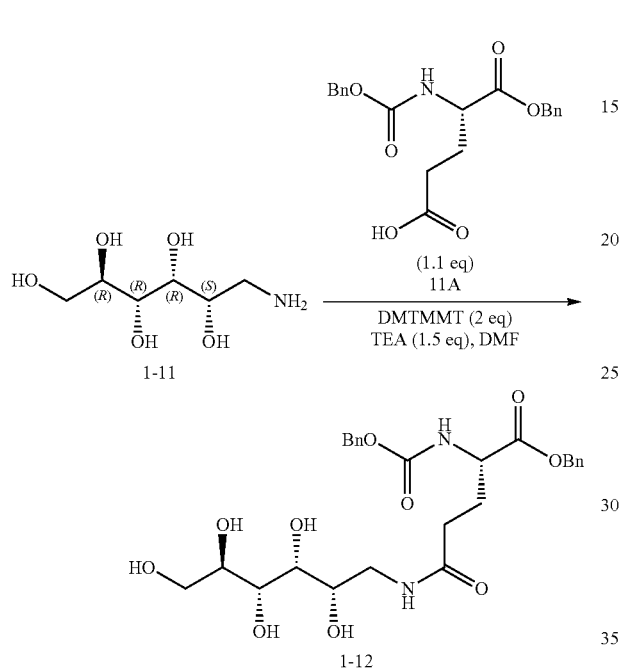

To a solution of compound 11A (6.03 g, 16.27 mmol, 1.1 eq) in N,N-dimethylformamide (27 mL) was added 4-(4,6-dimethoxy-1,3,5-triazin-2-yl)-4-methylmorpholinium tetrafluoroborate (DMTMMT) (9.7 g, 29.59 mmol, 2 eq) and triethylamine (2.24 g, 22.19 mmol, 1.5 eq) successively. After stirred at 25° C. for 0.5 hr, compound 1-11 (2.68 g, 14.79 mmol, 1 eq) was added and the reaction mixture was stirred at 25° C. for 12 hrs. LCMS (retention time of product=0.253) showed the starting material was consumed and new peak with desired MS was detected. The reaction mixture was diluted with water (50 mL) and extracted with dichloromethane (6×50 mL). The combined organic layers were washed with brine (3×130 mL), dried over $Na_2SO_4$ and filtered. The filtrate was concentrated under reduced pressure and the residue was high vacuumed to give an oil. The oil was purified by reverse phase HPLC (3 kg Agela $C_{18}$ column, $CH_3CN/H_2O$, 300 mL/min, gradient: 30% $CH_3CN$ for 10 min, 30% to 45% $CH_3CN$ in 30 min, 45% $CH_3CN$ for 35 min; about 15 grams of crude product was dissolved in 70 mL of DMF to load on the column) to afford product 1-12 (4 g, 6.74 mmol, yield 46.1%, purity 99%) as a white solid. $^1$H NMR (400 MHz, DMSO-d6) δ 1.72-1.85 (m, 1H) 1.91-2.03 (m, 1H) 2.18 (br t, J=7.44 Hz, 2H) 2.96-3.03 (m, 1H) 3.24 (dt, J=13.16, 5.17 Hz, 2H) 3.37-3.40 (m, 2H) 3.44 (br s, 2H) 4.04-4.11 (m, 1H) 4.29 (d, J=6.38 Hz, 1H) 4.39-4.45 (m, 2H) 4.51 (d, J=5.63 Hz, 1H) 4.75 (d, J=4.63 Hz, 1H) 4.96-5.14 (m, 4H) 7.19-7.46 (m, 10H) 7.68-7.85 (m, 2H).

General procedure for preparation of (2S)-2-amino-5-oxo-5-[[(2S,3R,4R,5R)-2,3,4,5,6-pentahydroxyhexyl]amino]pentanoic acid (1-13).

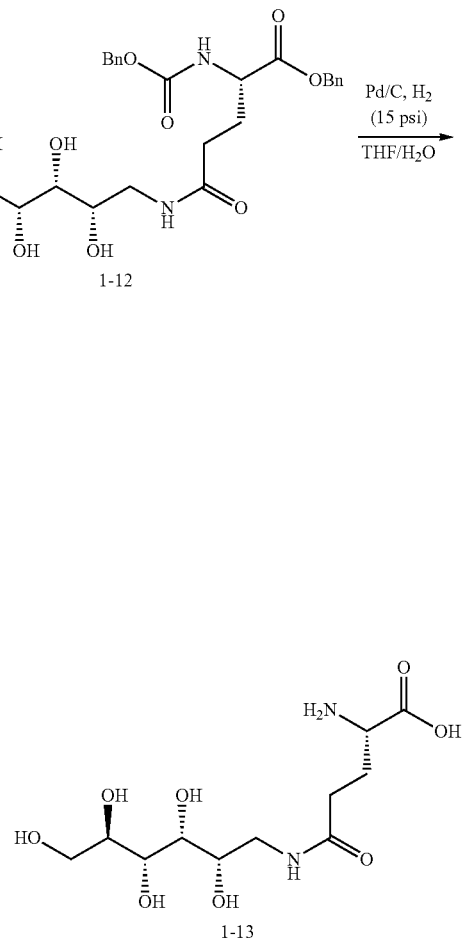

To a solution of compound 1-12 (4 g, 7.48 mmol, 1 eq) in water (192 mL) and tetrahydrofuran (48 mL) was added Pd/C (15.86 g, 14.96 mmol, 10 wt %, 2 eq). The mixture was stirred at 25° C. for 12 hrs under $H_2$ (15 psi). LCMS (retention time of product=0.137) showed the starting material was consumed and desired product was detected. The mixture was filtered through a celite pad and the filtrate was concentrated to give product 1-13 (2 g, 6.26 mmol, yield 83.6%, purity 97.1%) as a white solid. $^1$H NMR (400 MHz, DEUTERIUM OXIDE) δ 3.84 (dt, J=7.76, 4.74 Hz, 1H) 3.70-3.80 (m, 4H) 3.58-3.64 (m, 2H) 3.41 (dd, J=14.06, 4.03 Hz, 1H) 3.25 (dd, J=14.06, 7.83 Hz, 1H) 2.41 (br s, 2H) 2.10 (br s, 2H).

General procedure for preparation of (2S)-2-[6-(2,5-di-oxopyrrol-1-yl)hexanoylamino]-5-oxo-5-[[(2S,3R,4R,5R)-2,3,4,5,6-pentahydroxyhexyl]amino]pentanoic acid (1-14).

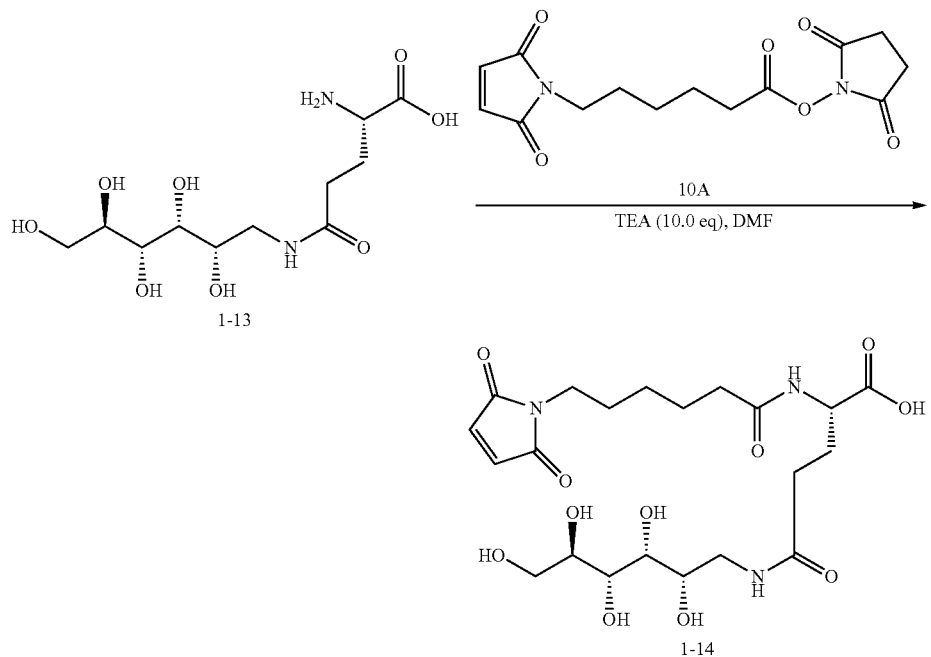

To a solution of compound 1-13 (1 g, 3.22 mmol, 1 eq) and compound 10A (993.51 mg, 3.22 mmol, 1 eq) in N,N-dimethylformamide (10 mL) was added triethylamine (3.26 g, 32.23 mmol, 4.49 mL, 10 eq). The mixture was stirred at 20° C. for 12 hrs. LCMS (retention time of product=1.054) showed the starting material was consumed and desired product was detected. One additional vial was set up as described above. After the reactions were completed, the reaction mixtures from the two reactions were combined and diluted with water (15 mL). It was directly purified by prep-HPLC to give product 1-14 (700 mg, 1.39 mmol, yield 21.57%, purity 100%) as a white solid. $^1$H NMR (400 MHz, DEUTERIUM OXIDE) δ 6.78 (s, 1H) 4.30 (dd, J=9.11, 5.07 Hz, 1H) 3.83 (dt, J=7.89, 4.74 Hz, 1H) 3.79-3.74 (m, 1H) 3.74-3.68 (m, 2H) 3.65-3.57 (m, 2H) 3.46 (t, J=6.91 Hz, 2H) 3.40 (dd, J=14.06, 4.16 Hz, 1H) 3.23 (dd, J=14.00, 7.89 Hz, 1H) 2.39-2.30 (m, 2H) 2.24 (t, J=7.27 Hz, 2H) 2.20-2.08 (m, 1H) 2.04-1.89 (m, 1H) 1.55 (dquin, J=14.04, 7.19, 7.19, 7.19, 7.19 Hz, 4H) 1.28-1.17 (m, 2H).

Prep-HPLC Method:
Column: Phenomenex luna c18 250 mm×100 mm×15 um
Mobile phase: A for H$_2$O (0.075% trifluoroacetic acid) and B for acetonitrile
Gradient: B from 1% to 30% in 20 min; Flow rate: 250 mL/min; Wavelength: 220&254 nm General procedure for preparation of (2,5-dioxopyrrolidin-1-yl) (2S)-2-[6-(2,5-dioxopyrrol-1-yl)hexanoylamino]-5-oxo-5-[[(2S,3R,4R,5R)-2,3,4,5,6-pentahydroxyhexyl]amino]pentanoate (14A)

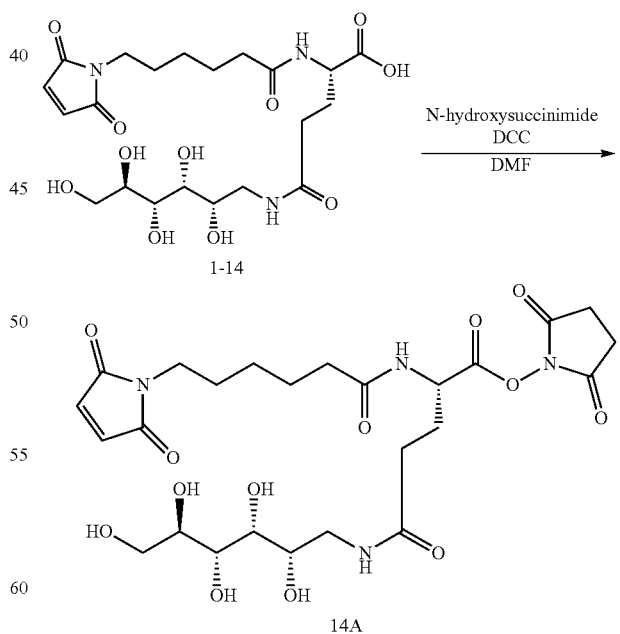

To a solution of compound 1-14 (100 mg, 198.61 μmol, 1 eq) and N-hydroxysuccinimide (45.71 mg, 397.22 μmol, 2 eq) in N,N-dimethylformamide (2 mL) was added N,N-dicyclohexylcarbodiimide (DCC) (81.96 mg, 397.22 μmol, 80.35 μL, 2 eq). The reaction mixture was stirred at 20° C.

for 6 hrs. LCMS (retention time=1.418) showed that most of the starting materials were consumed and about 65% of product with desired MS was detected. Four additional vials were set up as described above and another vial was set up in 80 mg scale. The reaction mixtures from the six reactions were combined. It was filtered to remove the solid and the filtrate containing product 14A was used in next step directly. LCMS (ESI+): m/z 601.3 (M+H)$^+$, RT: 1.418 min.

General procedure for preparation of (2S)-2-[6-(2,5-dioxopyrrol-1-yl)hexanoylamino]-N-[(1S)-1-[[(1S)-2-[4-[(19S)-19-ethyl-6-fluoro-19-hydroxy-7-methyl-14,18-dioxo-17-oxa-3,13-diazapentacyclo[11.8.0.0$^{2,11}$.0$^{4,9}$.0$^{15,20}$]henicosa-1(21),2,4,6,8,10,15(20)-heptaen-8-yl]butoxymethylamino]-1-methyl-2-oxo-ethyl]carbamoyl]-2-methyl-propyl]-N'-[(2S,3R,4R,5R)-2,3,4,5,6-pentahydroxyhexyl]pentanediamide (MB-3) (meditecan) (PL3)

vial was set up as 67.12 mg scale. The reaction solutions from the six reactions were combined and filtered. The filtrate was purified by prep-HPLC to give product MB-3 (meditecan) (PL3) (260 mg, 221.18 μmol, yield 18.6%, purity 96.74%) as a off-white solid. $^1$H NMR (400 MHz, DMSO-d$_6$) δ 8.87 (s, 1H), 8.60 (br s, 1H), 8.08 (br d, J=6.2 Hz, 1H), 8.00 (br d, J=7.7 Hz, 1H), 7.77 (br d, J=11.5 Hz, 1H), 7.72 (br s, 1H), 7.63 (br d, J=9.3 Hz, 1H), 7.32 (s, 1H), 6.99 (s, 2H), 6.53 (s, 1H), 5.43 (br s, 2H), 5.29 (br s, 2H), 4.74 (br s, 1H), 4.57 (br s, 1H), 4.52 (br d, J=6.6 Hz, 1H), 4.47 (br d, J=5.5 Hz, 1H), 4.38 (br d, J=5.1 Hz, 1H), 4.33 (br s, 1H), 4.26 (br d, J=6.4 Hz, 1H), 4.23 (br d, J=6.6 Hz, 2H), 4.13 (br s, 1H), 3.55 (br d, J=4.4 Hz, 3H), 3.45 (br s, 7H), 3.14 (br s, 3H), 3.00 (br s, 1H), 2.42 (br s, 3H), 2.08 (br d, J=5.7 Hz, 4H), 1.96-1.78 (m, 1H), 1.96-1.78 (m, 4H), 1.69

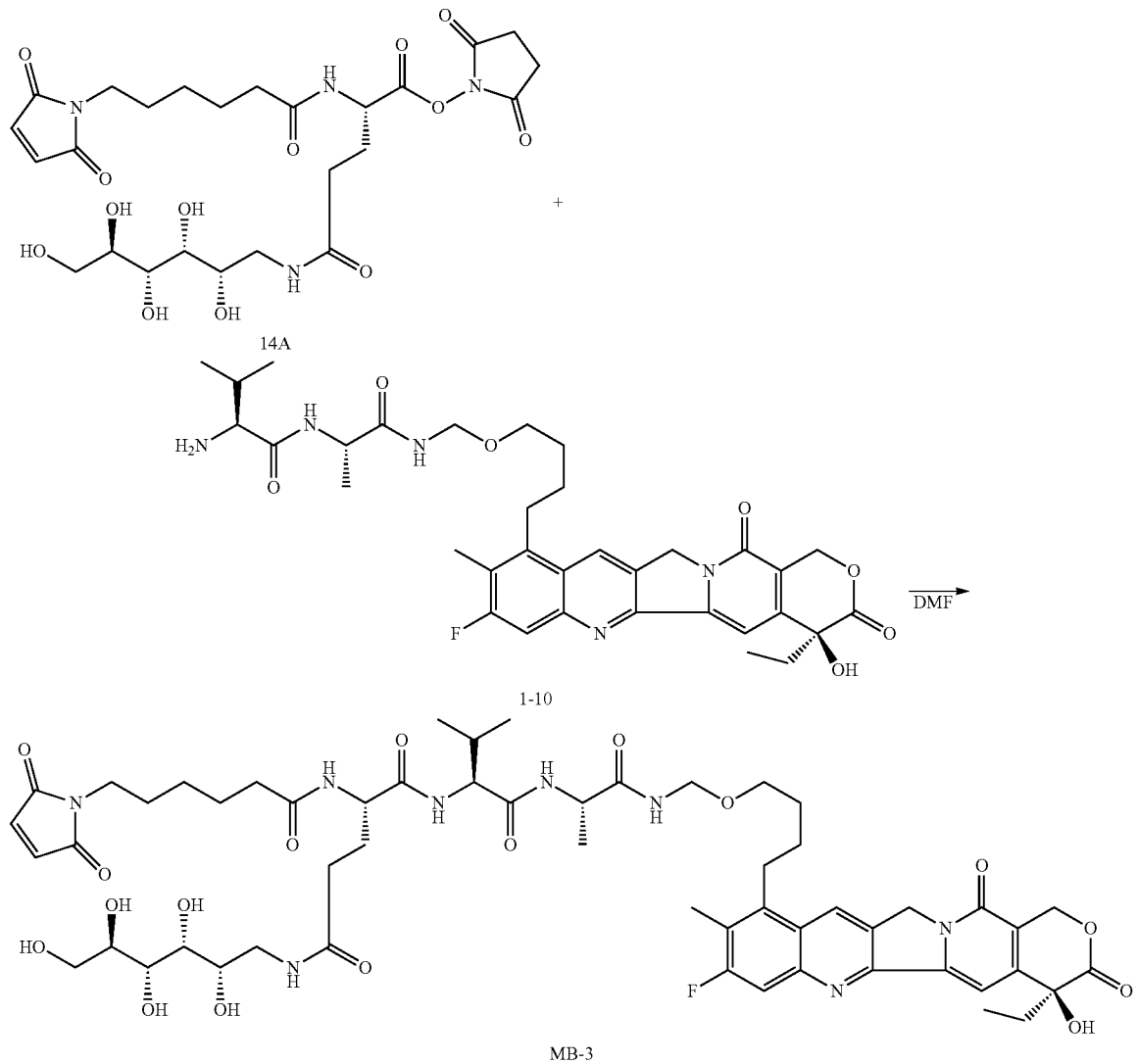

A mixture of compound 1-10 (83.9 mg, 128.79 μmol, 0.65 eq) and compound 14A in 2 mL of N,N-dimethylformamide (crude product from above reactions, 119 mg, 198.14 μmol) was stirred at 25° C. for 15 hrs. LCMS (retention time=1.729) showed that most of the starting materials were consumed and product with desired MS was detected. Four additional vials were set up as described above and another (br s, 3H), 1.58 (br s, 2H), 1.45 (br s, 4H), 1.18 (br d, J=6.4 Hz, 5H), 0.88 (br t, J=7.1 Hz, 3H), 0.76-0.76 (m, 1H), 0.76 (br dd, J=6.9, 11.4 Hz, 5H). $^{13}$C NMR (101 MHz, DMSO-d6) δ 173.14, 172.49 (d, J=10.3 Hz, 1C), 172.08, 171.53, 171.14, 170.58, 163.06, 160.59, 156.93, 152.35, 150.07, 147.96 (d, J=13.9 Hz, 1C), 145.41, 140.24, 134.48, 129.34, 128.39, 125.08, 124.09, 119.08, 110.24 (br d, J=22.7 Hz, 1C), 96.83, 72.44, 72.10, 71.78, 71.55, 69.67, 69.25, 66.80, 65.33, 63.38, 57.25, 52.34, 50.52, 48.41, 42.09, 37.02, 34.99, 31.98, 30.69, 30.36, 29.01, 27.81, 27.65 (br s, 1C), 26.75, 25.82, 24.80, 19.12, 17.88 (d, J=11.7 Hz, 1C), 11.44 (d, J=5.9 Hz, 1C), 7.81. HRMS (ESI-TOF) m/z: [M+H]+ calcd 1137.52; found 1137.5140.

Prep-HPLC Method:
Instrument: Gilson 281 semi-preparative HPLC system; Column: Phenomenex Gemini-NX 150×30 mm×5 um; Mobile phase: A: H$_2$O; B: acetonitrile; Flow rate: 25 mL/min; Monitor wavelength: 220&254 nm; Gradient: 20% to 50% B in 10 minutes, 50% B for 0.1 minute, 50% to 100% B in 0.1 minute, 100% B for 2 minutes, 100% to 20% B in 0.1 minute, and 20% B for 1.2 minutes.

Example 5. Exemplary Synthesis of Antibody-Drug Conjugates MB-2a and MB-3a (trastuzumab meditecan)

General procedure for preparation of trastuzumab-drug conjugate MB-2a give an antibody concentration of 8.63 mg/ml (extinction coefficient of trastuzumab $\varepsilon_{280}$=213380 M$^{-1}$ cm$^{-1}$ was used).

Reduction of the antibody: To a tube containing 12.2 mL (105 mg, 0.000724 mmol of trastuzumab) of above prepared trastuzumab solution was added 6.2 mL of 50 mM conjugation buffer followed by the addition of 579.2 μl of TCEP (10 mM) and 2.1 mL of 10 mM DTPA. The tube was put into the Thermomixer and the reduction reaction was run at 25° C. for 2 hours.

Conjugation between antibody and payload: To the above trastuzumab reduction solution was added a solution of MB-2 (PL1) (7.45 mg, 0.00882 mmol) in DMSO (1.76 mL). The tube was put into the Thermomixer and the conjugation reaction was run at 25° C. for 1 hour.

Purification: The above conjugation reaction solution was subjected to the purification using ultrafiltration tube (30KD) for 6 cycles with the 25 mM His/His-HCl formulation buffer to give 5.5 mL (15.1 mg/mL, antibody yield=83 mg, % yield=79%) of MB-2a in the formulation buffer.

Physicochemical characterization of MB-2a (extinction coefficient of the payload $\varepsilon_{280}$=4546 M$^{-1}$ cm$^{-1}$ and $\varepsilon_{360}$=17513 M$^{-1}$ cm$^{-1}$ were used) (Table 1):

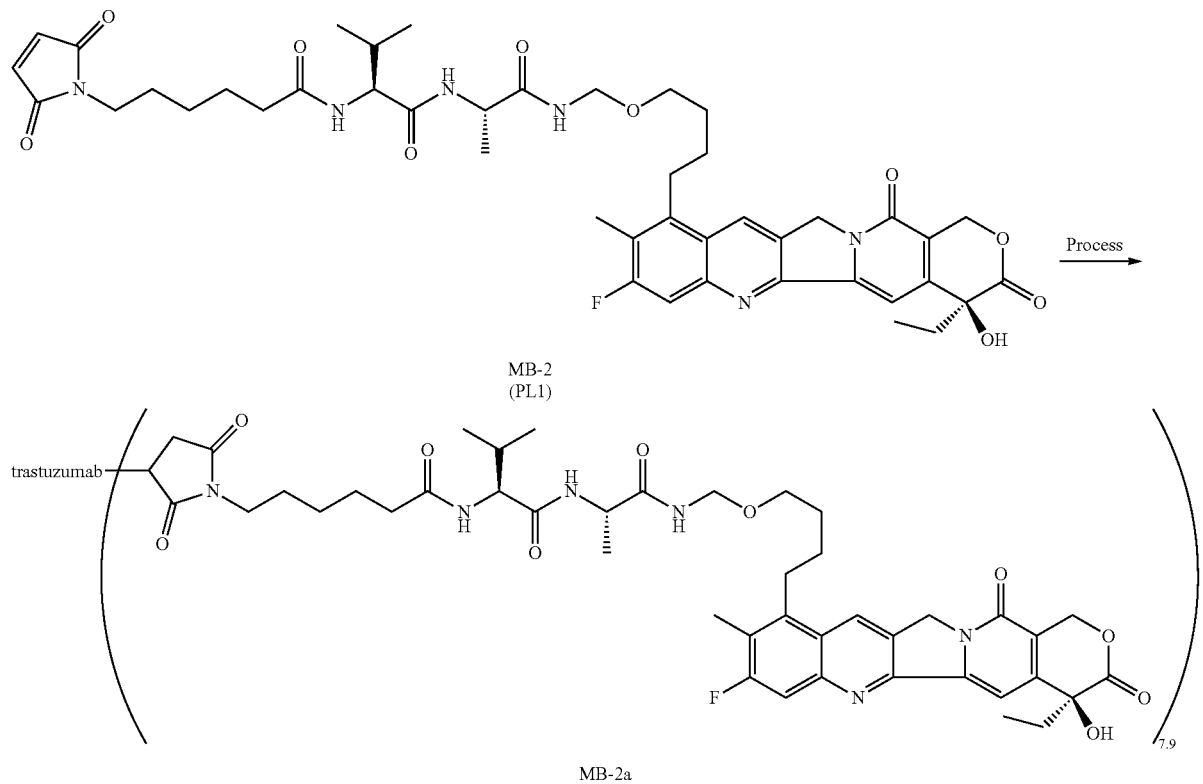

MB-2 (PL1)

MB-2a 50 mM conjugation buffer (pH 7.4): One liter contains 6.86 g of Na$_2$HPO$_4$·2H$_2$O and 1.58 g of NaH$_2$PO$_4$·H$_2$O.

10 mM DTPA (pentetic acid) solution: One liter contains 3.90 g of DTPA and 1.20 g of NaOH.

25 mM His/His-HCl formulation buffer (pH 5.5): One liter contains 0.90 g of L-histidine and 4.04 g of L-histidine hydrochloride monohydrate.

Antibody preparation: 452 mg of lyophilized trastuzumab powder was dissolved in 22 mL of purified water. The obtained antibody solution was dialyzed 4 cycles with the 50 mM conjugation buffer using ultrafiltration tube (30KD) to

TABLE 1

| Analysis Items | Methods | Results | | |
|---|---|---|---|---|
| Monomer level | SEC-HPLC | 99.4% | | |
| DAR | HIC-HPLC | DAR = 7.9 | | |
| | | D6 = 5.9% | | |
| | | D8 = 94.1% | | |
| Concentration | UV-Vis | Mass concentration | 15.1 | mg/ml |
| | | Molarity  Antibody | 98.9 | μmol/L |
| | | Payload | 797.3 | μmol/L |

General procedure for preparation of trastuzumab-drug conjugate MB-3a (trastuzumab meditecan)

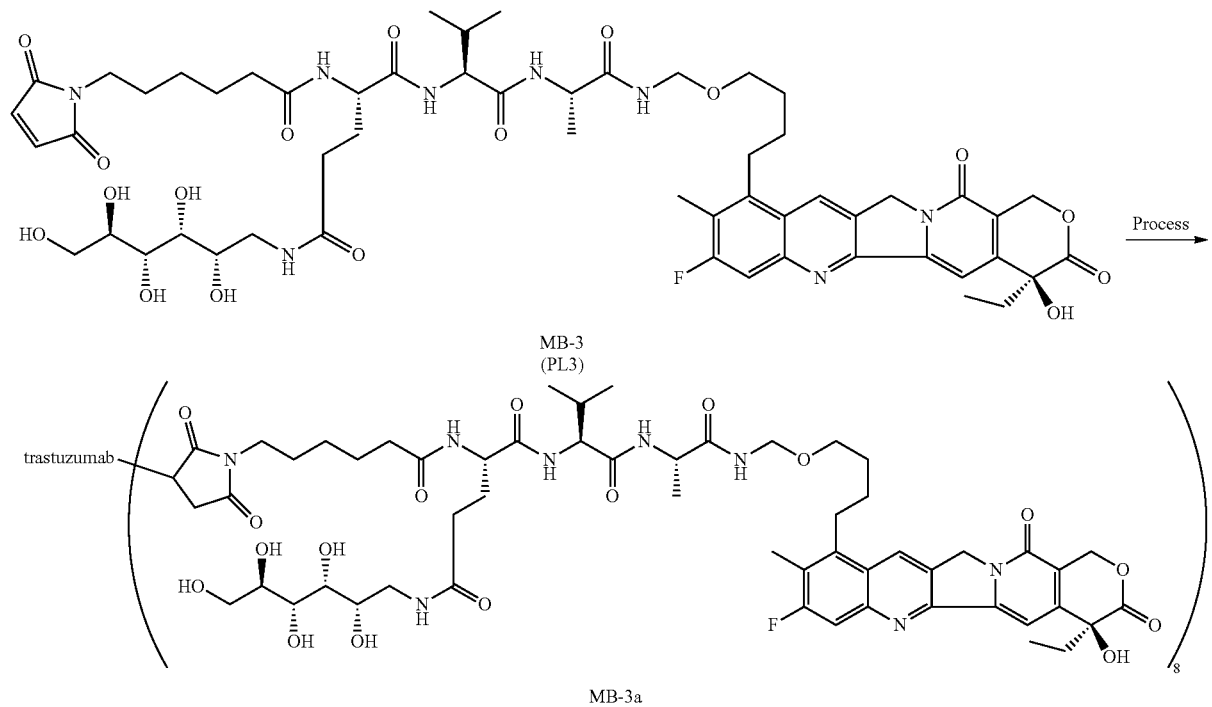

MB-3a 50 mM conjugation buffer (pH 7.4): One liter contains 6.86 g of $Na_2HPO_4 \cdot 2H_2O$ and 1.58 g of $NaH_2PO_4 \cdot H_2O$.

10 mM DTPA (pentetic acid) solution: One liter contains 3.90 g of DTPA and 1.20 g of NaOH.

25 mM His/His-HCl formulation buffer (pH 5.5): One liter contains 0.90 g of L-histidine and 4.04 g of L-histidine hydrochloride monohydrate.

Antibody preparation: 452 mg of lyophilized trastuzumab powder was dissolved in 22 mL of purified water. The obtained antibody solution was dialyzed 4 cycles with the 50 mM conjugation buffer using ultrafiltration tube (30KD) to give an antibody concentration of 8.63 mg/ml (extinction coefficient of trastuzumab $\varepsilon_{280}$=213380 $M^{-1}$ $cm^{-1}$ was used).

Reduction of the antibody: To a tube containing 12.2 mL (105 mg, 0.000724 mmol of trastuzumab) of above prepared trastuzumab solution was added 6.2 mL of 50 mM conjugation buffer followed by the addition of 579.2 μl of TCEP (10 mM) and 2.1 mL of 10 mM DTPA. The tube was put into the Thermomixer and the reduction reaction was run at 25° C. for 2 hours.

Conjugation between antibody and payload: To the above trastuzumab reduction solution was added a solution of MB-3 (meditecan) (PL3) (10.02 mg, 0.00886 mmol) in DMSO (1.77 mL). The tube was put into the Thermomixer and the conjugation reaction was run at 25° C. for 1 hour.

Purification: The above conjugation reaction solution was subjected to purification using ultrafiltration tube (30KD) for 6 cycles with the 25 mM His/His-HCl formulation buffer to give 6.2 mL (14.6 mg/mL, antibody yield=90.5 mg, % yield=86%) of MB-3a (trastuzumab meditecan) in the formulation buffer.

Physicochemical characterization of MB-3a (trastuzumab meditecan) (extinction coefficient of the payload $\varepsilon_{280}$=4546 $M^{-1}$ $cm^{-1}$ and $\varepsilon_{360}$=17513 $M^{-1}$ $cm^{-1}$ were used) (Table 2):

TABLE 2

| Analysis Items | Methods | Results | | |
|---|---|---|---|---|
| Monomer level | SEC-HPLC | 98.4% | | |
| DAR | HIC-HPLC | DAR = 8 | | |
| | | D8 = 100% | | |
| Concentration | UV-Vis | Mass concentration | | 14.6 mg/ml |
| | | Molarity | Antibody | 94.8 μmol/L |
| | | | Payload | 772.5 μmol/L |

Example 6. Exemplary Synthesis of Compound P2

General procedure for preparation of 1-(6-amino-2-bromo-4-fluoro-3-methyl-phenyl)propan-1-ol (6a).

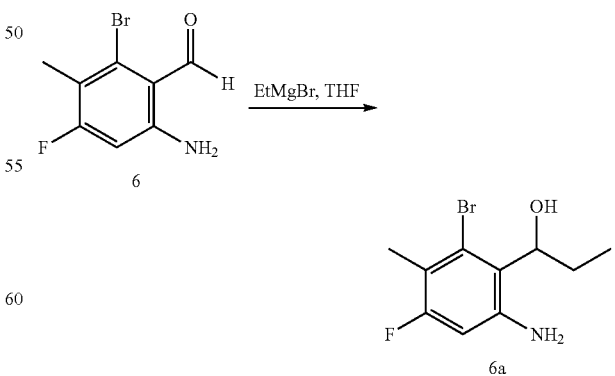

To a stirring solution of ethylmagnesium bromide in THF (3 M, 2.01 mL, 2 eq) was added compound 6 (700 mg, 3.02 mmol, 1 eq) in tetrahydrofuran (5 mL) at 0° C. The resulting suspension was allowed to warm to 20° C. and stirred for 4 hrs. The reaction was quenched with saturated aqueous NH₄Cl solution (4 mL) carefully at 0° C. and extracted with ethyl acetate (4 mL×3). The combined organic layers were washed with brine, dried over Na₂SO₄, filtered and concentrated in vacuo to give a residue. The residue was purified by prep-TLC (petroleum ether/ethyl acetate=5/1) to give product 6a (240 mg, yield 18.21%, purity 60%) as a yellow oil. ¹H NMR (400 MHz, CHLOROFORM-d) δ=6.39 (d, J=10.8 Hz, 1H), 4.02 (br s, 2H), 2.93-2.86 (m, 2H), 2.22 (d, J=2.2 Hz, 3H), 1.23-1.18 (m, 3H).

General procedure for preparation of 1-(6-amino-2-bromo-4-fluoro-3-methyl-phenyl)propan-1-one (10).

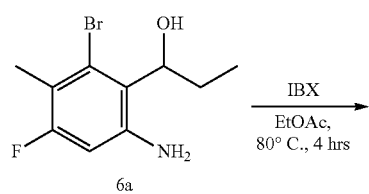

A mixture of compound 6a (80 mg, 0.305 mmol, 1 eq) and 2-iodoxybenzoicacid (213.66 mg, 0.763 mmol, 2.5 eq) in ethyl acetate (3 mL) was stirred at 80° C. for 4 hrs. The reaction completed based on the TLC (petroleum ether/ethyl acetate=8/1, Rf=0.31). Two additional vials were set up as described above and all three reaction mixtures were combined. The combined mixture was filtered and the filter cake was washed with ethyl acetate. The filtrate was concentrated under reduced pressure to give a residue. The residue was purified by prep-TLC (petroleum ether/ethyl acetate=8/1) to give the crude product which was further purified by prep-HPLC under neutral condition to give product 10 (80 mg, 276.81 umol, yield 30.23%, purity 90%) as a yellow oil. ¹H NMR (400 MHz, CHLOROFORM-d) δ=6.39 (d, J=10.6 Hz, 1H), 4.02 (br s, 2H), 2.90 (q, J=7.3 Hz, 2H), 2.22 (d, J=2.0 Hz, 3H), 1.22 (t, J=7.2 Hz, 3H).

Preparative HPLC method:

Column: Kromasil C₁₈ (250×50 mm×10 um)

Mobile phase: A for H₂O (10 mM NH₄HCO₃) and B for acetonitrile

Gradient: B from 45% to 65% in 20 min; Flow rate: 80 mL/min

General procedure for preparation of (19S)-8-bromo-10,19-diethyl-6-fluoro-19-hydroxy-7-methyl-17-oxa-3,13-diazapentacyclo[11.8.0.0²,¹¹.0⁴,⁹.0¹⁵,²⁰]henicosa-1(21),2,4,6,8,10,15(20)-heptaene-14,18-dione (11).

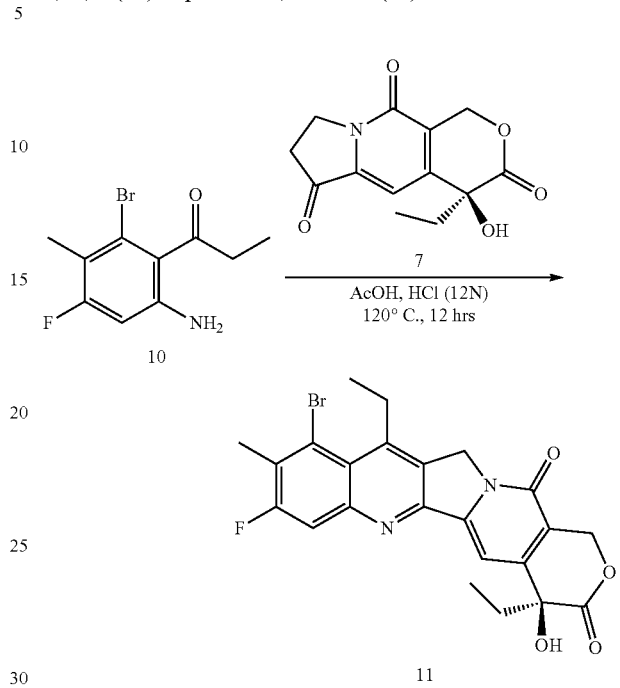

A mixture of compound 10 (80 mg, 0.307 mmol, 1 eq) and compound 7 (80.97 mg, 0.307 mmol, 1 eq) in AcOH (2.5 mL) was heated to 120° C. and then 12 N HCl (0.125 mL, 4.8 eq) was added. The reaction mixture was stirred at 120° C. for 12 hrs. TLC (petroleum ether/ethyl acetate=2/1, product Rf=0.2) showed that the starting material was consumed. The reaction mixture was concentrated under reduced pressure to give a residue which was purified by prep-TLC (petroleum ether/ethyl acetate=1/1, product Rf=0.5) to give product 11 (80 mg, 0.131 mmol, yield 42.7%, purity 80%) as a brown solid ¹H NMR (400 MHz, DMSO-d6) δ=8.09 (d, J=9.5 Hz, 1H), 7.35 (s, 1H), 5.45 (s, 2H), 5.35 (s, 2H), 3.61 (br d, J=8.2 Hz, 2H), 2.67 (s, 3H), 1.90-1.84 (m, 2H), 1.37 (q, J=7.6 Hz, 3H), 0.92-0.87 (m, 3H).

General procedure for preparation of (19S)-8-[4-[tert-butyl(dimethyl)silyl]oxybut-1-ynyl]-10,19-diethyl-6-fluoro-19-hydroxy-7-methyl-17-oxa-3,13-diazapentacyclo[11.8.0.0²,¹¹.0⁴,⁹.0¹⁵,²⁰]henicosa-1(21),2,4,6,8,10,15(20)-heptaene-14,18-dione (12).

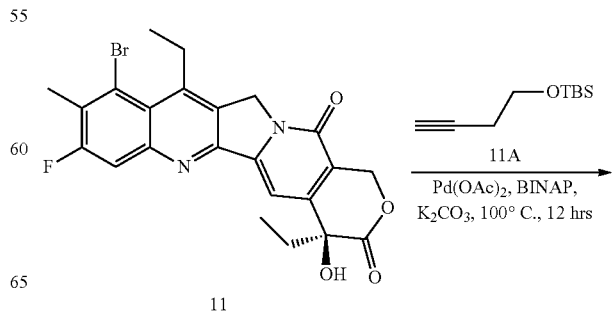

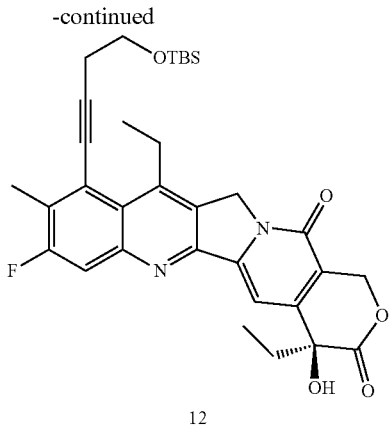

12

To a solution of compound 11 (40 mg, 0.0821 mmol, 1 eq) in toluene (2 mL) was added compound 11A (60.53 mg, 0.328 mmol, 4 eq), Pd(OAc)$_2$ (7.37 mg, 0.0328 mmol, 0.4 eq), (+/−)-2,2-Bis(diphenylphosphino)-1,1-dinaphthalene (25.56 mg, 0.0410 mmol, 0.5 eq) and K$_2$CO$_3$ (56.72 mg, 0.410 mmol, 5 eq) under N$_2$ protection. The reaction mixture was stirred at 100° C. for 12 hrs under N$_2$ protection. TLC (petroleum ether/ethyl acetate=1/2, Rf=0.5) showed that most of starting materials were consumed. One additional vial was set up as described above. The reaction mixtures from the two reactions were combined and concentrated under reduced pressure to give a residue which was purified by prep-TLC (petroleum ether/ethyl acetate=1/2, product Rf=0.5) to give product 12 (30 mg, 0.0508 mmol, yield 30.9%) as a brown solid. LCMS (ESI+): m/z (M+H)$^+$, calculated 591.3, found 591.4.

General procedure for preparation of (19S)-10,19-diethyl-6-fluoro-19-hydroxy-8-(4-hydroxybutyl)-7-methyl-17-oxa-3,13-diazapentacyclo[11.8.0.0$^{2,11}$.0$^{4,9}$.0$^{15,20}$]henicosa-1(21),2,4,6,8,10,15(20)-heptaene-14,18-dione (P2)

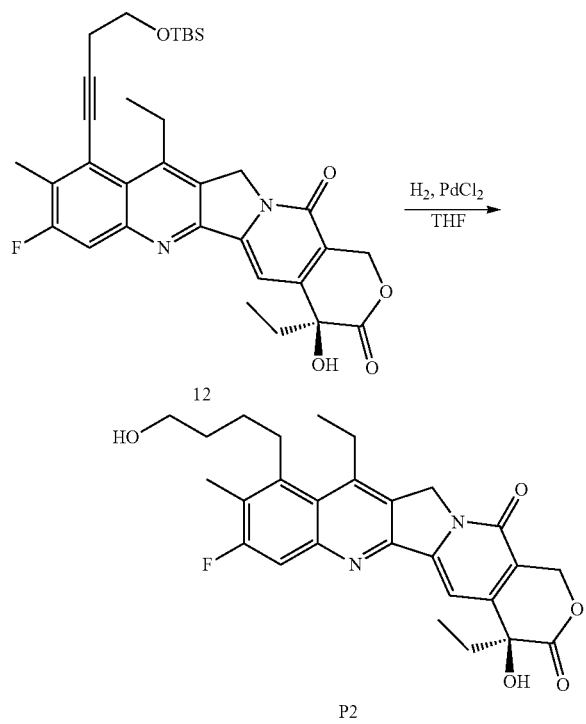

To a solution of compound 12 (10 mg, 0.0169 mmol, 1 eq) in tetrahydrofuran (2 mL) was added PdCl$_2$ (4.50 mg, 0.0254 mmol, 1.5 eq) under H$_2$ (15 psi) protection. The reaction mixture was stirred at 25° C. for 2 hrs. TLC (petroleum ether/ethyl acetate=1/1, product Rf=0; ethyl acetate/methanol=10/1, product Rf=0.45) and LCMS (retention time=1.204) showed that the starting material was consumed and new peak with desired MS detected. One additional vial was set up as described above. The reaction mixtures from the two reactions were combined and filtered via a celite pad. The filtrate was concentrated under reduced pressure to give a residue which was purified by prep-HPLC to give product P2 (2.5 mg, yield 19.7%, purity 97.45%) as a white solid. $^1$H NMR (400 MHz, METHANOL-d4) δ=7.60 (s, 1H), 7.37 (d, J=10.6 Hz, 1H), 5.61 (d, J=16.3 Hz, 1H), 5.41 (d, J=16.3 Hz, 1H), 5.38 (s, 1H), 3.60 (t, J=6.2 Hz, 2H), 3.35 (br s, 2H), 3.25 (br s, 2H), 2.73 (d, J=2.2 Hz, 3H), 2.02-1.94 (m, 2H), 1.76 (br d, J=7.5 Hz, 2H), 1.72-1.63 (m, 2H), 1.40 (t, J=7.5 Hz, 3H), 1.02 (t, J=7.4 Hz, 3H). $^{13}$C NMR (101 MHz, METHANOL-d4) δ=188.26-187.89 (m, 1C), 188.02, 174.99, 157.34, 153.76, 152.96, 148.59, 146.32, 135.47, 121.49, 121.23, 120.19, 119.52, 111.49, 99.28, 86.57, 74.50, 66.91, 62.65, 51.49, 37.51, 33.44, 32.24, 30.61, 27.20, 15.71, 10.14, 8.33. HRMS (ESI-TOF) m/z: [M+H]$^+$ calcd 481.21; found 481.2103

Prep-HPLC Method:
Instrument: Gilson 281 semi-preparative HPLC system
Mobile phase: A: H$_2$O; B: acetonitrile; Column: Waters Xbridge BEH C18 100×25 mm×5 um;
Flow rate: 25 mL/min; Gradient: 30% to 60% of B in 10 minutes, 60% to 100% of B in 0.2 minute, 100% of B for 2 minutes, 100% to 30% of B in 0.1 minute, then 30% of B for 1.2 minutes.

Example 7. In Vitro Cytotoxicity Assays of the Toxins and ADCs

Dispensed 175 µL cell suspension in 96-well plate at 1500 cells per well and incubate for 24 hours in a humidified incubator (37° C., 5% CO$_2$). For antibody blocking, incubate cells (15000 cells/mL) with 2×10$^{-6}$ M of trastuzumab (final concentration 1 µM). Added 25 µL various concentrations of compound as a 5× solution into the cell culture medium (Fetal bovine serum, Invitrogen) in the plate and incubated for 120 hours in the incubator. Thawed CCK-8 on the bench top or in a 37° C. water bath, added 10 µL of CCK-8 to each well of the incubated plate (be careful not introducing air bubbles into the wells since they would interfere with the O. D. reading) and then further incubated for 1-4 hours in the incubator. Measured the absorbance at 450 nm using a SpectraMax i3× Microplate Reader and calculated the cell inhibition rate. The IC$_{50}$ curves were generated along with the IC$_{50}$ values by using GraphPad Prism software.

The results of the in vitro cytotoxicity assay of the toxins (the expected metabolites of the ADCs) are summarized in the following Table 3. The cytotoxicities of metabolite MB-1 are comparable to DXd which is the metabolite of DS-8201a (Enhertu) in multiple cell lines, except in moderate Her-2 expression and trastuzumab-resistant cell line JIMT-1, in which MB-1 is ten folds more potent than DXd.

TABLE 3

| | Cell Lines (IC$_{50}$, nM) | | | | | |
|---|---|---|---|---|---|---|
| Compound | SK-BR-3 | MCF-7 | NCI-N87 | SK-OV-3 | MDA-MB-468 | JIMT-1 |
| MB-1 | 0.77 | 0.37 | 1.3 | 1.0 | 0.42 | 0.78 |
| P2 | >30 | | >30 | >30 | | >30 |
| DXd | 1.9 | 0.57 | 3.6 | 4.7 | 0.57 | 8.7 |

The results of the in vitro cytotoxicity assay of the ADCs are summarized in the following Table 4. In addition to exemplary compounds of Formula III such as MB-2a and MB-3a (trastuzumab meditecan), the activity of trastuzumab and the ADC trastuzumab deruxtecan (DS-8201a, Enhertu) were also evaluated for the sake of comparison. As shown in Table 4, trastuzumab ADCs MB-2a and MB-3a showed the same potency as DS-8201a in a Her2 high expression cell line, NCI-N87. However, when the Her2 antigens were blocked with trastuzumab, the cell growth inhibition ability of the ADCs decreased. In addition, the ADCs are not potent in Her2 negative cell line MDA-MB-468, demonstrating specificity of the ADCs for Her2-expressing cells. Although the ADCs are not sensitive in the in vitro assay in JIMT-1 cells which has moderate level of Her2 expression, MB-2a and MB-3a are still relative more potent than DS-8201a in this cell line.

TABLE 4

| | Cell Lines (IC$_{50}$, nM) | | | |
|---|---|---|---|---|
| Compound | NCI-N87 | NCI-N87 with trastuzumab blocking | JIMT-1 | MDA-MB-468 |
| Trastuzumab | 495 | | | |
| MB-2a | 11.5 | 37.8 | 3773 | >1000 |
| MB-3a | 11.1 | 36.4 | 1815 | >1000 |
| DS-8201a | 11.3 | 29 | 6496 | >1000 |

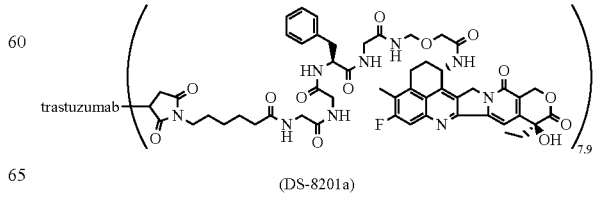

(DS-8201a)

Example 8. In Vivo Efficacy of the ADCs in NCI-N87 CDX Model

Each mouse (female Balb/c-Nude from Vital Rivers) was inoculated subcutaneously at the right flank with NCI-N87 tumor cells ($5 \times 10^6$) mixed with Matrigel (50:50) in 0.2 mL of PBS for tumor development. The animals were randomly grouped on day 6 after tumor inoculation, when the average tumor volume reached around 160 mm³, then treatment started for the efficacy study. Each group contained 8 mice. The test and control articles were administered to the tumor-bearing mice via tail vein at a volume of 5 mL/kg.

Tumor size was measured twice a week in two dimensions using a caliper, and the volume was expressed in mm³ using the formula: $V=0.5\ a \times b^2$ where a and b were the long and short dimensions of the tumor, respectively. Results were represented by mean and the standard error (Mean±SEM).

Statistical analysis: Two-way ANOVA was performed to compare tumor volume between two groups. All data were analyzed using Graphpad Prism 6.0 and $P<0.05$ was considered to be statistically significant. Both statistical analysis and biological observations were taken into consideration.

Tumor growth inhibition: The tumor size was used for calculations of T/C values. T/C (%) of relative tumor proliferation rate was calculated using the formula: T/C (%)=(Ti/T0)/(Vi/V0)×100%. The relative tumor growth inhibition was calculated by formula: TGI (%)=[1−(Ti/T0)/(Vi/V0)]×100%. Ti refer to the mean tumor volume of treatment group measured at each indicated time point following treatment; T0 refer to the tumor volume of treatment group when grouping; Vi refer to the mean tumor volume of vehicle control group measured at each indicated time point following treatment; V0 refer to the tumor volume of vehicle control group when grouping. If T/C>40%, there is no efficacy; if T/C=<40%, and p value<0.05, there is tumor inhibition.

The antitumor effects of the ADCs in the NCI-N87 CDX model is illustrated in FIG. 1 and Table 5. As illustrated in FIG. 1, both MB-2a (1 mg/kg and 4 mg/kg) and MB-3a (trastuzumab meditecan) (1 mg/kg and 4 mg/kg dosages) demonstrated a strong antitumor effect and are more efficacious than DS-8201a (Enhertu).

Example 9. In Vivo Efficacy of the ADCs in JIMT-1 CDX Model

Each mouse (Scid-Beige from Shanghai Lingchang Biotech) was inoculated subcutaneously at the right flank with JIMT-1 tumor cells ($1 \times 10^7$) mixed with Matrigel (50:50) in 0.2 mL of PBS for tumor development. The animals were randomly grouped on day 6 after tumor inoculation, when the average tumor volume reached around 175 mm³, then treatment started for the efficacy study. Each group contained 8 mice. The test and control articles were administered to the tumor-bearing mice via tail vein at a volume of 5 mL/kg.

Tumor size was measured twice a week in two dimensions using a caliper, and the volume was expressed in mm³ using the formula: $V=0.5 a \times b^2$ where a and b were the long and short dimensions of the tumor, respectively. Results were represented by mean and the standard error (Mean±SEM).

Statistical analysis: Two-way ANOVA was performed to compare tumor volume between two groups. All data were analyzed using Graphpad Prism 6.0 and $P<0.05$ was considered to be statistically significant. Both statistical analysis and biological observations were taken into consideration.

Tumor growth inhibition: The tumor size was used for calculations of T/C values. T/C (%) of relative tumor proliferation rate was calculated using the formula: T/C (%)=(Ti/T0)/(Vi/V0)×100%. The relative tumor growth inhibition was calculated by formula: TGI (%)=[1−(Ti/T0)/(Vi/V0)]×100%. Ti refer to the mean tumor volume of treatment group measured at each indicated time point following treatment; T0 refer to the tumor volume of treatment group when grouping; Vi refer to the mean tumor volume of vehicle control group measured at each indicated time point following treatment; V0 refer to the tumor volume of vehicle control group when grouping. If T/C>40%, there is no efficacy; if T/C=<40%, and p value<0.05, there is tumor inhibition.

Figure 2:
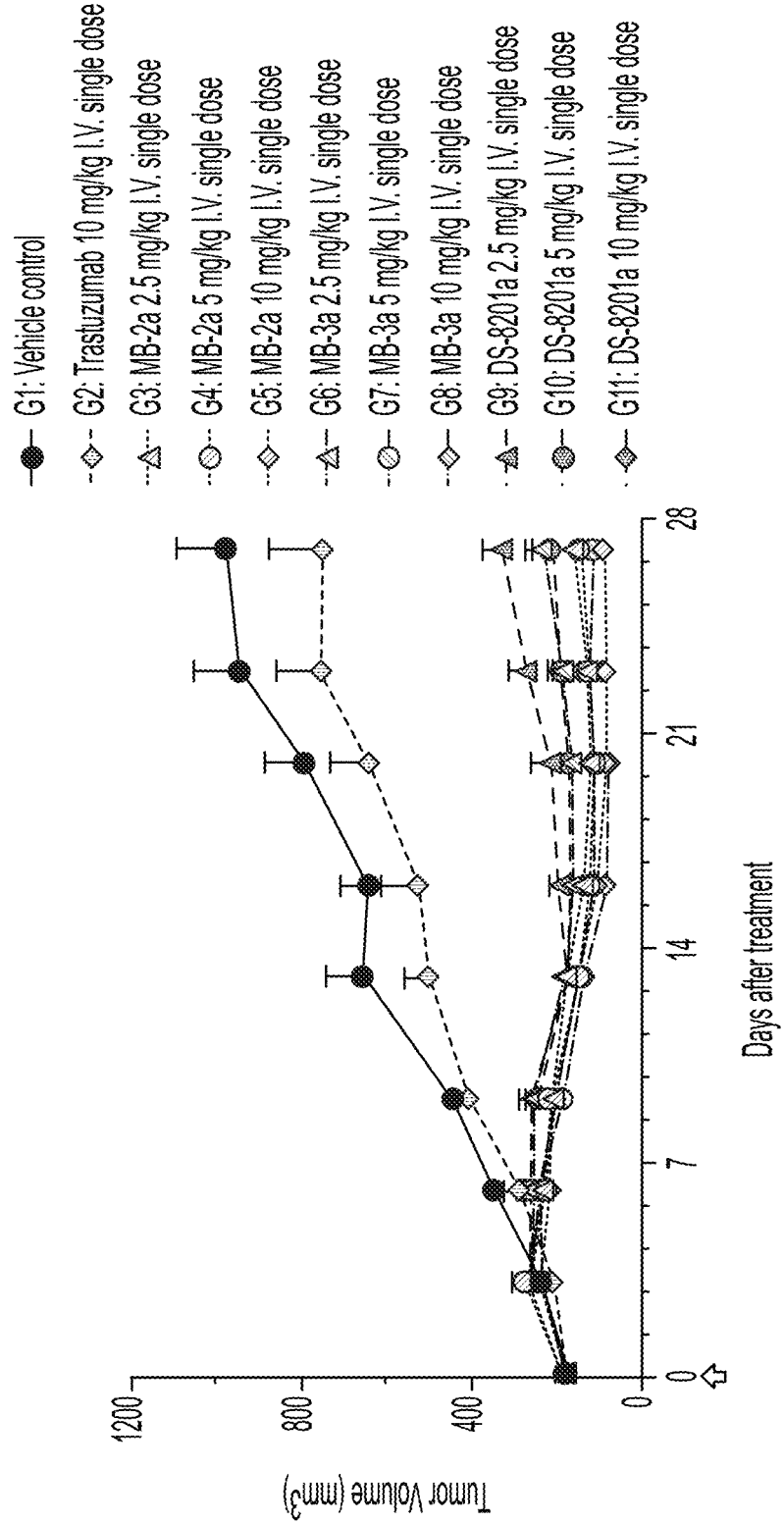
FIG. 2 illustrates effects of antibody drug conjugates (ADCs) in the JIMT-1 CDX model. In this study, all three doses of MB-2a and MB-3a studied showed a significant antitumor effect.
Figure 3:
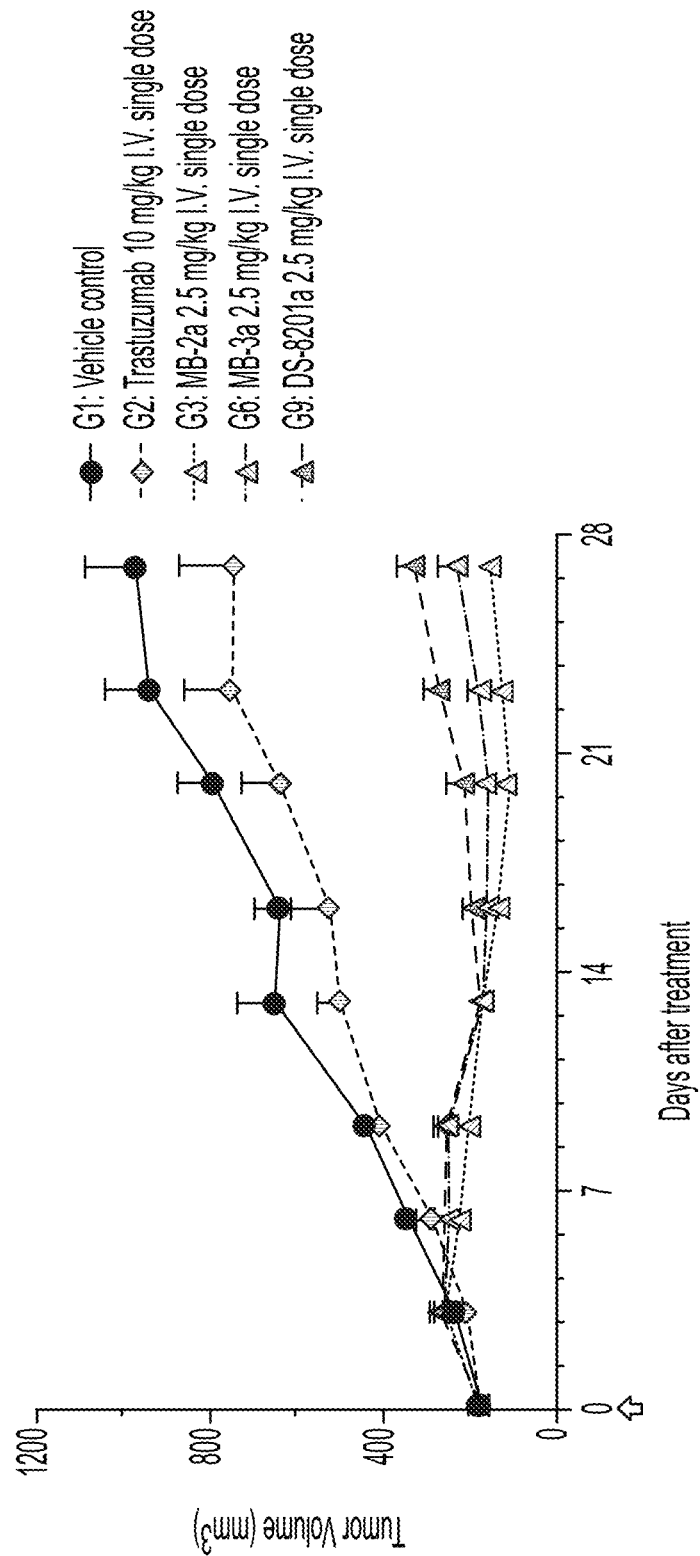
Figure 4:
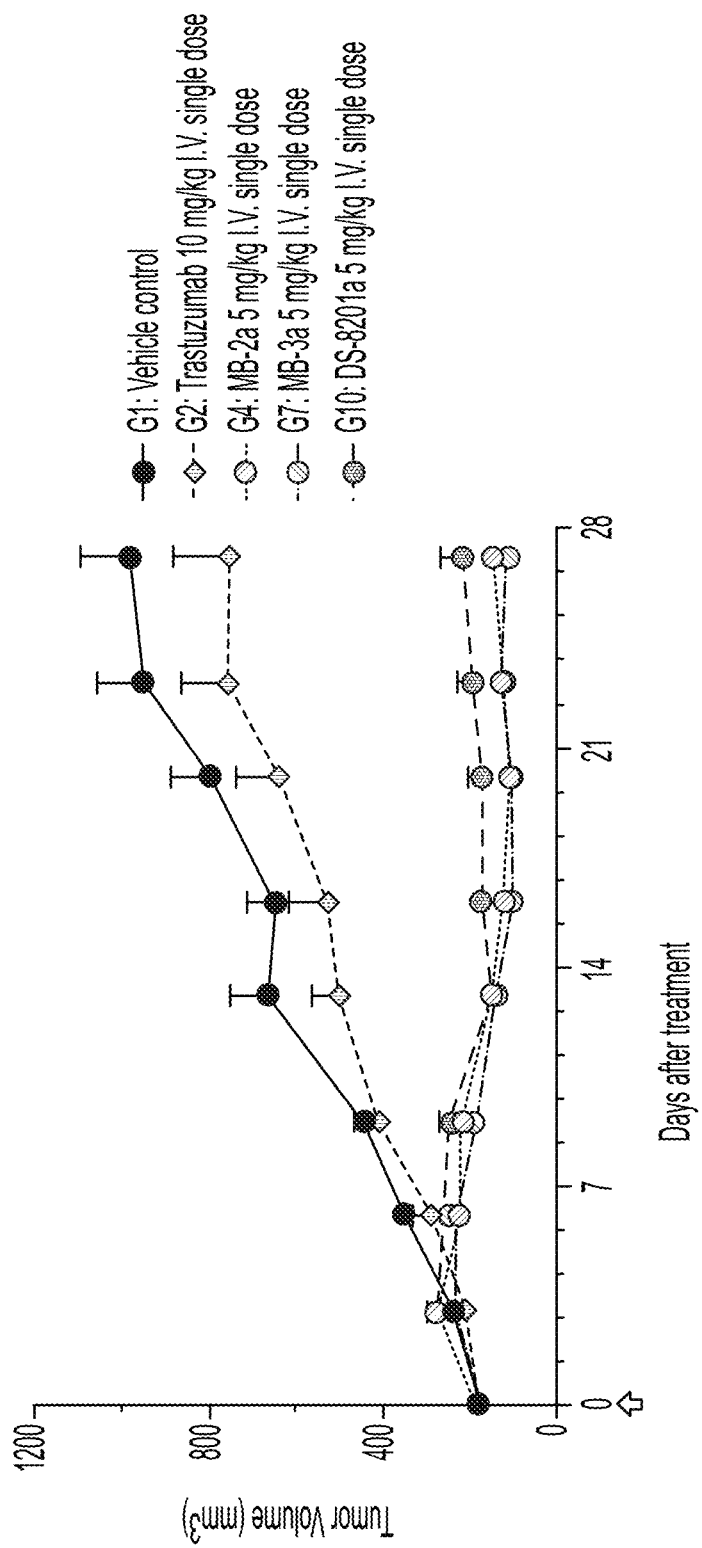
Figure 5:
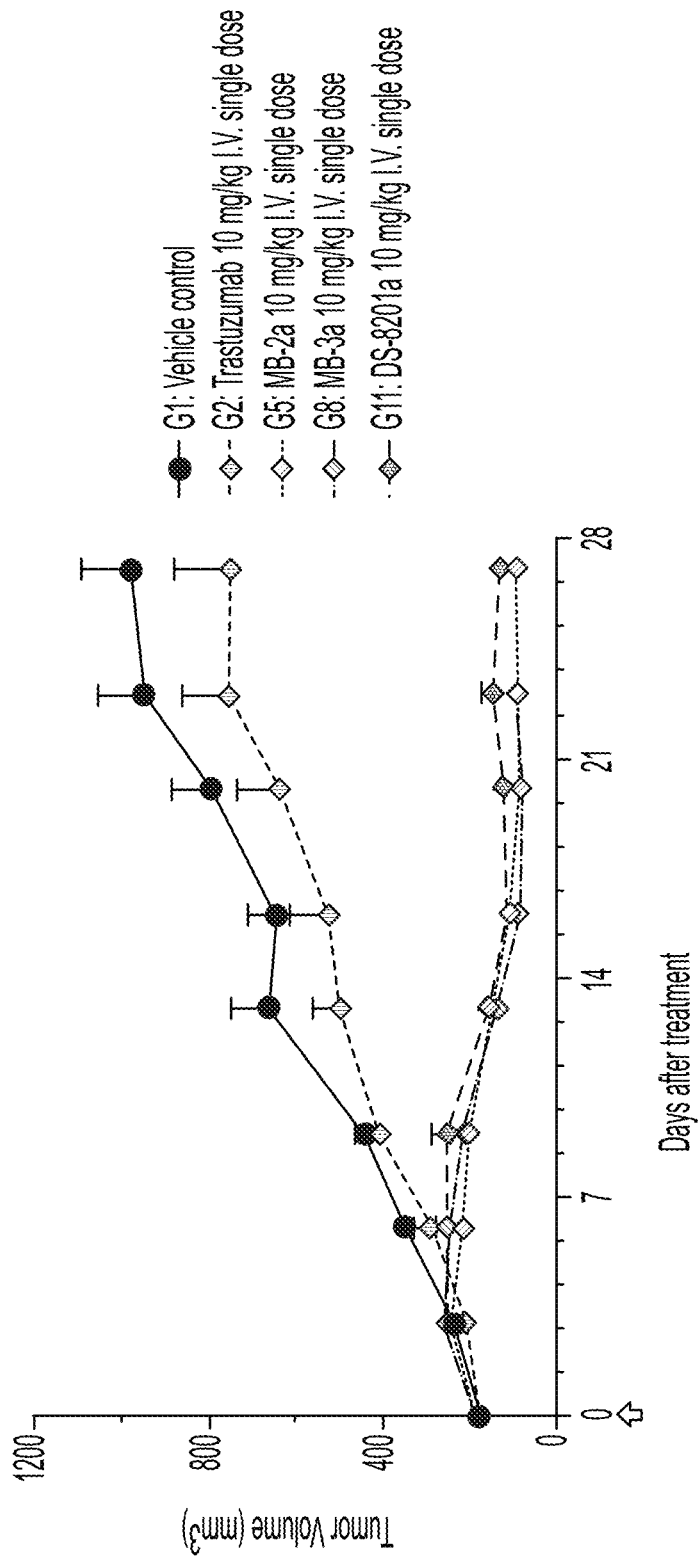

The antitumor effect of the ADCs in the JIMT-1 CDX model is illustrated in FIGS. 2-5 and in Table 6. FIG. 2 illustrates effects of antibody drug conjugates (ADCs) in the JIMT-1 CDX model at three different doses. In this study, all three doses of MB-2a and MB-3a (trastuzumab meditecan) studied showed a significant antitumor effect. MB-2a and MB-3a are more efficacious than DS-8201a (Enhertu) at low and moderate doses. The different doses studied in these experiments are also separately illustrated in FIG. 3 (2.5 mg/kg, i.v. single doses), FIG. 4 (5 mg/kg, i.v. single doses), and FIG. 5 (10 mg/kg, i.v. single doses).

TABLE 5

| Model | ADCs | Dosage (mg/Kg, single i.v.) | Regressions Partial | Regressions Complete | TGI (%) (day 23) | Comments |
|---|---|---|---|---|---|---|
| NCI-N87 | Vehicle | N/A | — | — | — | — |
|  | Trastuzumab | 4 | 0/8 | 0/8 | 16.8 | inactive |
|  | MB-2a | 0.25 | 0/8 | 0/8 | 12.0 | inactive |
|  | MB-3a | 0.25 | 0/8 | 0/8 | 28.1 | inactive |
|  | DS-8201a | 0.25 | 0/8 | 0/8 | 24.7 | inactive |
|  | MB-2a | 1 | 2/8 | 0/8 | 75.5 | active |
|  | MB-3a | 1 | 3/8 | 0/8 | 82.4 | highly active |
|  | DS-8201a | 1 | 0/8 | 0/8 | 52.2 | active |
|  | MB-2a | 4 | 5/8 | 3/8 | 97.1 | highly active |
|  | MB-3a | 4 | 5/8 | 3/8 | 97.6 | highly active |
|  | DS-8201a | 4 | 8/8 | 0/8 | 97.3 | highly active |

TABLE 6

| Model | ADCs | Dosage (mg/Kg, single i.v.) | Regressions Partial | Regressions Complete | TGI (%) (day 27) | Comments |
|---|---|---|---|---|---|---|
| JIMT-1 | Vehicle | N/A | — | — | — | — |
| | Trastuzumab | 10 | 0/8 | 0/8 | 22.5 | inactive |
| | MB-2a | 2.5 | 5/8 | 0/8 | 83.9 | highly active |
| | MB-3a | 2.5 | 3/8 | 0/8 | 76.2 | active |
| | DS-8201a | 2.5 | 1/8 | 0/8 | 66.3 | active |
| | MB-2a | 5 | 6/8 | 0/8 | 85.1 | highly active |
| | MB-3a | 5 | 7/8 | 0/8 | 88.4 | highly active |
| | DS-8201a | 5 | 4/8 | 0/8 | 78.4 | active |
| | MB-2a | 10 | 8/8 | 0/8 | 90.9 | highly active |
| | MB-3a | 10 | 6/8 | 1/8 | 90.9 | highly active |
| | DS-8201a | 10 | 7/8 | 0/8 | 87.5 | highly active |

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

I claim:

1. A compound of Formula (I),

or a pharmaceutically acceptable salt thereof, wherein:
D is represented by the following structural formula:

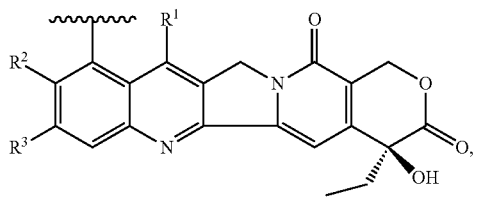

$R^1$ independently is —H or unsubstituted $C_1$-$C_6$ alkyl;
$R^2$ independently is —H, —F, —N($R^4$)$_2$, —N($R^4$)($R^5$), —O$R^4$, —S$R^4$, —S(=O)$R^5$, —SO$_2R^5$, $C_1$-$C_6$ alkyl, or $C_1$-$C_6$ fluoroalkyl; and $R^3$ independently is —H, —F, —CN, —OCH$_3$, —CH$_3$, or —CF$_3$; or
$R^2$ and $R^3$ together form a group of the formula —O(CH$_2$)$_n$O—, wherein n is 2, or —O(CF$_2$)$_n$O—, wherein n is 1 or 2;
$R^4$ independently is —H or $C_1$-$C_4$ alkyl;
$R^5$ independently is $C_1$-$C_4$ alkyl;
$L_1$ independently is absent or —($C_1$-$C_{10}$ alkylene)-;
$L_2$ independently is absent or is —OCH$_2$-$L_3$-*, —SCH$_2$-$L_3$-*, ~S(=O)-$L_3$-*, —SO$_2$-$L_3$-*, —C(=O)-$L_3$-*, —N($R^6$)CH$_2$-$L_3$-*, —N($R^6$)C(=O)-$L_3$-*, —N($R^6$)C(=O)N($R^7$)-$L_3$-*, —C(=O)N($R^6$)CH$_2$-$L_3$-*, —OC(=O)N($R^6$)CH$_2$-$L_3$-*, or —N($R^6$)C(=O)OCH$_2$-$L_3$-*;
wherein * denotes the site covalently linked to Q;
$L_3$ independently is —($C_1$-$C_{10}$ alkylene)-, —CH$_2$OCH$_2$CH$_2$—, or —CH$_2$CH$_2$OCH$_2$CH$_2$—;
each $R^6$ and $R^7$ independently is —H, $C_1$-$C_6$ alkyl, $C_1$-$C_6$ fluoroalkyl, $C_3$-$C_6$ cycloalkyl, aryl, heteroaryl, or benzyl; and
Q is —OH or —SH; and
wherein
when $R^1$ is —H or —CH$_2$CH$_3$, $R^2$ is —OH or alkoxy and $R^3$ is —H, then -$L_1$-$L_2$-Q is not —CH($R'$)CH$_2$OH or —CH($R'$)(CH$_2$)$_2$OH, wherein $R'$ is —H or $C_1$-$C_6$ alkyl, alkoxy, substituted alkyl, phenyl or PhCH$_2$—.

2. The compound of claim 1, wherein
$R^2$ independently is $C_1$-$C_6$ alkyl, $C_1$-$C_6$ fluoroalkyl, or —F; and/or
$R^3$ independently is —H, —F, —CN, or —CF$_3$.

3. The compound of claim 1, wherein D is represented by one of the following structures:

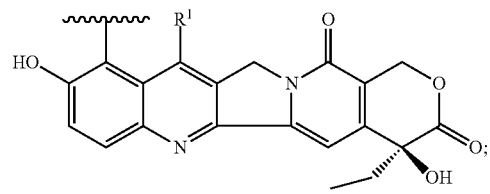
(D-I)

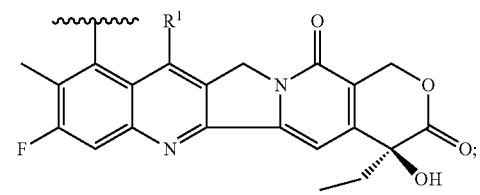
(D-II)

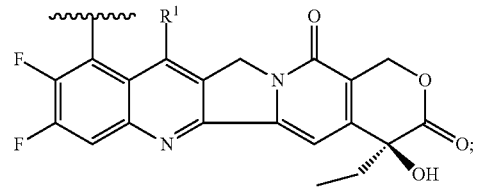
(D-III)

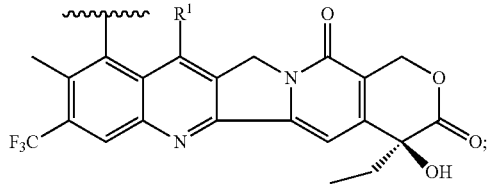
(D-IV)

(D-V)
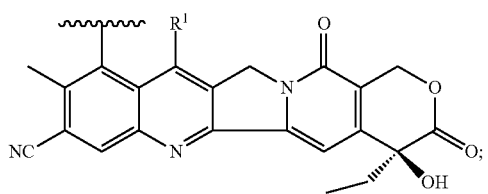
(D-VI)
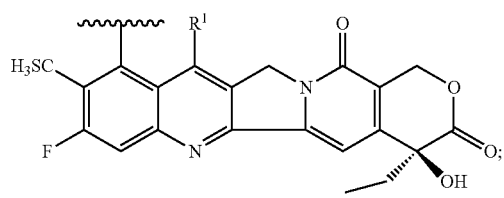
(D-VIII)
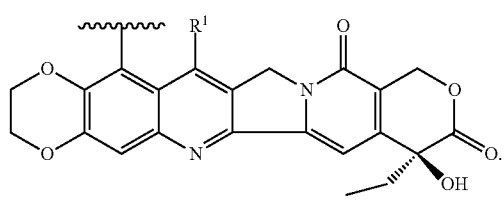
4. The compound of claim 3, wherein D is represented by one of the following structures:
(D1)
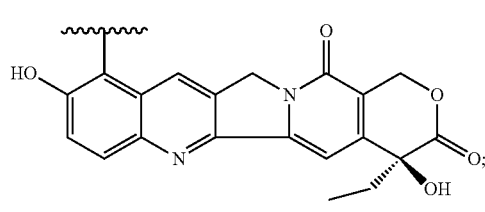
(D2)
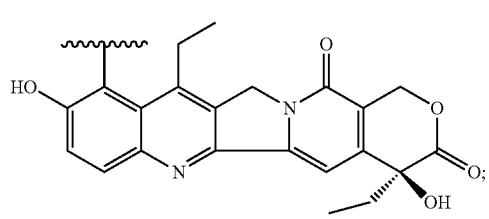
(D3)
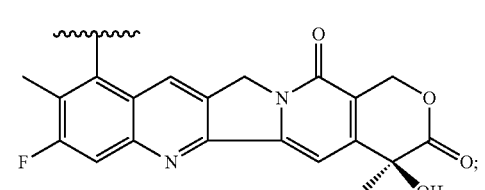
(D4)
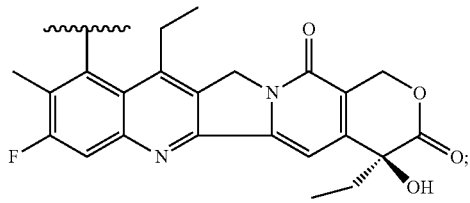
(D5)
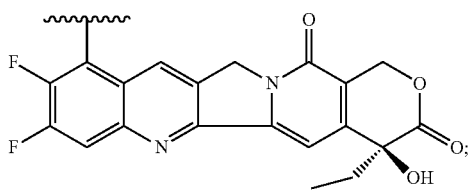
(D6)
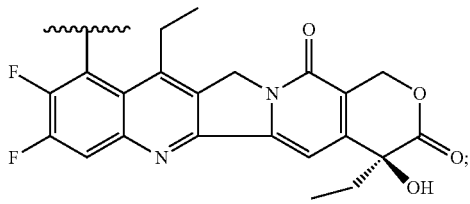
(D7)
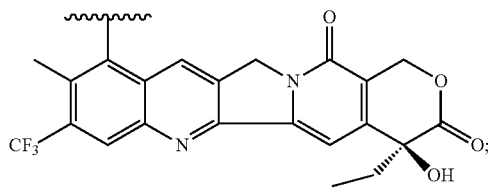
(D8)
(D9)
(D10)
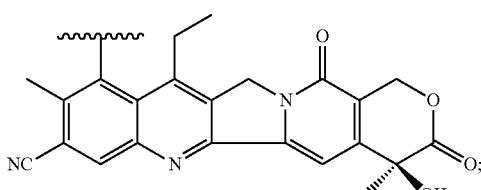

(D11)
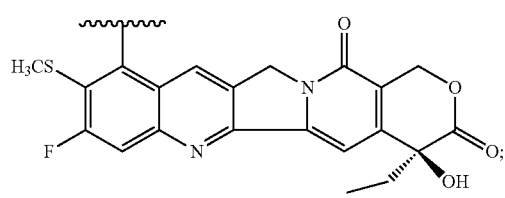

(D12)
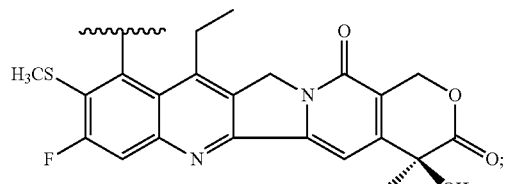

(D15)
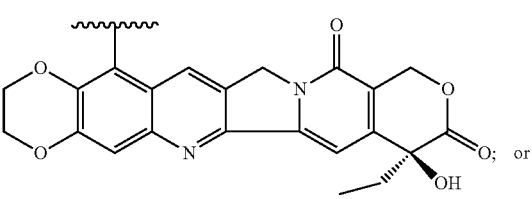

or (D16)
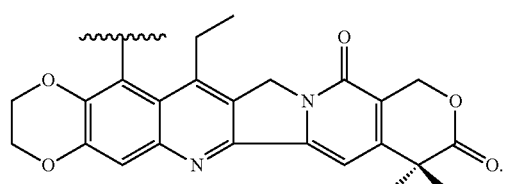

5. The compound of claim 1, wherein $L_1$ is —($C_1$-$C_{10}$ alkylene)- and $L_2$ is absent.

6. The compound of claim 1, wherein $L_1$-$L_2$ is —$CH_2$—, —$CH_2CH_2$—, —$CH_2CH_2CH_2$—, or —$CH_2CH_2CH_2CH_2$—.

7. The compound of claim 1, wherein D-$L_1$-$L_2$ is represented by a structure that is (P-I)
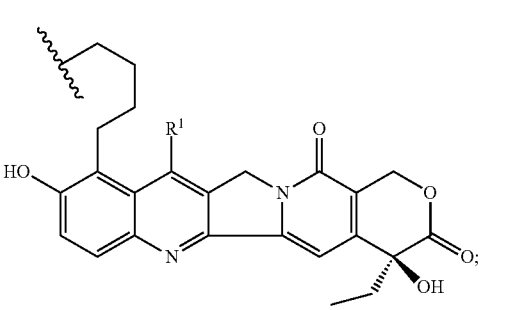

(P-II)
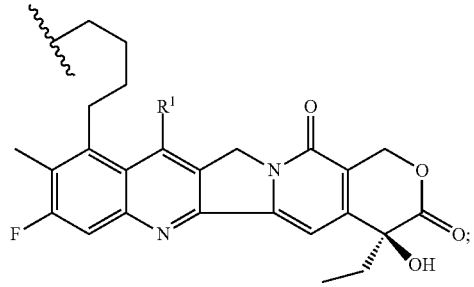

(P-III)
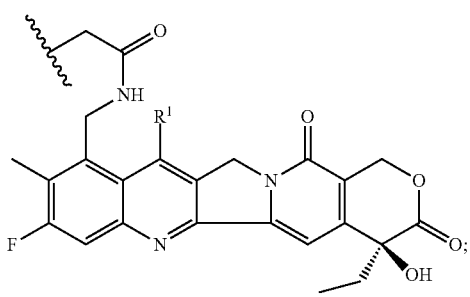

(P-IV)
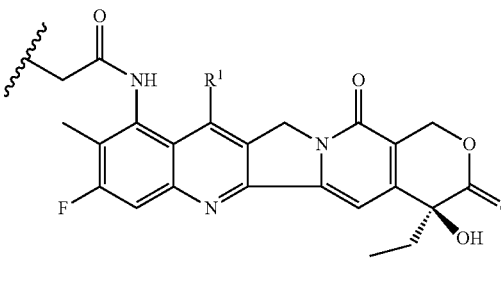

or (P-V)
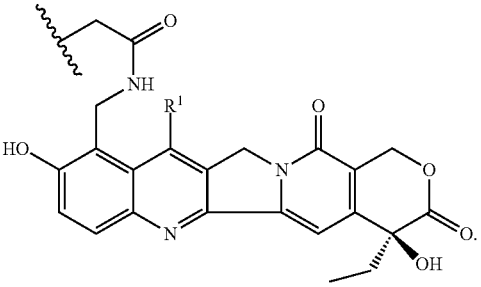

8. The compound of claim 1, wherein Q is —OH.

9. The compound of claim 1, wherein the compound has one of the following structures, (P1)
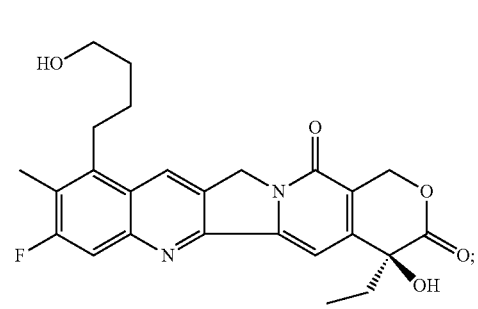

-continued (P2)
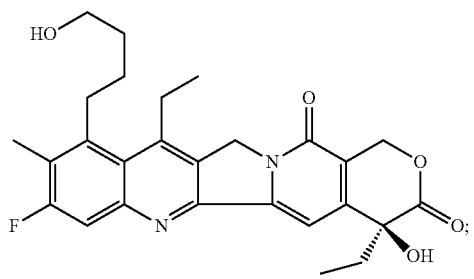

(P3)
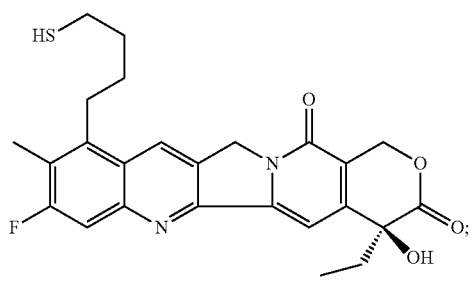

(P4)
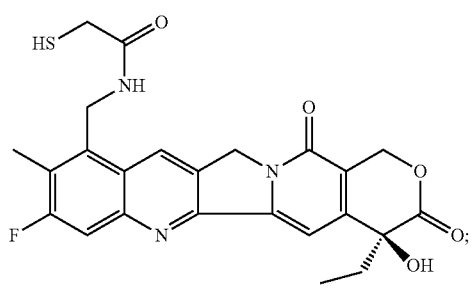

(P5)
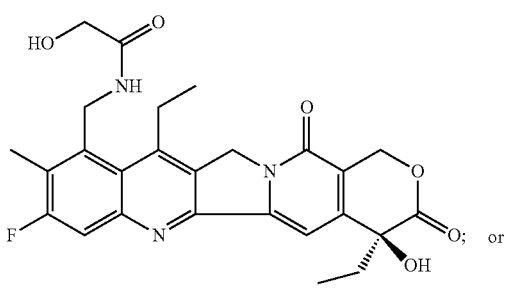

(P6)
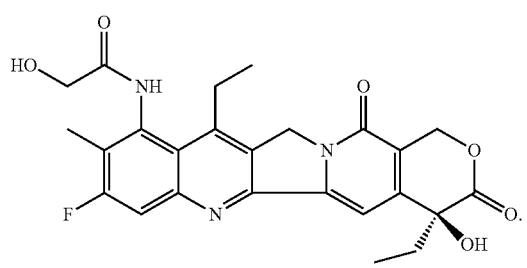

or a pharmaceutically acceptable salt thereof.

10. A compound of Formula (II), $$D\text{-}L_1\text{-}L_2\text{-}Q'\text{—}CH_2\text{—}NH\text{-}E\text{-}Z \quad (II),$$

or a pharmaceutically acceptable salt thereof, wherein:

D is represented by the following structural formula:

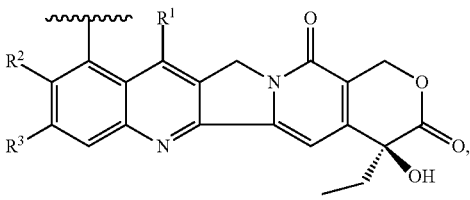

wherein $R^1$ independently is —H or unsubstituted $C_1$-$C_6$ alkyl;

$R^2$ independently is —H, —F, —N($R^4$)$_2$, —N($R^4$)($R^5$), —O$R^4$, —S$R^4$, —S(=O)$R^5$, —SO$_2R^5$, $C_1$-$C_6$ alkyl, or $C_1$-$C_6$ fluoroalkyl; and $R^3$ is —H, —F, —CN, —OCH$_3$, —CH$_3$, —CF$_3$; or $R^2$ and $R^3$ together form a group of the formula —O(CH$_2$)$_n$O—, wherein n is 2, or —O(CF$_2$)$_n$O— wherein n is 1 or 2;

$R^4$ independently is —H or $C_1$-$C_4$ alkyl;

$R^5$ independently is $C_1$-$C_4$ alkyl;

$L_1$ independently is absent or —($C_1$-$C_{10}$ alkylene)-;

$L_2$ independently is absent or is —OCH$_2$-$L_3$-*, —SCH$_2$-$L_3$-*, —S(=O)-$L_3$-*, —SO$_2$-$L_3$-*, —C(=O)-$L_3$-*, —N($R^6$)CH$_2$-$L_3$-*, —N($R^6$)C(=O)-$L_3$-*, —N($R^6$)C(=O)N($R^7$)-$L_3$-*, —C(=O)N($R^6$)CH$_2$-$L_3$-*; —OC(=O)N($R^6$)CH$_2$-$L_3$-*, or —N($R^6$)C(=O)OCH$_2$-$L_3$-* wherein denotes the site covalently linked to Q';

$L_3$ independently is —($C_1$-$C_{10}$ alkylene)-, —CH$_2$OCH$_2$CH$_2$—, or —CH$_2$CH$_2$OCH$_2$CH$_2$—;

each $R^6$ and $R^7$ independently is —H, $C_1$-$C_6$ alkyl, $C_1$-$C_6$ fluoroalkyl, $C_3$-$C_6$ cycloalkyl, aryl, heteroaryl, or benzyl; and Q' is —O— or —S—;

E is a peptide comprising 2 to 10 amino acids; wherein E is optionally substituted with one or more polyol; and wherein the N terminal of the peptide is covalently attached to Z;

Z is —C(=O)-$L_4$-Y,

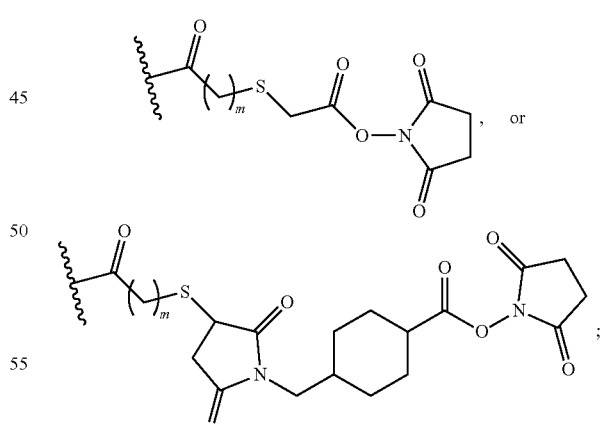

wherein m represents an integer of 1-10;

$L_4$ is —($C_1$-$C_{10}$ alkylene)-*, —CH$_2$CH$_2$(OCH$_2$CH$_2$)$_n$N($R^8$)C(=O)-$L_5$-* or —CH$_2$(OCH$_2$CH$_2$)$_n$N($R^8$)C(=O)-$L_5$-*; wherein n represents an integer of 1-10; and wherein * denotes the site covalently linked to Y;

$L_5$ is —($C_1$-$C_{10}$ alkylene)-;

$R^8$ is —H or —CH$_3$; and

Y is an electrophilic group.

11. The compound of claim 10, wherein E is a peptide of 2, 3, or 4 amino acids, wherein each amino acid in said peptide is an L amino acid or at least one amino acid in said peptide is a D amino acid.

12. The compound of claim 10, wherein E comprises one or more amino acids selected from glycine, alanine, valine, glutamine, glutamic acid, phenylalanine, and leucine, and wherein said glutamine or glutamic acid is optionally substituted by a polyol.

13. The compound of claim 10, wherein E comprises an amino acid having the following structure,

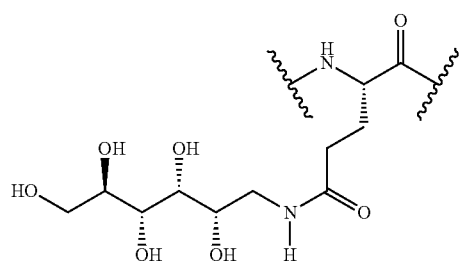

14. The compound of claim 10, wherein -E-NH—CH$_2$— has one of the following structures, wherein * denotes the N-terminal of the peptides covalently attached to Z:

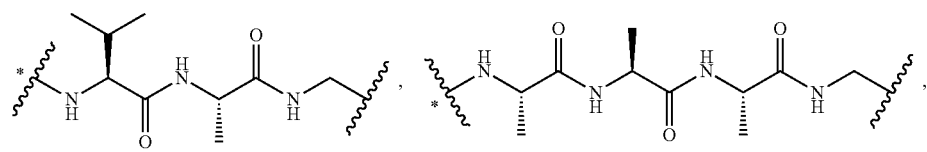

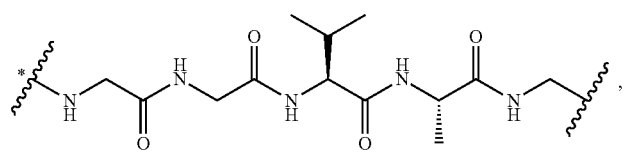

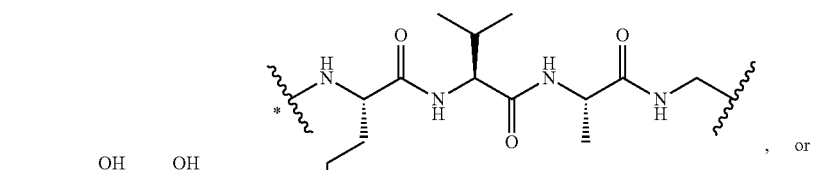

, or

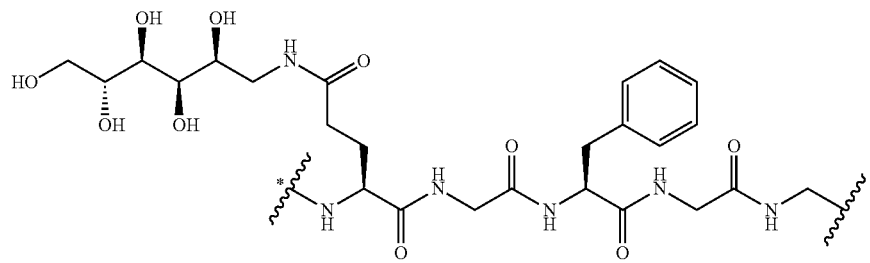

15. The compound of claim 10, wherein Z is

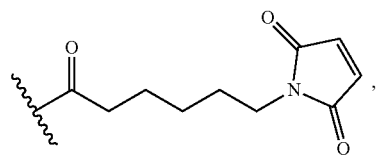

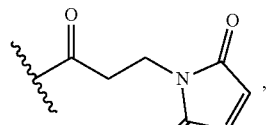

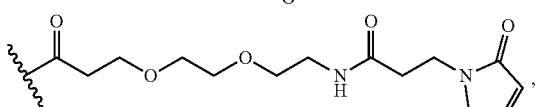

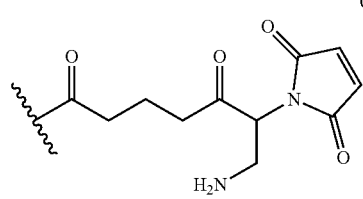

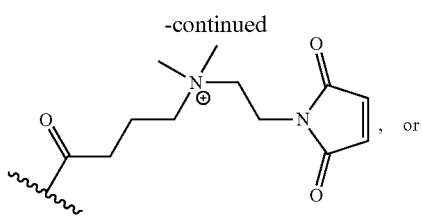, or
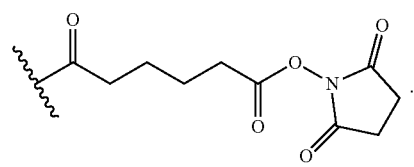.
16. The compound of claim 10, wherein Z-E-NH—CH$_2$— has one of the following structures.
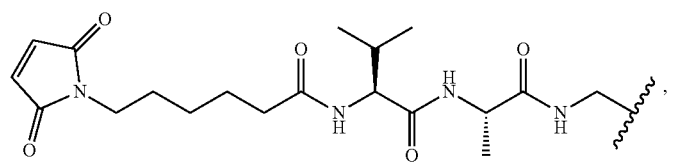,
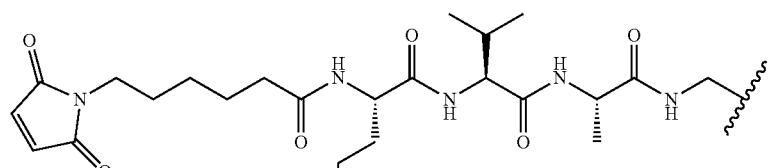,
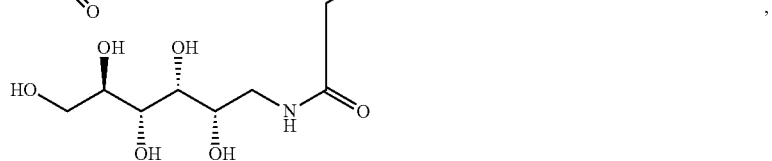,
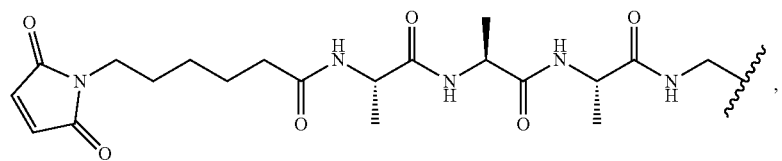, or
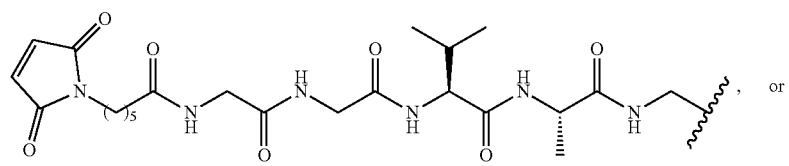.

17. The compound of claim 10, wherein D is represented by one of the following structures:
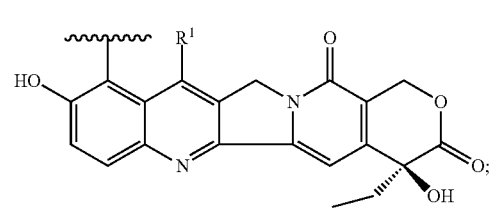
(D-I)
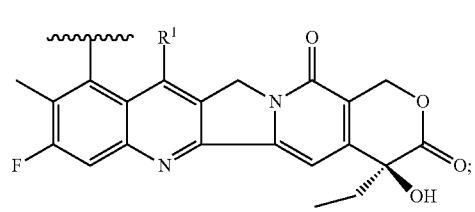
(D-II)
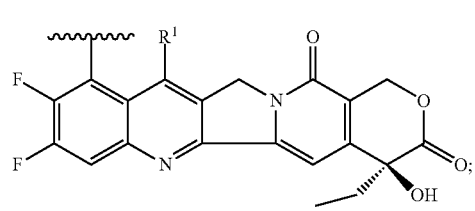
(D-III)
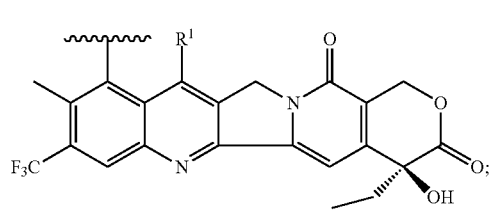
(D-IV)
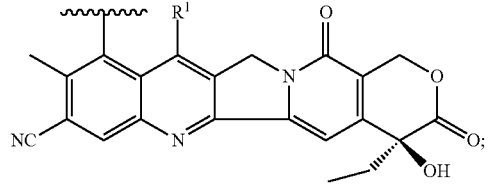
(D-V)
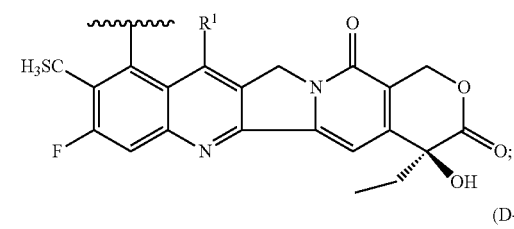
(D-VI)
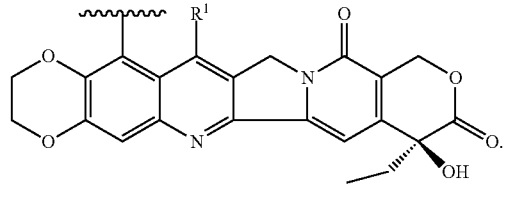
(D-VIII)
18. The compound of claim 17, wherein D is represented by one of the following structures:
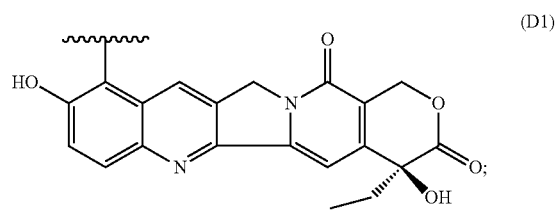
(D1)
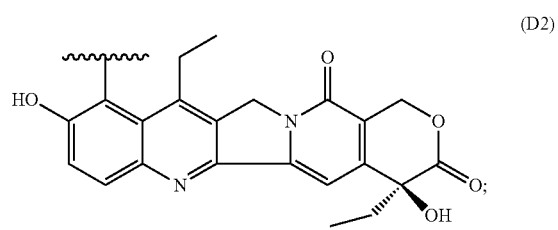
(D2)
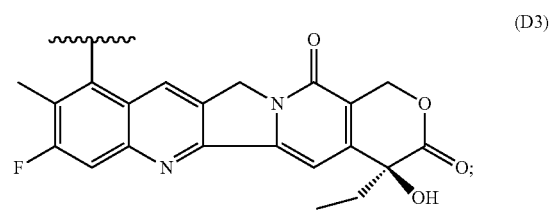
(D3)
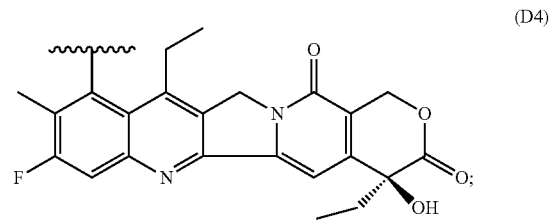
(D4)
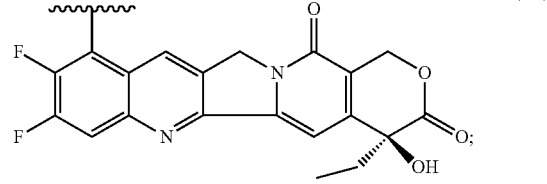
(D5)
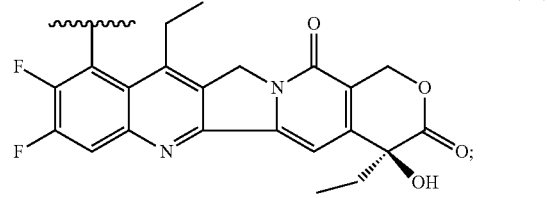
(D6)
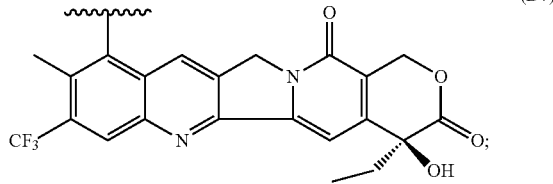
(D7)

-continued
(D8) 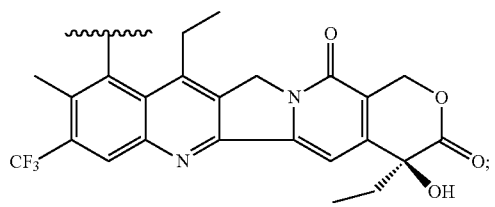
(D9) 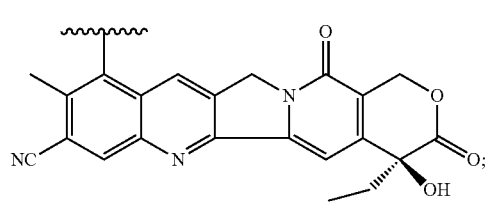
(D10) 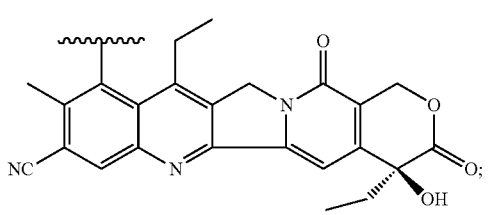
(D11) 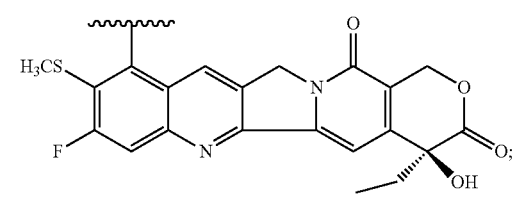
(D12) 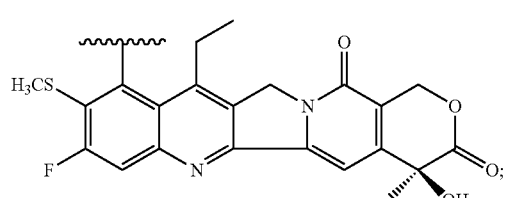
(D15) 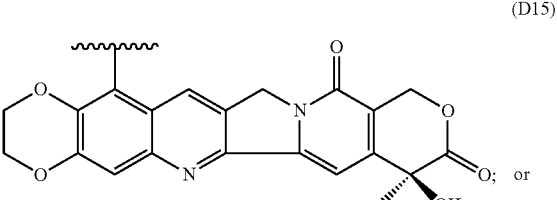
(D16) 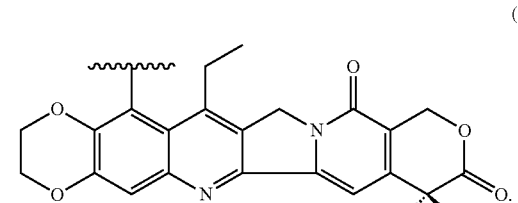
19. The compound of claim 10, wherein $D-L_1-L_2$ is represented by a structure that is
(P-I) 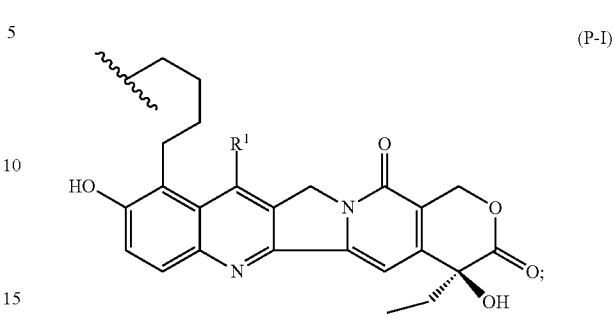
(P-II) 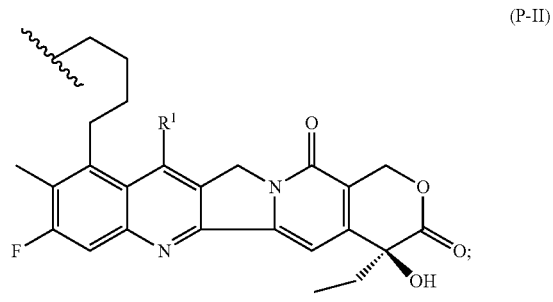
(P-III) 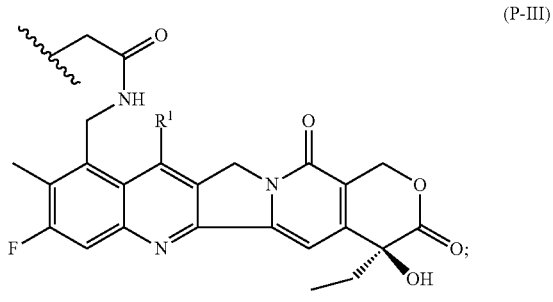
(P-IV) 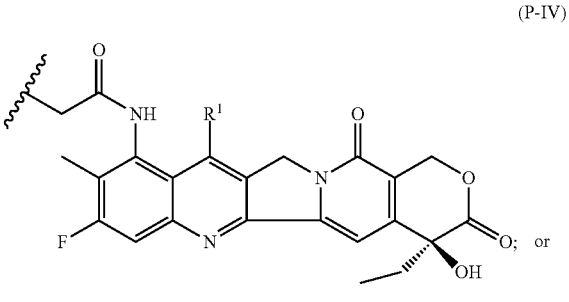
or
(P-V) 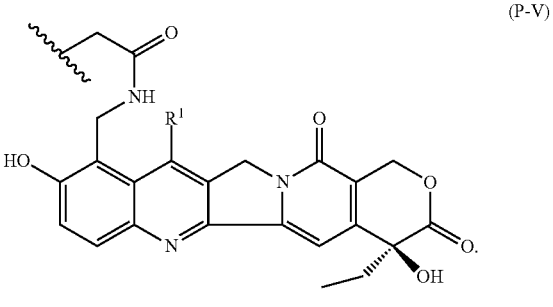

20. The compound of claim 10, wherein D-L$_1$-L$_2$-Q'— has one of the following structures:
(P1')
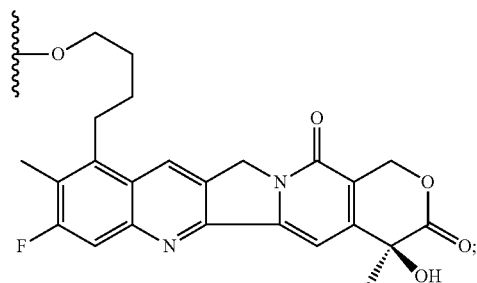
(P2')
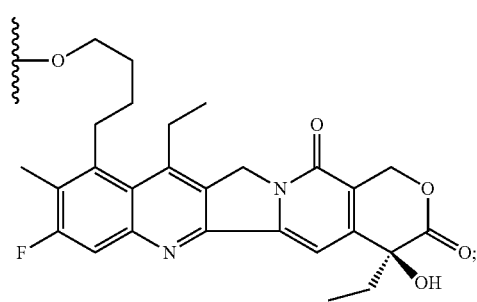
(P3')
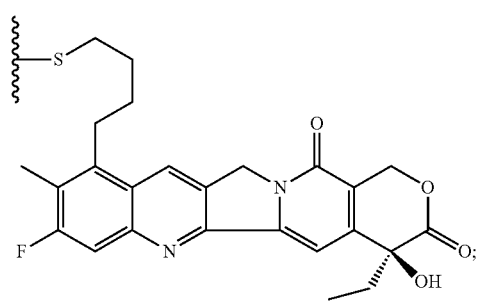
(P4')
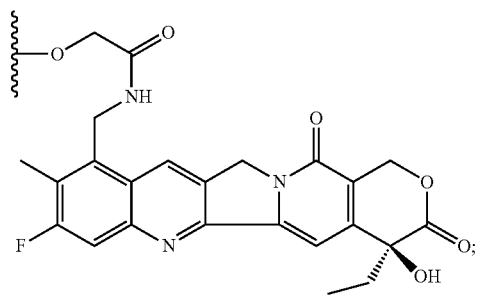
(P5')
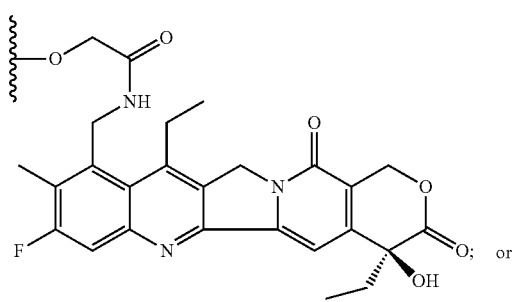
or
(P6')
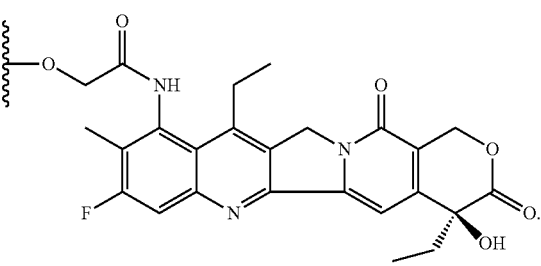
21. The compound of claim 10, wherein the compound has one of the following structures,
(PL1)
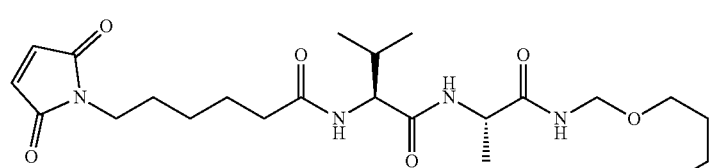
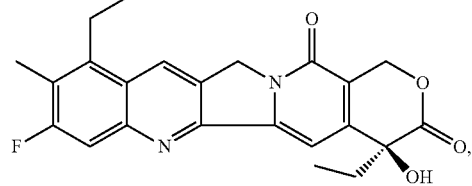

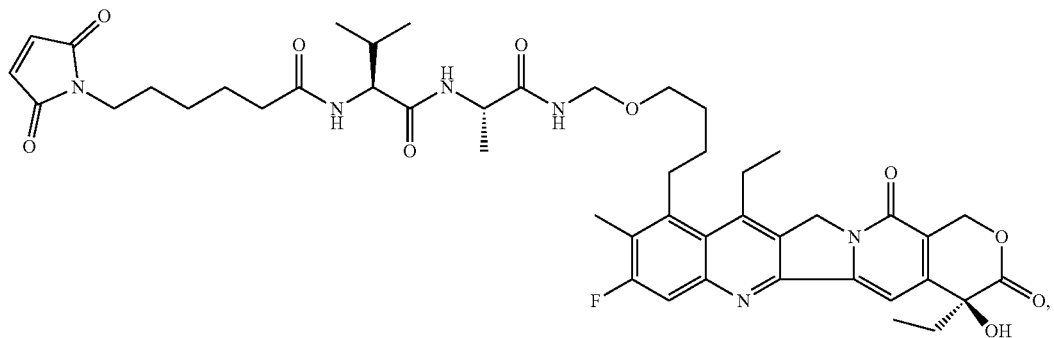
(PL2)
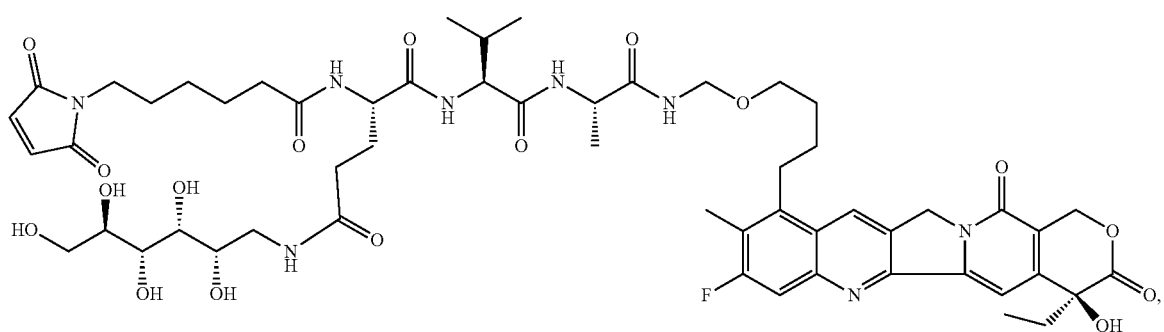
(PL3)
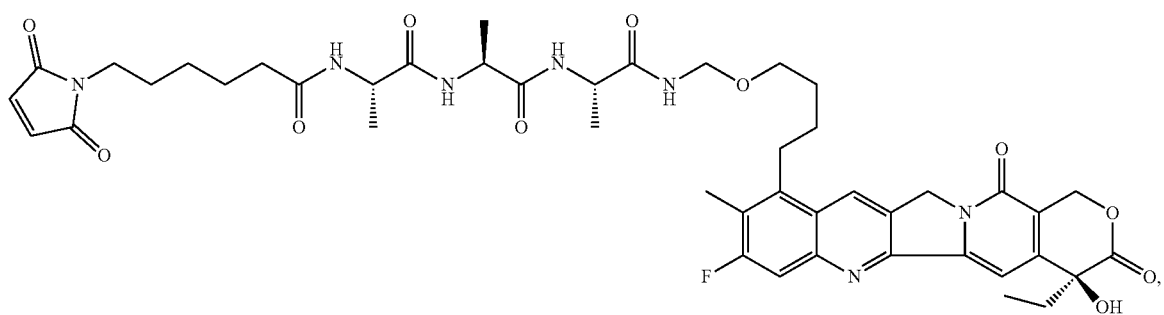
(PL4)
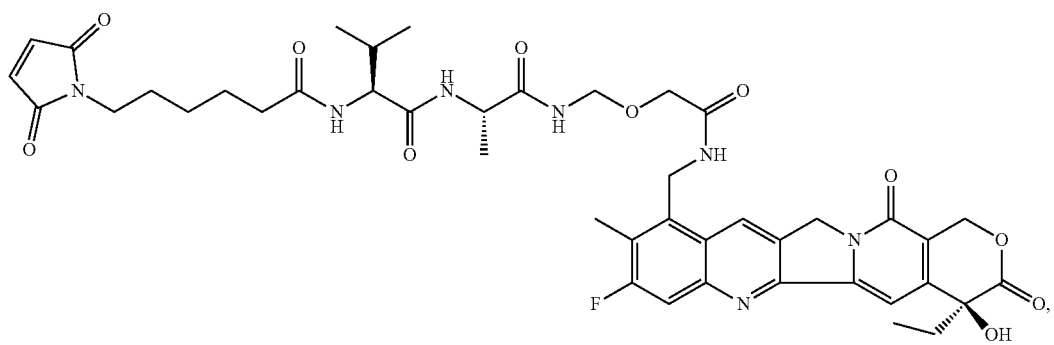
(PL5)

-continued
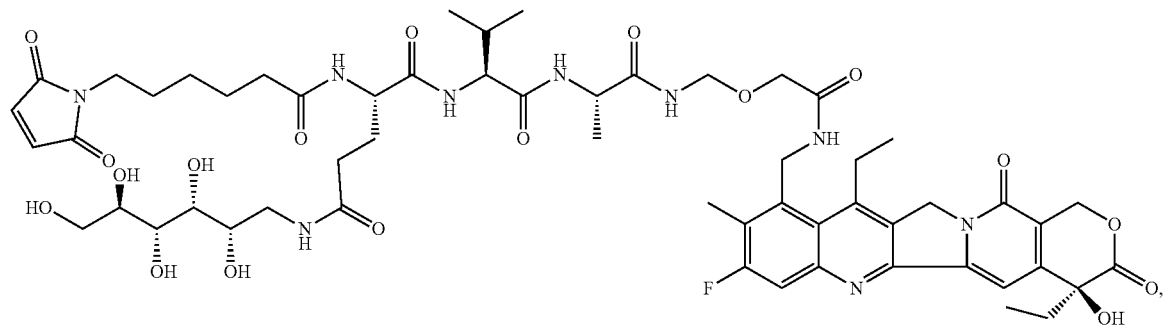
(PL6)
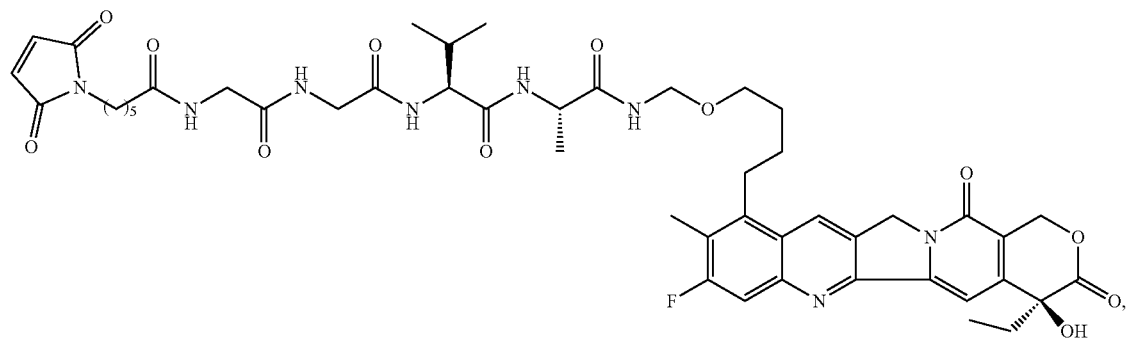
(PL7)
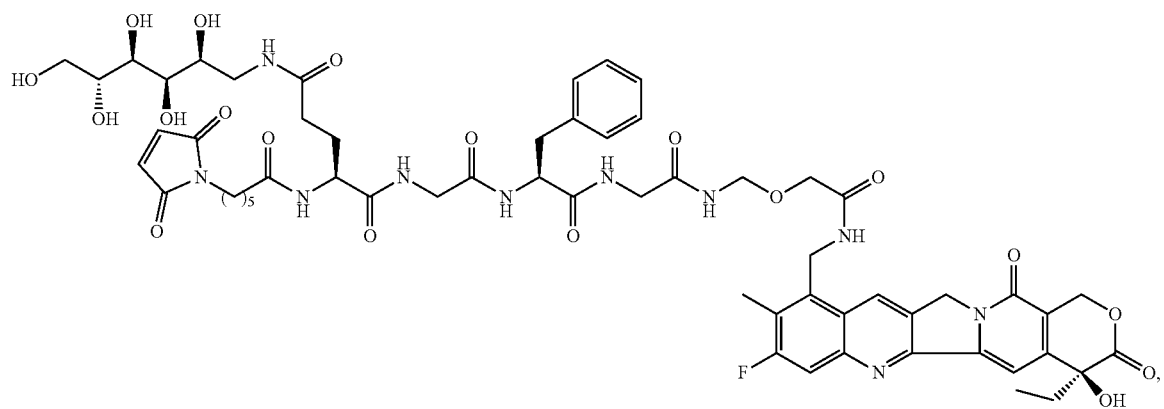
(PL8)
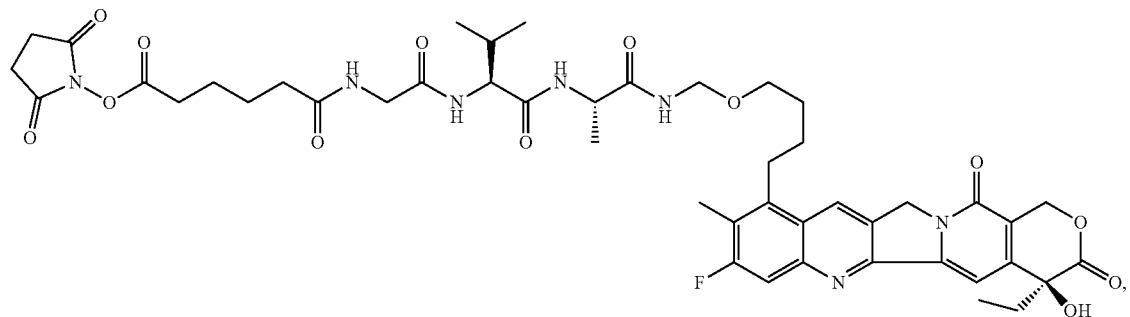
(PL9)

-continued
(PL10)
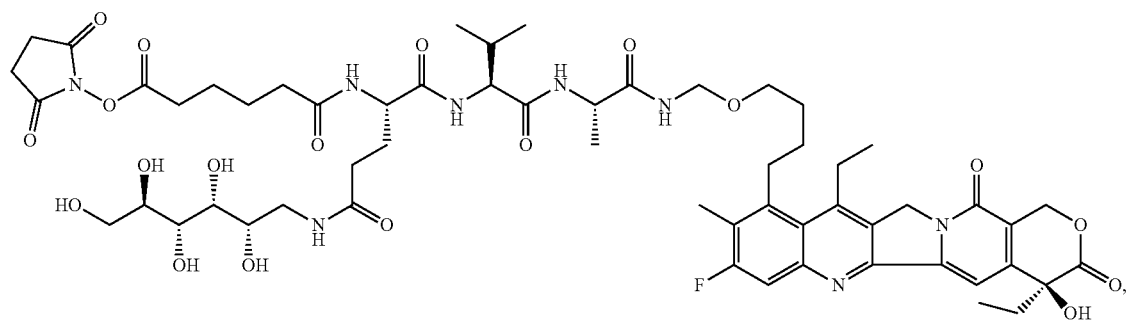
(PL11)
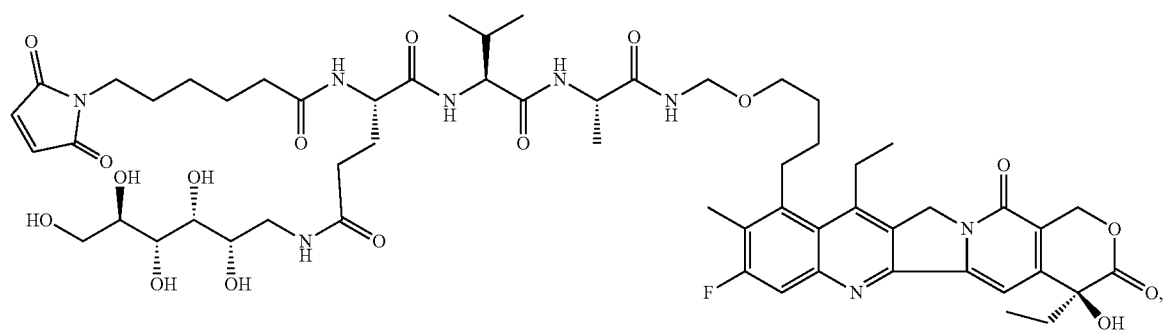
(PL12)
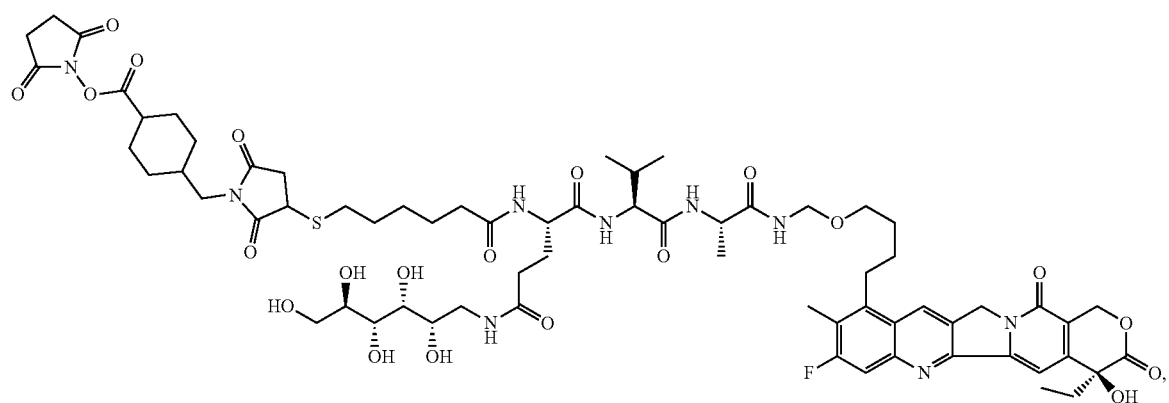
(PL13)
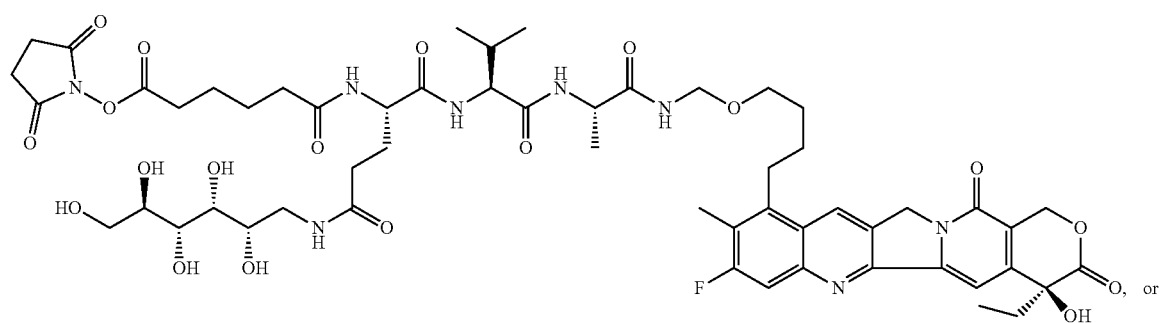

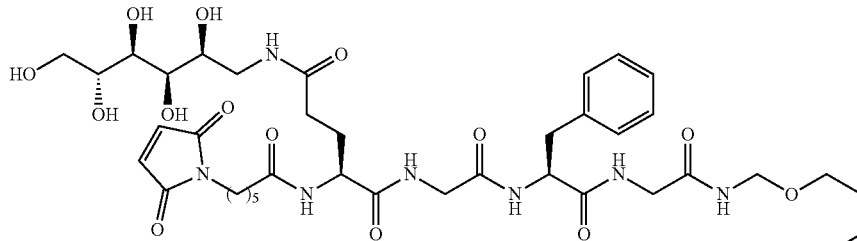

(PL14)

or a pharmaceutically acceptable salt thereof.

22. A compound of Formula (III),

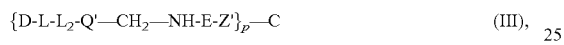

or a pharmaceutically acceptable salt thereof, wherein:

D is represented by the following structural formula:

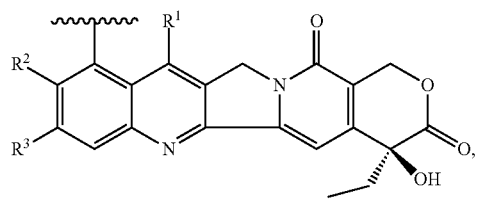

wherein $R^1$ independently is —H, or unsubstituted $C_1$-$C_6$ alkyl;

$R^2$ independently is —H, —F, —N($R^4$)$_2$, —N($R^4$)($R^5$), —O$R^4$, —S$R^4$, —S(=O)$R^5$, —SO$_2$$R^5$, $C_1$-$C_6$ alkyl, or $C_1$-$C_6$ fluoroalkyl; and $R^3$ is —H, —F, —CN, —OCH$_3$, —CH$_3$, or —CF$_3$; or $R^2$ and $R^3$ together form a group of the formula —O(CH$_2$)$_n$O—, wherein n is 2, or —O(CF$_2$)$_n$O—, wherein n is 1 or 2;

$R^4$ independently is —H or $C_1$-$C_4$ alkyl;

$R^5$ independently is $C_1$-$C_4$ alkyl;

$L_1$ independently is absent or —($C_1$-$C_{10}$ alkylene)-;

$L_2$ independently is absent or is —OCH$_2$-$L_3$-*, ~SCH$_2$-L-*, —S(=O)-$L_3$-*, —SO$_2$-$L_3$-*, —C(=O)-$L_3$-*, —N($R^6$)CH$_2$-L-*, —N($R^6$)C(=O)-$L_3$-*, —N($R^6$)C(=O)N($R^7$)-$L_3$-*, —C(=O)N($R^6$)CH$_2$-L-*, —OC(=O)N($R^6$)CH$_2$-$L_3$*, or —N($R^6$)C(=O)OCH$_2$-$L_3$-*; wherein * denotes the site covalently linked to Q';

$L_3$ independently is —($C_1$-$C_1$ alkylene)-, —CH$_2$OCH$_2$CH$_2$—, or —CH$_2$CH$_2$OCH$_2$CH$_2$—;

each $R^1$ and $R^7$ independently is —H, $C_1$-$C_6$ alkyl, $C_1$-$C_6$ fluoroalkyl, $C_3$-$C_6$ cycloalkyl, aryl, heteroaryl, or benzyl;

Q' is —O— or —S—;

E is a peptide comprising 2 to 10 amino acids; wherein E is optionally substituted with one or more polyol; and wherein the N terminal of the peptide is covalently attached to Z';

Z' is —C(=O)-$L_4$-Y',

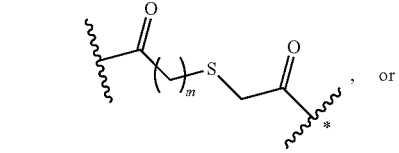

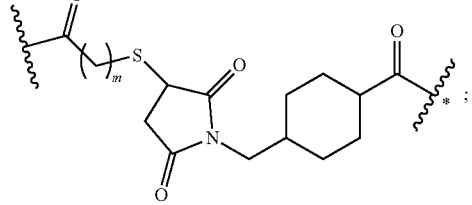

wherein m represents an integer of 1-10 and * denotes the site covalently linked to said C;

$L_4$ is —($C_1$-$C_{10}$ alkylene)-, —CH$_2$CH$_2$(OCH$_2$CH$_2$)$_n$N($R^8$)C(=O)-$L_5$-*, or —CH$_2$(OCH$_2$CH$_2$)$_n$N($R^8$)C(=O)-$L_5$-*; wherein n represents an integer of 1-10; and wherein * denotes the site covalently linked to Y';

$L^5$ is —($C_1$-$C_{10}$ alkylene)-;

$R^8$ is —H or —CH$_3$;

C represents a cell binding agent;

Y' is a group formed by the reaction of an electrophilic group with a reactive nucleophilic group present on said cell binding agent; and p has a value between 1 to 18.

23. The compound of claim 22, wherein D is represented by one of the following structures:

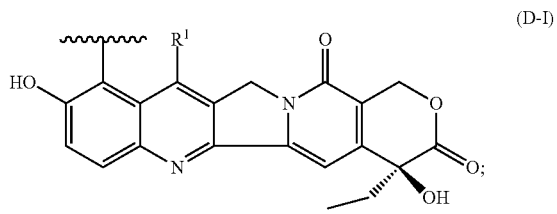

(D-I)

(D-II) 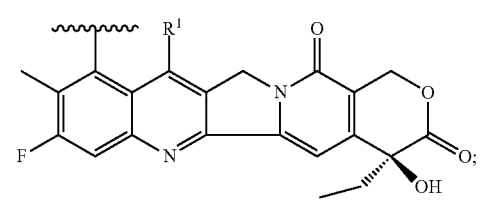
(D-III) 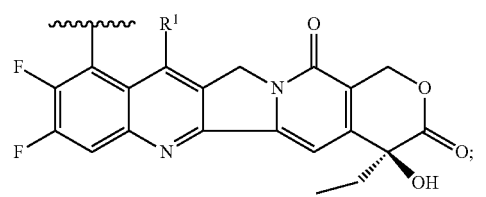
(D-IV) 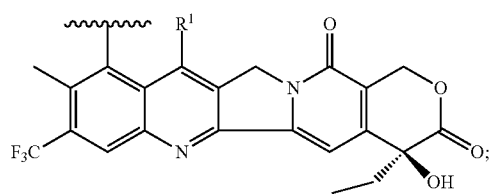
(D-V) 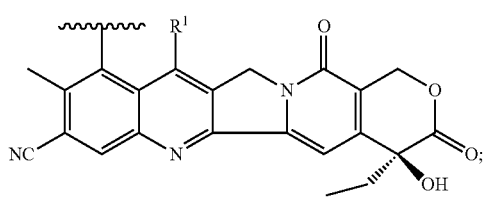
(D-VI) 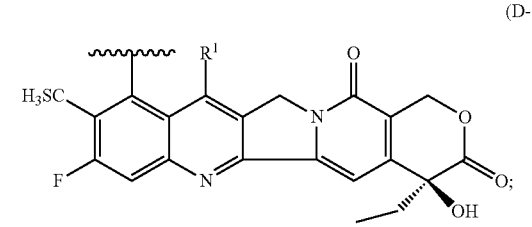
(D-VIII) 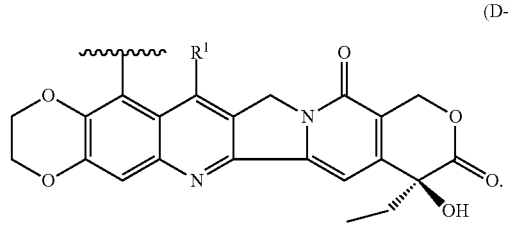
24. The compound of claim 23, wherein D is represented by one of the following structures:
(D1) 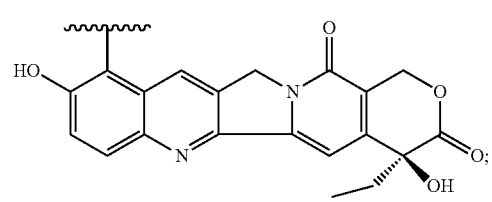
(D2) 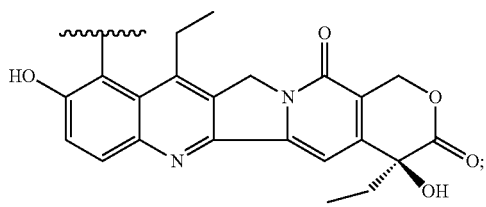
(D3) 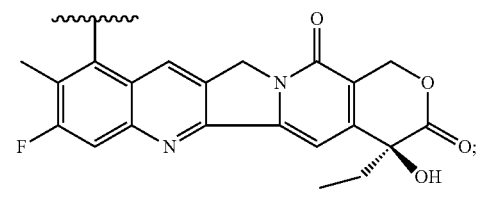
(D4) 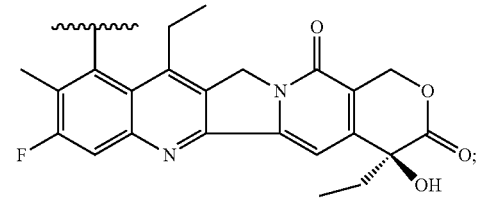
(D5) 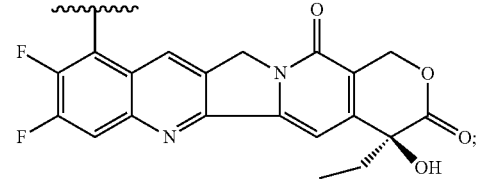
(D6) 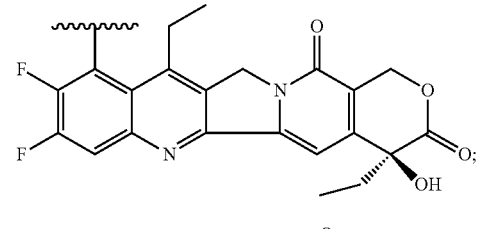
(D7) 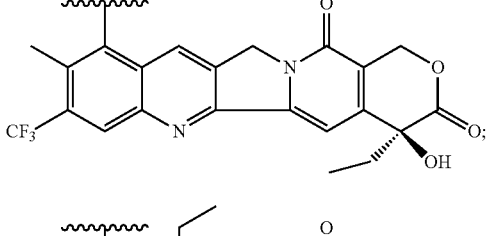
(D8) 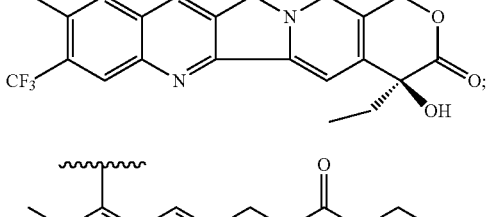
(D9) 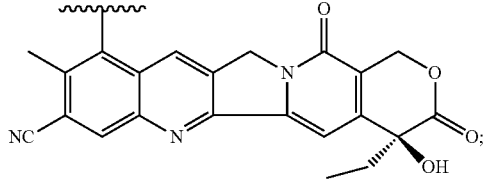

-continued
(D10)
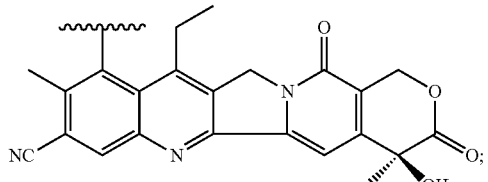
(D11)
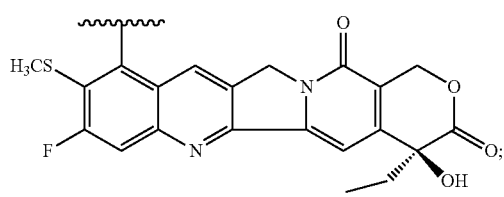
(D12)
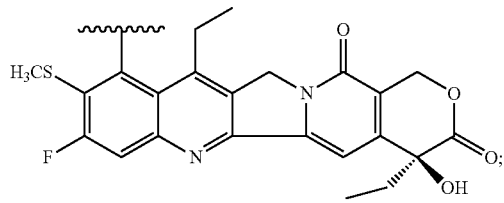
(D15)
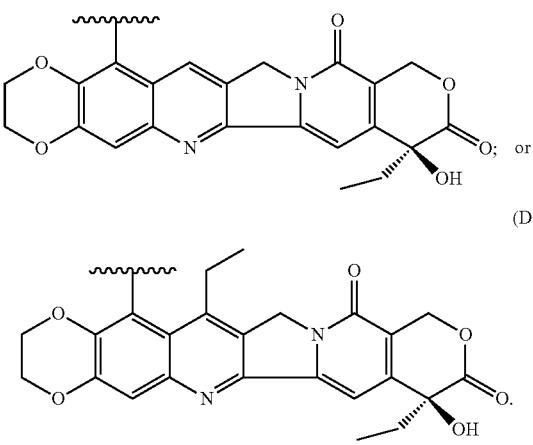
(D16)
25. The compound of claim 22, wherein D-L$_1$-L$_2$ is represented by a structure that is
(P-I)
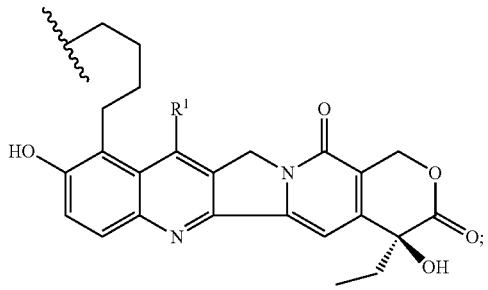
-continued
(P-II)
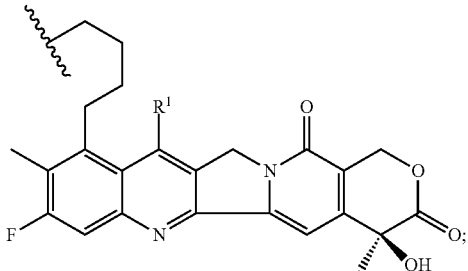
(P-III)
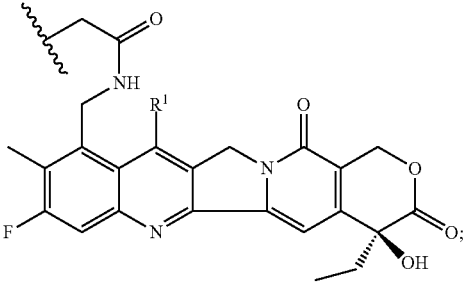
(P-IV)
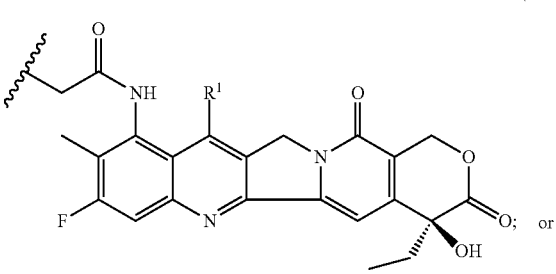
(P-V)
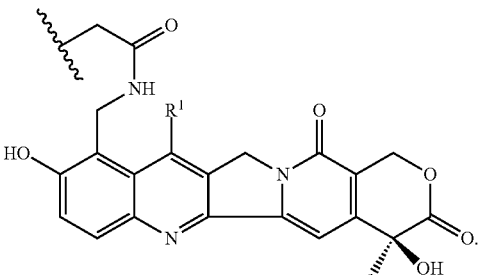
26. The compound of claim 22, wherein D-L$_1$-L$_2$-Q'— has one of the following structures:
(P1')
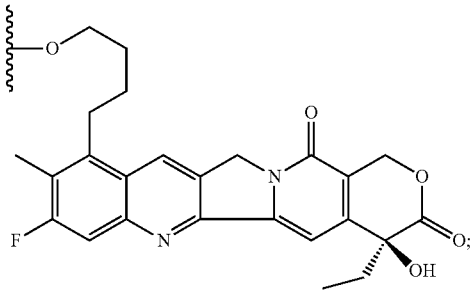

(P2′)
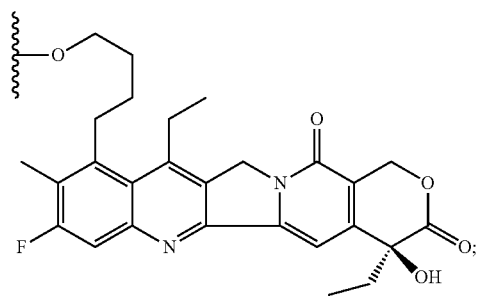
(P3′)
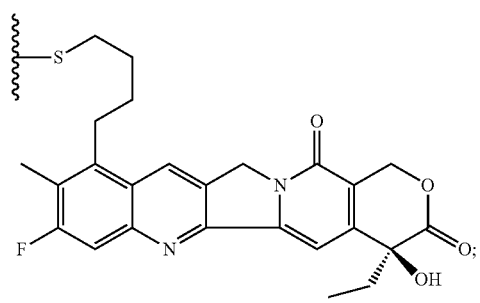
(P4′)
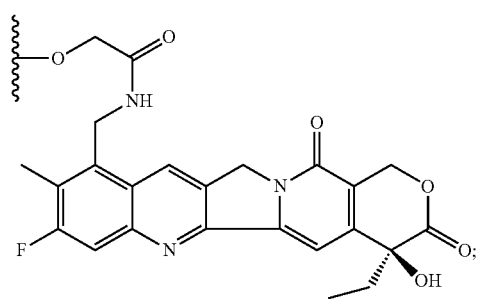
(P5′)
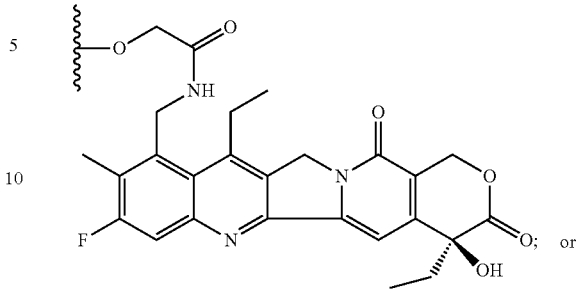
or
(P6′)
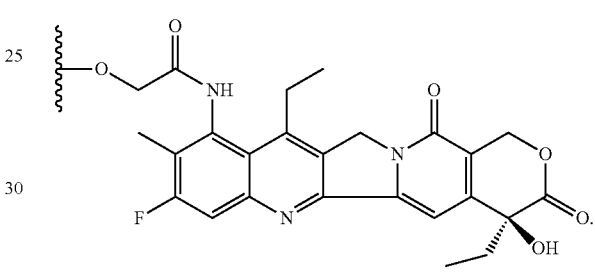
27. The compound of claim 22, wherein D-L$_1$-L$_2$-Q′—CH$_2$—NH-E-Z′— is formed from one of the following structures,
(PL1)
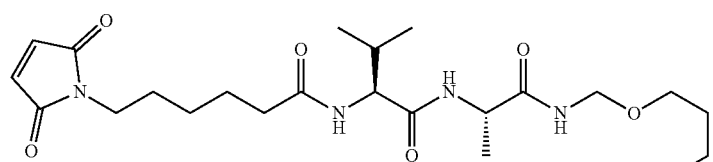
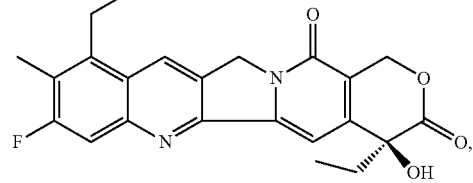
(PL2)
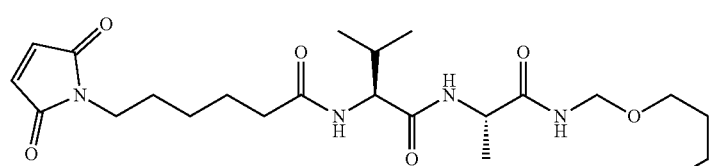
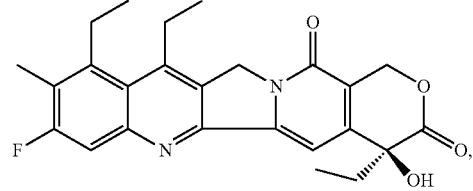

(PL3)
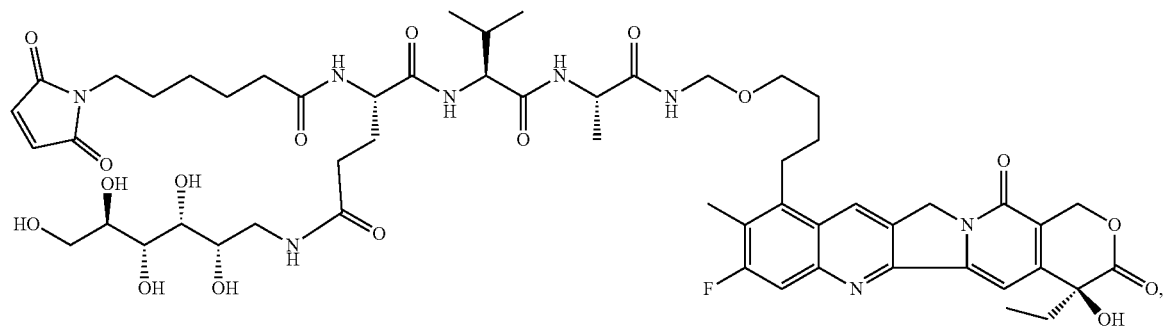
(PL4)
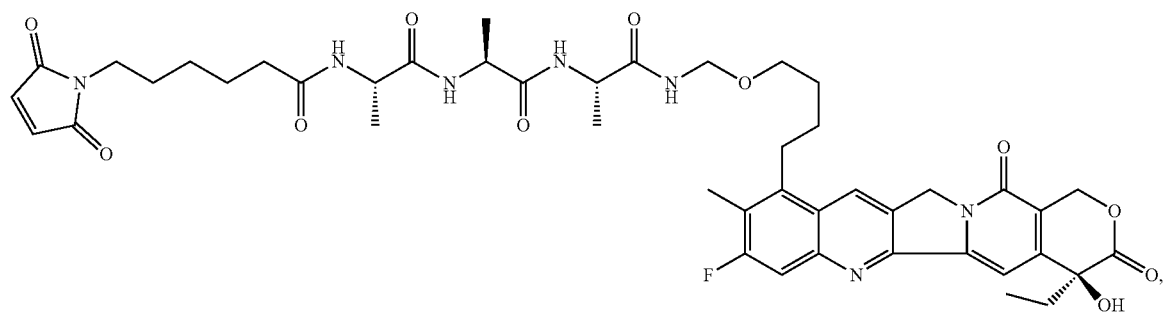
(PL5)
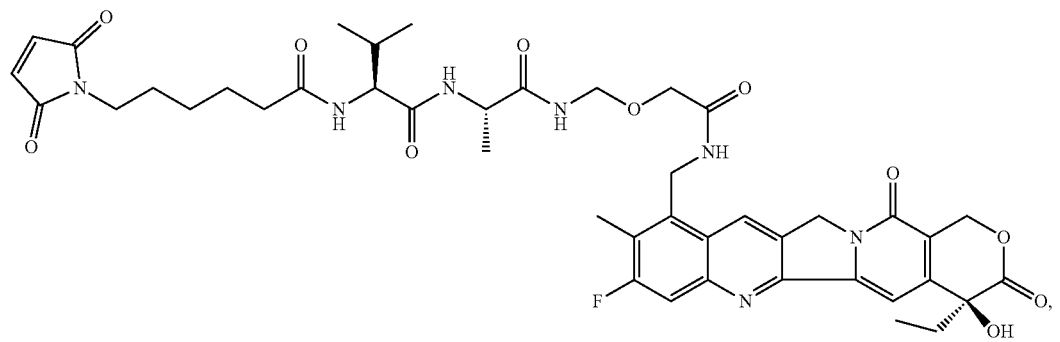
(PL6)
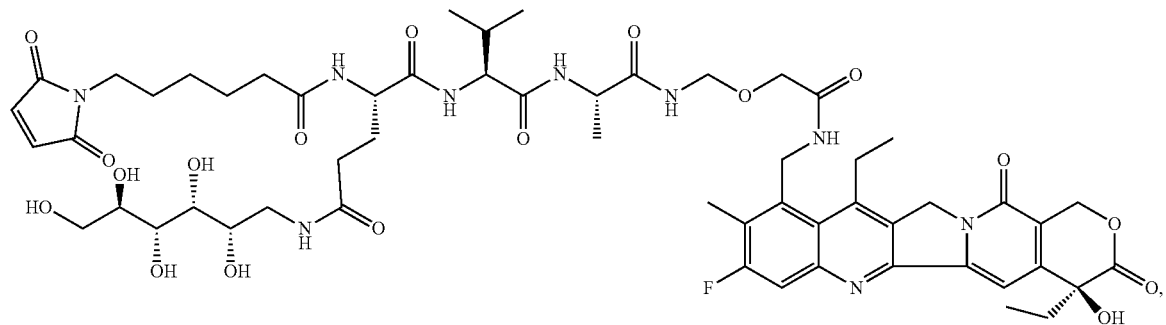

-continued
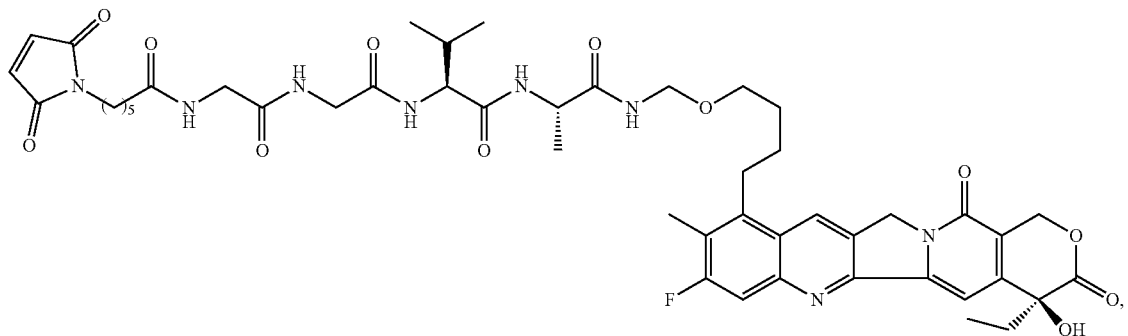
(PL7)
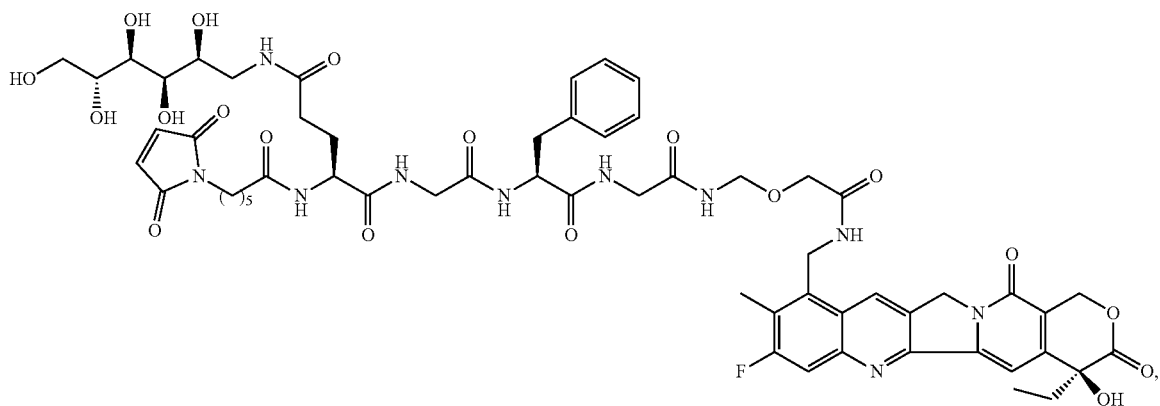
(PL8)
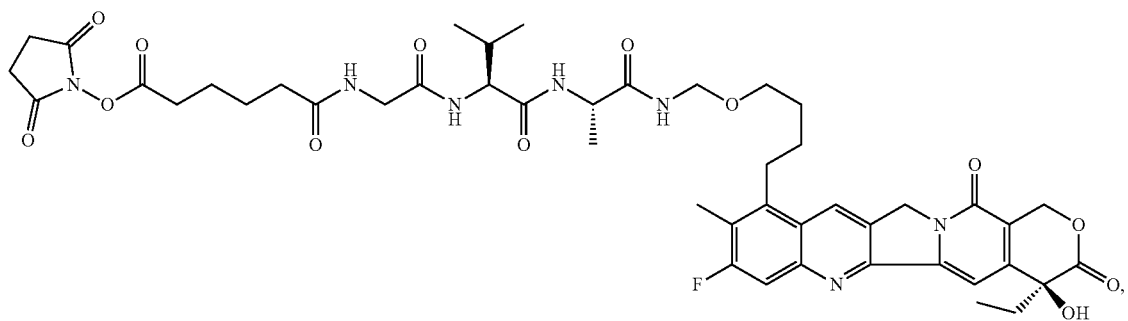
(PL9)
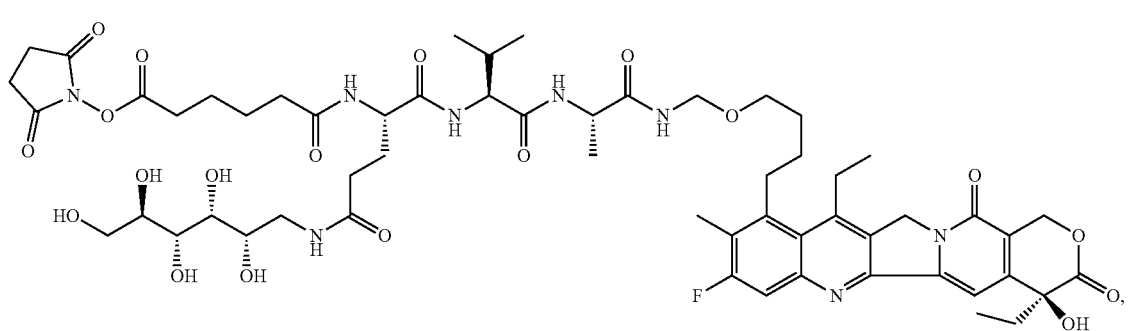
(PL10)

-continued
(PL11)
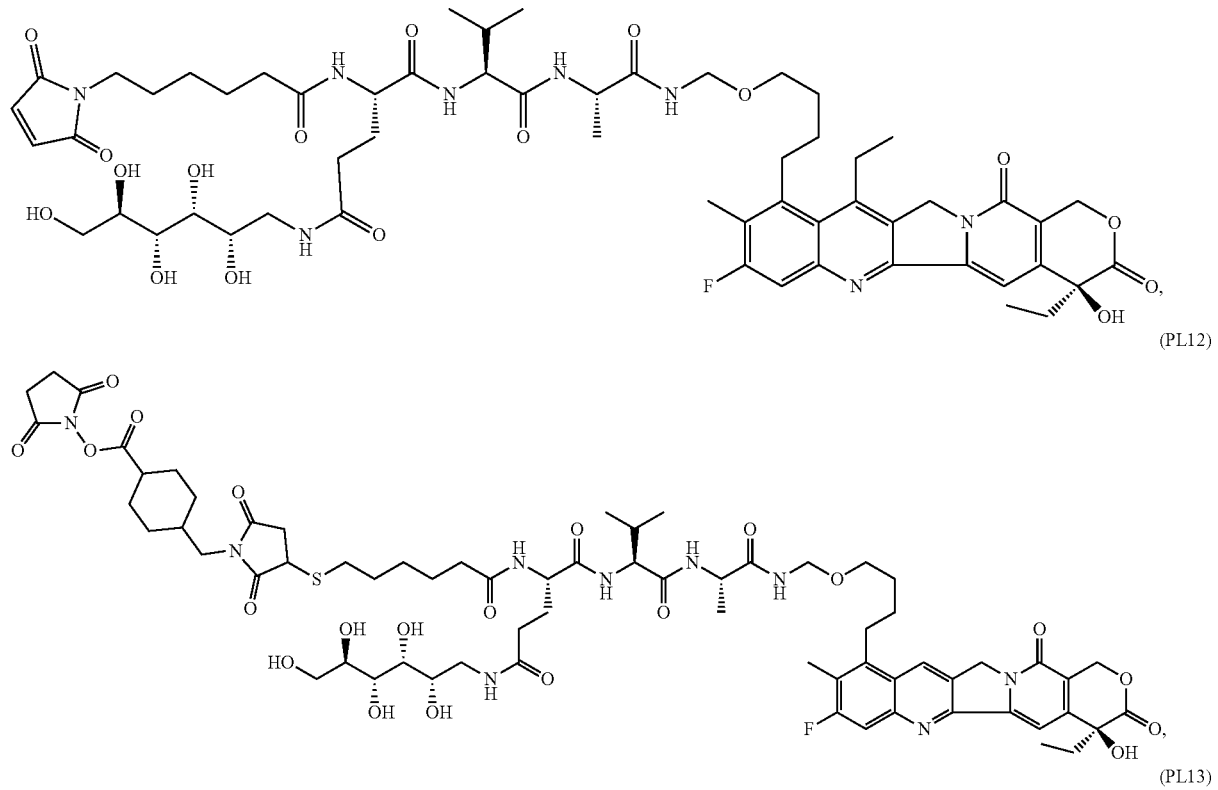
(PL12)
(PL13)
(PL14)
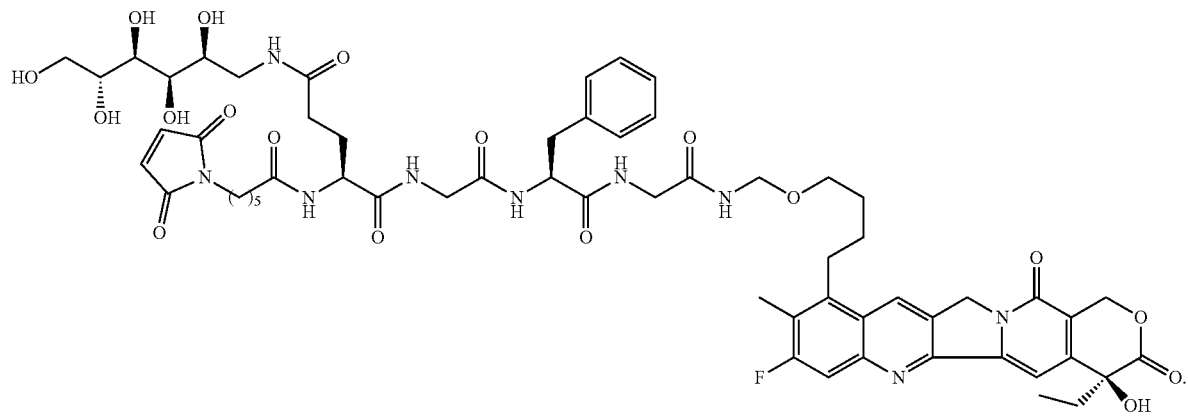

28. The compound of claim 22, wherein {D-L$_1$-L$_2$-Q'—CH$_2$—NH-E-Z'}$_p$—C is one of the following structures, wherein C is a monoclonal antibody and p is the drug to antibody ratio (DAR) and p is a average number ranging from about 2-10, 4-8, 7-8, or 3.2 to 8.0,
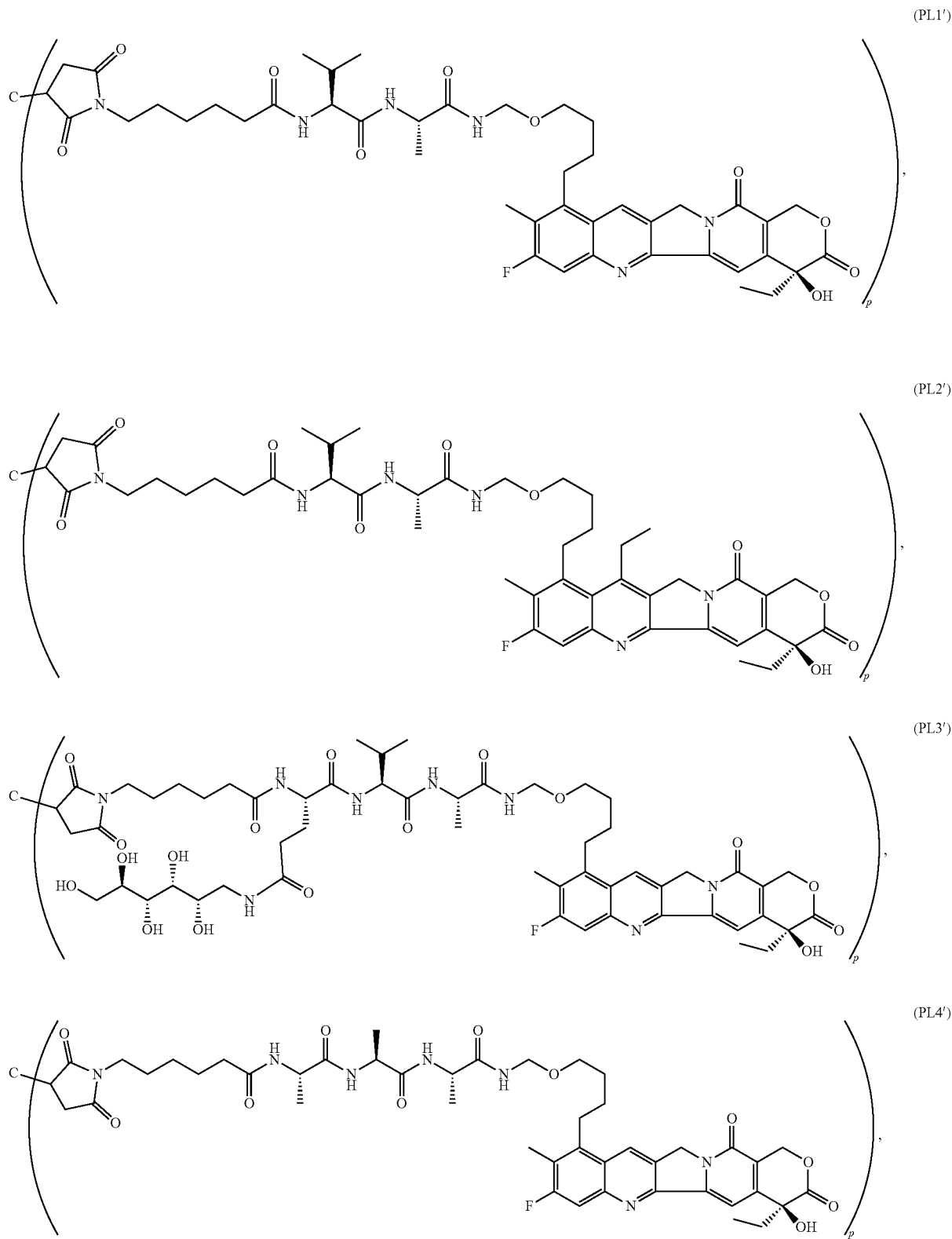

-continued
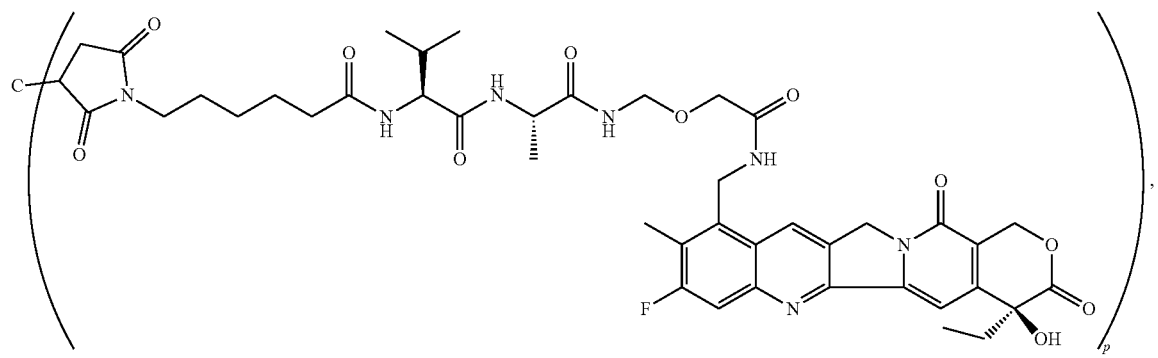
(PL5')
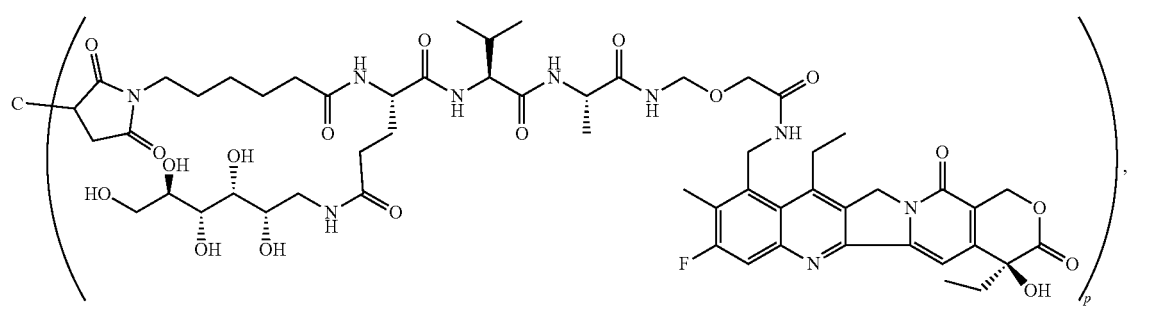
(PL6')
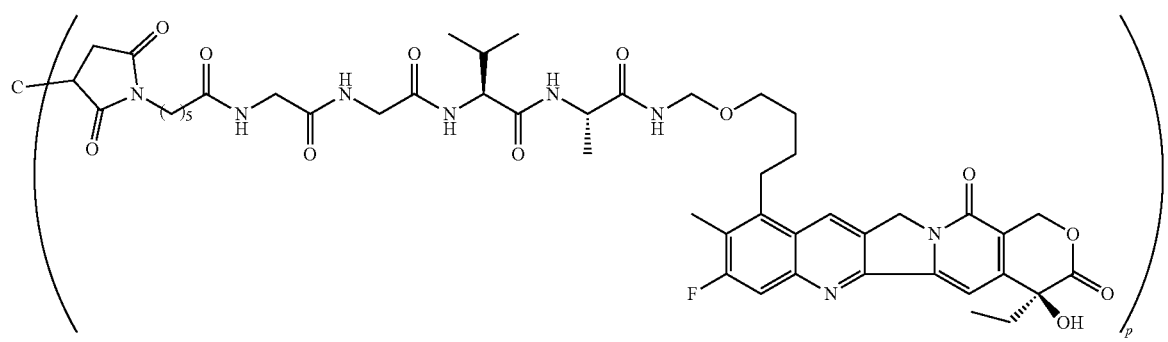
(PL7')
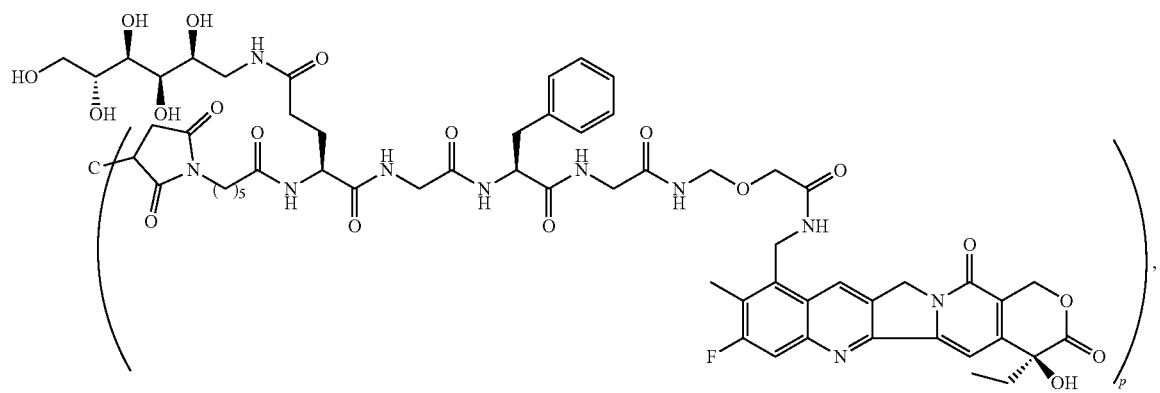
(PL8')

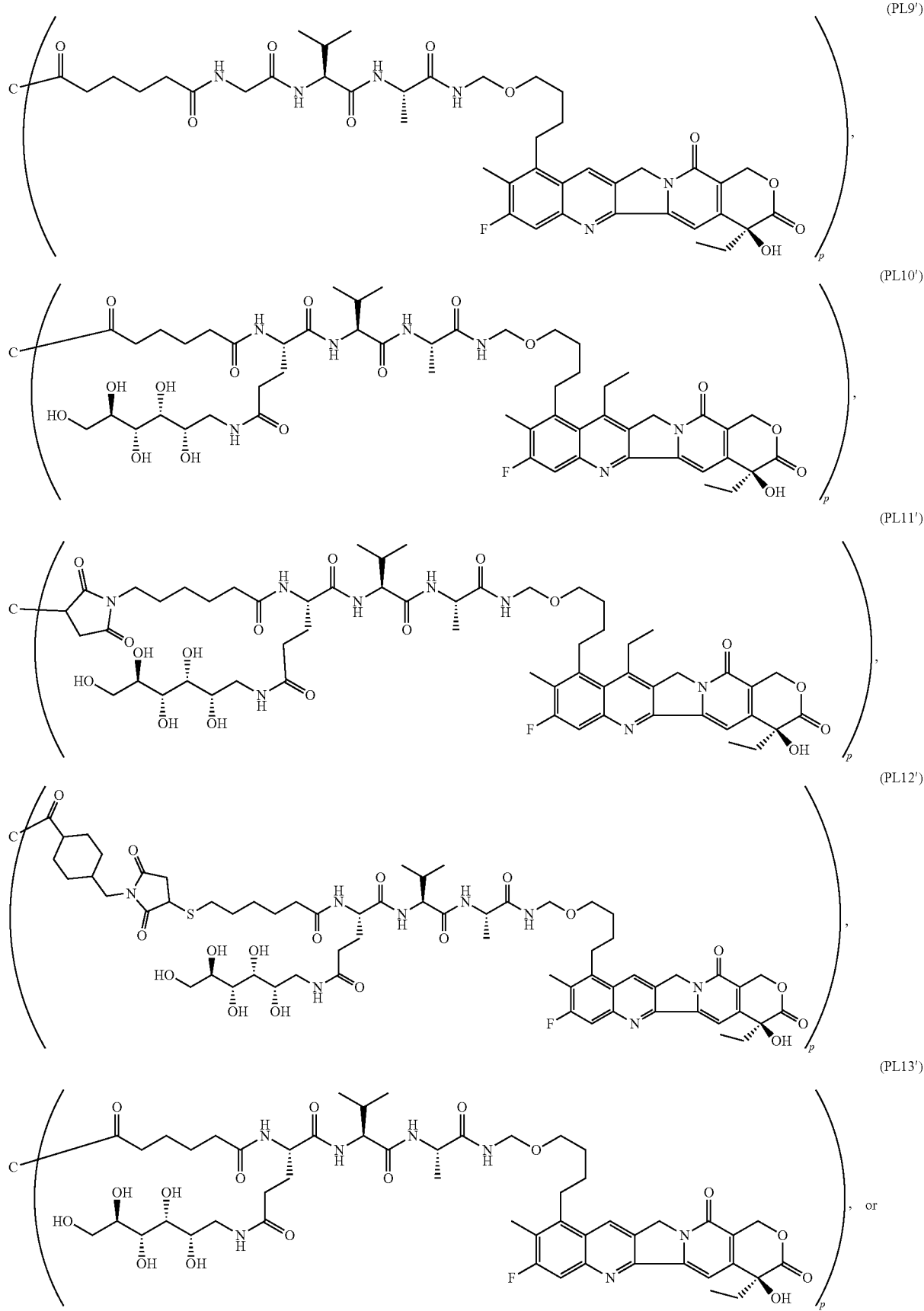

(PL14')

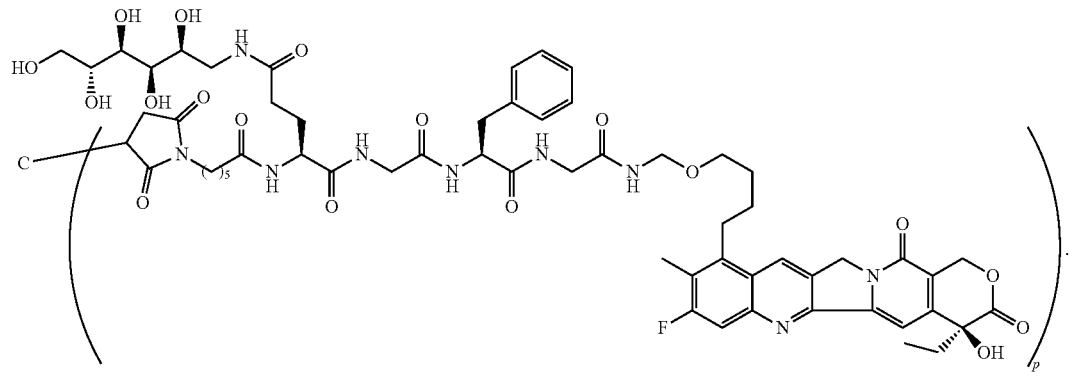

29. The compound of claim 22, wherein the cell binding agent is a monoclonal antibody or an antigen-binding fragment thereof.

30. A pharmaceutical composition comprising the compound of claim 22.

31. The compound of claim 22 having the following structure:

(PL3')

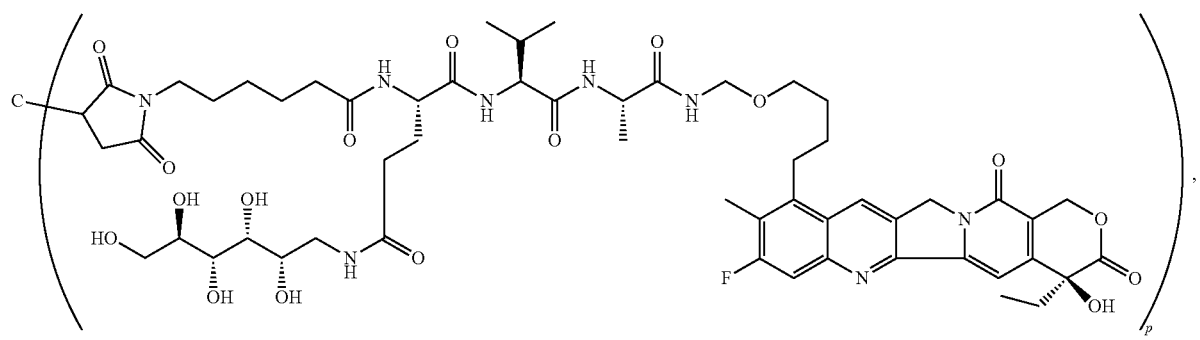

where C is a monoclonal antibody and p is the drug to antibody ratio (DAR) and p is a average number ranging from about 2-10, 4-8, 7-8, or 3.2 to 8.0.

32. The compound of claim 1, having the following structure:

(P1)

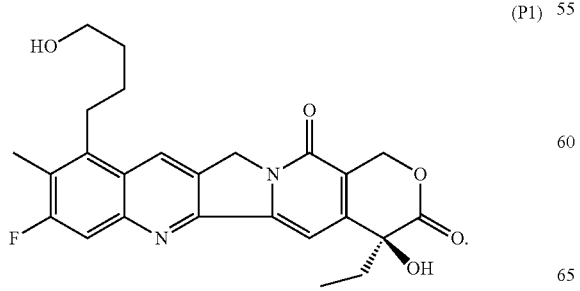

33. The compound of claim 10, having the following structure:
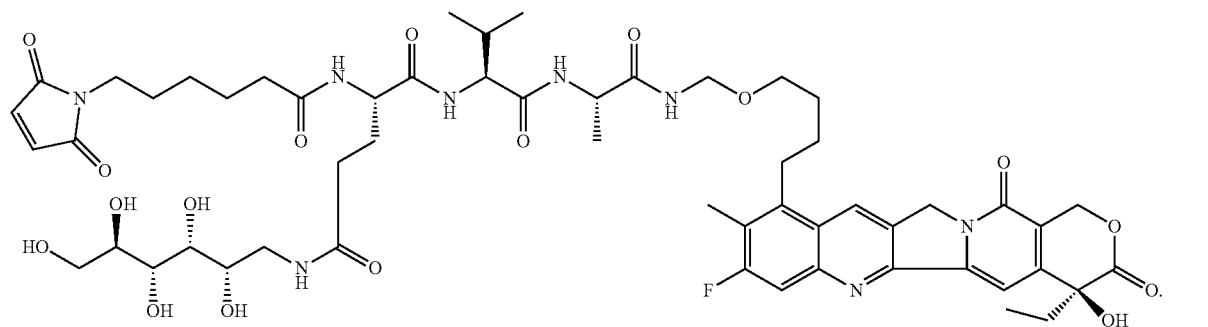
(PL3)

UNITED STATES PATENT AND TRADEMARK OFFICE
CERTIFICATE OF CORRECTION

PATENT NO. : 12,029,736 B2
APPLICATION NO. : 17/185012
DATED : July 9, 2024
INVENTOR(S) : Wei Li Page 1 of 1

It is certified that error appears in the above-identified patent and that said Letters Patent is hereby corrected as shown below:

In the Claims

Column 237, Claim 1, Line 40 at the end of figure (I), add ", wherein"
Column 243, Claim 9, Line 26, Figure (P4) the top left side of this figure should be "HO"
Column 244, Claim 10, Line 29, there should be an "*" after "wherein"

Signed and Sealed this
Third Day of December, 2024

Katherine Kelly Vidal
*Director of the United States Patent and Trademark Office*